United States Patent
Schramm et al.

(10) Patent No.: US 10,519,222 B2
(45) Date of Patent: Dec. 31, 2019

(54) BROADLY NEUTRALIZING MONOCLONAL ANTIBODIES AGAINST HIV-1 V1V2 ENV REGION

(71) Applicants: The United States of America, as represented by the Secretary, Department of Health and Human SERVICES, Bethesda, MD (US); The Trustees of Columbia University in the City of New York, New York, NY (US); Centre for the AIDS Programme of Research in South Africa, Durban (ZA); University of the Witwatersrand, Johannesburg, Johannesburg (ZA); National Health Laboratory Service, Sandringham (ZA)

(72) Inventors: Chaim Aryeh Schramm, Bronx, NY (US); Jason Gorman, Washington, DC (US); John Mascola, Rockville, MD (US); Lawrence Stewart Shapiro, New York, NY (US); Lynn Morris, Randburg (ZA); Nicole Amy Doria-Rose, Kensington, MD (US); Penelope Linda Moore, Modderfontein (ZA); Peter Dak Pin Kwong, Washington, DC (US); Salim Safurdeen Abdool Karim, Durban (ZA)

(73) Assignees: THE UNITED STATES OF AMERICA, AS REPRESENTED BY THE SECRETARY, DEPARTMENT OF HEALTH AND HUMAN SERVICES, Bethesda, MD (US); THE TRUSTEES OF COLUMBIA UNIVERSITY IN THE CITY OF NEW YORK, New York, NY (US); CENTRE FOR THE AIDS PROGRAMME OF RESEARCH IN SOUTH AFRICA, Durban (ZA); UNIVERSITY OF THE WITWATERSRAND, JOHANNESBURG, Johannesburg (ZA); NATIONAL HEALTH LABORATORY SERVICE, Sandringham (ZA)

( * ) Notice: Subject to any disclaimer, the term of this patent is extended or adjusted under 35 U.S.C. 154(b) by 64 days.

(21) Appl. No.: 15/121,051

(22) PCT Filed: Feb. 27, 2015

(86) PCT No.: PCT/IB2015/051465
§ 371 (c)(1),
(2) Date: Aug. 24, 2016

(87) PCT Pub. No.: WO2015/128846
PCT Pub. Date: Sep. 3, 2015

(65) Prior Publication Data
US 2016/0362479 A1    Dec. 15, 2016

(30) Foreign Application Priority Data

Feb. 28, 2014 (GB) .................................... 1403613.1
Dec. 19, 2014 (ZA) ................................ 2014/09416

(51) Int. Cl.
*C07K 16/10*       (2006.01)
*A61K 39/42*       (2006.01)
(Continued)

(52) U.S. Cl.
CPC .......... *C07K 16/1063* (2013.01); *A61K 39/42* (2013.01); *A61K 45/06* (2013.01); *C12N 7/00* (2013.01); *G01N 33/6854* (2013.01); *C07K 2317/21* (2013.01); *C07K 2317/54* (2013.01); *C07K 2317/55* (2013.01);
(Continued)

(58) Field of Classification Search
CPC ............ C07K 16/1063; C07K 2317/56; C07K 2317/565; C07K 2317/76; A61K 39/42
See application file for complete search history.

(56) References Cited

U.S. PATENT DOCUMENTS

2003/0105282 A1    6/2003  Pinter

FOREIGN PATENT DOCUMENTS

WO    WO 2013/039792    3/2013
WO    WO 2013/085550    6/2013

OTHER PUBLICATIONS

Franchini, G., and M. L. Bosch, 1989, Genetic Relatedness of the Human Immunodeficiency Viruses Type 1 and 2 (HIV-1, HIV-2) and the Simian Immunodeficiency Virus (SIV), Annals New York Academy of Science, 554(1):81-87.*

(Continued)

*Primary Examiner* — Jeffrey S Parkin
(74) *Attorney, Agent, or Firm* — Buchanan Ingersoll & Rooney PC

(57) ABSTRACT

The present invention relates anti-HIV therapies and prophylaxis. Specifically, the invention relates to broadly neutralizing antibodies against HIV-1, nucleic acids encoding these antibodies, vectors comprising the nucleic acids and cells and pharmaceutical compositions Comprising said vectors and/or antibodies. The present invention also relates to use of the antibodies and/or vectors for the treatment and/or prevention of HIV-1 infection in a subject. Furthermore, the invention also relates to a kit containing the antibodies of the invention.

10 Claims, 13 Drawing Sheets

Specification includes a Sequence Listing.

(51) Int. Cl.
A61K 45/06 (2006.01)
C12N 7/00 (2006.01)
G01N 33/68 (2006.01)
(52) U.S. Cl.
CPC .... C07K 2317/56 (2013.01); C07K 2317/565 (2013.01); C07K 2317/622 (2013.01); C07K 2317/76 (2013.01); C07K 2317/92 (2013.01); C12N 2740/16122 (2013.01); C12N 2740/16134 (2013.01); G01N 2469/20 (2013.01)

(56) References Cited

OTHER PUBLICATIONS

Chen, C., et al., Sep. 1992, Generation and Analysis of Random Point Mutations in an Antibody CDR2 Sequence: Many Mutated Antibodies Lose Their Ability to Bind Antigen, J. Exp. Med. 176:855-866.*
Xiange, J., et al., 1995, Framework Residues 71 and 93 of the Chimeric B72.3 Antibody are Major Determinants of the Conformation of Heavy-chain Hypervariable Loops, J. Mol. Biol. 253:385-390.*
Liu, Z., et al., 1999, Fine Mapping of the Antigen-Antibody Interaction of scFv215, a Recombinant Antibody Inhibiting RNA Polymerase II from *Drosophila mlanogaster*, J. Mol. Recog. 12:103-111.*
Bansal, G. P., 2007, A summary of the workshop on passive immunization using monoclonal antibodies for HIV/AIDS, held at the National Institute of Allergy and Infectious Diseases, Bethesda, Mar. 10, 2006, Biologicals 35:367-371.*
Gong, R., et al., 2012, Candidate Antibody-Based Therapeutics Against HIV-1, Biodrugs 26(3):143-162.*
Abela, I. A., et al., Apr. 2012, Cell-Cell Transmission Enables HIV-1 to Evade Inhibition by Potent CD4bs Directed Antibodies, PLoS Pathogens, 8(4):e1002634 (pp. 1-21).*
Kwong, P. D., et al., Sep. 2013, Broadly neutralizing antibodies and the search for an HIV-1 vaccine: the end of the beginning, Nat. Rev. Immunol. 13:693-701.*
Haigwood, N. L., 2004, Predictive Value of Primate Models for AIDS, AIDS Rev. 6:187-198.*
Doria-Rose et al., *A Family of Broad and Highly Potent V1V2-Directed HIV-1 Neutralizing Antibodies with Long CDRH3s from a South African Seroconverter*, 29(11) AIDS Research and Human Retroviruses A-48 (2013), (abstract only).
Doria-Rose et al., *New Member of the V1V2-Directed CAP256-VRC26 Lineage That Shows Increased Breadth and Exceptional Potency*, 90(1) Journal of Virology 76-91 (Jan. 2016).
Gorman et al., *Structures of HIV-1-Env V1B2 with broadly neutralizing antibodies reveal commonalties that enable vaccine design*, 23(1) Nat. Struct. Mol. Biol. 81-90 (Jan. 2016).
McLellan et al., *V1/V2-directed antibodies elicited in RV144 vaccinees bind to a structurally polymorphic site*, 9(Suppl. 2) Retrovirology P107 (2012) (abstract only).
Moore et al., *Multiple Pathways of Escape from HIV Broadly Cross-Neutralizing V2-Dependent Antibodies*, 87(9) J. Virol. 4882-4894 (May 2013).
Moore et al., *Ontogeny-based immunogens for the induction of V2-directed HIV broadly neutralizing antibodies*, 275 Immunological Reviews 217-229 (2017).
AIDS vaccine, Oct. 7-10, 2013, Barcelona, Spain, 29(11) AIDS Research and Human Retroviruses, 29(11) (Nov. 1, 2013).
Haynes et al., *B-cell-lineage immunogen design in vaccine development with HIV-1 as a case study*, 30(5) Nature Biotechnology 423-433 (May 1, 2012).
Klein et al., *Antibodies in HIV-1 Vaccine Development and Therapy*, 341 Science 1199-1204 (Sep. 13, 2013).

Kwong et al., *Human Antibodies that Neutralize HIV-1: Identification, Structures, and B Cell Ontogenies*, 37(3) Immunity 412-425 (Sep. 21, 2012).
McLellan et al., *Structure of HIV-a gp120 V1/V2 domain with broadly neutralizing antibody PG9*, 480 Nature 336-343 (Dec. 15, 2011).
Moore et al., *Potent and Broad Neutralization of HIV-1 Subtype C by Plasma Antibodies Targeting a Quaternary Epitope Including Residues in the V2 Loop*, 85(7) Journal of Virology 3128-3141 (Apr. 2011).
Pancera et al., *Structural basis for diverse N-glycan recognition by HIV-1-neutralizing V1-V2-directed antibody PG16*, 20(7) Nature Structural & Molecular Biology 804-814 (Jul. 2013).
Schramm et al., *Origin of an Ultra-Long CDR H3 in a V1V2-directed Broadly HIV-1 Neutralizing HIV-1 Antibody Lineage*, http://epostersonline.com/aidsvax2013/?q=node/1165&posterview=true&first=true retrieved May 6, 2015.
Walker et al., *Broad neutralization coverage of HIV by multiple highly potent antibodies*, 477 Nature 466-471 (Sep. 22, 2011).
International Search Report issued in corresponding International Patent Application No. PCT/IB2015/051465, dated Jun. 11, 2015.
Adams et al., *Recent developments in the PHENIX software for automated crystallographic structure determination*, 11 Journal of Synchrotron Radiation 53-55 (2004).
Alamyar et al., *IMGT/HIGHV-QUEST: The IMGT® Web Portal for Immunoglobulin (IG) or Antibody and T Cell Receptor (TR) Analysis from NGS High Throughput and Deep Sequencing*, 8(1)(2) Immunome-Research 1-15 (2012).
Ashkenazy et al., *FastML: a web server for probabilistic reconstruction of ancestral sequences*, 40 Nucleic Acids Research W580-W584 (2012) (Online May 31, 2012).
Bonsignori et al., *Analysis of a Clonal Lineage of HIV-1 Envelope V2/V3 Conformational Epitope-Specific Broadly Neutralizing Antibodies and Their Inferred Unmutated Common Ancestors*, 85(19) Journal of Virology 9998-10009 (Oct. 2011) (Ahead of Print Jul. 27, 2011).
Boyd et al., *Individual Variation in the Germline Ig Gene Repertoire Inferred from Variable Region Gene Rearrangements*, 184(12) Journal of Immunology 6986-6992 (2010) (Online May 2010).
Briney et al., *High-throughput antibody sequencing reveals genetic evidence of global regulation of the naive and memory repertoires that extends across individuals*, 13 Genes and Immunity 469-473 (2012) (Online May 24, 2012).
Briney et al., *Human Peripheral Blood Antibodies with Long HCDR3s Are Extablished Primarily at Original Recombination Using a Limited Subset of Germline Genes*, 7(5) PLoS ONE 1-13 (May 9, 2012).
Bunnik et al., *Autologous Neutralizing Humoral Immunity and Evolution of the Viral Envelope in the Course of Subtype B Human Immunodeficiency Virus Type 1 Infection*, 82(16) Journal of Virology 7932-7941 (Aug. 2008) (Published ahead Jun. 4, 2008).
Burton et al., *A Blueprint for HIV Vaccine Discovery*, 12 Cell Host & Microbe 396-407 (Oct. 18, 2012).
Crooks et al., *WebLogo: A Sequence Logo Generator*, 14 Genome Research 1188-1190 (2004).
Davis et al., *MolProbity: structure validation and all-atom contact analysis for nucleic acids and their complexes*, 32 Nucleic Acids Research W615-W619 (2004).
Ditzel et al., *Determinants of Polyreactivity in a Large Panel of Recombinant Human Antibodies from HIV-1 Infection*, 157 Journal of Immunology 739-749 (1996).
Doria-Rose et al., *Breadth of Human Immunodeficiency Virus-Specific Neutralizing Activity in Sera: Clustering Analysis and Association with Clinical Variables*, 84(3) Journal of Virology 1631-1636 (Feb. 2010) (Published ahead of Print Nov. 18, 2009).
Doria-Rose et al., *A Short Segment of the HIV-1 gp120 V1/V2 Region Is a Major Determinant of Resistance to V1/V2 Neutralizing Antibodies*, 86(15) Journal of Virology 8319-8323 (Aug. 2012).
Emsley et al., *Coot: model building tools for molecular graphics*, D60 Acta Crystalographica 2126-2132 (2004).
Gao et al., *The Heterosexual Human Immunodeficiency Virus Type 1 Epidemic in Thailand is Caused by an Intersubtype (A/E) Recombinant of African Origin*, 70(10) 7013-7029 (Oct. 1996).

(56) References Cited

OTHER PUBLICATIONS

Georgiev et al., *Delineating Antibody Recognition in Polyclonal Sera from Patterns of HIV-1 Isolate Neutralization*, 340 Science 751-756 (May 10, 2013).
Glanville et al., *Precise determination of the diversity of a combinatorial antibody library gives insight into the human immunoglobulin repertoire*, 106(48) PNAS 20216-20221 (Dec. 1, 2009).
Gray et al., *The Neutralization Breadth of HIV-1 Develops Incrementally Over Four Years and Is Associated with CD4+ T Cell Decline and High Viral Load During Acute Infection*, 85(10) Journal of Virology 4828-4840 (May 2011) (Published ahead of Print Mar. 9, 2011).
Haynes et al., *Cardiolipin Polyspecific Autoreactivity in Two Broadly Neutralizing HIV-1 Antibodies*, 308 Science 1906-1909 (Jun. 24, 2005).
Huang et al., *Broad and potent neutralization of HIV-1 by a gp41-specific human antibody*, 491 Nature 406-414 (Nov. 15, 2012).
Huang et al., *Isolation of human monoclonal antibodies from peripheral blood B cells*, 8(10) Nature Protocols 1907-1915 (2013) (Online Sep. 12, 2013).
Julien et al., *Asymmetric recognition of the HIV-1 trimer by broadly neutralizing antibody PG9*, 110(11) PNAS 4351-4356 (Mar. 12, 2013).
Kabat et al., *Sequences of Proteins of Immunological Interest* (1983).
Kong et al., *Antigenicity and Immunogenicity in HIV-1 Antibody-Based Vaccine Design*, 8(003) Journal AIDS Clinical Research 1-23 (2012).
Kosakovsky et al., *A Maximum Likelihood Method for Detecting Directional Evolution in Protein Sequences and Its Application to Influenza A Virus*, 25(9) Molecular Biology and Evolution 1089-1824 (2008) (Advanced access publication May 29, 2008).
Kraus et al., *A Rev1-vpu polymorphism unique to HIV-1 subtype A and C strains impairs envelope glycoprotein expression from rev-vpu-env cassettes and reduces virion infectivity in pseudotyping assays*, 397 Virology 346-357 (2010).
Larkin et al., *Clustal W and Clustal X Version 2.0*, 23(21) Bioinformatics 2947-2948 (2007) (Advanced access publication Sep. 10, 2007).
Li et al., *Clustering of highly homologous sequences to reduce the size of large protein databases*, 17(3) Bioinformatics 282-283 (2001).
Liao et al., *Co-evolution of a broadly neutralizing HIV-1 antibody and founder virus*, 496 Nature 469-479 (Apr. 25, 2013).
Liu et al., *Molecular architecture of native HIV-1 gp120 trimers*, 455 Nature 109-114 (Sep. 4, 2008).
Lynch et al., *The B Cell Response Is Redundant and Highly Focused on V1V2 during Early Subtype C Infection in a Zambian Seroconverter*, 85(2) Journal of Virology 905-915 (Jan. 2011).
Mascola et al., *HIV-1 neutralizing antibodies: understanding nature's pathways*, 254 Immunological Reviews 225-244 (2013).
McCoy et al., *Neutralizing antibodies to HIV-1 induced by immunization*, 210(2) Journal of Experimental Medicine 209-223 (2013).
McLellan et al., *Structure of HIV-1 gp120 V1/V2 domain with broadly neutralizing antibody PG9*, 480 Nature 336-345 (Dec. 15, 2011).
Moir et al., *Prospects for an HIV vaccine: leading B cells down the right path*, 18(12) Nature Structural & Molecular Biology 1317-1322 (Dec. 2011).
Montefiori, *Homotypic Antibody Responses to Fresh Clinical Isolates of Human Immunodeficiency Virus*, 182 Virology 635-643 (1991).
Montefiori et al., *Measuring HIV Neutralization in a Luciferase Reporter Gene Assay*, 2 Ed. 485 HIV Protocols 394-405 (2009).
Moore et al., *Multiple Pathways of Escape from HIV Broadly Cross-Neutralizing V2-Dependent Antibodies*, 87(9) Journal of Virology 4882-4894 (May 2013) (Published ahead of print Feb. 6, 2013).
Murrell et al., *Detecting Individual Sites Subject to Episodic Diversifying Selection*; 8(7) PLoS Genetics 1-10 (Jul. 2012).
Overbaugh et al., *The Antibody Response against HIV-1*, Cold Spring Harb Perspectives in Medicine 1-17 (2012).
Pancera et al., *Selective recognition of oligomeric HIV-1 primary isolate envelope glycoproteins by potently neutralizing ligands requires efficient precursor cleavage*, 332 Virology 145-156 (2005) (Online Dec. 10, 2004).
Pantophlet et al., *GP120: Target for Neutralizing HIV-1 Antibodies*, 24 Annual Review of Immunology 739-769 (2006) (Online advanced review Jan. 16, 2006).
Pejchal et al., *Structure and function of broadly reactive antibody PG16 reveal an H3 subdomain that mediates potent neutralization of HIV-1*, 107(25) PNAS 11483-11488 (Jun. 22, 2010).
Pejchal et al., *A Potent and Broad Neutralizing Antibody Recognizes and Penetrates the HIV Glycan Shield*, 334 Science 1097-1103 (Nov. 25, 2011).
Pettersen et al., *UCSF Chimera—A Visualization System for Exploratory Research and Analysis*, 25 Journal of Computational Chemistry 1605-1612 (2004).
Piantadosi et al., *Breadth of Neutralizing Antibody Response to Human Immunodeficiency Virus Type 1 Is Affected by Factors Early in Infection but Does Not Influence Disease Progression*, 83(19) Journal of Virology 10269-10274 (Oct. 2009) (Published ahead of print Jul. 29, 2009).
Pond et al., *HyPhy: hypothesis testing using phylogenies*, 21(5) Bioinformatics 676-679 (2005) (Advanced access publication Oct. 27, 2004).
Price et al., *FastTree 2—Approximately Maximum-Likelihood Trees for Large Alignments*, 5(3) PLos ONE 1-10 (Mar. 2010).
Richman et al., *Rapid evolution of the neutralizing antibody response to HIV type 1 infection*, 100(7) PNAS 4144-4149 (Apr. 1, 2003).
Rolland et al., *Increased HIV-1 vaccine efficacy against viruses with genetic signatures in Env V2*, 490 Nature 417-420 (Oct. 18, 2012).
Salazar-Gonzalez et al., *Deciphering Human Immunodeficiency Virus Type 1 Transmission and Early Envelope Diversification by Single-Genome Amplification and Sequencing*, 82(8) Journal of Virology 3952-3970 (Apr. 2008) (Published ahead of print Feb. 6, 2008).
Sather et al., *Factors Associated with the Development of Cross-Reactive Neutralizing Antibodies during Human Immunodeficiency Virus Type 1 Infection*, 83(2) Journal of Virology 757-769 (Jan. 2009) (Published ahead of print Nov. 5, 2008).
Shu et al., *Efficient protein boosting after plasmid DNA or recombinant adenovirus immunization with HIV-1 vaccine constructs*, 25 Vaccine 1398-1408 (2007).
Soto et al., *loop modeling: sampling, filtering, and scoring*, 70 Proteins 834-843 (2008).
Souto-Carneiro et al., *Characterization of the Human Ig Heavy Chain Antigen Binding Complementarity Determining Region 3 Using a Newly Developed Software Algorithm, JOINSOLVER*, 172 Journal of Immunology 6789-6802 (2004).
Tamura et al., *MEGA5—Molecular Evolutionary Genetics Analysis Using Maximum Likelihood, Evolutionary Distance, and Maximum Parsimony Methods*, 28(10) Molecular Biology and Evolution 2731-2739 (2011) (Advanced access publication May 4, 2011).
Tian et al., *Immunodominance of the $V_H$1-46 Antibody Gene Segment in the Primary Repertoire of Human Rotavirus—Specific B Cells Is Reduced in the Memory Compartment through Somatic Mutation of Nondominant Clones*, 180 Journal of Immunology 3279-3288 (2008).
Tiller et al., *Efficient generation of monoclonal antibodies from single human B cells by single cell RT-PCR and expression vector cloning*, 329 Journal of Immunological Methods 112-124 (2008) (Available online Oct. 31, 2007).
Tomaras et al., *Polyclonal B Cell Responses to Conserved Neutralization Epitopes in a Subset of HIV-1-Infected Individuals*, 85(21) Journal of Virology 11502-11519 (Nov. 2011) (Published ahead of print Aug. 17, 2011).
Tong et al., *HIV-1 Virus-Like Particles Bearing Pure Env Trimers Expose Neutralizing Epitopes but Occlude Nonneutralizing Epitopes*, 86(7) Journal of Virology 3574-3587 (2012) (Published ahead of print Feb. 1, 2012).
Tran et al., *Structural Mechanism of Trimeric HIV-1 Envelope Glycoprotein Activation*, 8(7) PLoS Pathogens 1-18 (Jul. 2012).

(56) References Cited

OTHER PUBLICATIONS

Van Gils et al., *Prevalence of cross-reactive HIV-1-neutralizing activity in HIV-1-infected patients with rapid or slow disease progression*, 23 AIDS 2405-2414 (2009).

Van Loggerenberg et al., *Establishing a Cohort at High Risk of HIV Infection in South Africa: Challenges and Experiences of the CAPRISA 002 Acute Infection Study*, 3(4) PLoS ONE 1-8 (Apr. 16, 2008).

Verkoczy et al., *Autoreactivity in an HIV-1 broadly reactive neutralizing antibody variable region heavy chain induces immunologic tolerance*, 107(1) PNAS 181-186 (Jan. 5, 2010).

Walker et al., *Broad and Potent Neutralizing Antibodies from an African Donor Reveal a New HIV-1 Vaccine Target*, 326 Science 285-289 (Oct. 9, 2009).

Walker et al., *A limited Number of Antibody Specificities Mediate Broad and Potent Serum Neutralization in Selected HIV-1 Infected Individuals*, 6(8) PLoS Pathogens 1-14 (Aug. 2010).

Wardemann et al., *Predominant Autoantibody Production by Early Human B Cell Precursors*, 301 Science 1374-1377 (Sep. 5, 2003).

Wei et al., *Antibody neutralization and escape by HIV-1*, 422 Nature 307-312 (Mar. 20, 2003).

Wu et al., *Rational Design of Envelope Identifies Broadly Neutralizing Human Monoclonal Antibodies to HIV-1*, 329 Science 856-862 (Aug. 13, 2010).

Wu et al., *Focused Evolution of HIV-1 Neutralizing Antibodies Revealed by Structures and Deep Sequencing*, 333 Science 1593-1602 (Sep. 16, 2011).

Zhou et al., *Structural Basis for Broad and Potent Neutralization of HIV-1 by Antibody VRC01*, 329 Science 811-818 (Aug. 13, 2010).

Zhu et al., *Somatic populations of PGT135-137 HIV-1-neutralizing antibodies identified by 454 pyrosequencing and bioinformatics*, 3(Article 315) Frontiers in Microbiology 1-18 (Sep. 2012).

Zhu et al., *Mining the antibodyome for HIV-1-neutralizing antibodies with next-generation sequencing and phylogenetic pairing of heavy/light chains*, 110(16) PNAS 6470-3475 (Apr. 16, 2013).

Klein et al., *Somatic mutations of the immunoglobulin framework are generally required for broad and potent HIV-1 neutralization*, 153(1) Cell 126-138 (Mar. 28, 2013).

Sela-Culang et al., *The structural basis of an antibody-antigen recognition*, 4(Article 302) Frontiers in Immunology 1-13 (Oct. 2013).

\* cited by examiner

| Antibody name | Mutation From VH3-30*18 | Mutation From Vλ1-51*02 | CDRH3 Length | Neut of 46 strains | |
|---|---|---|---|---|---|
| | | | | % Breadth | Geomean IC50 |
| CAP256-VRC26.01 | 8.3% | 3.9% | 35 | 20% | 1.88 |
| CAP256-VRC26.02 | 8.7% | 4.9% | 35 | 17% | 0.40 |
| CAP256-VRC26.03 | 8.7% | 7.4% | 35 | 35% | 0.07 |
| CAP256-VRC26.04 | 9.0% | 8.1% | 35 | 30% | 0.32 |
| CAP256-VRC26.05 | 10% | 5.6% | 35 | 22% | 0.10 |
| CAP256-VRC26.06 | 11% | 7.4% | 36 | 17% | 0.38 |
| CAP256-VRC26.07 | 12% | 7.7% | 35 | 13% | 1.51 |
| CAP256-VRC26.08 | 12% | 9.8% | 37 | 46% | 0.09 |
| CAP256-VRC26.09 | 14% | 9.8% | 37 | 46% | 0.08 |
| CAP256-VRC26.10 | 12% | 3.9% | 35 | 24% | 0.60 |
| CAP256-VRC26.11 | 13% | 14% | 35 | 26% | 0.94 |
| CAP256-VRC26.12 | 15% | 8.4% | 35 | 7% | 0.49 |
| CAP256-VRC26.13 | 15% | 9.5% | 35 | 7% | 0.24 |
| CAP256-VRC26.14 | 10% | 7.7% | 35 | 24% | 0.29 |
| CAP256-VRC26.15 | 10% | 6.7% | 35 | 33% | 0.75 |
| CAP256-VRC26.16 | 10% | 7.7% | 35 | 28% | 0.52 |
| CAP256-VRC26.17 | 12% | 8.1% | 35 | 28% | 0.17 |
| CAP256-VRC26.18 | 12% | 7.4% | 35 | 26% | 0.45 |
| CAP256-VRC26.19 | 13% | 10% | 35 | 46% | 0.27 |
| CAP256-VRC26.20 | 16% | 13% | 37 | 2% | 1.87 |
| CAP256-VRC26.21 | 18% | 14% | 37 | 13% | 0.30 |
| CAP256-VRC26.22 | 16% | 13% | 37 | 46% | 0.07 |
| CAP256-VRC26.23 | 9.7% | 6.3% | 35 | 7% | 0.17 |
| CAP256-VRC26.24 | 4.2% | 2.5% | 35 | 37% | 4.18 |
| CAP256-VRC26.25 | 12% | 9.8% | 36 | 63% | 0.007 |
| CAP256-VRC26.26 | 17% | 9.8% | 37 | 59% | 0.08 |
| CAP256-VRC26.27 | 16% | 9.5% | 37 | 59% | 0.08 |
| CAP256-VRC26.28 | 15% | 12% | 37 | 41% | 0.12 |
| CAP256-VRC26.29 | 15% | 13% | 37 | 46% | 0.16 |
| CAP256-VRC26.30 | 16% | 13% | 37 | 28% | 0.84 |
| CAP256-VRC26.31 | 15% | 10% | 37 | 20% | 0.39 |
| CAP256-VRC26.32 | 11% | 15% | 35 | 20% | 0.18 |
| CAP256-VRC26.33 | 9.4% | 6.5% | 35 | 22% | 0.23 |

FIGURE 1

A
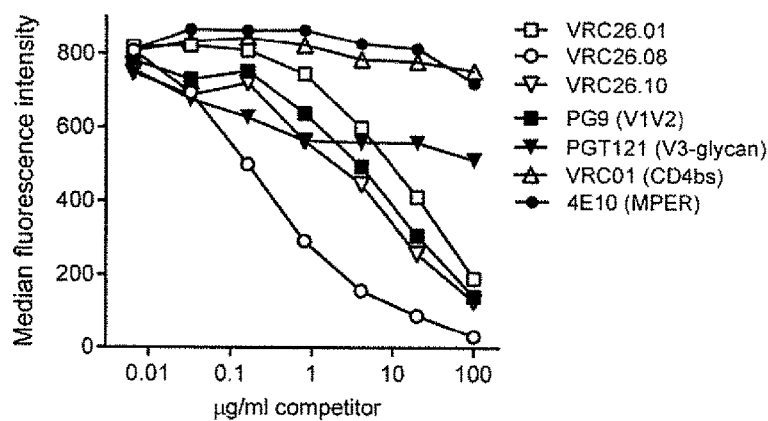
B
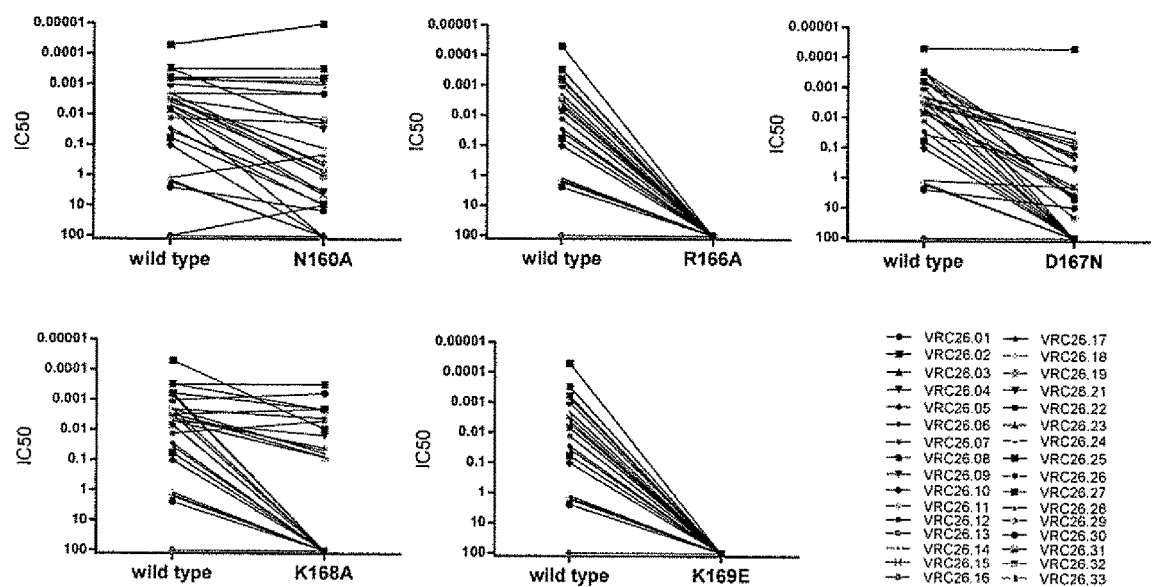
FIGURE 2

| Virus ID | CAP256-VRC26.08 | | CAP256-VRC26.25 | | Virus ID | CAP256-VRC26.08 | | CAP256-VRC26.25 | |
|---|---|---|---|---|---|---|---|---|---|
| | IC50 | IC80 | IC50 | IC80 | | IC50 | IC80 | IC50 | IC80 |
| Du156.12 | 0.011 | 0.296 | <0.0003 | 0.114 | 21261106_C12_H2 | 0.0004 | 0.003 | <0.0003 | 0.001 |
| Du172.17 | >25 | >25 | >25 | >25 | 21369737_G11_F2 | 11.009 | >25 | 0.002 | 1.792 |
| Du422.1 | 0.004 | 0.213 | 0.001 | 0.055 | 21399975_E2_B3 | 0.003 | 0.098 | <0.0003 | <0.0003 |
| ZM197M.PB7 | 0.008 | 0.037 | <0.0003 | 0.004 | 21492713_B11_E3 | >25 | >25 | >25 | >25 |
| ZM214M.PL15 | >25 | >25 | 0.008 | >25 | 21502011_F12_E2 | >25 | >25 | >25 | >25 |
| ZM233M.PB6 | <0.0003 | 0.005 | <0.0003 | <0.0003 | 21561324_D3_B5 | 0.066 | 1.126 | 0.013 | 2.083 |
| ZM53M.PB12 | <0.0003 | 0.002 | <0.0003 | <0.0003 | 19314479_A2_5 | <0.0003 | <0.0003 | <0.0003 | <0.0003 |
| ZM109F.PB4 | >25 | >25 | <0.0003 | 4.997 | 98-F4_H5-13 | >25 | >25 | >25 | >25 |
| ZM135M.PL10a | >25 | >25 | >25 | >25 | 234-F1-16-57 | <0.0003 | <0.0003 | <0.0003 | <0.0003 |
| CAP45.2.00.G3 | 0.007 | 0.721 | <0.0003 | 0.001 | 541-F1_A7_2 | 0.005 | 0.226 | <0.0003 | 0.046 |
| Du151.2 | 0.095 | 4.394 | <0.0003 | 0.004 | 569-F1_37_10 | >25 | >25 | >25 | >25 |
| CAP244.2.00.D3 | >25 | >25 | >25 | >25 | 304_F2_1_11 | 0.183 | 12.503 | <0.0003 | 0.213 |
| ZM215F.PB8 | >25 | >25 | >25 | >25 | 346_F4_D2_12 | >25 | >25 | 0.052 | 20.774 |
| ZM55F.PB28a | 0.022 | 0.117 | 0.003 | 0.087 | 556_F2_3_25 | >25 | >25 | >25 | >25 |
| ZM106F.PB9 | 0.034 | 0.364 | 0.002 | 0.013 | CAP69.1.12_TA7.1 | 0.005 | 0.151 | <0.0003 | <0.0003 |
| 6644.v2.c33 | >25 | >25 | >25 | >25 | CAP136.1.16_E6_1 | >25 | >25 | >25 | >25 |
| 0077.v1.c16 | 0.003 | 0.030 | <0.0003 | 0.004 | CAP174.1.06_F3_1B | >25 | >25 | >25 | >25 |
| 3728.v2.c6 | 0.0004 | 0.005 | <0.0003 | <0.0003 | CAP220.2.00_A8_5B | >25 | >25 | >25 | >25 |
| 6838.v1.c35 | 0.042 | 1.018 | <0.0003 | 0.022 | CAP224.1.18_C7_3 | 0.002 | 0.010 | <0.0003 | 0.006 |
| 6785.v5.c14 | 0.001 | 0.013 | <0.0003 | 0.001 | CAP225.1.06_A2_18 | 18.885 | >25 | >25 | >25 |
| 0041.v3.c18 | 1.742 | 21.248 | 0.008 | 0.332 | CAP269.2.00_F11_1 | >25 | >25 | >25 | >25 |
| 3168.v4.c10 | >25 | >25 | 1.538 | >25 | CAP37.1.18_D2_19 | 11.518 | >25 | <0.0003 | 0.011 |
| 3873.v1.c24 | 0.002 | 0.007 | 0.0004 | 0.003 | CAP40.2.01_A3_5 | >25 | >25 | >25 | >25 |
| 6322.v4.c1 | 0.003 | 0.017 | <0.0003 | 0.003 | CAP129.1.15_B2_13 | <0.0003 | 0.001 | <0.0003 | <0.0003 |
| 0921.v2.c14 | 0.0005 | 0.049 | <0.0003 | <0.0003 | CAP237.1.22_B2_2_39 | <0.0003 | <0.0003 | <0.0003 | 0.002 |
| 3637.v5.c3 | >25 | >25 | >25 | >25 | CAP258.2.00_X_23 | 1.785 | >25 | 0.084 | >25 |
| 6471.v1.c16 | >25 | >25 | >25 | >25 | CAP260.2.00_TA1_1B | 0.066 | 1.591 | <0.0003 | 0.014 |
| 0984.v2.c2 | >25 | >25 | >25 | >25 | CAP266.2.00_E9_h6 | 0.056 | 1.441 | 0.001 | 0.146 |
| 6040.v4.c15 | 0.042 | 1.862 | <0.0003 | 0.009 | TRP290.2.00_23_6 | 0.055 | 0.753 | 0.007 | 0.195 |
| 6631.v3.c10 | >25 | >25 | >25 | >25 | TRP292.2.00_12_4 | >25 | >25 | >25 | >25 |
| 933.v4.c4 | 0.009 | 0.078 | <0.0003 | 0.010 | TRP307.2.00_24_1 | <0.0003 | 0.002 | <0.0003 | 0.001 |
| 6980.v0.c31 | <0.0003 | 0.002 | <0.0003 | <0.0003 | TRP310.2.00_20_2 | 0.167 | 2.442 | 0.020 | 0.604 |
| 3426.v5.c17 | 0.930 | 17.930 | 0.020 | 2.814 | TRP343.2.00_21_2 | >25 | >25 | >25 | >25 |
| 377.v4.c09 | 0.679 | 8.918 | 0.002 | 0.361 | TRP347.2.00_B1_1 | <0.0003 | <0.0003 | <0.0003 | <0.0003 |
| Ce1086_B2 | 1.254 | >25 | 0.0004 | 0.168 | TRP363.2.00_10_3 | 0.035 | 3.668 | 1.228 | >25 |
| Ce0393_C3 | 1.095 | 10.350 | 0.004 | 0.112 | 722_G4_16 | >25 | >25 | >25 | >25 |
| Ce1176_A3 | 1.264 | >25 | 0.041 | >25 | So431_C1_1 | >25 | >25 | >25 | >25 |
| Ce2010_F5 | >25 | >25 | >25 | >25 | CT885_H3_2 | >25 | >25 | >25 | >25 |
| Ce0682_E4 | 0.011 | 0.454 | <0.0003 | 0.001 | So186_H6_5 | 0.099 | 23.634 | <0.0003 | 0.018 |
| Ce1172_H1 | 5.526 | >25 | 3.188 | >25 | So405_T24_5 | >25 | >25 | >25 | >25 |
| Ce2060_G9 | 0.002 | 0.022 | <0.0003 | <0.0003 | So225_H11_12 | >25 | >25 | >25 | >25 |
| Ce2103_E8 | 0.002 | 0.008 | <0.0003 | 0.001 | So706_T10b_3 | 3.252 | >25 | 0.108 | >25 |
| Ce0965_H7(Rev-) | 0.259 | 5.825 | 0.119 | >25 | CT072_56_7 | 9.989 | >25 | 0.002 | 24.704 |
| Ce703010131_1E2 | 3.425 | >25 | 0.005 | 6.488 | CT966_E1-7 | 0.080 | 1.065 | <0.0003 | 0.013 |
| Ce703010054_2A2 | >25 | >25 | 0.033 | >25 | CT977_69_12 | 0.002 | 0.013 | <0.0003 | 0.002 |
| Ce703010217_B6 | 0.135 | 7.110 | <0.0003 | 0.335 | CT140_140_B6 | 0.286 | 4.884 | 0.012 | 0.089 |
| Ce703010228_1C4 | 0.001 | 0.011 | <0.0003 | 0.001 | CT349_39_16 | 0.0004 | 0.011 | <0.0003 | 0.002 |
| Ce704010083_B8 | 0.237 | 5.778 | 0.016 | >25 | CT431_G6_6 | >25 | >25 | >25 | >25 |
| Ce704809221_1B3 | >25 | >25 | 0.541 | >25 | CT823_B6_1 | >25 | >25 | >25 | >25 |
| Ce0626_E6 | <0.0003 | 0.001 | <0.0003 | <0.0003 | Ko426_T78_10 | >25 | >25 | >25 | >25 |
| Ce0665_F2 | >25 | >25 | >25 | >25 | Ko459_T68_4 | 0.008 | >25 | <0.0003 | 0.005 |
| Ce0089_G2 | >25 | >25 | >25 | >25 | Ko870_C2_10 | <0.0003 | 0.001 | <0.0003 | <0.0003 |
| Ce2052_G10 | <0.0003 | 0.002 | <0.0003 | <0.0003 | Ko224_T87_2_4 | >25 | >25 | 0.023 | 11.593 |
| Ce704010069_C6 | <0.0003 | 0.001 | <0.0003 | <0.0003 | Ko756_38_Tb12 | 0.052 | 4.573 | <0.0003 | <0.0003 |
| Ce703010010_C4 | <0.0003 | 0.003 | <0.0003 | <0.0003 | CA327_D2_2 | >25 | >25 | >25 | >25 |
| Ce704810053_2B7 | 0.001 | 0.014 | <0.0003 | <0.0003 | CA392_H2_6 | 1.984 | >25 | 0.112 | >25 |
| CeCAP210_TA5 | <0.0003 | 0.006 | <0.0003 | <0.0003 | CA457_H1_1 | >25 | >25 | >25 | >25 |
| CeCAP200_B8a | 0.009 | 0.477 | 0.002 | 0.311 | ME067_A10-15 | 0.001 | 0.019 | <0.0003 | 0.003 |
| CeCAP221_B14 | 14.566 | >25 | 0.328 | >25 | CA146_H3_3 | >25 | >25 | 0.053 | >25 |
| CeCAP188_1_D1_14(Rev-) | >25 | >25 | >25 | >25 | CA240_A5.5 | >25 | >25 | >25 | >25 |
| CeCAP177_1A3 | 0.002 | 0.051 | <0.0003 | 0.012 | 1811_B3.23 | >25 | >25 | >25 | >25 |

FIGURE 9

| Clade | Sample | Combined mAbs (IC50) | | | CAP256 plasma (ID50) | | | |
|---|---|---|---|---|---|---|---|---|
| | | wk59 | wk120 | wk 206 | wk 59 | wk106 | wk159 | wk 220 |
| C | ZM53.12 | 0.103 | 0.002 | 0.072 | 979 | 14218 | 13474 | 15460 |
| | ZM233.6 | >50 | 0.0003 | 0.228 | 238 | 4360 | 13476 | 5261 |
| | CAP210.E8 | 0.217 | 0.002 | 0.072 | 7091 | 7830 | 13580 | 5250 |
| | DU422.01 | >50 | 0.008 | 8.2 | <45 | 346 | 1907 | 1968 |
| | ZM197.7 | 10.4 | 0.008 | 0.055 | <45 | 151 | 1062 | 1245 |
| | DU156.12 | >50 | 0.016 | >50 | <45 | 394 | 1363 | 1116 |
| | CAP<45.G3 | >50 | 4.7 | >50 | 287 | 7898 | 13402 | 1006 |
| | ZM214.15 | >50 | 0.33 | >50 | <45 | <45 | 920 | 538 |
| | ZM109.4 | >50 | 26.5 | >50 | <45 | 70 | 398 | 156 |
| | ZM249.1 | >50 | 0.01 | 34.5 | <45 | <45 | 230 | 119 |
| | CAP244.D3 | >50 | >50 | >50 | <45 | <45 | 58 | 62 |
| | DU172.17 | >50 | >50 | >50 | <45 | <45 | <45 | <45 |
| | ZM135.10a | >50 | >50 | >50 | <45 | 68 | 69 | <45 |
| A | Q842.d12 | >50 | 10.1 | >50 | <45 | 47 | 658 | 602 |
| | Q23.17 | >50 | 9.5 | 2.6 | <45 | 171 | 1107 | 448 |
| | Q259.d2.17 | >50 | 0.008 | 24.6 | <45 | 792 | 114 | 433 |
| | Q168.a2 | >50 | 0.181 | >50 | <45 | 70 | 2349 | 352 |
| | Q461.e2 | >50 | 0.705 | >50 | <45 | <45 | 422 | 127 |
| | Q769.d22 | >50 | >50 | >50 | <45 | <45 | <45 | <45 |
| B | 6535.3 | >50 | >50 | >50 | <45 | 214 | 788 | 284 |
| | WITO.33 | >50 | 0.003 | >50 | 56 | 219 | 293 | 99 |
| | TRO.11 | >50 | >50 | >50 | <45 | <45 | <45 | 69 |
| | AC10.29 | >50 | 0.022 | >50 | <45 | 64 | 48 | 66 |
| | RHPA.7 | >50 | >50 | >50 | <45 | <45 | <45 | 49 |
| | PVO.04 | >50 | >50 | 2.48 | 47 | 53 | 86 | 47 |
| | CAAN.A2 | >50 | >50 | >50 | <45 | <45 | <45 | <45 |
| | QH0692.42 | >50 | >50 | >50 | <45 | <45 | 49 | <45 |
| | REJO.67 | >50 | >50 | >50 | <45 | <45 | <45 | <45 |
| | SC422.8 | >50 | 0.178 | >50 | <45 | <45 | <45 | <45 |
| | THRO.18 | >50 | 4.25 | >50 | <45 | <45 | <45 | <45 |
| | TRJO.58 | >50 | 0 | >50 | <45 | <45 | 56 | <45 |

FIGURE 10

| | PI | SU | 23.14 | 23.10 | 23.13 | 23.11 | 23.16 | 30.2 | 30.4 | 34.18 | 34.22 | 34.31 | 38.19 | 38.38 | 38.16 | 48.10 | 48.18. | 48.8 | 59.10b |
|---|---|---|---|---|---|---|---|---|---|---|---|---|---|---|---|---|---|---|---|
| | | | | | | | | | | | | IC50 (ug/ml) | | | | | | | |
| CAP256.20 | 50 | 50 | 50 | 50 | 50 | 50 | 50 | 50 | 50 | 50 | 50 | 50 | 50 | 50 | 50 | 0.454 | 50 | 50 | 50 |
| CAP256.12 | 50 | 0.01 | 50 | 50 | 50 | 50 | 50 | 28.09 | 6.51 | 50 | 50 | 50 | 50 | 50 | 5.132 | 50 | 50 | 50 | 50 |
| CAP256.13 | 50 | 0.0345 | 50 | 50 | 50 | 50 | 50 | 50 | 50 | 50 | 50 | 50 | 50 | 50 | 50 | 50 | 50 | 50 | 50 |
| CAP256.23 | 50 | 0.125 | 50 | 50 | 50 | 50 | 50 | 50 | 50 | 50 | 50 | 50 | 50 | 50 | 50 | 50 | 50 | 50 | 50 |
| CAP256.07 | 50 | 0.00819 | 50 | 50 | 50 | 50 | 50 | 50 | 8.073 | 50 | 50 | 1 | 50 | 50 | 50 | 12.45088 | 6.9799 | 0.49076 | 5.43 |
| CAP256.21 | 50 | 0.004 | 50 | 50 | 50 | 50 | 50 | 50 | 50 | 50 | 50 | 0.085 | 50 | 50 | 50 | <0.02 | <0.02 | 0.2815 | 0.02 |
| CAP256.02 | 50 | 0.00774 | 50 | 50 | 50 | 50 | 50 | 50 | 19.57 | 50 | 50 | 0.04875 | 50 | 50 | 50 | 0.19591 | 0.59979 | 0.15198 | 0.3475 |
| CAP256.06 | 0.03 | 0.06273 | 0.1123 | 0.0939 | 0.086 | 0.0591 | 0.115 | 0.006 | 0.02 | 0.02 | 0.02 | 0.2 | 0.17777 | 0.1878 | 0.5985 | 50 | 1.0754 | 0.2462 | 0.2025 |
| CAP256.01 | 50 | 0.04188 | 50 | 50 | 50 | 50 | 50 | 50 | 50 | 50 | 50 | 50 | 50 | 50 | 50 | 50 | 50 | 50 | 50 |
| CAP256.05 | 50 | 0.00944 | 50 | 50 | 50 | 50 | 50 | 50 | 50 | 50 | 50 | 0.1 | 50 | 50 | 50 | 0.6476 | 0.94541 | 0.18103 | 0.7225 |
| CAP256.10 | 50 | 0.01123 | 50 | 50 | 50 | 50 | 50 | 50 | 50 | 50 | 50 | 0.08 | 50 | 50 | 50 | 0.22674 | 0.38362 | 0.13538 | 0.265 |
| CAP256.11 | 50 | 0.01433 | 50 | 50 | 50 | 50 | 50 | 11.285 | 50 | 50 | 50 | 0.0395 | 50 | 50 | 24 | 0.2746 | 0.2447 | 0.49224 | 0.54 |
| CAP256.14 | 50 | 0.011 | 50 | 50 | 50 | 50 | 50 | 50 | 50 | 50 | 50 | 0.166 | 50 | 50 | 50 | 0.105 | 2.277 | 0.8005 | 0.581 |
| CAP256.18 | 50 | 0.03 | 50 | 50 | 50 | 50 | 50 | 50 | 50 | 50 | 50 | 0.257 | 50 | 50 | 50 | 0.582 | 50 | 0.4305 | 0.137 |
| CAP256.04 | 50 | 0.00452 | 50 | 50 | 50 | 50 | 50 | 50 | 20.873 | 50 | 50 | 0.689 | 50 | 50 | 50 | 0.3824 | 0.5179 | 0.03 | 0.26 |
| CAP256.16 | 50 | 0.008 | 50 | 50 | 50 | 50 | 50 | 50 | 50 | 50 | 50 | 0.079 | 50 | 50 | 50 | 0.1485 | 0.6621 | 0.1755 | 0.261 |
| CAP256.17 | 50 | 0.022 | 50 | 50 | 50 | 50 | 50 | 50 | 50 | 50 | 50 | 0.0395 | 50 | 50 | 50 | 0.111 | <0.02 | <0.02 | 0.0625 |
| CAP256.15 | 50 | 0.0345 | 50 | 50 | 50 | 50 | 50 | 50 | 50 | 50 | 50 | 0.259 | 50 | 50 | 50 | 0.026 | 50 | 0.331 | 0.644 |
| CAP256.03 | 50 | 0.00299 | 50 | 50 | 50 | 50 | 50 | 50 | 8.09 | 50 | 50 | 0.02 | 50 | 50 | 20.26 | 0.07941 | 0.1052 | 0.02 | 0.185 |
| CAP256.24 | 50 | 0.054 | 50 | 50 | 50 | 50 | 50 | 50 | 50 | 50 | 50 | 2 | 50 | 50 | 50 | 50 | <0.02 | 50 | 50 |
| CAP256.08 | 50 | 0.00355 | 50 | 50 | 50 | 50 | 50 | 15.12 | 9.09 | 50 | 50 | 0.05 | 50 | 50 | 50 | 0.04339 | 0.04509 | 0.0404 | 0.05 |
| CAP256.09 | 50 | 0.0034 | 50 | 50 | 50 | 50 | 50 | 17.77 | 8.49 | 50 | 50 | 0.03 | 50 | 50 | 50 | 0.0741 | 0.02713 | <0.02 | 0.03895 |
| CAP256.19 | 50 | 0.023 | 50 | 50 | 50 | 50 | 50 | 27.314 | 50 | 50 | 50 | 0.2765 | 50 | 27.393 | 50 | 0.243 | 0.414 | 0.267 | 0.142 |
| CAP256.22 | 50 | 0.0045 | 50 | 50 | 50 | 50 | 50 | 50 | 1.546 | 50 | 50 | 0.0145 | 50 | 5 | 50 | 0.02 | 0.059 | 0.02 | 0.02 |
| CAP256.25 | 1.33 | 0.0009 | 3.207 | 3.912 | 0.613 | 3.3153 | 1.1657 | 0.0459 | nd | 25.526 | 9.8955 | 0.0009 | 50 | | | 0.02 | 0.02 | 0.02 | 0.02 |

| mAb | | CAP256-VRC26 | | | | | | | | | | | | | | | | |
|---|---|---|---|---|---|---|---|---|---|---|---|---|---|---|---|---|---|---|
| breadth | | 6.38 | 6.38 | 6.38 | 6.38 | 12.77 | 12.77 | 17.02 | 17.02 | 19.15 | 19.57 | 19.57 | 21.28 | 21.74 | 23.4 | 25.53 | 25.53 | 27.66 |
| mAb ID | Residues 160-171 | 20 | 12 | 13 | 23 | 7 | 21 | 2 | 6 | 1 | 31 | 32 | 5 | 33 | 10 | 11 | 14 | 18 |
| PI | NTITEVRDKQKK | >50 | >50 | >50 | >50 | >50 | >50 | >50 | 0.03 | >50 | >50 | >50 | >50 | >50 | >50 | >50 | >50 | >50 |
| SU | NATTELRDKKKK | >50 | 0.010 | 0.02 | 0.09 | 0.008 | 0.005 | 0.008 | 0.06 | 0.04 | 0.002 | 0.015 | 0.009 | 0.015 | 0.01 | 0.030 | 0.010 | 0.01 |
| T162I | NAITELRDKKKK | >50 | 0.100 | 0.63 | >50 | 0.010 | 22.881 | 0.050 | 0.04 | 0.02 | 0.061 | 0.533 | 1.700 | 2.013 | 0.40 | 0.100 | 0.239 | 0.06 |
| K169T | NATTELRDKTKK | >50 | >50 | >50 | >50 | 6 | 0.050 | 4 | >50 | >50 | 0.104 | 5 | 5 | 4 | 0.87 | 0.4 | 5 | 5 |
| K169I | NATTELRDKIKK | >50 | >50 | >50 | >50 | 1 | 0.010 | 0.1 | 0.05 | >50 | 0.014 | 0.220 | 0.20 | 0.366 | 0.08 | 0.1 | 0.267 | 0.23 |
| K169Q | NATTELRDKQKK | >50 | >50 | >50 | 7 | 1 | 0.018 | 0.05 | 0.8 | >50 | 0.014 | 0.263 | 0.1 | 0.413 | 0.10 | 0.090 | 0.448 | 0.45 |
| K169R | NATTELRDKRKK | >50 | 2 | 11 | 0.086 | 0.0 | 0.010 | 0.002 | 25 | 27 | 0.005 | 0.010 | 0.00 | 0.006 | 0.00 | 0.0 | 0.018 | 0.01 |
| K169E | NATTELRDKEKK | >50 | >50 | >50 | >50 | >50 | >50 | >50 | >50 | >50 | >50 | >50 | >50 | >50 | >50 | >50 | >50 | >50 |
| R166K | NATTELKDKKKK | >50 | >50 | >50 | >50 | >50 | >50 | >50 | >50 | >50 | 3.490 | >50 | >50 | 8.795 | >50 | >50 | >50 | >50 |
| R166S | NATTELSDKKKK | >50 | >50 | >50 | >50 | >50 | >50 | >50 | >50 | >50 | >50 | >50 | >50 | >50 | >50 | >50 | >50 | >50 |

| mAb | | CAP256-VRC26 | | | | | | | | | | | | | | | | |
|---|---|---|---|---|---|---|---|---|---|---|---|---|---|---|---|---|---|---|
| breadth | | 28.26 | 29.79 | 29.79 | 29.79 | 31.91 | 36.17 | 36.96 | 41.3 | 45.65 | 46.81 | 46.81 | 46.81 | 46.81 | 58.7 | 58.7 | 63.04 | |
| mAb ID | Residues 160-171 | 30 | 4 | 16 | 17 | 15 | 3 | 24 | 28 | 29 | 8 | 9 | 19 | 22 | 27 | 26 | 25 | |
| PI | NTITEVRDKQKK | >50 | >50 | >50 | >50 | >50 | >50 | >50 | >50 | >50 | >50 | >50 | >50 | >50 | >50 | >50 | 1.330 | |
| SU | NATTELRDKKKK | 0.001 | 0.005 | 0.005 | 0.007 | 0.009 | 0.003 | 0.038 | 0.006 | 0.024 | 0.004 | 0.003 | 0.012 | 0.006 | 0.005 | 0.01 | 0.002 | |
| T162I | NAITELRDKKKK | 0.018 | 0.003 | 0.188 | 0.006 | 0.040 | 0.002 | 0.417 | 0.219 | 0.324 | 0.005 | 0.004 | 0.032 | 0.079 | 0.002 | 0.01 | 0.001 | |
| K169T | NATTELRDKTKK | 0.049 | 0.29 | 3 | 0.487 | 2 | 0.09 | >50 | 0.370 | 1 | 0.18 | 0.07 | 0.998 | 0.411 | 0.05 | 0.087 | 0.020 | |
| K169I | NATTELRDKIKK | 0.007 | 0.05 | 0.140 | 0.045 | 0.218 | 0.02 | >50 | 0.033 | 0.140 | 0.04 | 0.02 | 0.133 | 0.026 | 0.02 | 0.034 | 0.006 | |
| K169Q | NATTELRDKQKK | 0.005 | 0.06 | 0.146 | 0.153 | 0.294 | 0.03 | >50 | 0.018 | 0.115 | 0.04 | 0.02 | 0.199 | 0.027 | 0.04 | 0.058 | 0.009 | |
| K169R | NATTELRDKRKK | 0.003 | 0.00 | 0.006 | 0.006 | 0.005 | 0.00 | >50 | 0.004 | 0.032 | 0.00 | 0.00 | 0.008 | 0.007 | 0.00 | 0.006 | 0.002 | |
| K169E | NATTELRDKEKK | >50 | >50 | >50 | >50 | >50 | >50 | >50 | >50 | >50 | >50 | >50 | >50 | >50 | >50 | >50 | >50 | |
| R166K | NATTELKDKKKK | 0.639 | 16 | >50 | >50 | >50 | 4.8 | >50 | 3.777 | 5.000 | 0.1 | 0.2 | 27.383 | 0.528 | 0.02 | 0.026 | 0.007 | |
| R166S | NATTELSDKKKK | >50 | >50 | >50 | >50 | >50 | >50 | >50 | >50 | >50 | >50 | >50 | >50 | >50 | >50 | >50 | >50 | |

A

| Controls | Hep2 staining |
|---|---|
| CAP256-VRC26-UCA | - |
| CAP256-VRC26.01 | - |
| CAP256-VRC26.02 | - |
| CAP256-VRC26.03 | - |
| CAP256-VRC26.04 | - |
| CAP256-VRC26.05 | - |
| CAP256-VRC26.06 | - |
| CAP256-VRC26.07 | - |
| CAP256-VRC26.08 | - |
| CAP256-VRC26.09 | - |
| CAP256-VRC26.10 | - |
| CAP256-VRC26.11 | - |
| CAP256-VRC26.12 | - |
| CAP256-VRC26.19 | - |
| CAP256-VRC26.22 | - |
| CAP256-VRC26.25 | - |

| Control | Hep2 staining |
|---|---|
| 4E10 | ++ |
| VRC01 | - |

B

BROADLY NEUTRALIZING MONOCLONAL ANTIBODIES AGAINST HIV-1 V1V2 ENV REGION

CROSS-REFERENCE TO RELATED APPLICATIONS

This application is a U.S. National Stage Application pursuant to 35 U.S.C. § 371 of International Patent Application PCT/IB2015/051465, filed on Feb. 27, 2015, and published as WO 2015/128846 on Sep. 3, 2015, which claims priority to South African Patent Application No. 2014/09416, filed on Dec. 19, 2014, and Great Britain Patent Application No. 1403613.1, filed on Feb. 28, 2014, all of which are incorporated herein by reference in their entireties for all purposes.

BACKGROUND OF THE INVENTION

The present invention relates anti-HIV therapies and prophylaxis. Specifically, the invention relates to broadly neutralizing antibodies against HIV-1, nucleic acids encoding these antibodies, vectors comprising the nucleic acids and cells and pharmaceutical compositions Comprising said vectors and/or antibodies. The present invention also relates to use of the antibodies and/or vectors for the treatment and/or prevention of HIV-1 infection in a subject. Furthermore, the invention also relates to a kit containing the antibodies of the invention.

Antibodies that effectively neutralize HIV-1 represent potential templates to guide HIV-1 vaccination strategies if the molecular events that led to their elicitation could be understood and reproduced (Haynes et al. 2012; Kong et al. 2012; Moir et al. 2011; McCoy et al. 2013; Overbaugh & Morris 2012; Burton et al. 2012). Virtually all infected individuals mount a potent antibody response within a few months of infection, but these antibodies preferentially neutralise the autologous virus that rapidly escapes (Montefiori et al. 1991; Richman et al. 2003; Wei et al. 2003; Bunnik et al. 2008). Cross-reactive antibodies capable of neutralising a majority of HIV-1 strains arise in about 20% of donors after 2-3 years of infection (van Gils et al. 2009; Gray et al. 2011; Piantadosi et al. 2009; Sather et al. 2009; Doria-Rose et al. 2010). The challenge with studying (and eliciting) broadly neutralising antibodies is that they are generally subdominant responses and are vastly outnumbered by ineffective or strain-specific antibody responses (Kong et al. 2012; Overbaugh & Morris 2012; Pantophlet et al. 2006; Kwong et al. 2012; Mascola & Haynes et al. 2013). Importantly, it is unclear if broadly neutralizing antibodies develop from early strain-specific B cell lineages that mature over years of infection, or if breadth results from rare stochastic events stimulating new B cell lineages that rapidly become cross-reactive for HIV-1.

One means to map molecular events leading to the development of an HIV-1-specific antibody response involves the isolation of broadly neutralizing monoclonal antibodies and examination of the B cell genetic record with next-generation sequencing (NGS) (Glanville et al. 2009; Tian et al. 2008; Briney et al. 2012; Boyd et al. 2010). Sampling at a single time point after the development of a neutralizing antibody lineage allows the study of an expanded antibody family and the elucidation of earlier lineage sequences with lower levels of somatic mutation (Wu et al. 2011; Zhu et al. 2012; Zhu et al. 2013). Even greater insight can be gained with longitudinal sampling from early after the time of infection, as was shown for the CH103 antibody lineage that targets the CD4-binding site of the HIV-1 envelope glycoprotein (Env) (Liao et al. 2013). Several mature CH103 neutralizing monoclonal antibodies were isolated 2 antigen-specific B cells at 136 weeks after infection. NGS was then used to identify transcripts of the CH103 lineage, which were observed as early as 14 weeks after infection, well before plasma cross-neutralizing activity was detected in this donor. Notably, the inferred unmutated common ancestor (UCA) of CH103 bound the autologous transmitted/founder virus, and evolved in response to viral diversification to gain the necessary somatic mutations to effectively neutralize heterologous strains of HIV-1. Since the CD4 binding site is only one of the several conserved neutralization epitopes on the HIV-1 Env, additional studies are needed to understand the genetic determinants and maturation pathway of potent neutralizing antibodies that target other vulnerable regions of HIV-1.

Serum neutralizing antibodies from HIV-1 infected donors often target the V1V2 region of HIV-1 Env (Gray et al. 2011; Walker et al. 2010; Lynch et al. 2011; Tomaras et al. 2011), and binding antibodies to this region were shown to correlate with protection in the RV144 HIV vaccine trial (Haynes et al. 2012). In addition, potent neutralizing monoclonal antibodies to the V1V2 region have been isolated from several donors. These include PG9 and PG16, which neutralize 70-80% of circulating HIV-1 isolates (Walker et al. 2009), CH01-04, which neutralize 40-50% (Bonsignori et al. 2011), and PGT141-145 which neutralize 40-80% (Walker et al. 2011). All of these antibodies are characterized by long $3^d$-heavy-chain complementarity-determining regions (CDR H3), which are protruding, anionic, and tyrosine sulphated (Pejchal et al. 2010; McLellan et al. 2011; Pancera et al. 2013). Crystal and electron microscopy structures of Env complexes with PG9 and PG16 reveal that the CDR H3s penetrate the HIV-1 glycan shield, recognizing a quaternary glycopeptide epitope at the membrane-distal apex of the HIV-1 spike, formed by the association of V1V2s from three gp120 protomers (McLellan et al. 2011; Pancera et al. 2013; Julien et al. 2013). To understand more precisely which factors are crucial in the pathway toward effective V1V2-directed antibodies, we analyzed donor CAP256 who was previously shown to develop a potent V1V2-directed plasma response (Moore et al. 2011; Moore et al. 2013; Georgiev et al. 2013). This donor was analyzed by longitudinal sampling, found to be superinfected at week 15, and showed modest neutralization breadth at one year. By three years post-infection, plasma from CAP256 neutralized 77% of all HIV-1 strains but particularly those from subtypes A and C (Gray et al. 2011). Here we isolate potent V1V2-directed broadly neutralizing antibodies from this donor, perform NGS to enable a detailed understanding of the evolution of lineage, and determine crystal structures to define their molecular characteristics. Circulating plasma virus was also analyzed longitudinally to understand the interplay between viral Env evolution and the immune response. The results allow for a precise delineation of the molecular events that gave rise to this category of potent antibodies.

SUMMARY OF THE INVENTION

In a first aspect of the invention there is provided for an isolated anti-HIV antibody that binds to the V1V2 epitope of HIV, wherein the antibody comprises one or both of a heavy chain variable region comprising a consensus amino acid sequence of SEQ ID NO:121 and a light chain variable region comprising a consensus amino acid sequence of SEQ ID NO:122.

In one embodiment the isolated anti-HIV antibody neutralizes autologous HIV virus CAP256.SU at an $IC_{50}$ concentration of less than 0.5 µg/ml, or heterologous HIV virus ZM53.12 at an $IC_{50}$ concentration of less than 0.5 µg/ml.

In another aspect of the invention there is provided for an isolated anti-HIV antibody selected from the group consisting of CAP256-VRC26-UCA, CAP256-VRC26-11, CAP256-VRC26-12, CAP256-VRC26.01, CAP256-VRC26.02, CAP256-VRC26.03, CAP256-VRC26.04, CAP256-VRC26.05, CAP256-VRC26.06, CAP256-VRC26.07, CAP256-VRC26.08, CAP256-VRC26.09, CAP256-VRC26.10, CAP256-VRC26.11, CAP256-VRC26.12, CAP256-VRC26.25, CAP256-VRC26.26 and CAP256-VRC26.27.

In one embodiment of the invention the antibody is CAP256-VRC26.01 and the antibody effectively neutralises at least 19% of HIV-1 strains selected from the group consisting of 96ZM651.02, CAP210.E8, CAP244.D3, CAP45.G3, DU156.12, DU172.17, DU422.01, ZM109.4, ZM135.10a, ZM197.7, ZM214.15, ZM233.6, ZM249.1, ZM53.12, 0260.v5.c36, BG505.w6m, KER2008.12, KER2018.11, MB201, MB539.2B7, Q168.a2, Q23.17, Q259.d2.17, Q461.e2, Q769.d22, Q842.d12, RW020.2, UG037.8, 6535.3, AC10.29, CAAN.A2, PVO.04, QH0692.42, REJO.67, RHPA.7, SC422.8, THRO.18, TRJO.58, TRO.11, WITO.33, 191821.E6.1, 3016.V5.c36, 6405.v4.c34, C1080.c3, CM244.ec1, CNE3 and TH976.17.

In one embodiment of the invention the antibody is CAP256-VRC26.02 and the antibody effectively neutralises at least 17% of HIV-1 strains selected from the group of strains mentioned above; or the antibody is CAP256-VRC26.03 and the antibody effectively neutralises at least 36% of HIV-1 strains selected from the group of strains mentioned above; the antibody is CAP256-VRC26.04 and the antibody effectively neutralises at least 30% of HIV-1 strains selected from the group of strains mentioned above; the antibody is CAP256-VRC26.05 and the antibody effectively neutralises at least 21% of HIV-1 strains selected from the group of strains mentioned above; the antibody is CAP256-VRC26.06 and the antibody effectively neutralises at least 17% of HIV-1 strains selected from the group of strains mentioned above; the antibody is CAP256-VRC26.07 and the antibody effectively neutralises at least 13% of HIV-1 strains selected from the group of strains mentioned above; the antibody is CAP256-VRC26.08 and the antibody effectively neutralises at least 47% of HIV-1 strains selected from the group of strains mentioned above; the antibody is CAP256-VRC26.09 and the antibody effectively neutralises at least 47% of HIV-1 strains selected from the group of strains mentioned above; the antibody is CAP256-VRC26.10 and the antibody effectively neutralises at least 23% of HIV-1 strains selected from the group of strains mentioned above; the antibody is CAP256-VRC26.11 and the antibody effectively neutralises at least 23% of HIV-1 strains selected from the group of strains mentioned above; the antibody is CAP256-VRC26.12 and the antibody effectively neutralises at least 6% of HIV-1 strains selected from the group of strains mentioned above; the antibody is CAP256-VRC26.13 and the antibody effectively neutralises at least 6% of HIV-1 strains selected from the group of strains mentioned above; the antibody is CAP256-VRC26.14 and the antibody effectively neutralises at least 26% of HIV-1 strains selected from the group of strains mentioned above; the antibody is CAP256-VRC26.15 and the antibody effectively neutralises at least 32% of HIV-1 strains selected from the group of strains mentioned above; the antibody is CAP256-VRC26.16 and the antibody effectively neutralises at least 30% of HIV-1 strains selected from the group of strains mentioned above; the antibody is CAP256-VRC26.17 and the antibody effectively neutralises at least 30% of HIV-1 strains selected from the group of strains mentioned above; the antibody is CAP256-VRC26.18 and the antibody effectively neutralises at least 28% of HIV-1 strains selected from the group of strains mentioned above; the antibody is CAP256-VRC26.19 and the antibody effectively neutralises at least 47% of HIV-1 strains selected from the group of strains mentioned above; the antibody is CAP256-VRC26.20 and the antibody effectively neutralises at least 2% of HIV-1 strains selected from the group of strains mentioned above; the antibody is CAP256-VRC26.21 and the antibody effectively neutralises at least 13% of HIV-1 strains selected from the group of strains mentioned above; the antibody is CAP256-VRC26.22 and the antibody effectively neutralises at least 47% of HIV-1 strains selected from the group of strains mentioned above; the antibody is CAP256-VRC26.23 and the antibody effectively neutralises at least 6% of HIV-1 strains selected from the group of strains mentioned above; the antibody is CAP256-VRC26.24 and the antibody effectively neutralises at least 37% of HIV-1 strains selected from the group of strains mentioned above; or the antibody is CAP256-VRC26.25 and the antibody effectively neutralises at least 63% of HIV-1 strains selected from the group of strains mentioned above; the antibody is CAP256-VRC26.26 and the antibody effectively neutralises at least 59% of HIV-1 strains selected from the group of strains mentioned above; the antibody is CAP256-VRC26.27 and the antibody effectively neutralises at least 59% of HIV-1 strains selected from the group of strains mentioned above; the antibody is CAP256-VRC26.28 and the antibody effectively neutralises at least 41% of HIV-1 strains selected from the group of strains mentioned above; the antibody is CAP256-VRC26.29 and the antibody effectively neutralises at least 46% of HIV-1 strains selected from the group of strains mentioned above; the antibody is CAP256-VRC26.30 and the antibody effectively neutralises at least 28% of HIV-1 strains selected from the group of strains mentioned above; the antibody is CAP256-VRC26.31 and the antibody effectively neutralises at least 20% of HIV-1 strains selected from the group of strains mentioned above; the antibody is CAP256-VRC26.32 and the antibody effectively neutralises at least 20% of HIV-1 strains selected from the group of strains mentioned above; or the antibody is CAP256-VRC26.33 and the antibody effectively neutralises at least 22% of HIV-1 strains selected from the group of strains mentioned above.

A further aspect provides for an isolated anti-HIV antibody comprising an amino acid sequence selected from the group consisting of SEQ ID NOs:1-60, SEQ ID NOs:170-173, SEQ ID NOs:178-181 or SEQ ID NOs:186-189.

In another embodiment the anti-HIV antibody comprises:
i) a heavy chain sequence comprising the amino acid sequence of SEQ ID NO:3 and a light chain sequence comprising the amino acid sequence of SEQ ID NO:4; or
ii) a heavy chain sequence comprising the amino acid sequence of SEQ ID NO:7 and a light chain sequence comprising the amino acid sequence of SEQ ID NO:8; or
iii) a heavy chain sequence comprising the amino acid sequence of SEQ ID NO:11 and a light chain sequence comprising the amino acid sequence of SEQ ID NO:12; or iv) a heavy chain sequence comprising the amino acid sequence of SEQ ID NO:15 and a light chain sequence comprising the amino acid sequence of SEQ ID NO:16; or v) a heavy chain sequence comprising the amino acid sequence of SEQ ID NO:19 and a light chain sequence comprising the amino acid sequence of SEQ ID NO:20; or vi) a heavy chain sequence comprising the amino acid sequence of SEQ ID NO:23 and a light chain sequence comprising the amino acid sequence of SEQ ID NO:24; or vii) a heavy chain sequence comprising the amino acid sequence of SEQ ID NO:27 and a light chain sequence comprising the amino acid sequence of SEQ ID NO:28; or viii) a heavy chain sequence comprising the amino acid sequence of SEQ ID NO:31 and a light chain sequence comprising the amino acid sequence of SEQ ID NO:32; or ix) a heavy chain sequence comprising the amino acid sequence of SEQ ID NO:35 and a light chain sequence comprising the amino acid sequence of SEQ ID NO:36; or x) a heavy chain sequence comprising the amino acid sequence of SEQ ID NO:39 and a light chain sequence comprising the amino acid sequence of SEQ ID NO:40; or xi) a heavy chain sequence comprising the amino acid sequence of SEQ ID NO:43 and a light chain sequence comprising the amino acid sequence of SEQ ID NO:44; or xii) a heavy chain sequence comprising the amino acid sequence of SEQ ID NO:47 and a light chain sequence comprising the amino acid sequence of SEQ ID NO:48; or xiii) a heavy chain sequence comprising the amino acid sequence of SEQ ID NO:51 and a light chain sequence comprising the amino acid sequence of SEQ ID NO:52; or xiv) a heavy chain sequence comprising the amino acid sequence of SEQ ID NO:55 and a light chain sequence comprising the amino acid sequence of SEQ ID NO:56; or xv) a heavy chain sequence comprising the amino acid sequence of SEQ ID NO:59 and a light chain sequence comprising the amino acid sequence of SEQ ID NO:60; or xvi) a heavy chain sequence comprising the amino acid sequence of SEQ ID NO:172 and a light chain sequence comprising the amino acid sequence of SEQ ID NO: 173; or xvi) a heavy chain sequence comprising the amino acid sequence of SEQ ID NO:180 and a light chain sequence comprising the amino acid sequence of SEQ ID NO: 181; or xvi) a heavy chain sequence comprising the amino acid sequence of SEQ ID NO:188 and a light chain sequence comprising the amino acid sequence of SEQ ID NO: 189.

In one embodiment of the invention the antibody includes a heavy chain with a CDR1 comprising the amino acids at positions 26-33 of SEQ ID NO:3, a CDR2 comprising the amino acids at positions 51-58 of SEQ ID NO:3, and a CDR3 comprising the amino acids at positions 97-133 of SEQ ID NO:3, and a light chain with a CDR1 comprising the amino acids at positions 26-33 of SEQ ID NO:4, a CDR2 comprising the amino acids at positions 51-53 of SEQ ID NO:4, and a CDR3 comprising the amino acids at positions 90-101 of SEQ ID NO:4.

Alternatively, in another embodiment the isolated anti-HIV antibody includes a heavy chain with a CDR1 comprising the amino acids at positions 26-33 of SEQ ID NO:7, a CDR2 comprising the amino acids at positions 51-58 of SEQ ID NO:7, and a CDR3 comprising the amino acids at positions 97-133 of SEQ ID NO:7, and a light chain with a CDR1 comprising the amino acids at positions 26-33 of SEQ ID NO:8, a CDR2 comprising the amino acids at positions 51-53 of SEQ ID NO:8, and a CDR3 comprising the amino acids at positions 90-101 of SEQ ID NO:8.

In another embodiment the isolated anti-HIV antibody may include a heavy chain with a CDR1 comprising the amino acids at positions 26-33 of SEQ ID NO:11, a CDR2 comprising the amino acids at positions 51-58 of SEQ ID NO:11, and a CDR3 comprising the amino acids at positions 97-133 of SEQ ID NO:11, and a light chain with a CDR1 comprising the amino acids at positions 26-33 of SEQ ID NO:12, a CDR2 comprising the amino acids at positions 51-53 of SEQ ID NO:12, and a CDR3 comprising the amino acids at positions 90-101 of SEQ ID NO:12.

Alternatively, in another embodiment the isolated anti-HIV antibody may include a heavy chain with a CDR1 comprising the amino acids at positions 26-33 of SEQ ID NO:15, a CDR2 comprising the amino acids at positions 51-58 of SEQ ID NO:15, and a CDR3 comprising the amino acids at positions 97-133 of SEQ ID NO:15, and a light chain with a CDR1 comprising the amino acids at positions 26-33 of SEQ ID NO:16, a CDR2 comprising the amino acids at positions 51-53 of SEQ ID NO:16, and a CDR3 comprising the amino acids at positions 90-101 of SEQ ID NO:16.

In yet another embodiment the isolated antibody includes a heavy chain with a CDR1 comprising the amino acids at positions 26-33 of SEQ ID NO:19, a CDR2 comprising the amino acids at positions 51-58 of SEQ ID NO:19, and a CDR3 comprising the amino acids at positions 97-133 of SEQ ID NO:19, and a light chain with a CDR1 comprising the amino acids at positions 26-33 of SEQ ID NO:20, a CDR2 comprising the amino acids at positions 51-53 of SEQ ID NO:20, and a CDR3 comprising the amino acids at positions 90-98 of SEQ ID NO:20.

In another embodiment the isolated antibody includes a heavy chain with a CDR1 comprising the amino acids at positions 26-33 of SEQ ID NO:23, a CDR2 comprising the amino acids at positions 51-58 of SEQ ID NO:23, and a CDR3 comprising the amino acids at positions 97-133 of SEQ ID NO:23, and a light chain with a CDR1 comprising the amino acids at positions 26-33 of SEQ ID NO:24, a CDR2 comprising the amino acids at positions 51-53 of SEQ ID NO:24, and a CDR3 comprising the amino acids at positions 90-101 of SEQ ID NO:24.

In a further embodiment the isolated antibody may include a heavy chain with a CDR1 comprising the amino acids at positions 26-33 of SEQ ID NO:27, a CDR2 comprising the amino acids at positions 51-58 of SEQ ID NO:27, and a CDR3 comprising the amino acids at positions 97-133 of SEQ ID NO:27, and a light chain with a CDR1 comprising the amino acids at positions 26-33 of SEQ ID NO:28, a CDR2 comprising the amino acids at positions 51-53 of SEQ ID NO:28, and a CDR3 comprising the amino acids at positions 90-101 of SEQ ID NO:28.

In another embodiment the isolated antibody includes a heavy chain with a CDR1 comprising the amino acids at positions 26-33 of SEQ ID NO:31, a CDR2 comprising the amino acids at positions 51-58 of SEQ ID NO:31, and a CDR3 comprising the amino acids at positions 97-133 of SEQ ID NO:31, and a light chain with a CDR1 comprising the amino acids at positions 23-30 of SEQ ID NO:32, a CDR2 comprising the amino acids at positions 48-50 of SEQ ID NO:32, and a CDR3 comprising the amino acids at positions 90-98 of SEQ ID NO:32.

A further embodiment provides for an isolated antibody which includes a heavy chain with a CDR1 comprising the amino acids at positions 26-33 of SEQ ID NO:35, a CDR2 comprising the amino acids at positions 51-58 of SEQ ID NO:35, and a CDR3 comprising the amino acids at positions 97-134 of SEQ ID NO:35, and a light chain with a CDR1 comprising the amino acids at positions 26-33 of SEQ ID NO:36, a CDR2 comprising the amino acids at positions 51-53 of SEQ ID NO:36, and a CDR3 comprising the amino acids at positions 90-98 of SEQ ID NO:36.

According to another embodiment, the isolated antibody includes a heavy chain with a CDR1 comprising the amino acids at positions 26-33 of SEQ ID NO:39, a CDR2 comprising the amino acids at positions 51-58 of SEQ ID NO:39, and a CDR3 comprising the amino acids at positions 97-133 of SEQ ID NO:39, and a light chain with a CDR1 comprising the amino acids at positions 26-33 of SEQ ID NO:40, a CDR2 comprising the amino acids at positions 51-53 of SEQ ID NO:40, and a CDR3 comprising the amino acids at positions 90-101 of SEQ ID NO:40.

In another embodiment of the invention the antibody includes a heavy chain with a CDR1 comprising the amino acids at positions 26-33 of SEQ ID NO:43, a CDR2 comprising the amino acids at positions 51-58 of SEQ ID NO:43, and a CDR3 comprising the amino acids at positions 97-135 of SEQ ID NO:43, and a light chain with a CDR1 comprising the amino acids at positions 26-33 of SEQ ID NO:44, a CDR2 comprising the amino acids at positions 51-53 of SEQ ID NO:44, and a CDR3 comprising the amino acids at positions 90-101 of SEQ ID NO:44.

In yet another embodiment of the invention the antibody includes a heavy chain with a CDR1 comprising the amino acids at positions 26-33 of SEQ ID NO:47, a CDR2 comprising the amino acids at positions 51-58 of SEQ ID NO:47, and a CDR3 comprising the amino acids at positions 97-135 of SEQ ID NO:47, and a light chain with a CDR1 comprising the amino acids at positions 26-33 of SEQ ID NO:48, a CDR2 comprising the amino acids at positions 51-53 of SEQ ID NO:48, and a CDR3 comprising the amino acids at positions 90-101 of SEQ ID NO:48.

In a further embodiment of the invention the antibody includes a heavy chain with a CDR1 comprising the amino acids at positions 26-33 of SEQ ID NO:51, a CDR2 comprising the amino acids at positions 51-58 of SEQ ID NO:51, and a CDR3 comprising the amino acids at positions 97-133 of SEQ ID NO:51, and a light chain with a CDR1 comprising the amino acids at positions 26-33 of SEQ ID NO:52, a CDR2 comprising the amino acids at positions 51-53 of SEQ ID NO:52, and a CDR3 comprising the amino acids at positions 90-101 of SEQ ID NO:52.

In an alternative embodiment of the invention the antibody includes a heavy chain with a CDR1 comprising the amino acids at positions 26-33 of SEQ ID NO:55, a CDR2 comprising the amino acids at positions 51-58 of SEQ ID NO:55, and a CDR3 comprising the amino acids at positions 96-132 of SEQ ID NO:55, and a light chain with a CDR1 comprising the amino acids at positions 26-33 of SEQ ID NO:56, a CDR2 comprising the amino acids at positions 51-53 of SEQ ID NO:56, and a CDR3 comprising the amino acids at positions 90-97 of SEQ ID NO:56.

In yet another embodiment of the invention the antibody includes a heavy chain with a CDR1 comprising the amino acids at positions 26-33 of SEQ ID NO:59, a CDR2 comprising the amino acids at positions 51-58 of SEQ ID NO:59, and a CDR3 comprising the amino acids at positions 97-133 of SEQ ID NO:59, and a light chain with a CDR1 comprising the amino acids at positions 26-33 of SEQ ID NO:60, a CDR2 comprising the amino acids at positions 51-53 of SEQ ID NO:60, and a CDR3 comprising the amino acids at positions 90-97 of SEQ ID NO:60.

A further embodiment of the invention provides for an antibody which includes a heavy chain with a CDR1 comprising the amino acids at positions 31-35 of SEQ ID NO:172, a CDR2 comprising the amino acids at positions 50-66 of SEQ ID NO:172, and a CDR3 comprising the amino acids at positions 99-134 of SEQ ID NO:172, and a light chain with a CDR1 comprising the amino acids at positions 23-35 of SEQ ID NO:173, a CDR2 comprising the amino acids at positions 51-57 of SEQ ID NO:173, and a CDR3 comprising the amino acids at positions 90-101 of SEQ ID NO:173.

A further embodiment of the invention provides for an antibody which includes a heavy chain with a CDR1 comprising the amino acids at positions 31-35 of SEQ ID NO:180, a CDR2 comprising the amino acids at positions 50-66 of SEQ ID NO:180, and a CDR3 comprising the amino acids at positions 99-135 of SEQ ID NO:180, and a light chain with a CDR1 comprising the amino acids at positions 23-35 of SEQ ID NO:181, a CDR2 comprising the amino acids at positions 51-57 of SEQ ID NO:181, and a CDR3 comprising the amino acids at positions 90-101 of SEQ ID NO:181.

A further embodiment of the invention provides for an antibody which includes a heavy chain with a CDR1 comprising the amino acids at positions 31-35 of SEQ ID NO:188, a CDR2 comprising the amino acids at positions 50-66 of SEQ ID NO:188, and a CDR3 comprising the amino acids at positions 99-135 of SEQ ID NO:188, and a light chain with a CDR1 comprising the amino acids at positions 23-35 of SEQ ID NO:189, a CDR2 comprising the amino acids at positions 52-57 of SEQ ID NO:189, and a CDR3 comprising the amino acids at positions 90-101 of SEQ ID NO:189.

A fourth aspect of the invention provides for a composition comprising the isolated anti-HIV antibody of the invention or a fragment thereof.

In one embodiment, the present invention provides for a nucleic acid molecule encoding the isolated anti-HIV antibody of the invention, or a fragment thereof.

Other embodiments provide for vectors comprising the nucleic acid molecules encoding the isolated anti-HIV antibody of the invention or a fragment thereof, as well as cells containing the vectors.

A fifth aspect of the invention provides for a composition comprising the nucleic acid molecule encoding the isolated anti-HIV antibody of the invention, or a fragment thereof, vectors comprising the nucleic acids or cells containing the vectors.

A further embodiment of the invention provides for a pharmaceutical composition comprising at least one antibody or fragment of the invention and a pharmaceutically acceptable carrier.

A further embodiment of the invention provides for a pharmaceutical composition comprising at least one nucleic acid molecule encoding the isolated anti-HIV antibody of the invention, or a fragment thereof, vectors comprising the nucleic acids or cells containing the vectors and a pharmaceutically acceptable carrier.

In a further aspect of the invention there is provided for a method of immunising against or treating an HIV infection or an HIV-related disease, the method comprising administering a therapeutically effective amount of at least one HIV antibody of the invention to a subject in need of immunisation or treatment. The administration may comprise administration of a second therapeutic agent. Preferably, the second therapeutic agent is an antiviral agent.

In a further aspect of the invention there is provided for a method of immunising against or treating an HIV infection or an HIV-related disease, the method comprising administering a therapeutically effective amount of at least one nucleic acid molecule encoding the isolated anti-HIV antibody of the invention, or a fragment thereof, a vector comprising the nucleic acids or cells containing the vectors to a subject in need of immunisation or treatment. The administration may comprise administration of a second therapeutic agent. Preferably, the second therapeutic agent is an antiviral agent.

The present specification also provides for a vaccine comprising an epitope that specifically binds to an antibody of the invention.

In yet a further aspect of the invention there is provided for a method of detecting the presence of an anti-HIV antibody of the invention or an antigen or epitope that binds to an anti-HIV antibody of the invention in a patient, the method comprising isolating a biological sample from the patient and assaying the biological sample for the presence of the anti-HIV antibody or the presence of an antigen or epitope that binds to an anti-HIV antibody of the invention or a cell that contains at least one of the DNA or mRNA encoding the antibody.

A further aspect makes provision for a kit comprising at least one antibody or fragment of the invention.

BRIEF DESCRIPTION OF THE FIGURES

Non-limiting embodiments of the invention will now be described by way of example only and with reference to the following figures:

FIG. 1: Development of broad neutralization by donor CAP256 and isolation of neutralizing antibodies. Genetic characteristics and neutralization breadth and potency of the 33 isolated antibodies, CAP256-VRC26.01-33. Neutralization was assessed against a panel of 46 Env-pseudoviruses.

FIG. 2: Epitope mapping of CAP256-VRC26 antibodies to the V1V2 region of the HIV-1 envelope glycoprotein (a) Binding competition indicates CAP256-VRC26 antibodies to be in the same competition group as V1V2-directed antibody PG9. Binding to ZM53-Env-expressing 293T cells by labeled CAP256-VRC26.08 and unlabeled competitor antibodies was measured by flow cytometry. (b) Neutralization of ConC (wild type) and it's V2 mutants by CAP256-VRC26 antibodies. Each pair of dots shows the $IC_{50}$s for one virus and respective mutant.

FIG. 6: Sequences of CAP256-VRC26 heavy chains. Sequences of the 33 B-cell culture derived antibodies inferred intermediates are compared to the germline V and J genes.

FIG. 7: Sequences of CAP256-VRC26 lambda light chains. Sequences of the 33 B-cell culture derived antibodies, inferred intermediates are compared to the germline V and J genes.

FIG. 9: Neutralization ($IC_{50}$ values) of 194 viruses by CAP256-VRC26.08 and CAP256-VRC26.25. Geometric mean is calculated for values <50.

FIG. 10: Neutralization of heterologous viruses by CAP256 plasma and mAbs. Neutralization of 31 viruses by CAP256-VRC26 mAbs and by plasma from CAP256 sampled at 4 timepoints. Plasma data are from Moore et al, 2011. Antibody values are shown as 50% inhibitory concentration ($IC_{50}$) of a theoretical combination of all 31 antibodies (calculated as the lowest $IC_{50}$ for each virus). Plasma is shown as 50% inhibitory dilution ($ID_{50}$) with a starting dilution of 1:45.

FIG. 11: Neutralization ($IC_{50}$ values) by each of the 31 CAP256-VRC26 mAbs tested against Env clones.

FIG. 12: Effect of V2 epitope polymorphisms and escape mutations on CAP256-VRC26 neutralization. CAP256-VRC26 mAb neutralization of the SU and PI viruses, and of the SU virus mutated to contain PI polymorphisms 162I, 165V or 169Q. The V2 epitope sequences (residues 160-171) are shown on the left and neutralization $IC_{50}$ values on the right.

SEQUENCE LISTING

Figure 3:
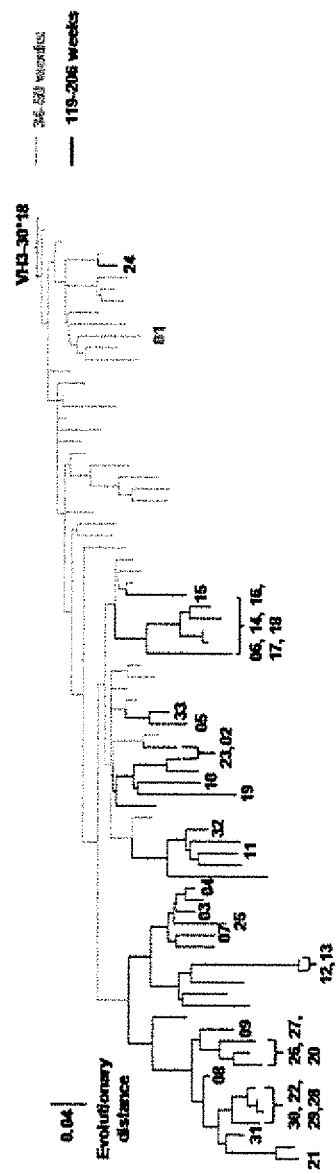
FIG. 3: Maturation of the CAP256-VRC26 lineage revealed by next-generation sequencing (NGS) of B cell transcripts. Phylogenetic trees of the CAP256-VRC26 clonal lineage for heavy chain and light chain.

The nucleic acid and amino acid sequences listed in the accompanying sequence listing are shown using standard letter abbreviations for nucleotide bases, and the standard three letter abbreviations for amino acids. It will be understood by those of skill in the art that only one strand of each nucleic acid sequence is shown, but that the complementary strand is included by any reference to the displayed strand. In the accompanying sequence listing:

SEQ ID NO:1 is the amino acid sequence of the antibody heavy chain of CAP256-VRC26-UCA.

SEQ ID NO:2 is the amino acid sequence of the antibody light chain of CAP256-VRC26-UCA.

SEQ ID NO:3 is the amino acid sequence of the antibody heavy chain variable domain of CAP256-VRC26-UCA.

SEQ ID NO:4 is the amino acid sequence of the antibody light chain variable domain of CAP256-VRC26-UCA.

SEQ ID NO:5 is the amino acid sequence of the antibody heavy chain of CAP256-VRC26-I1

SEQ ID NO:6 is the amino acid sequence of the antibody light chain of CAP256-VRC26-I1

SEQ ID NO:7 is the amino acid sequence of the antibody heavy chain variable domain of CAP256-VRC26-I1

SEQ ID NO:8 is the amino acid sequence of the antibody light chain variable domain of CAP256-VRC26-I1

SEQ ID NO:9 is the amino acid sequence of the antibody heavy chain of CAP256-VRC26-I2.

SEQ ID NO:10 is the amino acid sequence of the antibody light chain of CAP256-VRC26-I2

SEQ ID NO:11 is the amino acid sequence of the antibody heavy chain variable domain of CAP256-VRC26-I2

SEQ ID NO:12 is the amino acid sequence of the antibody light chain variable domain of CAP256-VRC26-I2

SEQ ID NO:13 is the amino acid sequence of the antibody heavy chain of CAP256-VRC26.01

SEQ ID NO:14 is the amino acid sequence of the antibody light chain of CAP256-VRC26.01

SEQ ID NO:15 is the amino acid sequence of the antibody heavy chain variable domain of CAP256-VRC26.01

SEQ ID NO:16 is the amino acid sequence of the antibody light chain variable domain of CAP256-VRC26.01

SEQ ID NO:17 is the amino acid sequence of the antibody heavy chain of CAP256-VRC26.02

SEQ ID NO:18 is the amino acid sequence of the antibody light chain of CAP256-VRC26.02

SEQ ID NO:19 is the amino acid sequence of the antibody heavy chain variable domain of CAP256-VRC26.02

SEQ ID NO:20 is the amino acid sequence of the antibody light chain variable domain of CAP256-VRC26.02

SEQ ID NO:21 is the amino acid sequence of the antibody heavy chain of CAP256-VRC26.03

SEQ ID NO:22 is the amino acid sequence of the antibody light chain of CAP256-VRC26.03

SEQ ID NO:23 is the amino acid sequence of the antibody heavy chain variable domain of CAP256-VRC26.03

SEQ ID NO:24 is the amino acid sequence of the antibody light chain variable domain of CAP256-VRC26.03

SEQ ID NO:25 is the amino acid sequence of the antibody heavy chain of CAP256-VRC26.04

SEQ ID NO:26 is the amino acid sequence of the antibody light chain of CAP256-VRC26.04

SEQ ID NO:27 is the amino acid sequence of the antibody heavy chain variable domain of CAP256-VRC26.04

SEQ ID NO:28 is the amino acid sequence of the antibody light chain variable domain of CAP256-VRC26.04

SEQ ID NO:29 is the amino acid sequence of the antibody heavy chain of CAP256-VRC26.05

SEQ ID NO:30 is the amino acid sequence of the antibody light chain of CAP256-VRC26.05

SEQ ID NO:31 is the amino acid sequence of the antibody heavy chain variable domain of CAP256-VRC26.05

SEQ ID NO:32 is the amino acid sequence of the antibody light chain variable domain of CAP256-VRC26.05

SEQ ID NO:33 is the amino acid sequence of the antibody heavy chain of CAP256-VRC26.06

SEQ ID NO:34 is the amino acid sequence of the antibody light chain of CAP256-VRC26.06

SEQ ID NO:35 is the amino acid sequence of the antibody heavy chain variable domain of CAP256-VRC26.06

SEQ ID NO:36 is the amino acid sequence of the antibody light chain variable domain of CAP256-VRC26.06

SEQ ID NO:37 is the amino acid sequence of the antibody heavy chain of CAP256-VRC26.07

SEQ ID NO:38 is the amino acid sequence of the antibody light chain of CAP256-VRC26.07

SEQ ID NO:39 is the amino acid sequence of the antibody heavy chain variable domain of CAP256-VRC26.07

SEQ ID NO:40 is the amino acid sequence of the antibody light chain variable domain of CAP256-VRC26.07

SEQ ID NO:41 is the amino acid sequence of the antibody heavy chain of CAP256-VRC26.08

SEQ ID NO:42 is the amino acid sequence of the antibody light chain of CAP256-VRC26.08

SEQ ID NO:43 is the amino acid sequence of the antibody heavy chain variable domain of CAP256-VRC26.08

SEQ ID NO:44 is the amino acid sequence of the antibody light chain variable domain of CAP256-VRC26.08

SEQ ID NO:45 is the amino acid sequence of the antibody heavy chain of CAP256-VRC26.09

SEQ ID NO:46 is the amino acid sequence of the antibody light chain of CAP256-VRC26.09

SEQ ID NO:47 is the amino acid sequence of the antibody heavy chain variable domain of CAP256-VRC26.09

SEQ ID NO:48 is the amino acid sequence of the antibody light chain variable domain of CAP256-VRC26.09

SEQ ID NO:49 is the amino acid sequence of the antibody heavy chain of CAP256-VRC26.10

SEQ ID NO:50 is the amino acid sequence of the antibody light chain of CAP256-VRC26.10

SEQ ID NO:51 is the amino acid sequence of the antibody heavy chain variable domain of CAP256-VRC26.10

SEQ ID NO:52 is the amino acid sequence of the antibody light chain variable domain of CAP256-VRC26.10

SEQ ID NO:53 is the amino acid sequence of the antibody heavy chain of CAP256-VRC26.11

SEQ ID NO:54 is the amino acid sequence of the antibody light chain of CAP256-VRC26.11

SEQ ID NO:55 is the amino acid sequence of the antibody heavy chain variable domain of CAP256-VRC26.11

SEQ ID NO:56 is the amino acid sequence of the antibody light chain variable domain of CAP256-VRC26.11

SEQ ID NO:57 is the amino acid sequence of the antibody heavy chain of CAP256-VRC26.12

SEQ ID NO:58 is the amino acid sequence of the antibody light chain of CAP256-VRC26.12

SEQ ID NO:59 is the amino acid sequence of the antibody heavy chain variable domain of CAP256-VRC26.12

SEQ ID NO:60 is the amino acid sequence of the antibody light chain variable domain of CAP256-VRC26.12

SEQ ID NO:61 is an exemplary nucleic acid sequence of the antibody heavy chain of CAP256-VRC26-UCA SEQ ID NO:62 is an exemplary nucleic acid sequence of the antibody light chain of CAP256-VRC26-UCA SEQ ID NO:63 is an exemplary nucleic acid sequence of the antibody heavy chain variable domain of CAP256-VRC26-UCA SEQ ID NO:64 is an exemplary nucleic acid sequence of the antibody light chain variable domain of CAP256-VRC26-UCA SEQ ID NO:65 is an exemplary nucleic acid sequence of the antibody heavy chain of CAP256-VRC26-11

SEQ ID NO:66 is an exemplary nucleic acid sequence of the antibody light chain of CAP256-VRC26-l1

SEQ ID NO:67 is an exemplary nucleic acid sequence of the antibody heavy chain variable domain of CAP256-VRC26-11

SEQ ID NO:68 is an exemplary nucleic acid sequence of the antibody light chain variable domain of CAP256-VRC26-11

SEQ ID NO:69 is an exemplary nucleic acid sequence of the antibody heavy chain of CAP256-VRC26-12

SEQ ID NO:70 is an exemplary nucleic acid sequence of the antibody light chain of CAP256-VRC26-12

SEQ ID NO:71 is an exemplary nucleic acid sequence of the antibody heavy chain variable domain of CAP256-VRC26-12

SEQ ID NO:72 is an exemplary nucleic acid sequence of the antibody light chain variable domain of CAP256-VRC26-12

SEQ ID NO:73 is an exemplary nucleic acid sequence of the antibody heavy chain of CAP256-VRC26.01

SEQ ID NO:74 is an exemplary nucleic acid sequence of the antibody light chain of CAP256-VRC26.01

SEQ ID NO:75 is an exemplary nucleic acid sequence of the antibody heavy chain variable domain of CAP256-VRC26.01

SEQ ID NO:76 is an exemplary nucleic acid sequence of the antibody light chain variable domain of CAP256-VRC26.01

SEQ ID NO:77 is an exemplary nucleic acid sequence of the antibody heavy chain of CAP256-VRC26.02

SEQ ID NO:78 is an exemplary nucleic acid sequence of the antibody light chain of CAP256-VRC26.02

SEQ ID NO:79 is an exemplary nucleic acid sequence of the antibody heavy chain variable domain of CAP256-VRC26.02

SEQ ID NO:80 is an exemplary nucleic acid sequence of the antibody light chain variable domain of CAP256-VRC26.02

SEQ ID NO:81 is an exemplary nucleic acid sequence of the antibody heavy chain of CAP256-VRC26.03

SEQ ID NO:82 is an exemplary nucleic acid sequence of the antibody light chain of CAP256-VRC26.03

SEQ ID NO:83 is an exemplary nucleic acid sequence of the antibody heavy chain variable domain of CAP256-VRC26.03

SEQ ID NO:84 is an exemplary nucleic acid sequence of the antibody light chain variable domain of CAP256-VRC26.03

SEQ ID NO:85 is an exemplary nucleic acid sequence of the antibody heavy chain of CAP256-VRC26.04

SEQ ID NO:86 is an exemplary nucleic acid sequence of the antibody light chain of CAP256-VRC26.04

SEQ ID NO:87 is an exemplary nucleic acid sequence of the antibody heavy chain variable domain of CAP256-VRC26.04

SEQ ID NO:88 is an exemplary nucleic acid sequence of the antibody light chain variable domain of CAP256-VRC26.04

SEQ ID NO:89 is an exemplary nucleic acid sequence of the antibody heavy chain of CAP256-VRC26.05

SEQ ID NO:90 is an exemplary nucleic acid sequence of the antibody light chain of CAP256-VRC26.05

SEQ ID NO:91 is an exemplary nucleic acid sequence of the antibody heavy chain variable domain of CAP256-VRC26.05

SEQ ID NO:92 is an exemplary nucleic acid sequence of the antibody light chain variable domain of CAP256-VRC26.05

SEQ ID NO:93 is an exemplary nucleic acid sequence of the antibody heavy chain of CAP256-VRC26.06

SEQ ID NO:94 is an exemplary nucleic acid sequence of the antibody light chain of CAP256-VRC26.06

SEQ ID NO:95 is an exemplary nucleic acid sequence of the antibody heavy chain variable domain of CAP256-VRC26.06

SEQ ID NO:96 is an exemplary nucleic acid sequence of the antibody light chain variable domain of CAP256-VRC26.06

SEQ ID NO:97 is an exemplary nucleic acid sequence of the antibody heavy chain of CAP256-VRC26.07

SEQ ID NO:98 is an exemplary nucleic acid sequence of the antibody light chain of CAP256-VRC26.07

SEQ ID NO:99 is an exemplary nucleic acid sequence of the antibody heavy chain variable domain of CAP256-VRC26.07

SEQ ID NO:100 is an exemplary nucleic acid sequence of the antibody light chain variable domain of CAP256-VRC26.07

SEQ ID NO:101 is an exemplary nucleic acid sequence of the antibody heavy chain of CAP256-VRC26.08

SEQ ID NO:102 is an exemplary nucleic acid sequence of the antibody light chain of CAP256-VRC26.08

SEQ ID NO:103 is an exemplary nucleic acid sequence of the antibody heavy chain variable domain of CAP256-VRC26.08

SEQ ID NO:104 is an exemplary nucleic acid sequence of the antibody light chain variable domain of CAP256-VRC26.08

SEQ ID NO:105 is an exemplary nucleic acid sequence of the antibody heavy chain of CAP256-VRC26.09

SEQ ID NO:106 is an exemplary nucleic acid sequence of the antibody light chain of CAP256-VRC26.09

SEQ ID NO:107 is an exemplary nucleic acid sequence of the antibody heavy chain variable domain of CAP256-VRC26.09

SEQ ID NO:108 is an exemplary nucleic acid sequence of the antibody light chain variable domain of CAP256-VRC26.09

SEQ ID NO:109 is an exemplary nucleic acid sequence of the antibody heavy chain of CAP256-VRC26.10

SEQ ID NO:110 is an exemplary nucleic acid sequence of the antibody light chain of CAP256-VRC26.10

SEQ ID NO:111 is an exemplary nucleic acid sequence of the antibody heavy chain variable domain of CAP256-VRC26.10

SEQ ID NO:112 is an exemplary nucleic acid sequence of the antibody light chain variable domain of CAP256-VRC26.10

SEQ ID NO:113 is an exemplary nucleic acid sequence of the antibody heavy chain of CAP256-VRC26.11

SEQ ID NO:114 is an exemplary nucleic acid sequence of the antibody light chain of CAP256-VRC26.11

SEQ ID NO:115 is an exemplary nucleic acid sequence of the antibody heavy chain variable domain of CAP256-VRC26.11

SEQ ID NO:116 is an exemplary nucleic acid sequence of the antibody light chain variable domain of CAP256-VRC26.11

SEQ ID NO:117 is an exemplary nucleic acid sequence of the antibody heavy chain of CAP256-VRC26.12

SEQ ID NO:118 is an exemplary nucleic acid sequence of the antibody light chain of CAP256-VRC26.12

SEQ ID NO:119 is an exemplary nucleic acid sequence of the antibody heavy chain variable domain of CAP256-VRC26.12

SEQ ID NO:120 is an exemplary nucleic acid sequence of the antibody light chain variable domain of CAP256-VRC26.12

SEQ ID NO:121 is the consensus amino acid sequence of the antibody heavy chain variable domain of a CAP256-VRC26 antibody SEQ ID NO:122 is the consensus amino acid sequence of the antibody light chain variable domain of a CAP256-VRC26 antibody SEQ ID NOs:123-167 are the PCR primers used to prepare the amplicon for 454 pyrosequencing SEQ ID NO:168 is the sequence for oligonucleotide primer EnvM SEQ ID NO:169 is the sequence for oligonucleotide primer EnvAstop SEQ ID NO:170 is the amino acid sequence of the antibody heavy chain of CAP256-VRC26.25

SEQ ID NO:171 is the amino acid sequence of the antibody light chain of CAP256-VRC26.25

SEQ ID NO:172 is the amino acid sequence of the antibody heavy chain variable domain of CAP256-VRC26.25

SEQ ID NO:173 is the amino acid sequence of the antibody light chain variable domain of CAP256-VRC26.25

SEQ ID NO:174 is an exemplary nucleic acid sequence of the antibody heavy chain of CAP256-VRC26.25

SEQ ID NO:175 is an exemplary nucleic acid sequence of the antibody light chain of CAP256-VRC26.25

SEQ ID NO:176 is an exemplary nucleic acid sequence of the antibody heavy chain variable domain of CAP256-VRC26.25

SEQ ID NO:177 is an exemplary nucleic acid sequence of the antibody light chain variable domain of CAP256-VRC26.25

SEQ ID NO:178 is the amino acid sequence of the antibody heavy chain of CAP256-VRC26.26

SEQ ID NO:179 is the amino acid sequence of the antibody light chain of CAP256-VRC26.26

SEQ ID NO:180 is the amino acid sequence of the antibody heavy chain variable domain of CAP256-VRC26.26

SEQ ID NO:181 is the amino acid sequence of the antibody light chain variable domain of CAP256-VRC26.26

SEQ ID NO:182 is an exemplary nucleic acid sequence of the antibody heavy chain of CAP256-VRC26.26

SEQ ID NO:183 is an exemplary nucleic acid sequence of the antibody light chain of CAP256-VRC26.26

SEQ ID NO:184 is an exemplary nucleic acid sequence of the antibody heavy chain variable domain of CAP256-VRC26.26

SEQ ID NO:185 is an exemplary nucleic acid sequence of the antibody light chain variable domain of CAP256-VRC26.26

SEQ ID NO:186 is the amino acid sequence of the antibody heavy chain of CAP256-VRC26.27

SEQ ID NO:187 is the amino acid sequence of the antibody light chain of CAP256-VRC26.27

SEQ ID NO:188 is the amino acid sequence of the antibody heavy chain variable domain of CAP256-VRC26.27

SEQ ID NO:189 is the amino acid sequence of the antibody light chain variable domain of CAP256-VRC26.27

SEQ ID NO:190 is an exemplary nucleic acid sequence of the antibody heavy chain of CAP256-VRC26.27

SEQ ID NO:191 is an exemplary nucleic acid sequence of the antibody light chain of CAP256-VRC26.27

SEQ ID NO:192 is an exemplary nucleic acid sequence of the antibody heavy chain variable domain of CAP256-VRC26.27

SEQ ID NO:193 is an exemplary nucleic acid sequence of the antibody light chain variable domain of CAP256-VRC26.27

DETAILED DESCRIPTION OF THE INVENTION

The present invention will now be described more fully hereinafter with reference to the accompanying drawings, in which some, but not all embodiments of the invention are shown.

The invention as described should not be limited to the specific embodiments disclosed and modifications and other embodiments are intended to be included within the scope of the invention. Although specific terms are employed herein, they are used in a generic and descriptive sense only and not for purposes of limitation.

Where a value of ranges is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either or both of those included limits are also included in the invention.

As used throughout this specification and in the claims which follow, the singular forms "a", "an" and "the" include the plural form, unless the context clearly indicates otherwise.

The terminology and phraseology used herein is for the purpose of description and should not be regarded as limiting. The use of the terms "comprising", "containing", "having" and "including" and variations thereof used herein, are meant to encompass the items listed thereafter and equivalents thereof as well as additional items.

Unless otherwise defined herein, all technical and scientific terms used herein have the same meaning as commonly understood by one of ordinary skill in the art to which this invention belongs.

The present invention provides for isolated anti-HIV antibodies which are broadly neutralising to HIV-1 and which recognise and bind to a V1V2 epitope of HIV-1 Env.

The term "antibody" includes monoclonal antibodies, polyclonal antibodies, multispecific antibodies (for instance, bispecific antibodies and polyreactive antibodies), and antibody fragments. Accordingly, the term "antibody" as used in this specification includes, but is not limited to, any specific binding member, immunoglobulin class and/or isotype (for instance: IgG1, IgG2, IgG3, IgG4, IgM, IgA, IgD, IgE and IgM) or an antibody fragment thereof.

It is understood in the art that an antibody is a glycoprotein comprising at least two heavy (H) chains and two light (L) chains which are inter-connected by disulfide bonds, or an antigen binding portion thereof. A heavy chain comprises a heavy chain variable region (VH) and a heavy chain constant region (CH1, CH2 and CH3). A light chain comprises a light chain variable region (VL) and a light chain constant region (CL). The variable regions of both the heavy and the light chains comprise framework regions (FR's) and complementarity determining regions (CDR's). The four FR's are relatively conserved while the CDR regions (CDR1, CDR2 and CDR3) comprise hypervariable regions. The FR's and CDR's are arranged from the $NH_2$ terminus to the COOH terminus as follows: FR1, CDR1, FR2, CDR2, FR3, CDR3, FR4. The variable regions of the heavy and light chains contain a binding domain that interacts with an antigen. Further, the constant regions may mediate the binding of the immunoglobulin to host tissues or factors.

Also included in the definition of "antibody" are chimeric antibodies, humanized antibodies, recombinant antibodies, human antibodies generated from a transgenic non-human animal and antibodies selected from libraries using enrichment technologies available to those skilled in the art.

The term "epitope" as used herein means any antigenic determinant on an antigen to which the paratope of an antibody can bind. Epitopic determinants usually consist of chemically active surface groupings of molecules such as amino acids or sugar side chains and usually have specific three dimensional structural characteristics, as well as specific charge characteristics.

An "antibody fragment" comprises a portion of an intact antibody, such as the antigen binding or variable region of the intact antibody. Examples of antibody fragments include, but are not limited to, Fab, Fab', F(ab')2, Fv fragments, scFV fragments; diabodies; or linear antibodies.

Papain digestion of antibodies produces two identical "Fab" fragments or antigen-binding fragments, each with a single antigen-binding site, and a residual "Fc" fragment, whose name reflects its ability to crystallize readily. Pepsin treatment of antibodies yields an F(ab')2 fragment that has two antigen-combining sites and which retains its ability to cross-link an antigen.

The term "Fv" refers to the minimum antibody fragment that contains a complete antigen-recognition and antigen-binding site. This fragment contains a dimer of one heavy- and one light-chain variable region domain in tight, non-covalent association. The folding of these two domains results in the formation of six hypervariable loops (three loops each from the H and L chain) that contribute the amino acid residues for antigen binding and confer antigen binding specificity to the antibody. However, even a single variable region (or half of an Fv comprising only three CDRs specific for an antigen) has the ability to recognize and bind an antigen, although at a lower affinity. "Single-chain Fv" ("sFv" or "scFv") are antibody fragments that comprise the VH and VL antibody domains connected into a single polypeptide chain. The sFv polypeptide can further comprise a polypeptide linker between the VH and VL domains that enables the sFv to form the desired structure for antigen binding.

The "Fab" fragments contain the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known in the art.

Variant antibodies also are included within the scope of the invention. Thus, variants of the sequences recited in the application also are included within the scope of the invention. Further variants of the antibody sequences having improved affinity can be obtained using methods known in the art and are included within the scope of the invention. Those skilled in the art can modify the amino acid sequences of a polypeptide utilizing recombinant methods and/or synthetic chemistry techniques for the production of variant polypeptides. For example, amino acid substitutions can be used to obtain antibodies with further improved affinity. Alternatively, codon optimization of the nucleotide sequence can be used to improve the efficiency of translation in expression systems for the production of the antibody. Such variant antibody sequences will share 70% or more (i.e., 75%, 80%, 85%, 90%, 95%, 96%, 97%, 98%, 99% or greater) sequence identity with the sequences recited in the application. Such sequence identity is calculated with regard to the full length of the sequence recited in the application.

The present invention provides for anti-HIV antibodies, either alone or in combination with other antibodies, which have broad neutralizing activity in serum and as isolated antibodies.

The term "polypeptide" should be read to include "peptide" and "protein" and vice versa. As used herein, "polypeptide" refers to an amino acid sequence of a recombinant or non-recombinant polypeptide having an amino acid sequence of i) a native polypeptide, ii) a biologically active fragment of an polypeptide, or iii) a biologically active variant of a polypeptide.

As used herein, the term "isolated" means a nucleic acid or an antibody which has been removed from its natural environment. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids and/or polypeptides.

The terms "subject" and "patient" are used interchangeably herein to mean any animal that may have a need for the pharmaceutical compositions, treatments and vaccines described herein. Subjects and patients thus include, without limitation, primates (including humans), canines, felines, murines and other mammalian subjects. Preferably, the subjects are humans. As will be evidence from the context in which the term is used, subject and patient refer to a subject or patient susceptible to infection by Human Immunodeficiency Virus (HIV) and/or a subject or patient who is infected with HIV.

In a further embodiment of the invention, the cross-reactive, broadly neutralizing anti-HIV antibody comprises a heavy chain variable region comprising the consensus amino acid sequence of SEQ ID NO:121. In yet another embodiment, the cross-reactive, broadly neutralising anti-HIV antibody comprises a light chain variable region comprising the consensus amino sequence of SEQ ID NO:122.

A further embodiment of the present invention provides for an isolated anti-HIV antibody comprising the heavy chain sequence of SEQ ID NO:1, 5, 9, 13, 17, 21, 25, 29, 33, 37, 41, 45, 49, 53, 57, 170, 178 or 186 and a light chain sequence of SEQ ID NO:2, 6, 10, 14, 18, 22, 26, 30, 34, 38, 42, 46, 50, 54, 58, 171, 179 or 187 and an isolated anti-HIV antibody comprising a heavy chain variable region sequence of SEQ ID NO: 3, 7, 11, 15, 19, 23, 27, 31, 35, 39, 43, 47, 51, 55, 59, 172, 180 or 188 and a light chain variable sequence of SEQ ID NO: 4, 8, 12, 16, 20, 24, 28, 32, 36, 40, 44, 48, 52, 56, 60, 173, 181 or 189, or sequences having at least 70%, or at least 75%, or at least 80%, or at least 85%, or at least 90%, or at least 95%, or at least 96%, or at least 97%, or at least 98%, or at least 99% identity thereto.

In another embodiment, the present invention provides an isolated anti-HIV antibody comprising one or both of the heavy chain sequence of SEQ ID NO: 3, 7, 11, 15, 19, 23, 27, 31, 35, 39, 43, 47, 51, 55, 59, 172, 180 or 188 and the light chain sequence of SEQ ID NO: 4, 8, 12, 16, 20, 24, 28, 32, 36, 40, 44, 48, 52, 56, 60, 173, 181 or 189, and wherein the antibody neutralizes a panel of HIV virus strains at the $IC_{50}$ concentrations shown in Tables 3.1, 3.2 or 3.3.

In another embodiment, the present invention provides an isolated anti-HIV antibody selected from the group consisting of CAP256-VRC261-UCA, CAP256-VRC26-I1, CAP256-VRC26-12, CAP256-VRC26.01, CAP256-VRC26.02, CAP256-VRC26.03, CAP256-VRC26.04, CAP256-VRC26.05, CAP256-VRC26.06, CAP256-VRC26.07, CAP256-VRC26.08, CAP256-VRC26.09, CAP256-VRC26.10, CAP256-VRC26.11, CAP256-VRC26.12, CAP256-VRC26.13, CAP256-VRC26.14, CAP256-VRC26.15, CAP256-VRC26.16, CAP256-VRC26.17, CAP256-VRC26.18, CAP256-VRC26.19, CAP256-VRC26.20, CAP256-VRC26.21, CAP256-VRC26.22, CAP256-VRC26.23, CAP256-VRC26.24, CAP256-VRC26.25, CAP256-VRC26.26, CAP256-VRC26.27, CAP256-VRC26.28, CAP256-VRC26.29, CAP256-VRC26.30, CAP256-VRC26.31, CAP256-VRC26.32 and CAP256-VRC26.33.

In another embodiment, the present invention provides an isolated anti-HIV antibody comprising heavy chain CDR1, CDR2 and CDR3 regions and light chain CDR1, CDR2 and CDR3 regions comprising the amino acids sequences of the corresponding regions of an HIV antibody selected from the group consisting of CAP256-VRC261-UCA, CAP256-VRC26-11, CAP256-VRC26-12, CAP256-VRC26.01, CAP256-VRC26.02, CAP256-VRC26.03, CAP256-VRC26.04, CAP256-VRC26.05, CAP256-VRC26.06, CAP256-VRC26.07, CAP256-VRC26.08, CAP256-VRC26.09, CAP256-VRC26.10, CAP256-VRC26.11, CAP256-VRC26.12, CAP256-VRC26.25, CAP256-VRC26.26 and CAP256-VRC26.27.

The present invention also provides for methods of making an isolated anti-HIV antibody comprising a heavy chain sequence of SEQ ID NO:1, 5, 9, 13, 17, 21, 25, 29, 33, 37, 41, 45, 49, 53, 57, 170, 178 or 186 and a light chain sequence of SEQ ID NO:2, 6, 10, 14, 18, 22, 26, 30, 34, 38, 42, 46, 50, 54, 58, 171, 179 or 187 and methods of producing an isolated anti-HIV antibody comprising a heavy chain variable region sequence of SEQ ID NO: 3, 7, 11, 15, 19, 23, 27, 31, 35, 39, 43, 47, 51, 55, 59, 172, 180 or 188 and the light chain variable sequence of SEQ ID NO: 4, 8, 12, 16, 20, 24, 28, 32, 36, 40, 44, 48, 52, 56, 60, 173, 181 or 189, or sequences having at least 70%, or at least 75%, or at least 80%, or at least 85%, or at least 90%, or at least 95%, or at least 96%, or at least 97%, or at least 98%, or at least 99% identity thereto.

In another embodiment, the invention provides for isolated nucleic acids encoding the isolated anti-HIV antibodies, vectors and host cells containing the nucleic acids, and recombinant techniques for the production of the antibodies.

The invention also provides for polynucleotide variants that encode the peptide sequences of the heavy and light chains of the anti-HIV antibodies CAP256-VRC261-UCA, CAP256-VRC26-I1, CAP256-VRC26-12, CAP256-VRC26.01, CAP256-VRC26.02, CAP256-VRC26.03, CAP256-VRC26.04, CAP256-VRC26.05, CAP256-VRC26.06, CAP256-VRC26.07, CAP256-VRC26.08, CAP256-VRC26.09, CAP256-VRC26.10, CAP256-VRC26.11, CAP256-VRC26.12, CAP256-VRC26.25, CAP256-VRC26.26 and CAP256-VRC26.27. These polynucleotide variants may have at least 70%, or at least 75%, or at least 80%, or at least 85%, or at least 90%, or at least 95%, or at least 96%, or at least 97%, or at least 98%, or at least 99%, or greater, sequence identity compared to a polynucleotide sequence of this invention, as determined using the methods described herein. Such contiguous sequences may encode a CDR sequence, or may encode a complete variable region. As is known in the art, a variable region sequence may be fused to any appropriate constant region sequence. One skilled in this art will recognize that these values can be appropriately adjusted to determine corresponding identity of proteins encoded by two nucleotide sequences by taking into account codon degeneracy, amino acid similarity, reading frame positioning, and the like.

The terms "nucleic acid" and "polynucleotide" are used interchangeably herein to refer to single-stranded or double-stranded RNA, DNA, or mixed polymers.

For recombinant production of the antibody, the nucleic acid encoding it is inserted into a vector for further cloning (amplification of the DNA) or for expression. DNA encoding the antibodies of the invention was isolated according to the methods set out in the Examples. Those of skill in the art will appreciate that many vectors are available for use in the recombinant production of antibodies. Vector components generally include, but are not limited to, one or more of the following: a signal sequence, an origin of replication, one or more marker genes, an enhancer element, a promoter, and a transcription termination sequence.

The anti-HIV antibodies of this invention may also be produced recombinantly, for instance, as a fusion polypeptide with a heterologous or homologous polypeptide, which include a signal sequence or other polypeptide having a specific cleavage site at the N-terminus of the mature protein or polypeptide, an immunoglobulin constant region sequence, and the like. A heterologous signal sequence selected preferably may be one that is recognized and processed (i.e., cleaved by a signal peptidase) by the host cell. For prokaryotic host cells that do not recognize and process the native antibody signal sequence, the signal sequence is substituted by a prokaryotic signal sequence selected.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard to the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

Suitable host cells for cloning or expressing the DNA are prokaryotic, yeast, or higher eukaryotic cells. Host cells transformed with the above-described expression or cloning vectors for anti-HIV antibody production are cultured in conventional nutrient media, modified as appropriate, for inducing promoters, selecting transformants, or amplifying the genes encoding the desired sequences. Antibody compositions prepared from the cells can be purified using purification techniques known to those of ordinary skill in the art.

Preferably, the nucleotide sequences and/or antibodies of the invention are administered to a subject in vivo, in order to produce an immunogenic response or provide a prophylactic effect in the subject. In some embodiments it may be desired to express the nucleic acids of the invention or administer the antibodies of the invention in a laboratory animal, such as for pre-clinical testing of the HIV-1 immunogenic or prophylactic compositions of the invention. In other embodiments, it will be desirable to express or administer the antibodies of the invention in human subjects, such as in clinical trials and for actual clinical use of the immunogenic or prophylactic compositions of the invention. In preferred embodiments the subject is a human, for example a human that is infected with, or is at risk of infection with, HIV-1.

According to another embodiment, the present invention provides a method for treating a mammal infected with a virus, such as, for example, HIV, comprising administering to said mammal a pharmaceutical composition comprising the anti-HIV antibodies disclosed herein or nucleotide sequences expressing the anti-HIV antibodies disclosed herein. According to one embodiment, the method for treating a mammal infected with HIV comprises administering to said mammal a pharmaceutical composition that comprises an antibody of the present invention, or a fragment thereof. The compositions of the invention can include more than one antibody having the characteristics disclosed (for example, a plurality or pool of antibodies). It also can include other HIV neutralizing antibodies as are known in the art. According to a further embodiment, the method for treating a mammal infected with HIV comprises administering to said mammal a pharmaceutical composition that comprises nucleotide sequences expressing the anti-HIV antibody of the present invention, or a fragment thereof, vectors containing the nucleic acids and cells containing the vectors.

In in vivo applications the antibodies or nucleic acids of the invention are preferably administered as a component of a pharmaceutical composition comprising the nucleotide sequences, vectors containing the nucleic acids, cells containing the vectors, and/or antibodies in admixture with a pharmaceutically acceptable carrier. When used for in vivo therapy, the nucleotide sequences, vectors containing the nucleic acids, cells containing the vectors and/or the antibodies of the invention are administered to the patient in therapeutically effective amounts. The nucleotide sequences, vectors containing the nucleic acids, cells containing the vectors and/or antibodies are administered to a human patient, in accord with methods known in the art, such as, but not limited to intravenous administration.

The term "pharmaceutical composition" is used herein to define a solid or liquid composition in a form, concentration and level of purity suitable for administration to a patient upon which administration it can elicit physiological changes which treat and/or ameliorate the effects of infection with HIV.

The pharmaceutical composition may further be used as one or more components of a prophylactic or therapeutic vaccine against HIV-1 and for the prevention, amelioration or treatment of AIDS. The nucleic acids and vectors of the invention are particularly useful for providing genetic vaccines, i.e. vaccines for delivering the nucleic acids encoding the antibodies of the invention to a subject, such as a human, such that the antibodies are expressed in the subject in order to elicit an immune response and/or to provide direct protection against HIV-1 infection. Alternatively, the antibodies of the invention may be administered to the subject in order to elicit an immune response against HIV-1 and/or to provide direct protection against HIV-1 infection.

Antibodies of the invention, nucleotide sequences, vectors containing the nucleic acids, and/or cells containing the vectors may be administered to the subject by any suitable means, including parenteral, subcutaneous, intraperitoneal, intrapulmonary, and intranasal administration. The antibody or antigen-binding portion thereof can either be administered alone or in combination with another therapeutic agent, for instance a second human antibody or antigen binding portion thereof. In one example, the second antibody or antigen binding portion thereof specifically binds to a second HIV epitope that differs from the epitope bound to the first antibody. In another example, the antibody is administered together with another agent, for example, an antiviral agent. Antiviral agents include, but are not limited to, for instance: Abacavir, Aciclovir, Adefovir, Amantadine, Amprenavir, Ampligen, Aplaviroc, Arbidol, Atazanavir, Atripla, Boceprevir, Cidofovir, Combivir, Darunavir, Delavirdine, Didanosine, Docosanol, Edoxudine, Efavirenz, Emtricitabine, Enfuvirtide, Entecavir, Entry inhibitors, Famciclovir, Fomivirsen, Fosamprenavir, Foscarnet, Fosfonet, Fusion inhibitor, Ganciclovir, Ibacitabine, Imunovir, Idoxuridine, Imiquimod, Indinavir, Inosine, Integrase inhibitor, Interferon I, II or III, Lamivudine, Lopinavir, Loviride, Maraviroc, Moroxydine, Methisazone, Nelfinavir, Nevirapine, Nexavir, Nucleoside analogues, Oseltamivir (Tamiflu), Peginterferon alfa-2a, Penciclovir, Peramivir, Pleconaril, Podophyllotoxin, Protease inhibitor, Raltegravir, Reverse transcriptase inhibitor, Ribavirin, Rimantadine, Ritonavir, Pyramidine, Saquinavir, Stavudine, Tenofovir, Tenofovir disoproxil, Tipranavir, Trifluridine, Trizivir, Tromantadine, Truvada, Valaciclovir (Valtrex), Valganciclovir, Vicriviroc, Vidarabine, Viramidine, Vicriviroc, Zalcitabine, Zanamivir (Relenza) or Zidovudine or any combination thereof.

For the prevention or treatment of disease, the appropriate dosage of antibody, nucleotide sequences, vectors containing the nucleic acids, and/or cells containing the vectors will depend on the type of disease to be treated, the severity and course of the disease, whether the antibody, nucleotide sequences, vectors containing the nucleic acids, and/or cells containing the vectors are administered for preventive purposes, previous therapy, the patient's clinical history and response to the antibody, and the discretion of the attending physician. The antibody, nucleotide sequences, vectors containing the nucleic acids, and/or cells containing the vectors are suitably administered to the patient at one time or over a series of treatments.

The term "effective dose" or "effective dosage" is defined as an amount sufficient to achieve or at least partially achieve the desired effect. The term "therapeutically effective dose" is defined as an amount sufficient to cure or at least partially arrest a disease and its symptoms and effects in a patient suffering from the disease. The effective dose for use is dependent upon the severity of the disorder being treated and the general state of the subject's immune system.

Pharmaceutical compositions comprising one or more antibodies of the invention are prepared for storage by mixing the antibody having the desired degree of purity with optional physiologically acceptable carriers, excipients or stabilizers, in the form of lyophilized formulations or aqueous solutions. The antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the antibody to be administered will be governed by such considerations, and is the minimum amount necessary to reduce virus titer in an infected individual.

Pharmaceutical compositions comprising one or more nucleic acids encoding antibodies of the invention, vectors containing the nucleic acids, and/or cells containing the vectors are prepared for storage by mixing the nucleic acids, vectors or cells having the desired degree of purity with optional physiologically acceptable carriers, excipients or stabilizers, in the form of lyophilized formulations or aqueous solutions. The composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the nucleic acids, vectors or cells to be administered will be governed by such considerations, and is the minimum amount necessary to reduce virus titer in an infected individual.

In another embodiment of the invention the antibodies of the invention may be used in a diagnostic composition. A diagnostic composition is a composition containing a compound or antibody, e.g., a labelled compound or antibody, that is used to detect the presence in a sample, such as a biological sample, of an antibody that binds to the compound or an immunogen, antigen or epitope that binds to the antibody; for instance, an anti-HIV antibody or an HIV immunogen, antigen or epitope.

In another embodiment of the invention, an article of manufacture, such as a kit, containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is one or more antibodies in a formulation of the invention as described above. The label on, or associated with, the container indicates that the composition is used for treating the condition of choice. The article of manufacture may further comprise a second container comprising a pharmaceutically-acceptable buffer, such as phosphate-buffered saline, Ringers solution and dextrose solution. It may further include other materials desirable from a commercial and user standpoint, including other buffers, diluents, filters, needles, syringes, and package inserts with instructions for use.

Study Subject

CAPRISA participant CAP256 was enrolled into the CAPRISA Acute Infection study (van Loggerenberg et al. 2008) that was established in 2004 in KwaZulu-Natal, South Africa for follow-up and subsequent identification of HIV seroconversion. CAP256 was one of the 7 women in this cohort who developed neutralization breadth (Gray et al. 2011). The CAPRISA 002 Acute Infection study was reviewed and approved by the research ethics committees of the University of KwaZulu-Natal (E013/04), the University of Cape Town (025/2004), and the University of the Witwatersrand (MM040202). CAP256 provided written informed consent for study participation.

The following examples are offered by way of illustration and not by way of limitation.

Example 1

Isolation and expression of CAP256-VRC26 family genes

PBMC isolated from CAP256 blood draws at weeks 59, 119, and 206 were stained and sorted for IgG+ B cells on a FACS Aria II (Georgiev et al. 2013). Cells were plated at 2 B cells/well in 384 well plates and cultured for 14 days in the presence of IL-2, IL-21, and CD40L-expressing irradiated feeder cells, (Huang et al. (2012), (2013). Culture supernatants were screened by microneutralization as described in (Doria-Rose et al, 2013. Protocol Exchange, in press) against HIV-1 ZM53.12 and CAP45.G3 Env-pseudoviruses. The numbers of screened wells are in Table 1. Kappa and lambda light chain gene and IgG heavy chain gene variable regions were amplified from neutralization positive wells, subcloned, expressed, and purified (Georgiev et al. 2013). Heavy chains were reconstituted as $IgG_1$. One antibody was recovered from week 59, 8 from week 119, and 3 from week 206.

TABLE 1

Summary of B cell cloning from donor CAP256

| Week of PBMC | 59 | 119 | 206 |
|---|---|---|---|
| Total B cells plated (2/well) | 15000 | 45000 | 42000 |
| % of IgG positive wells | 8.3% | 48% | 29% |
| # neutralization-positive wells | 4 | 49 | 34 |
| # antibodies recovered | 1 | 8 | 3 |

Example 2

Neutralization Assays

Single round of replication Env-pseudoviruses were prepared, titered, and used to infect TZM-bl target cells (Shu et al. 2007, Montefiori et al. 2009). Neutralization breadth of CAP256-VRC26.08 and 0.25 were determined using a panel of 195 geographically and genetically diverse Env-pseudoviruses representing the major subtypes and circulating recombinant forms (Georgiev et al. 2013, Wu et al. 2010). The data were calculated as a reduction in luminescence units compared with control wells, and reported as 50% inhibitory concentration ($IC_{50}$) in micrograms per microlitre for monoclonal antibodies, or reciprocal dilution ($ID_{50}$) for plasma samples.

Neutralization Correlations

The correlations between the neutralization fingerprints of the CAP256-VRC26 antibodies and the neutralization patterns of four longitudinal serum timepoints (at 59, 106, 159, and 220 weeks post infection) were computed over a set of 29 HIV-1 strains (6535.3, AC10.29, CAAN.A2, CAP210.E8, CAP244.D3, CAP45.G3, DU156.12, DU172.17, DU422.01, PVO.04, Q168.a2, Q23.17, Q259.d2.17, Q461.e2, Q769.d22, Q842.d12, QH0692.42, REJO.67, RHPA.7, SC422.8, THRO.18, TRJO.58, TRO.11, WITO.33, ZM109.4, ZM135.10a, ZM197.7, ZM233.6, ZM53.12) (Georgiev et al. 2013). The correlations between the neutralization potencies of the CAP256-VRC26 antibodies and a reference set of antibodies targeting the four major sites of vulnerability, with at most two antibodies per unique donor, were computed over a set of 41 HIV-1 strains (6535.3, 0260.v5.c36, 6405.v4.c34, AC10.29, C1080.c3, CAAN.A2, CAP210.E8, CAP244.D3, CAP45.G3, CNE3, DU156.12, DU172.17, DU422.01, KER2008.12, KER2018.11, MB201.A1, MB539.2B7, PVO.04, Q168.a2, Q23.17, Q259.17, Q461.e2, Q769.d22, Q842.d12, QH0692.42, REJO.67, RHPA.7, RW020.2, SC422.8, TH976.17, THRO.18, TRJO.58, TRO.11, UG037.8, WITO.33, ZM109.4, ZM135.10a, ZM197.7, ZM214.15, ZM249.1, ZM53.12). The correlations between the neutralization patterns of the four longitudinal serum time points and the neutralization fingerprints of the reference antibodies were computed over a set of 28 HIV-1 strains (6535.3, AC10.29, CAAN.A2, CAP210.E8, CAP244.D3, CAP45.G3, DU156.12, DU172.17, DU422.01, PVO.04, Q168.a2, Q23.17, Q259.17, Q461.e2, Q769.d22, Q842.d12, QH0692.42, REJO.67, RHPA.7, SC422.8, THRO.18, TRJO.58, TRO.11, WITO.33, ZM109.4, ZM135.10a, ZM197.7, ZM53.12). For the reference antibodies, data from multiple neutralization experiments was averaged and consolidated. All correlations are based on the Spearman rank coefficient.

Virus-Like Particle ELISA

VLP ELISAs were performed as described in Tong et al. (2012). Briefly, VLPs were produced by PEI-based cotransfection of 293T cells with a pCAGGS-based, Env-expressing plasmid and the Env-deficient HIV-1 genomic backbone plasmid pNL-LucR-E-. VLPs were coated on ELISA wells at 20× the concentration in transfection supernatants. MAb binding was then assessed by ELISA, omitting detergent in PBS wash buffers and probing with an anti-human Fc alkaline phosphatase conjugate (Accurate, Westbury, N.Y.) and SigmaFAST p-nitrophenyl phosphate tablets (Sigma). Plates were read at 405 nm.

Cell-Surface Env Binding 293T cells were transiently transfected with Env ZM53.12 with a deletion of the cytoplasmic tail (Pancera & Wyatt (2005)). After 2 days, the cells were stained with ViVid viability dye (Invitrogen) followed by biotinylated CAP256-VRC26.01 (10 ug/ml) or CAP256-VRC26.08 (0.8 µg/ml) premixed with serially diluted unlabeled competitor antibodies. After incubation and 2 washes, cells were stained with streptavidin-PE (Invitrogen) at 1:200 dilution. Cells were analyzed on a BD LSRII (Becton Dickinson). Binding was measured as the median fluorescence intensity (MFI) for each sample minus the MFI of cells stained with streptavidin-PE only.

Example 3

Polyreactivity Analysis of Antibodies

Antibody binding to cardiolipin was determined as described in Haynes et al. (2005). Briefly, using the QUANTA Lite ACA IgG III ELISA kit (Zeus Scientific) per manufacturer's protocol, each antibody was diluted to 100 µg/ml in the kit sample diluent and tested in 3-fold serial dilutions. Results shown are representative of at least two independent ELISAs. Positive and negative controls were included on each plate, and values three times above background were considered positive. Antibody reactivity to a human epithelial cell line (HEp-2) was determined with the ANA/HEp-2 Cell Culture IFA Test System (Zeus Scientific) per manufacturer's protocol. Antibodies were diluted to 50 µg/ml and 25 µg/ml in ZOBRA-NS diluent. Positive and negative controls were included on each slide. Antibodies were scored negative, indeterminate, or positive (1+ to 4+) at each dilution. Results are representative of at least two independent experiments.

Example 4

Next-Gen Sequencing

Amplicon for next-generation sequencing was prepared according to the methods of Wu et al. (2011) and Zhu et al. (2012) with slight modifications as indicated. Briefly, mRNA was prepared from 10-15 million PBMC using an Oligotex kit (Qiagen). cDNA was synthesized using Superscript II reverse transcriptase (Invitrogen) and oligo-dT(12-18) primers. Individual PCR reactions were performed with Phusion polymerase for 30 cycles. Primers (Table S NDRx) consisted of pools of 5-7 oligonucleotides specific for all lambda gene families or VH3 family genes, and had adapters for 454 next generation sequencing. For week 176 only, heavy-chain PCR was performed with primers for all VH families, and mixed lambda and kappa primers were used for light chain (Table 2). PCR products were gelpurified (Qiagen). Pyrosequencing of the PCR products was performed on a GSFLX sequencing instrument (Roche-454 Life Sciences, Bradford, Conn., USA) on a half chip per reaction (full chips for week 176). On average, ~250,000 raw reads were produced.

TABLE 2

PCR Primers used to prepare amplicon for 454 pyrosequencing (A) primers used for all time points except week 176 (B) primers used for week 176 sample only (A)

| Chain | Primer Name | Primer Sequence | SEQ ID NO: |
|---|---|---|---|
| Primers used for all time points except week 176 | | | |
| Heavy Chain: VH3 only | 5' pool | | |
| | XLR-A_VH3 LEADER-A | CCATCTCATCCCTGCGTGTCTCCGACTCAG TAAAAGGTGTCCAGTGT | SEQ ID NO: 123 |
| | XLR-A_VH3 LEADER-B | CCATCTCATCCCTGCGTGTCTCCGACTCAG TAAGAGGTGTCCAGTGT | SEQ ID NO: 124 |
| | XLR-A_VH3 LEADER-C | CCATCTCATCCCTGCGTGTCTCCGACTCAG TAGAAGGTGTCCAGTGT | SEQ ID NO: 125 |
| | XLR-A_VH3 LEADER-D | CCATCTCATCCCTGCGTGTCTCCGACTCAG GCTATTTTTAAAGGTGTCCAGTGT | SEQ ID NO: 126 |
| | XLR-A_VH3 LEADER-E | CCATCTCATCCCTGCGTGTCTCCGACTCAG TACAAGGTGTCCAGTGT | SEQ ID NO: 127 |
| | XLR-A_VH3 LEADER-F | CCATCTCATCCCTGCGTGTCTCCGACTCAG TTAAAGCTGTCCAGTGT | SEQ ID NO: 128 |
| | 3' pool | | |
| | XLR-B_3xwCgammaCH1-2 | CCTATCCCCTGTGTGCCTTGGCAGTCTCAG GGGGAAGACCGATGGGCCCTTGGT | SEQ ID NO: 129 |
| | XLR-B_3CmuCH1 | CCTATCCCCTGTGTGCCTTGGCAGTCTCAG GGGAATTCTCACAGGAGACGA | SEQ ID NO: 130 |
| Lambda Chain | 5' pool | | |
| | XLR-A_5L-VL1/2 | CCATCTCATCCCTGCGTGTCTCCGACTCAG GCACAGGGTCCTGGGCCCAGTCTG | SEQ ID NO: 131 |
| | XLR-A_5L-VL3 | CCATCTCATCCCTGCGTGTCTCCGACTCAG GCTCTGTGACCTCCTATGAGCTG | SEQ ID NO: 132 |

TABLE 2-continued

PCR Primers used to prepare amplicon for 454 pyrosequencing (A) primers
used for all time points except week 176 (B) primers used for week 176 sample only

| | | | |
|---|---|---|---|
| | XLR-A_5L-VL4/5 | CCATCTCATCCCTGCGTGTCTCCGACTCAG GGTCTCTCTCSCAGCYTGTGCTG | SEQ ID NO: 133 |
| | XLR-A_5L-VL6 | CCATCTCATCCCTGCGTGTCTCCGACTCAG GTTCTTGGGCCAATTTTATGCTG | SEQ ID NO: 134 |
| | XLR-A_5L-VL7/8 | CCATCTCATCCCTGCGTGTCTCCGACTCAG GAGTGGATTCTCAGACTGTGGTG | SEQ ID NO: 135 |
| | XLR-A_5MP-VL1 | CCATCTCATCCCTGCGTGTCTCCGACTCAG GCTCACTGCACAGGGTCCTGGGCC | SEQ ID NO: 136 |
| | XLR-A_5MP-VL3-1 | CCATCTCATCCCTGCGTGTCTCCGACTCAG GCTTACTGCACAGGATCCGTGGCC | SEQ ID NO: 137 |
| | XLR-A_5MP-VL3-19 | CCATCTCATCCCTGCGTGTCTCCGACTCAG ACTCTTTGCATAGGTTCTGTGGTT | SEQ ID NO: 138 |
| | XLR-A_5MP-VL3-21 | CCATCTCATCCCTGCGTGTCTCCGACTCAG TCTCACTGCACAGGCTCTGTGACC | SEQ ID NO: 139 |
| | XLR-A_5MP-VL7-43 | CCATCTCATCCCTGCGTGTCTCCGACTCAG ACTTGCTGCCCAGGGTCCAATTC | SEQ ID NO: 140 |
| 3' primer | | | |
| | XLR-B_3CL | CCTATCCCCTGTGTGCCTTGGCAGTCTCAG CACCAGTGTGGCCTTGTTGGCTTG | SEQ ID NO: 141 |

(B)

| Chain | Primer Name | Primer Sequence | SEQ ID NO: |
|---|---|---|---|
| Primers used for week 176 sample only | | | |
| Heavy Chain: Vh_all 5' pool | | | |
| | XLR-A_5L-VH1 | CCATCTCATCCCTGCGTGTCTCCGACTCAG ACAGGTGCCCACTCCCAGGTGCAG | SEQ ID NO: 142 |
| | XLR-A_5L-VH3 | CCATCTCATCCCTGCGTGTCTCCGACTCAG AAGGTGTCCAGTGTGARGTGCAG | SEQ ID NO: 143 |
| | XLR-A_5L-VH4/6 | CCATCTCATCCCTGCGTGTCTCCGACTCAG CCCAGATGGGTCCTGTCCCAGGTGCAG | SEQ ID NO: 144 |
| | XLR-A_5L-VH5 | CCATCTCATCCCTGCGTGTCTCCGACTCAG CAAGGAGTCTGTTCCGAGGTGCAG | SEQ ID NO: 145 |
| | XLR-A_5xwL-VH1 | CCATCTCATCCCTGCGTGTCTCCGACTCAG GCAGCCACAGGTGCCCACTCC | SEQ ID NO: 146 |
| | XLR-A_5xwL-VH1-24 | CCATCTCATCCCTGCGTGTCTCCGACTCAG CAGCAGCTACAGGCACCCACGC | SEQ ID NO: 147 |
| | XLR-A_5xwL-VH1-69 | CCATCTCATCCCTGCGTGTCTCCGACTCAG GGCAGCAGCTACAGGTGTCCAGTCC | SEQ ID NO: 148 |
| | XLR-A_VH3-L1-MP | CCATCTCATCCCTGCGTGTCTCCGACTCAG GCTATTTTAAAAGGTGTCCAATGT | SEQ ID NO: 149 |
| | XLR-A_VH3/4-1_1-MP | CCATCTCATCCCTGCGTGTCTCCGACTCAG GTGGCAGCTCCCAGATGGGTCCTGTC | SEQ ID NO: 150 |
| | XLR-A_VH3/4-L3-MP | CCATCTCATCCCTGCGTGTCTCCGACTCAG GTTGCAGTTTTAAAAGGTGTCCAGTG | SEQ ID NO: 151 |
| | XLR-A_VH5-L1-MP | CCATCTCATCCCTGCGTGTCTCCGACTCAG GCTGTTCTCCAAGGAGTCTGTTCC | SEQ ID NO: 152 |
| Light Chains (kappa + lambda) | 5' pool | | |
| | XLR-A_5xwL-VIE1/2 | CCATCTCATCCCTGCGTGTCTCCGACTCAG ATGAGGSTCCCYGCTCAGCTCCTGGG | SEQ ID NO: 153 |
| | XLR-A_5L-VK3 | CCATCTCATCCCTGCGTGTCTCCGACTCAG CTCTTCCTCCTGCTACTCTGGCTCCCAG | SEQ ID NO: 154 |
| | XLR-A_5L-VK4 | CCATCTCATCCCTGCGTGTCTCCGACTCAG ATTTCTCTGTTGCTCTGGATCTCTG | SEQ ID NO: 155 |
| | XLR-A_5L-VL1/2 | CCATCTCATCCCTGCGTGTCTCCGACTCAG GCACAGGGTCCTGGGCCCAGTCTG | SEQ ID NO: 156 |
| | XLR-A_5L-VL3 | CCATCTCATCCCTGCGTGTCTCCGACTCAG GCTCTGTGACCTCCTATGAGCTG | 8E0 ID NO: 157 |
| | XLR-A_5L-VL4/5 | CCATCTCATCCCTGCGTGTCTCCGACTCAG GGTCTCTCTCSCAGCYTGTGCTG | SEQ ID NO: 158 |
| | XLR-A_5L-VL6 | CCATCTCATCCCTGCGTGTCTCCGACTCAG GTTCTTGGGCCAATTTTATGCTG | SEQ ID NO: 159 |
| | XLR-A_5L-VL7/8 | CCATCTCATCCCTGCGTGTCTCCGACTCAG GAGTGGATTCTCAGACTGTGOTG | SEQ ID NO: 160 |
| | XLR-A_5MP-VL1 | CCATCTCATCCCTGCGTGTCTCCGACTCAG GCTCACTGCACAGGGTCCTGGGCC | SEQ ID NO: 161 |
| | XLR-A_5MP-VL3-1 | CCATCTCATCCCTGCGTGTCTCCGACTCAG GCTTACTGCACAGGATCCGTGGCC | SEQ ID NO: 162 |
| | XLR-A_5MP-VL3-19 | CCATCTCATCCCTGCGTGTCTCCGACTCAG ACTCTTTGCATAGGTTCTGTGGTT | SEQ ID NO: 163 |

TABLE 2-continued

PCR Primers used to prepare amplicon for 454 pyrosequencing (A) primers used for all time points except week 176 (B) primers used for week 176 sample only

| | | | |
|---|---|---|---|
| | XLR-A_5MP-VL3-21 | CCATCTCATCCCTGCGTGTCTCCGACTCAG TCTCACTGCACAGGCTCTGTGACC | SEQ ID NO: 164 |
| | XLR-A_5MP-VL7-43 | CCATCTCATCCCTGCGTGTCTCCGACTCAG ACTTGCTGCCCAGGGTCCAATTC | SEQ ID NO: 165 |
| 3'pool | | | |
| | XLR-B_3xwCk1 | CCTATCCCCTGTGTGCCTTGGCAGTCTCAG CAGCAGGCACACAACAGAGGCAGTTCC | SEQ ID NO: 166 |
| | XLR-B_3CL | CCTATCCCCTGTGTGCCTTGGCAGTCTCAG CACCAGTGTGGCCTTGTTGGCTTG | SEQ ID NO: 167 |

Antibodyomics Pipeline

Raw 454 data was processed using a pipeline implemented in Python, similar to one we reported previously (Zhu et al. 2013). Briefly, reads were filtered for length, keeping only those between 300 and 600 nucleotides. Germline V genes were then assigned to each read using BLAST with empirically optimized parameters. Reads for which no V gene match was found with an e-value <10-10 were discarded. For reads assigned to any VH3-30 or VL1-51 allele, (the CAP256-VRC26 germline genes), ClustalW2 (Larkin et al. 2007) was used to calculate the sequence identity to the germline and each isolated antibody. These data were plotted as density heat maps using ggplot2 in R to produce identity-divergence plots (not shown).

Finding Clonally Related Sequences

Reads that were assigned to the same V genes as CAP256-VRC26, VH3-30 and VL1-51, were submitted to IMGT High-Vquest (Alamyar (2012)) (http://www.imgt.org/IMGTindex/IMGTHighV-QUEST.html), and the results, including automated sequence corrections, were used to further sieve for lineage-related sequences. Reads assigned to J genes matching CAP256-VRC26 (JH3*02 or JL1*01), and having similar divergence (+/−15%) in the V and J genes, similar (+/−10%) nucleotide and amino acid divergences in the V gene, and containing a continuous open reading frame throughout the entire variable region, were selected for further processing. Next, reads from all time points were pooled and clustered at 97.25% sequence identity (twice the standard deviation of expected 454 sequencing error) (Zhu et al. 2012) using CDHit (Li et al. 2001). For each cluster, a representative sequence was chosen from the earliest possible time point. The choice of cluster representatives from the earliest time points at which they appeared was critical to maintaining information on the chronology of lineage development in subsequent analyses. This procedure yielded 8,485 unique heavy chain and 6,410 unique light chain sequences.

To identify CAP256-VRC26 lineage-member heavy chains, we performed intra-donor phylogenetic analysis (Zhu et al. 2012) on the unique 454 sequence set using the heavy chain sequences of the 12 isolated CAP256-VRC26 antibodies. 707 sequences were identified as likely lineage members, of which 27 were discarded after manual inspection, resulting in a total of 680 unique CAP256-VRC26 lineage heavy chain sequences.

To identify light chain lineage members, a sieve requiring at least 92% sequence identity in CDR L3 to one of the isolated antibodies resulted in 495 sequences. Joinsolver (Souto-Carneiro (2004)) was used to examine the V-J junctions of these sequences in detail, to ensure that the recombination points matched those known for the isolated antibodies. This gave a total of 472 unique CAP256-VRC26 lineage light chain sequences.

Computation of Phylogenetic Trees

MEGA5 (Tamura et al. 2011) was used to select GTR+G as the best mathematical model for building a maximum-likelihood tree from the CAP256-VRC26 lineage sequences. FASTML (Ashkenazy et al. 2012) was then used to estimate the gamma parameter and build separate maximum likelihood trees for heavy and light chain sequences (including the isolated antibodies) and these were rooted on the germline V gene sequences. Two branches of the light chain tree were manually moved to match their positioning in the heavy chain tree based on the evidence from trees constructed solely with the 12 isolated antibodies. Analysis with DNAML and PHYLIP (Phylogeny Inference Package) version 3.6 (Felsenstein, J. 2005. PHYLIP (Phylogeny Inference Package) version 3.6. Distributed by the author. Department of Genome Sciences, University of Washington, Seattle) showed that these rearrangements did not significantly alter the log-likelihood score of the tree.

To create a condensed version of the heavy chain phylogenetic tree, CDR H3 sequences were clustered using a 95% sequence identity threshold and requiring that all CDR H3s in a cluster have the same length. Isolated antibodies and monophyletic clusters with at least five members were represented by a single leaf, while all other sequences were removed from the tree. In cases were an internal node was deleted, branch lengths above and below that node were summed, so that the tree depths of all remaining sequences were maintained.

UCA and Inferred Intermediates

The DNAML maximum likelihood software package (http://cmgm.stanford.edu/phylip/dnaml.html) was used to infer ancestral sequences from phylogenetic trees of all heavy and all light chain lineage members (FIG. 3 and FIGS. 6 and 7), including the isolated antibodies. The calculated heavy chain UCA was identical to the germline VH3-30*18 allele. Although the VH3-30*03 allele is only one nucleotide different, germline sequencing of this donor showed that she carries the *18 allele and not the *03 allele (Catherine Mitchell, personal communication).

To test intermediates in the development of CAP256-VRC26.01, two internal nodes were chosen from the phylogenetic trees to be approximately equally spaced in terms of evolutionary distance and the inferred sequences were retrieved using DNAML. Successful complementation of inferred heavy and light chains for each intermediate suggests that the lineage is well sampled by the 454 data and that the calculated phylogenetic trees successfully capture the coupled evolutionary dynamics of heavy and light chains.

Logograms for CDRH3s were generated with Weblogo (Crooks et al. 2004).

Example 5

Crystallization

VRC26.UCA Fab was prepared by digesting purified IgG with Lys-C at 37° C. for 2 hours. The reaction was then quenched by the addition of Complete protease inhibitors. For VRC26.01, VRC26.03, VRC26.04, VRC26.06, VRC26.07 and VRC26.10 Fab preparation, an HRV3C recognition site (GLEVLFQGP) was inserted after Lys235 and purified IgG was incubated with HRV3C protease overnight at 4° C. For all, the digested antibodies were passed over Protein A agarose to remove the Fc fragment. The Fab was further purified over a Superdex 200 gel filtration column and concentrated aliquots were stored at −80° C. All Fabs were screened against 576 crystallization conditions using a Cartesian Honeybee crystallization robot. Initial crystals were grown by the vapour diffusion method in sitting drops at 20° C. by mixing 0.2 µl of protein complex with 0.2 µl of reservoir solution. Crystals were manually reproduced in hanging drops by mixing 1.0 µl protein complex with 1.0 µl reservoir solution. VRC26-UCA was crystallized with a reservoir solution of 27% PEG 8000 and 0.1M Hepes pH 7.5 and was flash frozen in liquid nitrogen with 20% PEG 400 as a cryoprotectant. VRC26.01 was crystallized with a reservoir solution of 32% PEG 400, 4% PEG 3350 and 0.1M Na Acetate pH 5.5 and was flash frozen in liquid nitrogen with 20% ethylene glycol as a cryoprotectant. VRC26.03 was crystallized with a reservoir solution of 22% PEG 8000, 5% MPD and 0.1M imidazole pH 6.5 and was flash frozen in liquid nitrogen with 20% xylitol as a cryoprotectant. VRC26.04 was crystallized with a reservoir solution of 14% PEG 3350, 25% ispropanol and 0.1M Tris pH 8.5 and was flash frozen in liquid nitrogen with 20% ethylene glycol as a cryoprotectant. VRC26.06 was crystallized with a reservoir solution of 3M Na formate and 0.1M Tris pH 7.5 and was flash frozen in liquid nitrogen with 20% xylitol as a cryoprotectant. VRC26.07 was crystallized with a reservoir solution of 4% PEG 8000, 0.1M Zn acetate and 0.1M MES pH 6 and was flash frozen in liquid nitrogen with 20% glycerol as a cryoprotectant. VRC26.10 was crystallized with a reservoir solution of 22% PEG 4000, 0.4M Na Acetate and 0.1 M Tris pH 7.5 and was flash frozen in liquid nitrogen with no cryoprotectant.

Data for all crystals were collected at a wavelength of 1.00 Å at SER-CAT beamlines ID-22 and BM-22 (Advanced Photon Source, Argonne National Laboratory). All diffraction data were processed with the HKL2000 suite (Otwinowski & Minor (1997)) and model building and refinement were performed in COOT (Emsley & Cowtan (2004)) and PHENIX (Adams et al. 2004), respectively. For VRC26.03 Fab data, a molecular replacement solution consisting of one Fab molecule per asymmetric unit was obtained using PHASER with a search model from PDB ID 3F12. VRC26.03 then served as a search model for all remaining VRC26 Fabs. Throughout the refinement processes, a cross validation (Rfree) test set consisting of 5% of the data was used and hydrogen atoms were included in the refinement model. Structure validations were performed periodically during the model building/refinement process with MolProbity (Davis et al. 2004). All graphical representation with protein crystal structures were made with Pymol (DeLano Scientific, San Carlos, Calif. (2002)).

Example 6

Structure Modeling (Spike and V1V2, and 11 and 12)

Defined locations of the V1V2, V3-glycan and CD4-binding sites were mapped directly onto EM density of the unliganded HIV-1 BAL spike (EMD-5019) (Liu et al. 2008) using the software package UCSF Chimera (Pettersen et al. 2004). The CD4-binding site was defined by aligning density of the VRC01-bound BAL spike (EMD-5457) (Tran et al. 2012) with the unliganded map and fitting a crystal structure of VRC01-bound gp120 (PDB id 3NGB) (Zhou et al. 2010) to the density. EM density in close proximity to the Fab structure was colored to highlight the region of contact. The same procedure was used to define the V3-glycan region using a PGT128-bound trimer (EMD-1970) and crystal structure (PDB id 3TYG) (Pejchal et al. 2011) and the V1V2 region using the PG9-bound BG505 SOSIP trimer (EMD-2241) (Julien et al. 2013) and a crystal structure of V1V2-bound PG9 (PDB id 3U4E) (McClellan et al. 2011). The fit of the PG9-V1V2 crystal structure to the SOSIP trimer was used to model the trimeric orientation of V1V2 using the 3-fold symmetry of the HIV-1 spike.

Two intermediates were calculated at approximately equal maturation distance along the VRC26-UCA to VRC26.01 pathway. Mutations associated with the intermediates were mapped directly onto the structure of VRC26.01. 14 of the 35 residues in the VRC26.01 structure are disordered and were modelled with Loopy (Soto et al. 2008) and represented as grey dots. Mutations of the intermediates were coloured according to approximate time of occurrence based on the longitudinal phylogenetic tree highlighting the timeline of the structural development.

Tyrosine sulfation predictions were carried out in GPS-TPS (Pan et al, http://tsp.biocuckoo.org).

Example 7

Single Genome Amplification, Sequencing and Cloning

HIV-1 RNA was isolated from plasma using the Qiagen QIAamp Viral RNA kit, and reverse transcribed to cDNA using SuperScript III Reverse Transcriptase (Invitrogen, CA). The envelope genes were amplified from single genome templates (Salazar-Gonzalez (2008)) and amplicons were directly sequenced using the ABI PRISM Big Dye Terminator Cycle Sequencing Ready Reaction kit (Applied Biosystems, Foster City, Calif.) and resolved on an ABI 3100 automated genetic analyzer. The full-length env sequences were assembled and edited using Sequencher v.4.5 software (Genecodes, Ann Arbor, Mich.). Multiple sequence alignments were performed using Clustal X (ver. 1.83) and edited with BioEdit (ver. 7.0.9) Sequence alignments were visualized using Highlighter for Amino Acid Sequences v1.1.0 (beta).

For analysis of selection pressure, and to account for recombination between the SU and PI, sequences were partitioned into two alignments (an SU-related, and a PI-related alignment) based on the inferred recombination breakpoints using an in-house script. Breakpoints were identified by a shift in identity from one reference towards the other, and required at least two sequential polymorphisms in common with a corresponding PI/SU-related virus in order to be considered. Phylogenies for both alignments were then reconstructed using FastTree (Price et al. 2010) with a GTR+CAT model, and rooted on the PI/SU. Signals of selective pressure were detected with MEME (episodic diversifying selection) (Murrell et al. 2012) and DEPS (directional selection) (Kosakovsky et al. 2008) using the FastTree-generated trees, implemented in Hyphy (Pond et al. 2005).

The frequencies of specific amino acids at a site and the distribution of net charges in the V2 epitope were calculated from the 2012 filtered web alignment (N=3990) from the Los Alamos HIV database (http://www.hiv.lanl.gov/).

Selected envelope amplicons were cloned into the expression vector pcDNA 3.1 (directional) (Invitrogen) by re-amplification of SGA first-round products using Pfu Ultra II enzyme (Stratagene) with the EnvM primer, 5'-TAG CCC TTC CAG TCC CCC CTT TTC TTT TA-3' (SEQ ID NO:168) (Gao et al. 1996) and directional primer, EnvAstop, 5'-CAC CGG CTT AGG CAT CTC CTA TGG CAG GAA GAA-3' (SEQ ID NO:169) (Kraus et al. 2010). Cloned env genes were sequenced to confirm that they exactly matched the sequenced amplicon. Autologous clones were mutated at key residues within the C-strand using the Stratagene QuickChange II kit (Stratagene) as described by the manufacturer. Mutations were confirmed by sequencing. Envelope clones were used to generate single round of replication Env-pseudoviruses as described above.

Example 8

Isolation of Potent Neutralizing Antibodies from Donor CAP256

The CAPRISA acute infection cohort comprises high-risk women tested monthly for HIV-1 infection; 62 seroconverted and were enrolled in a long-term longitudinal study with regular blood draws. Plasma from seven seroconverters could neutralize over 40% of HIV-1 strains after 3 years of infection (Gray et al. 2011). Mapping of these antibody responses indicated most to be glycan-dependent, either targeting glycan N160 in V1V2 region, or glycan N332 in the third variable region (V3) (Gray et al. 2011). Of these, the V1V2 responses were the most broad and potent, notably in donor CAP256 whose plasma titers exceeded 1:40,000 against some viruses (Gray et al. 2011, Moore et al. 2011 and Moore et al. 2013).

Blood memory B cells from donor CAP256 were used to isolate 33 monoclonal antibodies at 59, 119 and 206 weeks post-infection by high-throughput B cell culture, functional screening by microneutralization, and reverse transcription-PCR to recover antibody variable regions (Huang et al. 2012, Huang et al. 2013 and Tiller et al. 2008) (Table 1). These antibodies, named CAP256-VRC26.01-33, were subcloned and reconstituted as IgG, antibodies. All 33 were somatically related and distinguished by exceptionally long CDR H3s of 35-37 amino acids (Kabat numbering) (Kabat et al. 1991) (FIG. 1). Both heavy and lambda chains showed somatic mutation of 4-15% from their germline encoded V-genes: Vλ1-51*02 for the light chain and VH3-30*18 for the heavy chain. The 33 antibodies showed varying degrees of heterologous virus neutralization, with a range of breadth and potency (FIG. 1 and Tables 3.1, 3.2 and 3.3). They were extremely potent on many strains, especially subtype A and C viruses, with 50% inhibitory concentrations ($IC_{50}$) in the nanomolar range. The broadest, CAP256-VRC26.25, was ~12% mutated from the germline VH gene and neutralized 63% of a 194-virus panel of global isolates with a geometric mean $IC_{50}$ of 0.03 µg/ml (FIG. 9). The earliest antibody, CAP256-VRC26.01, isolated at week 59 when plasma titers were low, showed cross-clade neutralization of 20% (FIG. 1, Tables 3.1, 3.2 and 3.3) despite having diverged only ~8% from germline VH and less than 4% from germline light chain (FIG. 1).

Example 9

CAP256-VRC26 Antibodies Recognize V1V2 Strands B and C

To understand the relationship between neutralization by CAP256 plasma and by antibodies of the CAP256-VRC26 lineage, we determined neutralization fingerprints for each of the 33 isolated antibodies and compared them to neutralization fingerprints of plasma from CAP256 years 1-4. These fingerprints were highly correlated; furthermore the combination of all 33 antibodies recapitulated the neutralization breadth of the plasma (FIG. 10). Neutralization fingerprints of CAP256-VRC26 antibodies were also compared to those of previously characterized HIV-1-neutralizing antibodies directed against the major sites of HIV-1 vulnerability. Strong correlation was observed with PG9 and other V1V2-directed broadly neutralizing antibodies, but not with antibodies targeting other HIV-1 Env regions. Notably, CAP256-VRC26 antibodies showed no binding to any of 23 constructs of gp120, gp140, or scaffolded V1V2) similar to other V1V2 directed neutralizing antibodies. However, they showed strong binding to virus-like particles and cell-surface expressed gp160 (FIG. 2), indicating a high degree of specificity for the native quaternary conformation of Env. To determine the antibody competition group, we therefore used a cell-surface-Env binding assay. Binding of CAP256-VRC26.08 (FIG. 2) and CAP256-VRC26.01 to cell-surface gp160 was competed by the V1V2-directed antibody PG9, and weakly by the V3-glycan antibody PGT121, but not by MPER-directed or CD4-binding site-directed antibodies.

We then focused on strands B and C of the four-stranded V1V2 domain, both because residues of these strands were previously shown to be required for neutralization by the donor CAP256 plasma (Moore et al. 2011 and Moore et al. 2013) and because V1V2-directed neutralizing antibodies depend on strands B and C (McClellan et al. 2011, Pancera et al. 2013 and Doria-Rosa et al. 2012). We tested CAP256-VRC26 antibodies for neutralization of a virus with the consensus clade C Env sequence (ConC) and variants containing a series of V1V2 strand B and C point mutants (FIG. 2). Neutralization was ablated by R166A and K169E mutations, which had previously been shown to abrogate neutralization by CAP256 plasma (Moore et al. 2011). Other residues had modest effects that varied between the CAP256-VRC26 family members. For example, unlike the PG9 class of V1V2-directed antibodies, the CAP256-VRC26 antibodies were partially and variably sensitive to the loss of glycans at N160 as well as N156 (FIG. 2). To corroborate these results, we used a pair of viruses designed for a gain of sensitivity to existing well-characterized broadly neutralizing V1V2 antibodies (Doria-Rosa et al. 2012). As expected, HIV-1 strain 6405 was highly resistant to CAP256-VRC26 antibodies (FIG. 2b, bottom left). The gain-of-function mutant of 6405, containing 5 amino acid changes in the strand B-C region (FIG. 2b, bottom right), was neutralized by 11 of the 12 CAP256-VRC26 antibodies (FIG. 2b, bottom). Mapping these mutations to a model of the V1V2 region in the functional viral spike 37 indicated the recognized epitope to be close to the trimer axis, providing a structural explanation for the observed quaternary specificity.

TABLE 3.1

Neutralization of autologous (CAP256-PI and CAP256-SU) and 46 heterologous viruses by CAP256-VRC26.01 - CAP256-VRC26.12 mAbs. Neutralization of each mAb was measured using a TZM-bl assay. Geometric mean was calculated for values <50 μg/ml.

|   |   | $IC_{50}$ | | | | | |
|---|---|---|---|---|---|---|---|
|   |   | CAP256-VRC26.01 | CAP256-VRC26.02 | CAP256-VRC26.03 | CAP256-VRC26.04 | CAP256-VRC26.05 | CAP256-VRC26.06 |
|   |   | Autologous | | | | | |
|   | CAP256.PI | >50 | >50 | >50 | >50 | >50 | >50 |
|   | CAP256.SU | 0.140 | 0.015 | 0.004 | 0.003 | 0.007 | 0.055 |
| Heterologous by clade | $IC_{50}$ | CAP256-VRC26.01 | CAP256-VRC26.02 | CAP256-VRC26.03 | CAP256-VRC26.04 | CAP256-VRC26.05 | CAP256-VRC26.06 |
| C | 96ZM651.02 | >50 | >50 | >50 | >50 | >50 | >50 |
|   | CAP210.E8 | 0.217 | 0.062 | 0.011 | 0.005 | 0.013 | 0.729 |
|   | CAP244.D3 | >50 | >50 | >50 | >50 | >50 | >50 |
|   | CAP45.G3 | >50 | >50 | >50 | >50 | >50 | >50 |
|   | DU156.12 | >50 | >50 | >50 | >50 | >50 | >50 |
|   | DU172.17 | >50 | >50 | >50 | >50 | >50 | >50 |
|   | DU422.01 | >50 | >50 | 0.134 | 4.170 | >50 | >50 |
|   | ZM109.4 | >50 | >50 | >50 | >50 | 26.500 | >50 |
|   | ZM135.10a | >50 | >50 | >50 | >50 | >50 | >50 |
|   | ZM197.7 | 10.400 | 1.970 | 0.160 | 0.254 | 0.113 | >50 |
|   | ZM214.15 | >50 | >50 | 1.500 | >50 | >50 | >50 |
|   | ZM233.6 | >50 | 0.701 | 0.032 | 0.060 | 0.003 | >50 |
|   | ZM249.1 | >50 | >50 | 0.039 | 11.400 | >50 | >50 |
|   | ZM53.12 | 0.103 | 0.043 | 0.008 | 0.004 | 0.012 | 0.222 |
| A | 0.260.v5.c36 | >50 | >50 | >50 | >50 | >50 | >50 |
|   | BG505.w6m | >50 | >50 | 4.760 | 8.430 | >50 | >50 |
|   | KER2008.12 | 30.900 | >50 | >50 | >50 | >50 | >50 |
|   | KER2018.11 | 8.100 | 0.180 | 0.003 | 0.008 | 0.012 | >50 |
|   | MB201 | >50 | >50 | >50 | >50 | >50 | >50 |
|   | MB539.2B7 | >50 | >50 | >50 | >50 | >50 | >50 |
|   | Q168.a2 | >50 | >50 | >50 | >50 | >50 | >50 |
|   | Q23.17 | >50 | >50 | >50 | 23.600 | >50 | >50 |
|   | Q259.d2.17 | >50 | >50 | 0.014 | 0.025 | 0.023 | >50 |
|   | Q461.e2 | >50 | >50 | >50 | >50 | >50 | >50 |
|   | Q769.d22 | >50 | >50 | >50 | >50 | >50 | >50 |
|   | Q842.d12 | >50 | >50 | >50 | >50 | >50 | >50 |
|   | RW020.2 | >50 | >50 | >50 | >50 | >50 | >50 |
|   | UG037.8 | >50 | >50 | >50 | >50 | >50 | >50 |
| B | 6535.3 | >50 | >50 | >50 | >50 | >50 | >50 |
|   | AC10.29 | >50 | >50 | >50 | >50 | >50 | 0.022 |
|   | CAAN.A2 | >50 | >50 | >50 | >50 | >50 | >50 |
|   | PVO.04 | >50 | 7.980 | >50 | >50 | 44.400 | 0.308 |
|   | QH0692.42 | >50 | >50 | >50 | >50 | >50 | >50 |
|   | REJO.67 | >50 | >50 | >50 | >50 | >50 | >50 |
|   | RHPA.7 | >50 | >50 | >50 | >50 | >50 | >50 |
|   | SC422.8 | >50 | >50 | >50 | >50 | >50 | 0.178 |
|   | THRO.18 | >50 | >50 | >50 | >50 | >50 | 4.250 |
|   | TRJO.58 | >50 | >50 | >50 | >50 | >50 | >50 |
|   | TRO.11 | >50 | >50 | >50 | >50 | >50 | >50 |
|   | WITO.33 | >50 | >50 | >50 | >50 | >50 | 0.003 |
| D | 191821.E6.1 | >50 | >50 | >50 | >50 | >50 | >50 |
|   | 3016.V5.c36 | 9.630 | 0.057 | 0.118 | 0.283 | 0.011 | >50 |
|   | 6405.v4.c34 | >50 | >50 | >50 | >50 | >50 | >50 |
| AE | C1080.c3 | >50 | >50 | 0.119 | 0.212 | >50 | >50 |
|   | CM244.ec1 | 3.320 | 2.030 | 0.003 | 0.361 | 0.517 | >50 |
|   | CNE3 | >50 | >50 | >50 | >50 | >50 | >50 |
|   | TH976.17 | >50 | >50 | >50 | >50 | >50 | >50 |
| nonHIV | SIVmac251.30 | >50 |   |   |   |   | >50 |
|   | % breadth | 19% | 17% | 36% | 30% | 21% | 17% |
|   | geomean $IC_{50}$ (μg/ml) | 1.88 | 0.40 | 0.08 | 0.32 | 0.10 | 0.38 |
|   | # neut | 9 | 8 | 17 | 14 | 10 | 8 |

TABLE 3.1-continued

Neutralization of autologous (CAP256-PI and CAP256-SU) and 46 heterologous viruses by CAP256-VRC26.01 - CAP256-VRC26.12 mAbs. Neutralization of each mAb was measured using a TZM-bl assay. Geometric mean was calculated for values <50 μg/ml.

|   |   | $IC_{50}$ | | | | | |
|---|---|---|---|---|---|---|---|
|   |   | CAP256-VRC26.07 | CAP256-VRC26.08 | CAP256-VRC26.09 | CAP256-VRC26.10 | CAP256-VRC26.11 | CAP256-VRC26.12 |
|   |   | | | Autologous | | | |
|   | CAP256.PI | >50 | >50 | >50 | >50 | >50 | >50 |
|   | CAP256.SU | 0.008 | 0.003 | 0.002 | 0.031 | 0.055 | 0.032 |
| Heterologous by clade | $IC_{50}$ | CAP256-VRC26.07 | CAP256-VRC26.08 | CAP256-VRC26.09 | CAP256-VRC26.10 | CAP256-VRC26.11 | CAP256-VRC26.12 |
| C | 96ZM651.02 | >50 | 2.820 | 0.991 | >50 | >50 | >50 |
|   | CAP210.E8 | 0.021 | 0.006 | 0.002 | 0.100 | 0.073 | 0.072 |
|   | CAP244.D3 | >50 | >50 | >50 | >50 | >50 | >50 |
|   | CAP45.G3 | >50 | 4.690 | 16.000 | >50 | >50 | >50 |
|   | DU156.12 | >50 | 0.059 | 0.016 | >50 | >50 | >50 |
|   | DU172.17 | >50 | >50 | >50 | >50 | >50 | >50 |
|   | DU422.01 | >50 | 0.008 | 0.023 | 8.200 | 11.500 | >50 |
|   | ZM109.4 | >50 | >50 | >50 | >50 | >50 | >50 |
|   | ZM135.10a | >50 | >50 | >50 | >50 | >50 | >50 |
|   | ZM197.7 | >50 | 0.008 | 0.011 | 0.346 | 0.055 | >50 |
|   | ZM214.15 | >50 | >50 | 0.333 | >50 | >50 | >50 |
|   | ZM233.6 | >50 | 0.000 | 0.001 | 0.228 | 0.322 | >50 |
|   | ZM249.1 | 44.100 | 0.076 | 0.010 | >50 | 34.500 | >50 |
|   | ZM53.12 | 0.014 | 0.004 | 0.002 | 0.072 | 0.081 | 0.211 |
| A | 0.260.v5.c36 | >50 | >50 | >50 | >50 | >50 | >50 |
|   | BG505.w6m | >50 | 0.143 | 0.054 | >50 | 4.200 | >50 |
|   | KER2008.12 | >50 | >50 | >50 | >50 | >50 | >50 |
|   | KER2018.11 | 3.100 | 0.003 | 0.002 | 0.335 | 1.760 | >50 |
|   | MB201 | >50 | >50 | >50 | >50 | >50 | >50 |
|   | MB539.2B7 | >50 | 31.700 | 40.700 | >50 | >50 | >50 |
|   | Q168.a2 | >50 | 0.256 | 0.181 | >50 | >50 | >50 |
|   | Q23.17 | >50 | 13.300 | 9.500 | 2.590 | >50 | >50 |
|   | Q259.d2.17 | 42.500 | 0.009 | 0.008 | 24.600 | >50 | >50 |
|   | Q461.e2 | >50 | 0.969 | 0.705 | >50 | >50 | >50 |
|   | Q769.d22 | >50 | >50 | >50 | >50 | >50 | >50 |
|   | Q842.d12 | >50 | 40.400 | 10.11 | >50 | >50 | >50 |
|   | RW020.2 | >50 | >50 | >50 | >50 | >50 | >50 |
|   | UG037.8 | >50 | >50 | >50 | >50 | >50 | >50 |
| B | 6535.3 | >50 | >50 | >50 | >50 | >50 | >50 |
|   | AC10.29 | >50 | >50 | >50 | >50 | >50 | >50 |
|   | CAAN.A2 | >50 | >50 | >50 | >50 | >50 | >50 |
|   | PVO.04 | >50 | 11.800 | >50 | 2.480 | 10.800 | >50 |
|   | QH0692.42 | >50 | >50 | >50 | >50 | >50 | >50 |
|   | REJO.67 | >50 | >50 | >50 | >50 | >50 | >50 |
|   | RHPA.7 | >50 | >50 | >50 | >50 | >50 | >50 |
|   | SC422.8 | >50 | >50 | >50 | >50 | >50 | >50 |
|   | THRO.18 | >50 | >50 | >50 | >50 | >50 | >50 |
|   | TRJO.58 | >50 | >50 | >50 | >50 | >50 | >50 |
|   | TRO.11 | >50 | >50 | >50 | >50 | >50 | >50 |
|   | WITO.33 | >50 | >50 | >50 | >50 | >50 | >50 |
| D | 191821.E6.1 | >50 | >50 | 0.054 | >50 | >50 | >50 |
|   | 3016.V5.c36 | >50 | 0.013 | 0.004 | 0.017 | 0.300 | 7.930 |
|   | 6405.v4.c34 | >50 | >50 | >50 | >50 | >50 | >50 |
| AE | C1080.c3 | >50 | 0.012 | 0.019 | >50 | 0.018 | >50 |
|   | CM244.ec1 | 40.100 | 1.090 | 0.105 | 0.914 | 26.700 | >50 |
|   | CNE3 | >50 | >50 | >50 | >50 | >50 | >50 |
|   | TH976.17 | >50 | >50 | >50 | >50 | >50 | >50 |
| nonHIV | SIVmac251.30 |   | >50 | >50 | >50 |   |   |
|   | % breadth | 13% | 47% | 47% | 23% | 26% | 6% |
|   | geomean $IC_{50}$ (ug/ml) | 1.51 | 0.08 | 0.07 | 0.60 | 0.94 | 0.49 |
|   | # neut | 6 | 22 | 22 | 11 | 12 | 3 |

TABLE 3.2

Neutralization of autologous (CAP256-PI and CAP256-SU) and 46 heterologous viruses by CAP256-VRC26.13-CAP256-VRC26.24 mAbs. Neutralization of each mAb was measured using a TZM-bl assay. Geometric mean was calculated for values <50 μg/ml.

| | | $IC_{50}$ | | | | | |
|---|---|---|---|---|---|---|---|
| | | CAP256-VRC26.13 | CAP256-VRC26.14 | CAP256-VRC26.15 | CAP256-VRC26.16 | CAP256-VRC26.17 | CAP256-VRC26.18 |
| | | Autologous | | | | | |
| | CAP256.PI | >50 | >50 | >50 | >50 | >50 | >50 |
| | CAP256.SU | 0.019 | 0.004 | 0.008 | 0.004 | 0.003 | 0.008 |
| Heterologous by clade | $IC_{50}$ | CAP256-VRC26.13 | CAP256-VRC26.14 | CAP256-VRC26.15 | CAP256-VRC26.16 | CAP256-VRC26.17 | CAP256-VRC26.18 |
| C | 96ZM651.02 | >50 | >50 | >50 | >50 | >50 | >50 |
| | CAP210.E8 | 0.094 | 0.012 | 0.019 | 0.009 | 0.006 | 0.019 |
| | CAP244.D3 | >50 | >50 | >50 | >50 | >50 | >50 |
| | CAP45.G3 | >50 | >50 | >50 | >50 | >50 | >50 |
| | DU156.12 | >50 | >50 | 10.400 | 48.700 | 18.700 | >50 |
| | DU172.17 | >50 | >50 | >50 | >50 | >50 | >50 |
| | DU422.01 | >50 | 49.000 | 0.153 | 3.900 | 0.510 | 5.400 |
| | ZM109.4 | >50 | >50 | >50 | >50 | >50 | >50 |
| | ZM135.10a | >50 | >50 | >50 | >50 | >50 | >50 |
| | ZM197.7 | >50 | 4.960 | 14.600 | 2.210 | 2.200 | 1.890 |
| | ZM214.15 | >50 | >50 | >50 | >50 | >50 | >50 |
| | ZM233.6 | >50 | 0.028 | 0.192 | 0.031 | 0.006 | 0.037 |
| | ZM249.1 | >50 | >50 | >50 | 45.000 | 1.230 | >50 |
| | ZM53.12 | 0.039 | 0.006 | 0.014 | 0.006 | 0.005 | 0.010 |
| A | 0.260.v5.c36 | >50 | >50 | >50 | >50 | >50 | >50 |
| | BG505.w6m | >50 | 0.750 | 11.700 | 0.360 | 0.400 | 1.900 |
| | KER2008.12 | >50 | >50 | >50 | >50 | >50 | >50 |
| | KER2018.11 | >50 | 0.030 | 0.040 | 0.062 | 0.064 | 0.030 |
| | MB201 | >50 | >50 | >50 | >50 | >50 | >50 |
| | MB539.2B7 | >50 | >50 | >50 | >50 | >50 | >50 |
| | Q168.a2 | >50 | >50 | >50 | >50 | >50 | >50 |
| | Q23.17 | >50 | >50 | 0.338 | >50 | 6.420 | 35.000 |
| | Q259.d2.17 | >50 | 2.130 | 0.657 | 5.780 | 0.076 | 5.310 |
| | Q461.e2 | >50 | >50 | 19.900 | >50 | >50 | >50 |
| | Q769.d22 | >50 | >50 | >50 | >50 | >50 | >50 |
| | Q842.d12 | >50 | >50 | 9.350 | >50 | >50 | >50 |
| | RW020.2 | >50 | >50 | >50 | >50 | >50 | >50 |
| | UG037.8 | >50 | >50 | >50 | >50 | >50 | >50 |
| B | 6535.3 | >50 | >50 | >50 | >50 | >50 | >50 |
| | AC10.29 | >50 | >50 | >50 | >50 | >50 | >50 |
| | CAAN.A2 | >50 | >50 | >50 | >50 | >50 | >50 |
| | PVO.04 | >50 | >50 | 30.000 | >50 | >50 | >50 |
| | QH0692.42 | >50 | >50 | >50 | >50 | >50 | >50 |
| | REJO.67 | >50 | >50 | >50 | >50 | >50 | >50 |
| | RHPA.7 | >50 | >50 | >50 | >50 | >50 | >50 |
| | SC422.8 | >50 | >50 | >50 | >50 | >50 | >50 |
| | THRO.18 | >50 | >50 | >50 | >50 | >50 | >50 |
| | TRJO.58 | >50 | >50 | >50 | >50 | >50 | >50 |
| | TRO.11 | >50 | >50 | >50 | >50 | >50 | >50 |
| | WITO.33 | >50 | >50 | >50 | >50 | >50 | >50 |
| D | 191821.E6.1 | >50 | 3.360 | >50 | 0.820 | 35.400 | 10.400 |
| | 3016.V5.c36 | 3.740 | 0.012 | 0.160 | 0.012 | 0.011 | 0.028 |
| | 6405.v4.c34 | >50 | >50 | >50 | >50 | >50 | >50 |
| AE | C1080.c3 | >50 | 0.779 | >50 | 5.900 | >50 | 2.150 |
| | CM244.ec1 | >50 | 6.160 | 0.112 | 0.670 | 0.140 | 1.420 |
| | CNE3 | >50 | >50 | >50 | >50 | >50 | >50 |
| | TH976.17 | >50 | >50 | >50 | >50 | >50 | >50 |
| nonHIV | SIVmac251.30 | | | | | | |
| | % breadth | 6% | 26% | 32% | 30% | 30% | 28% |
| | geomean $IC_{50}$ (ug/ml) | 0.24 | 0.36 | 0.75 | 0.54 | 0.25 | 0.57 |
| | # neut | 3 | 12 | 15 | 14 | 14 | 13 |

TABLE 3.2-continued

Neutralization of autologous (CAP256-PI and CAP256-SU) and 46 heterologous viruses by CAP256-VRC26.13-CAP256-VRC26.24 mAbs. Neutralization of each mAb was measured using a TZM-bl assay. Geometric mean was calculated for values <50 µg/ml.

|  |  | IC$_{50}$ | | | | | |
| --- | --- | --- | --- | --- | --- | --- | --- |
|  |  | CAP256-VRC26.19 | CAP256-VRC26.20 | CAP256-VRC26.21 | CAP256-VRC26.22 | CAP256-VRC26.23 | CAP256-VRC26.24 |
|  |  | | | Autologous | | | |
|  | CAP256.PI | >50 | >50 | >50 | >50 | >50 | >50 |
|  | CAP256.SU | 0.015 | >50 | 0.002 | 0.002 | 0.019 | 0.040 |
| Heterologous by clade | IC$_{50}$ | CAP256-VRC26.19 | CAP256-VRC26.20 | CAP256-VRC26.21 | CAP256-VRC26.22 | CAP256-VRC26.23 | CAP256-VRC26.24 |
| C | 96ZM651.02 | >50 | >50 | >50 | >50 | >50 | >50 |
|  | CAP210.E8 | 0.025 | >50 | 0.005 | 0.003 | 0.019 | 0.230 |
|  | CAP244.D3 | >50 | >50 | >50 | >50 | >50 | >50 |
|  | CAP45.G3 | >50 | >50 | >50 | 1.400 | >50 | 0.672 |
|  | DU156.12 | 1.340 | >50 | >50 | 0.150 | >50 | 10.800 |
|  | DU172.17 | >50 | >50 | >50 | >50 | >50 | >50 |
|  | DU422.01 | 0.057 | >50 | 1.100 | 0.012 | >50 | 21.600 |
|  | ZM109.4 | 2.820 | >50 | >50 | >50 | >50 | 16.500 |
|  | ZM135.10a | >50 | >50 | >50 | >50 | >50 | >50 |
|  | ZM197.7 | 0.135 | >50 | >50 | 0.090 | >50 | 12.600 |
|  | ZM214.15 | >50 | >50 | >50 | >50 | >50 | 32.000 |
|  | ZM233.6 | 0.009 | >50 | 26.500 | 0.001 | >50 | 1.670 |
|  | ZM249.1 | 0.076 | >50 | >50 | 0.130 | >50 | 13.600 |
|  | ZM53.12 | 0.020 | 1.870 | 0.003 | 0.002 | 0.028 | 0.047 |
| A | 0.260.v5.c36 | >50 | >50 | >50 | >50 | >50 | >50 |
|  | BG505.w6m | 0.130 | >50 | >50 | 0.035 | >50 | 5.630 |
|  | KER2008.12 | >50 | >50 | >50 | 1.230 | >50 | >50 |
|  | KER2018.11 | 0.005 | >50 | 0.060 | 0.002 | 10.000 | 1.100 |
|  | MB201 | >50 | >50 | >50 | >50 | >50 | >50 |
|  | MB539.2B7 | 0.431 | >50 | >50 | 17.900 | >50 | >50 |
|  | Q168.a2 | 7.040 | >50 | >50 | 0.007 | >50 | 3.410 |
|  | Q23.17 | 0.233 | >50 | >50 | 0.006 | >50 | 5.920 |
|  | Q259.d2.17 | 2.160 | >50 | 25.400 | 0.005 | >50 | 31.100 |
|  | Q461.e2 | 15.600 | >50 | >50 | 4.100 | >50 | >50 |
|  | Q769.d22 | >50 | >50 | >50 | >50 | >50 | >50 |
|  | Q842.d12 | 0.160 | >50 | >50 | 0.630 | >50 | >50 |
|  | RW020.2 | >50 | >50 | >50 | >50 | >50 | >50 |
|  | UG037.8 | >50 | >50 | >50 | >50 | >50 | >50 |
| B | 6535.3 | >50 | >50 | >50 | >50 | >50 | >50 |
|  | AC10.29 | 2.980 | >50 | >50 | >50 | >50 | >50 |
|  | CAAN.A2 | >50 | >50 | >50 | >50 | >50 | >50 |
|  | PVO.04 | 1.100 | >50 | >50 | 9.030 | >50 | >50 |
|  | QH0692.42 | >50 | >50 | >50 | >50 | >50 | >50 |
|  | REJO.67 | >50 | >50 | >50 | >50 | >50 | >50 |
|  | RHPA.7 | >50 | >50 | >50 | >50 | >50 | >50 |
|  | SC422.8 | >50 | >50 | >50 | >50 | >50 | >50 |
|  | THRO.18 | >50 | >50 | >50 | >50 | >50 | >50 |
|  | TRJO.58 | >50 | >50 | >50 | >50 | >50 | >50 |
|  | TRO.11 | >50 | >50 | >50 | >50 | >50 | >50 |
|  | WITO.33 | >50 | >50 | >50 | >50 | >50 | >50 |
| D | 191821.E6.1 | 29.200 | >50 | >50 | 2.120 | >50 | |
|  | 3016.V5.c36 | 0.039 | >50 | >50 | 0.022 | >50 | 2.120 |
|  | 6405.v4.c34 | >50 | >50 | >50 | >50 | >50 | >50 |
| AE | C1080.c3 | 14.500 | >50 | >50 | 0.013 | >50 | 17.400 |
|  | CM244.ec1 | 0.024 | >50 | >50 | 4.540 | >50 | >50 |
|  | CNE3 | >50 | >50 | >50 | >50 | >50 | >50 |
|  | TH976.17 | >50 | >50 | >50 | >50 | >50 | >50 |
| nonHIV | SIVmac251.30 | | | | | | >50 |
|  | % breadth | 47% | 2% | 13% | 47% | 6% | 37% |
|  | geomean IC$_{50}$ (ug/ml) | 0.33 | 1.87 | 0.30 | 0.09 | 0.17 | 4.18 |
|  | # neut | 22 | 1 | 6 | 22 | 3 | 17 |

TABLE 3.3

Neutralization of autologous (CAP256-PI and CAP256-SU) and 46 heterologous viruses by CAP256-VRC26.25-CAP256-VRC26.33 mAbs. Neutralization of each mAb was measured using a TZM-bl assay. Geometric mean was calculated for values <50 μg/ml.

| | | IC$_{50}$ | | | | | | | | |
|---|---|---|---|---|---|---|---|---|---|---|
| | | CAP256-VRC26.25 | CAP256-VRC26.26 | CAP256-VRC26.27 | CAP256-VRC26.28 | CAP256-VRC26.29 | CAP256-VRC26.30 | CAP256-VRC26.31 | CAP256-VRC26.32 | CAP256-VRC26.33 |
| | CAP256.PI | 1.330 | >50 | >50 | >50 | >50 | >50 | >50 | >50 | >50 |
| | CAP256.SU | 0.001 | 0.003 | <0.0006 | <0.0006 | <0.0006 | <0.0006 | 0.0006 | 0.004 | 0.007 |
| Heterologous by clade | IC$_{50}$ | CAP256-VRC26.13 | CAP256-VRC26.14 | CAP256-VRC26.15 | CAP256-VRC26.16 | CAP256-VRC26.17 | CAP256-VRC26.18 | CAP256-VRC26.19 | CAP256-VRC26.20 | CAP256-VRC26.21 |
| C | 96ZM651.02 | 0.173 | 0.111 | 0.047 | >50 | >50 | 37.800 | >50 | >50 | >50 |
| | CAP210.E8 | 0.001 | 0.007 | 0.002 | <0.0006 | <0.0006 | <0.0006 | 0.003 | 0.008 | 0.017 |
| | CAP244.D3 | >50 | 36.600 | >50 | >50 | >50 | >50 | >50 | >50 | >50 |
| | CAP45.G3 | 0.000 | 0.080 | 0.025 | 0.016 | 0.076 | 0.317 | >50 | >50 | >50 |
| | DU156.12 | 0.002 | 0.013 | 0.006 | 0.171 | 0.136 | 0.848 | 4.460 | >50 | >50 |
| | DU172.17 | >50 | 0.500 | 4.360 | >50 | >50 | >50 | >50 | >50 | >50 |
| | DU422.01 | 0.003 | 0.080 | 0.015 | 0.075 | 0.072 | 0.400 | 1.660 | >50 | 29.500 |
| | ZM109.4 | 0.001 | 0.025 | 0.027 | >50 | >50 | >50 | >50 | >50 | >50 |
| | ZM135.10a | >50 | >50 | >50 | >50 | >50 | >50 | >50 | >50 | >50 |
| | ZM197.7 | 0.002 | 0.011 | 0.004 | 0.193 | 0.136 | 1.000 | 3.220 | 0.097 | 1.730 |
| | ZM214.15 | 0.006 | 14.100 | 3.860 | 6.850 | 13.600 | >50 | >50 | >50 | >50 |
| | ZM233.6 | 0.000 | 0.001 | <0.0006 | 0.002 | 0.003 | 0.188 | 0.740 | 0.015 | 0.004 |
| | ZM249.1 | 0.001 | 0.023 | 0.004 | 0.082 | 0.093 | 0.762 | >50 | 16.800 | 22.500 |
| | ZM53.12 | 0.000 | 0.001 | <0.0006 | <0.0006 | 0.001 | <0.0006 | <0.0006 | 0.011 | 0.015 |
| A | 0.260.v5.c36 | 6.540 | 0.780 | 2.100 | >50 | >50 | >50 | >50 | >50 | >50 |
| | BG505.w6m | 0.001 | 0.066 | 0.102 | 0.044 | 0.046 | 9.040 | >50 | >50 | >50 |
| | KER2008.12 | 0.005 | >50 | 11.300 | 0.760 | 0.684 | >50 | >50 | >50 | >50 |
| | KER2018.11 | 0.000 | 0.001 | 0.001 | <0.0006 | <0.0006 | <0.0006 | 0.002 | 0.032 | 0.037 |
| | MB201 | >50 | >50 | >50 | >50 | >50 | >50 | >50 | >50 | >50 |
| | MB539.2B7 | 0.186 | 0.634 | 1.150 | 29.400 | 13.300 | >50 | >50 | >50 | >50 |
| | Q168.a2 | 0.001 | 0.005 | 0.003 | 0.003 | 0.007 | 0.199 | 4.160 | >50 | >50 |
| | Q23.17 | 0.001 | >50 | >50 | 0.005 | 0.023 | >50 | >50 | >50 | >50 |
| | Q259.d2.17 | 0.002 | 0.011 | 0.005 | 0.012 | 0.019 | 0.107 | 0.262 | >50 | >50 |
| | Q461.e2 | 0.007 | 0.024 | 0.014 | 1.590 | 2.000 | >50 | >50 | >50 | >50 |
| | Q769.d22 | >50 | >50 | >50 | >50 | >50 | >50 | >50 | >50 | >50 |
| | Q842.d12 | 0.005 | 17.100 | 10.600 | 0.779 | 1.690 | >50 | >50 | >50 | >50 |
| | RW020.2 | >50 | >50 | >50 | >50 | >50 | >50 | >50 | >50 | >50 |
| | UG037.8 | >50 | >50 | >50 | >50 | >50 | >50 | >50 | >50 | >50 |
| B | 6535.3 | >50 | >50 | >50 | >50 | >50 | >50 | >50 | >50 | >50 |
| | AC10.29 | 0.077 | >50 | >50 | >50 | 20.400 | >50 | >50 | >50 | >50 |
| | CAAN.A2 | >50 | >50 | >50 | >50 | >50 | >50 | >50 | >50 | >50 |
| | PVO.04 | 0.072 | 0.562 | 0.371 | 6.000 | 4.000 | 12.600 | >50 | 17.800 | >50 |
| | QH0692.42 | >50 | >50 | >50 | >50 | >50 | >50 | >50 | >50 | >50 |
| | REJO.67 | >50 | >50 | >50 | >50 | >50 | >50 | >50 | >50 | >50 |
| | RHPA.7 | >50 | >50 | >50 | >50 | >50 | >50 | >50 | >50 | >50 |
| | SC422.8 | 47.200 | 1.740 | 4.860 | >50 | >50 | >50 | >50 | >50 | >50 |
| | THRO.18 | 19.800 | 0.667 | 1.230 | >50 | >50 | >50 | >50 | >50 | >50 |
| | TRJO.58 | >50 | >50 | >50 | >50 | >50 | >50 | >50 | >50 | >50 |
| | TRO.11 | >50 | >50 | >50 | >50 | >50 | >50 | >50 | >50 | >50 |
| | WITO.33 | >50 | >50 | >50 | >50 | >50 | >50 | >50 | >50 | >50 |
| D | 191821.E6.1 | | | | | | | | | |
| | 3016.V5.c36 | 0.000 | 0.022 | 0.006 | 0.008 | 0.012 | 1.050 | >50 | 0.284 | 0.506 |
| | 6405.v4.c34 | >50 | >50 | >50 | >50 | >50 | >50 | >50 | >50 | >50 |
| AE | C1080.c3 | 0.004 | 0.016 | 0.149 | 0.012 | 0.009 | 0.073 | 1.670 | >50 | >50 |
| | CM244.ec1 | 0.092 | 0.047 | 0.056 | 0.640 | 1.130 | >50 | >50 | 0.561 | 0.036 |
| | CNE3 | >50 | >50 | >50 | >50 | >50 | >50 | >50 | >50 | >50 |
| | TH976.17 | 0.106 | >50 | >50 | >50 | >50 | >50 | >50 | >50 | >50 |
| nonHIV | SIVmac251.30 | >50 | | | | | | | | |
| | % breadth | 63% | 59% | 59% | 41% | 46% | 28% | 20% | 20% | 22% |
| | geomean IC$_{50}$ (ug/ml) | 0.007 | 0.077 | 0.082 | 0.121 | 0.159 | 0.843 | 0.387 | 0.180 | 0.234 |
| | # neut | 29 | 27 | 27 | 19 | 21 | 13 | 9 | 9 | 10 |

Overall, the quaternary specificity, neutralization fingerprints, competition with PG9, and long CDR H3s indicate that the CAP256-VRC26 antibodies resemble V1V2-directed broadly neutralizing antibodies from other donors and recognize a quaternary epitope including strand C of the V1V2 trimer cap at the membrane-distal apex of the HIV-1 spike.

Example 10

Temporal Characterization of the CAP256-VRC26 Lineage by NGS

To characterize the development of the CAP256-VRC26 antibody lineage, we analyzed B cell immunoglobulin transcripts through multiplex PCR of cDNA prepared from 5 million PBMCs per reaction, using primers specific for the VH3 and VA families. 454 pyrosequencing reads of the PCR products were analyzed for eight time points between 15 and 206 weeks postinfection. Although no CAP256-VRC26 lineage-related transcripts were detected at 15 and 30 weeks, 1,113 lineage-related heavy chain transcripts and 52 lineage-related light chain transcripts were found at 38 weeks post-infection. Transcripts encoding somatic variants of both heavy and light chains were identified at all later time points. To track varying longitudinal prevalence within the lineage, we utilized identity-divergence plots of all heavy chain reads assigned to the same VH3-30 germline gene as the isolated antibodies. With the week 59-isolated CAP256-VRC26.01 as the identity referent, a large population of heavy chain sequences appeared as a segregated island on the identity-divergence plot at week 38. By weeks 48 and 59, this island had expanded and divided with some sequences showing >95% identity to CAP256-VRC26.01. By week 119, this high-identity island has disappeared and the larger island had dropped to an average of ~80% identity, which further decreased to ~75% by week 206. Similarly, with the week 119-isolated CAP256-VRC26.08 as the referent, a distinct pattern of segregated sequences appeared at week 38. Both prevalence and identity peaked at week 119, where two segregated islands were observed: one at ~95% identity, and the other ~85% identity to CAP256-VRC26.08. Similar patterns of identity were seen for the other CAP256-VRC26 antibodies (not shown), with peaks in prevalence corresponding to the week of isolation.

To provide a more precise understanding of the longitudinal development of the CAP256-VRC26 lineage, maximum-likelihood phylogenetic trees of all unique lineage transcripts were constructed and rooted by germline V gene sequences (FIG. 3). The lineage bifurcates early, with one branch leading to CAP256-VRC26.01 and a second developing into CAP256-VRC26.02-12. The heavy and light chain phylogenetic trees showed similar positions of the matched heavy and light chains for the 12 B cell-culture-identified antibodies, as well as a similar pattern of where transcripts from each time point appeared within each tree. This concordance suggested that the NGS and resulting phylogenetic trees reflected the coupled evolutionary behaviour of the antibody heavy and light chains, with the tree architecture closely approximating the maturation of the CAP256-VRC26 antibody lineage. To understand the origin of the CAP256-VRC26 lineage, the unmutated common ancestors (UCAs) for both heavy and light chain were inferred from the phylogenetic trees using maximum likelihood (FIG. 3). For the light chain, the UCA had a 12 amino acid CDR L3, the same length as found in CAP256-VRC26.01. For the heavy chain, the inferred UCA had a 35-residue CDR H3, apparently the result of a VDJ recombination with a single D-gene, IgHD3-3*01 with N-nucleotide insertions of 34 and 31 nucleotides at each junction. Confirmation for this inferred UCA came from the identification of several transcripts containing a 35 amino acid CDR3, the correct V and J genes, and fewer than 3 total nucleotide mutations from germline. Thus, the CAP256-VRC26 lineage emerged between weeks 30 and 38, with a remarkable 35-residue CDR H3 formed in whole by recombination. The lineage rapidly expanded, with both phylogenetic and temporal concordance between heavy and light chains. We also found general concordance between time of HIV-1 infection and depth on the phylogenetic trees; i.e. sequences from later time points show up later on the tree, indicating continuous evolution of this B cell lineage. For each time point, only a small fraction of branches provide roots to the grouped sequences of the next time point. This tree structure appears to represent "snapshots" of B cell expansion (the many grouped sequences at each time point) and selection (the rooting of the next time point sequences from very few current sequences).

Example 11

Structural Characteristics of CAP256-VRC26 Lineage Antibodies

To provide atomic-level definition of the features associated with molecular recognition by the CAP256-VRC26 lineage, we determined crystal structures of the antigen-binding fragments (Fabs) for six of the isolated antibodies from weeks 59, 119 and 206 as well as of the UCA (Table 4). The structures reveal an extended CDR H3 that protrudes ~20A above the antigen-combining surface (FIG. 4) and contained several unique features including a 2-stranded P-sheet and an intra-CDR H3 disulfide bond with cysteines positioned C terminal to each strand. This disulfide bond was not present in the UCA or in CAP256-VRC26.01, but was present in all of the more mature CAP256 antibodies. Tyrosines 100H and 100I near the apex of CDR H3 are both predicted to be sulfated and electron density confirmed O-sulfation of Tyr100H; however sulfation of Tyr100I was inconclusive due to side chain disorder.

These crystal structures also provided insight into the development of the lineage over four years. The CDR H3 of the UCA and CAP256-VRC26.01 protrude over the light chain, whereas the CDR H3 of the more mature antibodies is directed towards the heavy chain. The diversity of space groups and unit cells suggests that the initial trajectory of the CDR H3 protrusion is maintained under a variety of crystal packing conditions. These results suggest maturation of the orientation of the CDR H3 between UCA and the later antibodies. Perhaps relevant to this, the appearance of the disulfide bond in all antibodies after CAP256-VRC26.01 correlated with adoption of the mature CDR H3 orientation. The functional importance of this disulfide bond was experimentally confirmed: mutation of the relevant Cys residues in VRC26.03 resulted in loss of neutralization potency and breadth. Additionally, a conserved glycine at residue 97 in the heavy chain sequences lacking a disulfide bond is mutated to arginine in the mature antibodies, coinciding with the appearance of the two cysteines, further limiting the flexibility at the base of the CDR H3. The CDR H3s were consistently anionic, with formal charges ranging from –10 to –4. Thus, antibodies of the CAP256-VRC26 lineage have CDR H3s with structural properties similar to previously determined V1V2-directed broadly neutralizing antibodies, including tyrosine-sulfation, overall anionic character, long-length, and protrusion above the framework region. Overall, the structural analysis indicates that the initial B cell recombination produces a flexible, tyrosine-sulfated CDR H3 loop. Maturation, including the evolution of an intra-CDR H3 disulfide bond, appears to select a conformation more compatible with broad HIV-1 recognition.

Example 12

Developmental Interplay Between HIV-1 and CAP256-VRC26 Lineage

Analysis of CAP256 gp160 sequences over ~3 years of infection showed high levels of diversity driven by recombination between the primary infecting (PI) virus and a superinfecting virus (SU). The SU virus was first detected 15 weeks postinfection (Moore et al. 2013) and differed from the PI virus by ~17% in Env. Differences included polymorphisms at V2 residues 165 and 169, and an intact glycosylation sequon at position 160 in the SU virus, which is more representative of global HIV-1 strains. Between 23 and 34 weeks, Env gp160 recombinants were largely SU-derived but the important V1V2 region originated from the PI virus. Segments of V1V2 from the SU virus were detected again at week 30, and by 48 weeks post-infection the PI V1V2 was largely replaced by a SU V1V2. Position 169 was under strong positive diversifying selective pressure in the SU virus (p=0.0001) consistent with immune pressure on this C-strand residue.

All CAP256-VRC26.01-12 antibodies neutralized the SU virus, but not the PI virus (with the exception of CAP256-VRC26.06), suggesting the SU V1V2 elicited these antibodies. Env clones isolated between 23 and 38 weeks were largely resistant, suggesting that recombination to obtain the PI V1V2 epitope was a dominant early escape mechanism. An exception was the highly sensitive 34 week clone containing an SU-like V1V2 region, with an N160 glycan (seen in only 1/26 week 34 sequences) (FIG. 11). Thereafter, sensitivity of clones from weeks 48 and 59 tracked with the SU V1V2 containing an N160 glycosylation sequon.

The earliest antibody, CAP256-VRC26.01 (from week 59), neutralized the SU virus but surprisingly failed to neutralize the highly sensitive 34-week clone or later viruses from weeks 48 and 59 that contained a SU-like V1V2. This 34 week clone had a K169I mutation, which when introduced into the SU virus, abrogated CAP256-VRC26.01 neutralization, but only slightly affected later antibodies (FIG. 12). Furthermore, strong evidence of directional selection (Bayes factor=77,095) for a K169I (present in <2% of subtype C viruses) suggests that CAP256-VRC26.01 or related antibodies drove early escape mutations, with maturation of this lineage allowing later antibodies to tolerate 169I.

Viruses from 94 weeks onwards escaped all 12 isolated antibodies of the lineage through R166S/K or K169E mutations (FIG. 12). While R166S and K169E mediated complete escape for all antibodies, the 4 broadest (CAP256-VRC26.03, 04, 08, 09) still showed low levels of neutralization of the SU R166K mutant (FIG. 12). The ability to tolerate a lysine (present in ~13% of all HIV-1 viruses), in addition to the more common arginine at position 166 may account for the greater breadth of these 4 antibodies (FIG. 1). Neutralization escape was also associated with a net charge change in the V2 epitope from +3 (SU) to a rare 0 at 176 weeks (seen in only ~4% of HIV-1 viruses). This contrasted with the antibody CDR H3s which became less negatively charged over time (−10 to −4, FIG. 4) reflecting continued co-evolution of the viral epitope and the antibody paratope. Despite viral escape, neutralization breadth continued to increase, suggesting that sensitive viruses persisted at low levels and continued to stimulate this lineage.

Overall, these results display a complex interplay between virus and antibody, with a low-prevalence virus (containing a SU-like V2 epitope) engaging the naive B cells of the CAP256-VRC26 lineage. Dramatic changes in the V2 epitope of circulating recombinants preceded increased neutralization breadth, with neutralization of 48 and 59-week clones by later CAP256-VRC26 antibodies suggesting that these viruses contributed to antibody maturation.

TABLE 4

Crystallographic data collection and refinement statistics, values in parenthesis are for highest-resolution shell

|  | VRC26.UCA | VRC26.01 | VRC26.03 | VRC26.04 | VRC26.06 | VRC26.07 | VRC26.10 |
| --- | --- | --- | --- | --- | --- | --- | --- |
| Data collection | | | | | | | |
| Space group | C2 | C2 | C2 | P1 | R32: H | I222 | P212121 |
| Cell constants | | | | | | | |
| a, b, c (Å) | 85.5, 81.2, 69.2 | 104.4 71.2 82.9 | 99.2, 80.9, 87.6 | 68.0, 85.5, 103.3 | 253.5, 253.5, 70.1 | 70.1, 87.3, 224.4 | 43.4, 46.2, 232.5 |
| a, b, g (°) | 90.0, 124.0, 90.0 | 90.0, 93.3, 90 | 90.0, 116.7, 90.0 | 97.9, 107.7, 91.7 | 90.0, 90.0, 120.0 | 90.0, 90.0, 90.0 | 90,0, 90.0, 90.0 |
| Wavelength (Å) | 1 | 1 | 1 | 1 | 1 | 1 | 1 |
| Resolution (Å) | 50.0-2.90 (3.0-2.9) | 50.0-1.90 (1.93-1.90) | 50.0-2.70 (2.75-2.70) | 50.0-3.15 (3.20-3.15) | 50.0-3.0 (3.11-3.0) | 40-2.6 (2.64-2.60) | 50-1.91 (1.94-1.91) |
| $R_{merge}$ | 11 (37) | 8 (54) | 15 (44) | 14 (39) | 13 (54) | 13 (51) | 13 (46) |
| I/s| | 5.9 (1.8) | 16.3 (2.1) | 6.9 (1.8) | 5.8 (1.8) | 16.6 (2.1) | 12.5 (1.7) | 8.4 (2.5) |
| Completeness (%) | 85.7 (82.8) | 100 (99.8) | 88.4 (51.1) | 95.9 (79.6) | 98.8 (88.5) | 93.9 (53.0) | 65.2 (50) |
| Redundancy | 2.3 (2.2) | 3.7 (3.2) | 2.9 (1.7) | 1.9 (1.8) | 10.0 (5.0) | 6.5 (3.9) | 4.1 (3.9) |
| MOLECULES/ASU | 1 | 1 | 1 | 4 | 1 | 1 | 1 |
| REFINEMENT | | | | | | | |
| Resolution (Å) | 33.1-2.9 (3.0-2.9) | 34.7-1.90 (1.96-1.90) | 40.1-2.69 (2.79-2.69) | 35.63-3.12 (3.2-3.12) | 40.9-3.0 (3.1-3.0) | 30.0-2.6 (2.71-2.62) | 32.77-1.90 (1.97-1.91) |
| Unique reflections | 7,500 (660) | 48,060 (3,241) | 13,071 (641) | 36,806 (2,685) | 16,997 (1,487) | 19,901 (1,816) | 24,684 (2,029) |
| $R_{work}/R_{free}$(%) | 21.1/24.6 | 18/19.9 | 20.3/24.5 | 25.6/28.5 | 19.3/23.3 | 22.1/24.5 | 21.0, 24.1 |
| No. atoms | | | | | | | |
| Protein | 3249 | 3324 | 3447 | 13,508 | 3477 | 3361 | 3323 |
| Water | 17 | 197 | 47 | 0 | 0 | 17 | 267 |
| B-factors (Å$^2$) | | | | | | | |
| Protein | 55 | 33.3 | 47.8 | 51.3 | 66.3 | 36.2 | 22.2 |
| Water | 27.5 | 43.7 | 39 | na | na | 33.2 | 25.1 |

TABLE 4-continued

Crystallographic data collection and refinement statistics, values in parenthesis are for highest-resolution shell

|  | VRC26.UCA | VRC26.01 | VRC26.03 | VRC26.04 | VRC26.06 | VRC26.07 | VRC26.10 |
|---|---|---|---|---|---|---|---|
| R.m.s. deviations | | | | | | | |
| Bond lengths (Å) | 0.004 | 0.008 | 0.003 | 0.009 | 0.003 | 0.005 | 0.005 |
| Bond angles (°) | 0.885 | 1.22 | 0.82 | 1.15 | 0.79 | 1.01 | 0.96 |
| Ramachandran | | | | | | | |
| Most favored regions (%) | 90.2 | 98.2 | 92 | 91 | 96 | 92.5 | 96.5 |
| Additional allowed regions (%) | 9.4 | 1.8 | 7.8 | 8.4 | 3.8 | 7.5 | 3.3 |
| Disallowed regions (%) | 0.6 | 0 | 0.2 | 0.6 | 0.2 | 0 | 0.2 |

Example 13

Rapid Development of CAP256-VRC26.01

Figure 4:
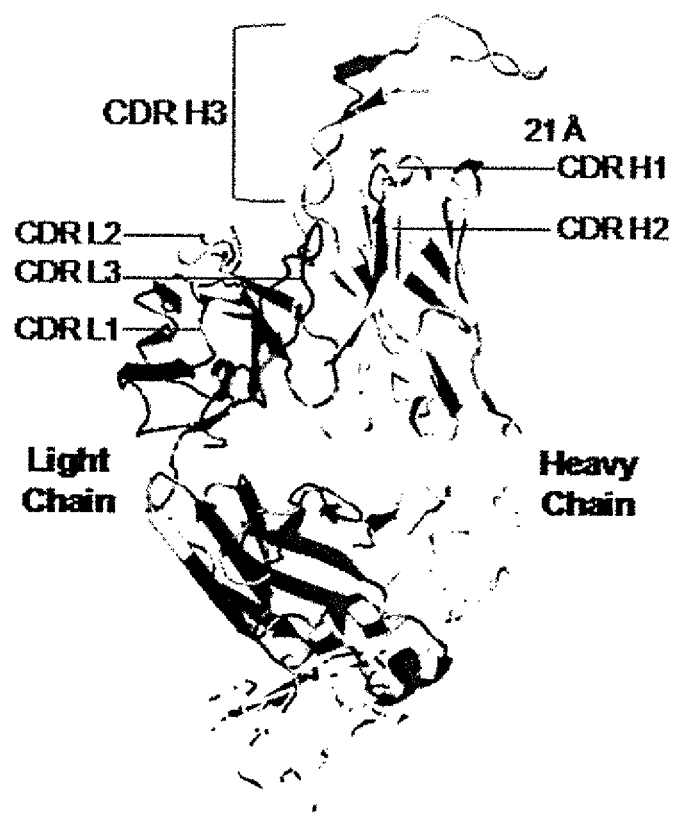
FIG. 4: Structural characteristics of the developing CAP256-VRC26 lineage. Crystal structure of the antigen-binding fragment (Fab) of CAP256-VRC26.03 shown in ribbon diagram representation.
Figure 6:
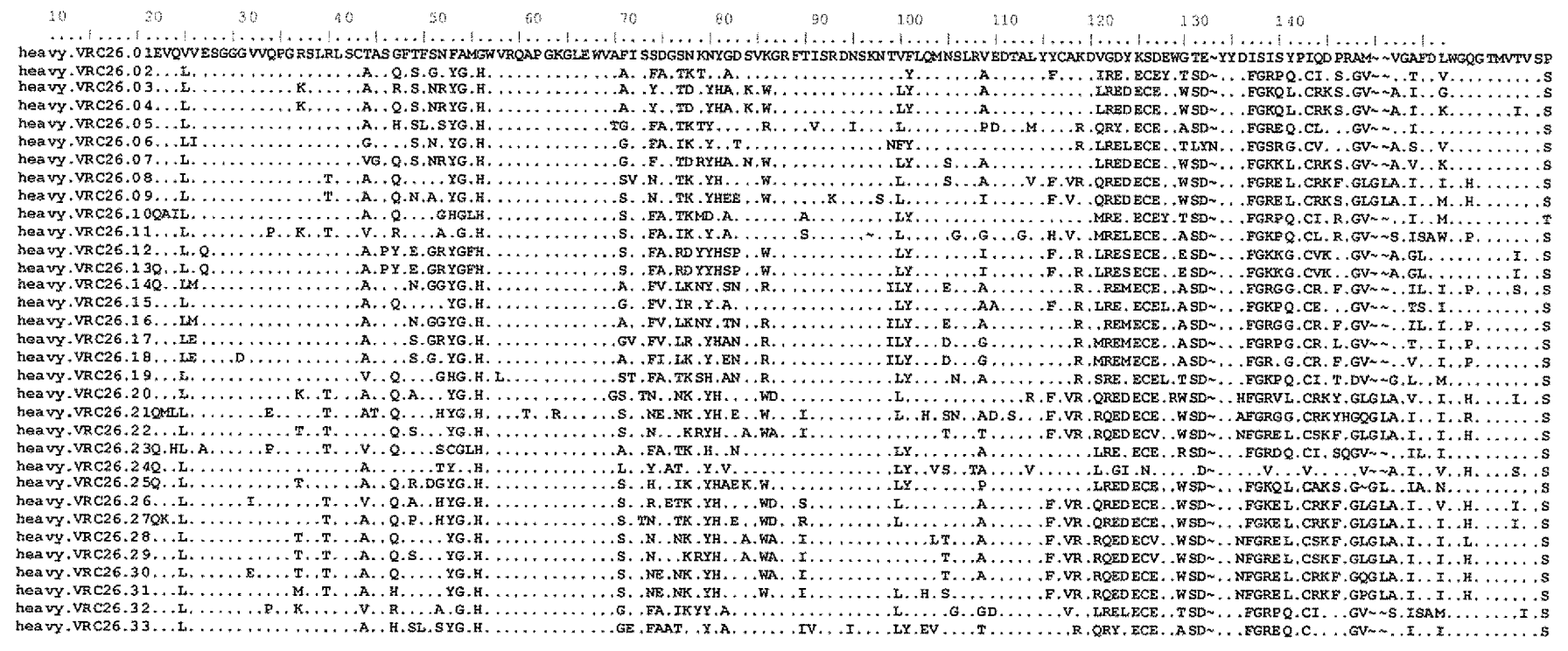
Figure 7:
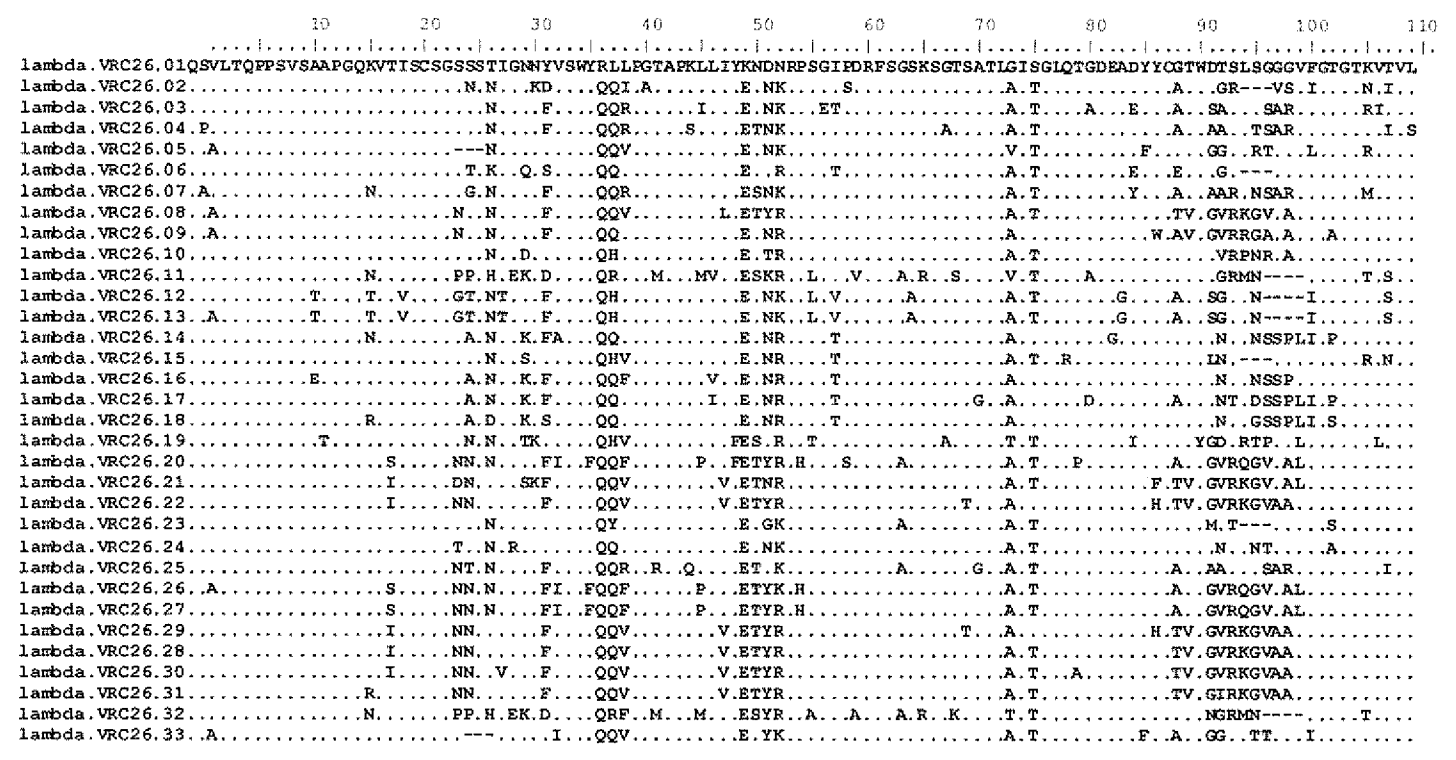

To understand the critical elements required for development of effective V1V2-directed antibodies, we focused on CAP256-VRC26.01, the earliest isolated antibody. This antibody neutralizes 15% of diverse HIV-1 strains, and has all the molecular characteristics required for neutralization by effective V1V2-directed antibodies (FIG. 4). We therefore inferred heavy and light chains for two developmental intermediates (VRC26-I1 and VRC26-I2) on the pathway between UCA and CAP256-VRC26.01 (FIGS. 6 and 7).

Figure 5:
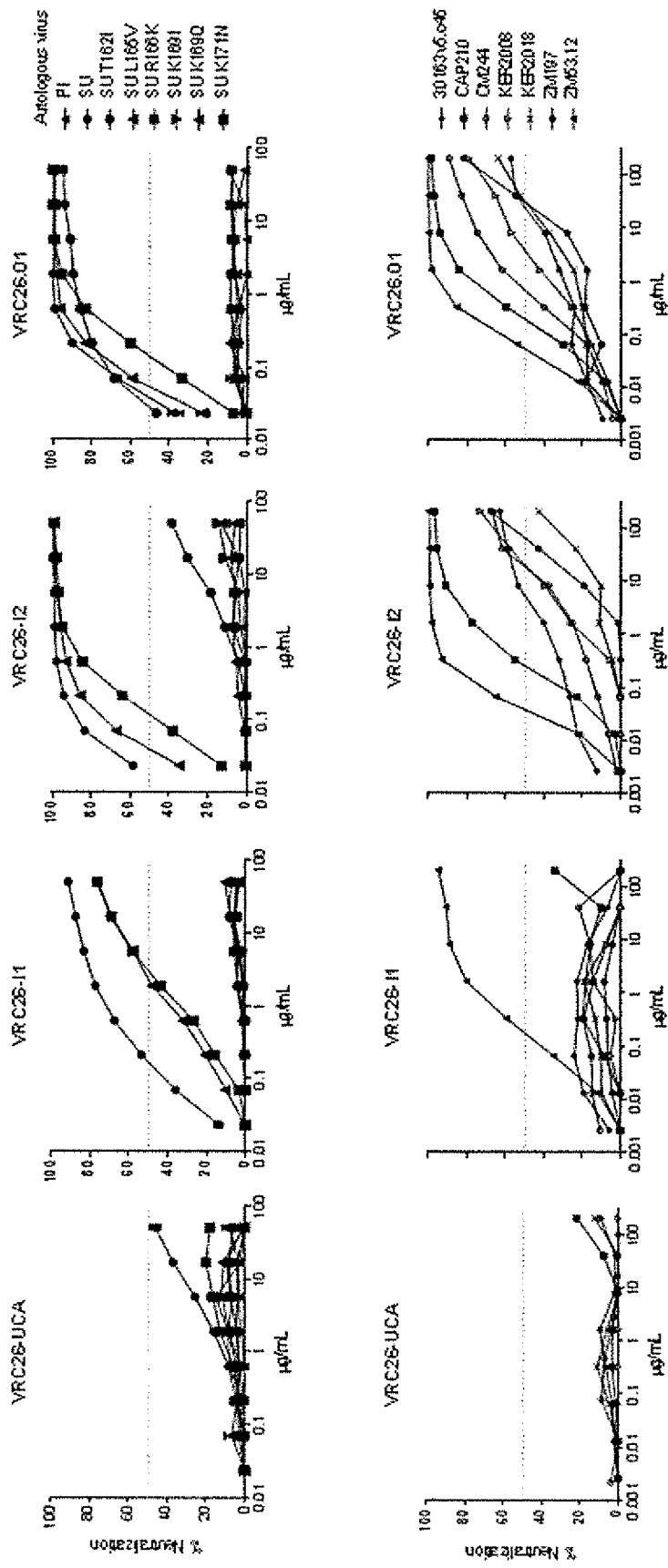
FIG. 5: Development from UCA to CAP256-VRC26.01. Top row shows neutralization by antibodies VRC26-UCA, VRC26-11, VRC26-12 and VRC26.01 against the autologous primary virus (PI), superinfecting virus (SU), and a set of SU viruses with escape mutations. Bottom row shows neutralization of heterologous viruses by CAP256-VRC26.01 lineage antibodies. Neutralization was assessed against a panel of seven VRC26.01-sensitive strains as shown.
Figure 8:
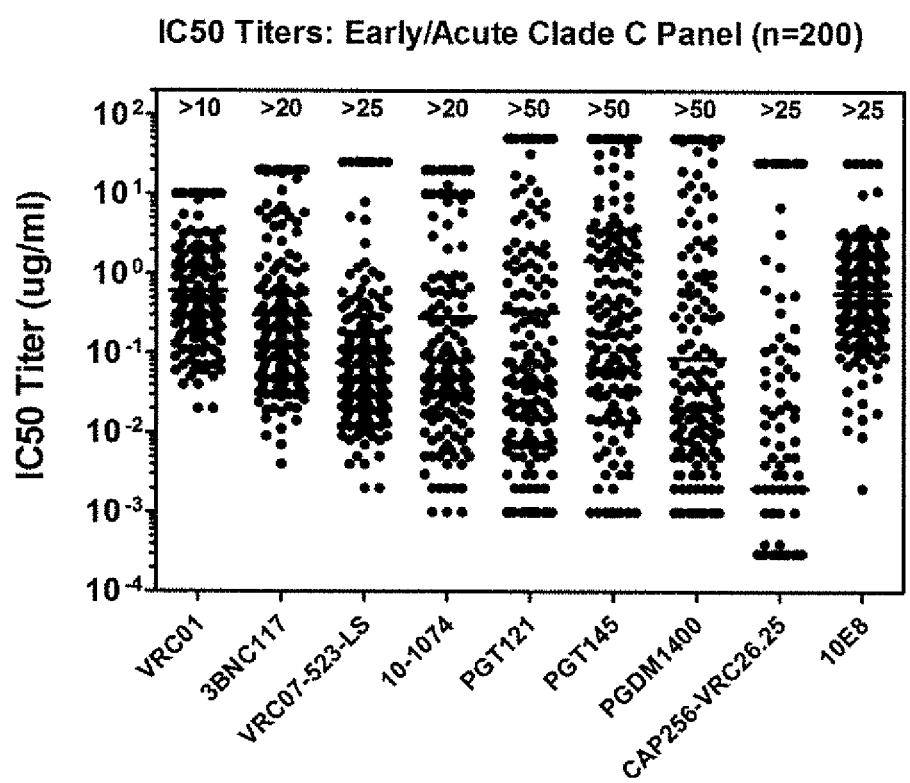
FIG. 8: Potency and breadth of CAP256-VRC26.25 against Clade C compared to other well known mAbs.

To assess the interactions between CAP256-VRC26.01 precursors and autologous virus, we reconstituted the UCA, I1, and I2 as IgGs and measured their neutralization activity. The UCA demonstrated weak but reproducible neutralization of the SU and no neutralization of the PI. The VRC26-I1, VRC26-I2 and CAP256-VRC26.01 antibodies demonstrated progressively improved potency against the SU. In each case, neutralization was reduced or eliminated by specific mutations on V1V2 strand C (FIG. 5). Breadth of neutralization also progressively increased, with VRC26-I2 neutralizing 6 of 7 CAP256-VRC26.01-sensitive heterologous viruses (FIG. 5). The frequencies of B-cell transcripts related to the UCA and intermediates support this sequential pathway of development leading to CAP256-VRC26.01.

We produced structural models of VRC26-I1 and I2 and compared them to the experimentally determined structures of UCA and CAP256-VRC26.01. I1 contained 12 mutations in the heavy chain (of 145 total residues) and 3 mutations in the light chain (of 110 total). Mutations accumulated primarily at solvent-exposed positions on the combining surface, suggestive of a functional role in binding. For the heavy chain, approximately half of the total amino acid mutations occurred in CDR H3 regions (FIGS. 6 and 7 and Table 5). Overall, compared to the UCA, CAP256-VRC26.01 contains 39 amino acid changes out of 255 amino acids total. This developmental pathway allows for an increase in neutralization from borderline neutralization of a single virus (SU) to cross-neutralization of heterologous HIV-1 strains. Throughout this development, the CDR H3 maintains its length, tyrosine sulfation and general anionic character.

TABLE 5

Heavy chain nucleotide and amino acid changes from VRC26-UCA to intermediates VRC26-I1 and VRC26-I2 to VRC 26.01.

|  | Compared to VH3-30*18 | | | | Compared to UCA | |
|---|---|---|---|---|---|---|
|  | nt % | nt # (out of 296) | aa % | aa # (out of 98) | aa % | aa # (out of 145) |
| VRC26-I1 | 2.0% | 6 | 5.1% | 5 | 8.3% | 12 |
| VRC26-I2 | 6.1% | 18 | 10.2% | 10 | 13.8% | 20 |
| VRC26-01 | 8.1% | 24 | 15.3% | 15 | 20.7% | 30 |

Example 14

Figure 13:
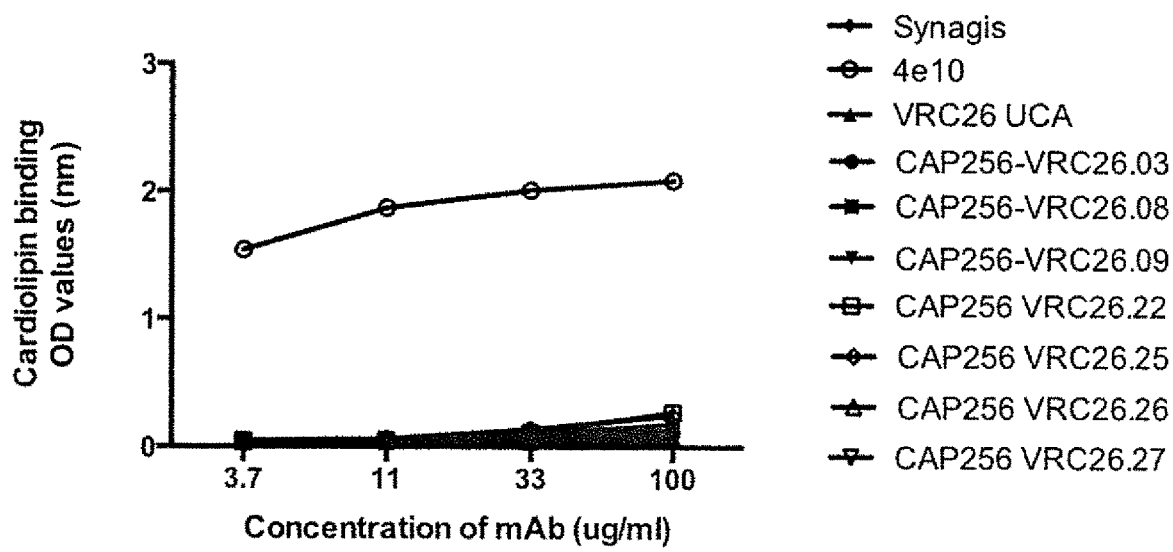
FIG. 13: Minimal autoreactivity of CAP256-VRC26 antibodies. (a). Staining on Hep2 cells was assessed at 50 and 25 µg/ml. Only the positive control, mAb 4E10, showed positive staining. (b) ELISA for binding to cardiolipin. 4E10 was strongly positive, CAP256-VRC26.03 was weakly positive, and the other CAP256-VRC26 mAbs and the UCA were negative along with control antibody VRC01.

Autoreactivity and frequency of long antigen-combining loops in the CAP256 donor A potential rate-limiting developmental step in the CAP256-VRC26 lineage is the recombination event that generated a 35-residue CDR H3 of the UCA. By one estimate, human B cells with recombined antibody genes encoding long (>24 residue, IMGT definition) or very long (>28 residue) CDR H3s constitute ~3.5% and 0.4% respectively of naive B cells (Briney et at 2012). These long B cell receptors have been associated with autoreactivity, and are subject to both central and peripheral deletion, resulting in an even smaller population of IgG+ memory B cells (Briney et al. 2012, Wardemann et al. 2003 and Ditzel et al. 1996). We therefore tested the CAP256-VRC26 UCA and 15 CAP256-VRC26 cloned antibodies for reactivity to autoantigens (Haynes et al. 2005). No reactivity with Hep2 cells was noted for the UCA or for any of the cloned antibodies. Likewise, no cardiolipin reactivity was noted for the UCA nor for 14 of the 15 selected antibodies; borderline reactivity was observed only for CAP256-VRC26.03 (FIG. 13). This suggests that tolerance and clonal deletion were not factors in the development of the CAP256-VRC26 lineage, in contrast to what has been found for some other HIV-1 broadly neutralizing antibodies (Haynes et al. 2005, Verkoczy et al. 2010) and for other antibodies with long CDR H3 loops (Briney et al. 2012, Wardemann et al. 2003 and Ditzel et al. 1996). We also asked whether long CDR H3 antibodies might be found at greater frequency in this donor. NGS of total B cells indicated that <0.4% of sequences had CDR H3s of greater than 28 amino acids in length suggesting that the CAP256 donor did not have an unusually high frequency of clonal lineages with long CDR H3 regions.

Example 15

Vaccine and Treatment Implications

The HIV-1 V1V2 region is a common target of serum neutralizing antibodies and is one of four known conserved neutralization epitopes on the HIV-1 Env (Overbaugh & Morris, 2012 and Kwong & Mascola, 2012). Thus, elicitation of V1V2 neutralizing antibodies is a major goal of HIV-1 vaccine design. Notably, in the RV144 Thai vaccine trial, an increased level of binding antibodies to the V1V2 region was associated with a reduced risk of infection (Haynes et al. 2012) and viral sieve analysis showed immune pressure in this same region (Rolland et al. 2012). While the vaccine used in the RV144 trial did not elicit broadly neutralizing V1V2-directed antibodies similar to those described here and elsewhere (Walker et al. 2009, Bonsignori et al. 2011 and Walker et al. 2011), the modest protective efficacy of the vaccine has highlighted a strong interest in the V1V2 region as a target of vaccine-elicited antibodies. Ideally, such antibody responses would be potently neutralizing and react with diverse HIV-1 strains similar to what is described here.

The previously well characterized V1V2 neutralizing antibodies, and the CAP256-VRC26 lineage, all have unusually long CDR H3 regions that appear to be necessary to penetrate the glycan shield and engage a V1V2 epitope. An important unanswered question has been how these long antigen binding loops originate. Until now, it was unclear if the CDR H3 region was elongated by insertions during the process of affinity maturation, or fully formed by V(D)J recombination and therefore present at the level of the naive B cell receptor. The ability to perform NGS of antibody gene transcripts from longitudinal samples allowed us to infer the UCA of the CAP256-VRC26 lineage, and to determine that it contained the requisite long antigen binding loop preformed prior to encountering HIV-1 antigen. We also inferred the virological events leading to the stimulation and evolution of the CAP256-VRC26 lineage. Similar to donor CH505, and the CH103 lineage that gave rise to broadly neutralizing anti-CD4 binding site antibodies, the autologous virus in CAP256 showed extensive variation prior to the development of breadth (Liao et al. 2013). Interestingly, the UCA did not recognize the primary infecting virus in donor CAP256, but weakly neutralized the superinfecting virus that occurred 15 weeks later, and contained a more common clade C V1V2 sequence. Subsequent antibody-virus interactions, including viral neutralization escape, appeared to drive somatic mutation and the development of more cross-reactive neutralization.

Finally, the distinct ontogeny of V1V2-directed broadly neutralizing antibodies revealed by the CAP256-VRC26 lineage suggests that neutralization potency and breadth can be achieved without extraordinary levels of somatic mutation. For example CAP256-VRC26.03 with ~8% Vgene somatic mutation neutralizes 30% of HIV-1 strains (FIG. 1). Thus, the primary requirement for eliciting V1V2-directed antibodies appears to be the availability of a suitably antigenic V1V2 epitope that is recognized by a relatively rare naive B cell receptor with a protruding, anionic CDR H3. While some neutralizing antibodies appear to require years of maturation (Haynes et al. 2012, Burton et al. 2012, Kwong et al. 2012 and Mascola et al. 2013), we show that quite unexpectedly a V1V2 directed B cell lineage can acquire HIV-1 neutralization breadth relatively rapidly. The quaternary-specificity of the V1V2 epitope may help this lineage to avoid decoy strategies, as viral debris and monomeric forms of gp120 are unlikely to bind this category of antibodies. Thus, identifying key features of antigens able to engage naive B cells with long CDR H3 is a critical step in design of vaccines targeting this site of vulnerability. It remains to be determined whether one can elicit neutralizing V1V2 antibodies merely by providing the appropriate trimeric V1V2 constructs or whether multiple/sequential immunogens that mirror viral evolution are needed. Overall, the precise delineation of the developmental pathway for the CAP256-VRC26 lineage reported here should provide a basis for attempts to elicit effective V1V2-directed HIV-1-neutralizing antibodies.

REFERENCES

Adams, P. D. et al. (2004) *J Synchrotron Radiat* 11, 53-55.
Alamyar, E., et al. (2012) *Immunome research* 8, 26.
Ashkenazy, H. et al. (2012) *Nucleic acids research* 40, 580-584.
Bonsignori, M., et al. (2011) *Journal of virology* 85, 9998-10009.
Boyd, S. D. et al. (2010) *J Immunol* 184, 6986-6992.
Briney, B. S. et al. (2012) *Genes and immunity* 13, 469-473.
Briney, B. S. et al. (2012) *PloS one* 7, e36750.
Bunnik, E. M. et al. (2008) *Journal of virology* 82, 7932-7941.
Burton, D. R. et al. (2012). *Cell host & microbe* 12, 396-407.
Crooks, G. E., et al. (2004) *Genome research* 14, 1188-1190.
Davis, I. W., et al. (2004) *Nucleic acids research* 32, 615-619.
Ditzel, H. J. et al. (1996) *J Immunol* 157, 739-749.
Doria-Rose, N. A., et al. (2010) *Journal of virology* 84, 1631-1636.
Doria-Rose, N. A., et al. (2012) *Journal of virology* 86, 8319-8323.
Emsley, P. & Cowtan, K. (2004) *Acta Crystallogr D Biol Crystallogr* 60, 2126-2132.
Gao, F. et al. (1996) *Journal of virology* 70.
Georgiev, I. S., et al. (2013) *Science* 340, 751-756.
Glanville, J. et al. (2009) *Proc Natl Acad Sci.* 106, 20216-20221.
Gray, E. S. et al. (2011) *Journal of virology* 85, 4828-4840.
Haynes, B. F. et al. (2005) *Science* 308, 1906-1908.
Haynes, B. F. et al. (2012) *Nature biotechnology* 30, 423-433.
Huang, J. et al. (2012) *Nature* 491, 406-412.
Huang, J. et al. (2013) *Nature Protocols*.
Julien, J. P. et al. (2013) *Proc Natl Acad Sci* 110, 4351-4356.
Kabat, E. A. et al. (1991) Sequences of Proteins of Immunological Interest, (U.S. Department of Health and Human Service, National Institutes of Health, Bethesda Md.).
Kong, L. & Sattentau, Q. J. (2012) *J AIDS Clinic Res* S8, 003.
Kosakovsky et al. (2008) *Molecular biology and evolution* 25, 1809-1824.
Kraus, M. H., et al. (2010) *Virology* 397, 346-357.
Kwong, P. D. & Mascola, J. R. (2012) *Immunity* 37, 412-425.
Larkin, M. A. et al. (2007) *Bioinformatics* 23, 2947-2948.
Li, W., et al. (2001) *Bioinformatics* 17, 282-283.
Liao, H. X., et al. (2013) *Nature* 496, 469-476.
Liu, J., et al. (2008) *Nature* 455, 109-113.
Lynch, R. M. et al. (2011) *Journal of virology* 85, 905-915.
Mascola, J. R. & Haynes, B. F. (2013) *Immunological reviews* 254, 225-244.
McCoy, L. E. & Weiss, R. A. (2013) *The Journal of experimental medicine* 210, 209-223.
McLellan, J. S. et al. (2011) *Nature* 480, 336-343.
Moir, S. et al. (2011) *Nature structural & molecular biology* 18, 1317-1321.

Montefiori, D. C. et al. (1991) *Virology* 182, 635-643. (1991).
Montefiori, D. C. (2009) *Methods Mol Biol* 485, 395-405.
Moore, P. L., et al. (2011) *Journal of virology* 85, 3128-3141.
Moore, P. L. et al. (2013) *Journal of virology* 87, 4882-4894.
Murrell, B. et al. (2012) *PLoS genetics* 8.
Otwinowski, Z. & Minor, W. (1997) *Methods in enzymology* 276, 307-326.
Overbaugh, J. & Morris, L. (2012) The Antibody Response against HIV-1. Cold Spring Harbor perspectives in medicine 2.
Pancera, M. & Wyatt, R. (2005) *Virology* 332, 145-156.
Pancera, M., et al. (2013) *Nature structural & molecular biology* 20, 804-813.
Pantophlet, R. & Burton, D. R. (2006) *Annual review of immunology* 24, 739-769.
Pejchal, R. et al. (2010) *Proc Natl Acad Sci* 107, 11483-11488.
Pejchal, R. et al. (2011) *Science* 334, 1097-1103.
Pettersen, E. F. et al. (2004) *J Comput Chem* 25, 1605-1612.
Piantadosi, A., et al. (2009) *Journal of virology* 83, 10269-10274.
Pond, S. L., et al. (2005) *Bioinformatics* 21, 676-679.
Price, M. N., et al. (2010) *PLoS one* 5.
Richman, D. D. et al. (2003) *Proc Natl Acad Sci.* 100, 4144-4149.
Rolland, M., et al. (2012) *Nature* 490, 417-420.
Salazar-Gonzalez, J. F. et al. (2008) *Journal of virology* 82, 3952-3970.
Sather, D. N., et al. (2009) *Journal of virology* 83, 757-769.
Shu, Y. et al. (2007) *Vaccine* 25, 1398-1408.
Soto, C. S., et al. (2008) *Proteins* 70, 834-843.
Souto-Carneiro, M. M., et al. (2004) *Journal of Immunology* 172, 6790-6802.
Tamura, K. et al. (2011) *Molecular biology and evolution* 28, 2731-2739.
Tian, C. et al. (2008) *J Immunol* 180, 3279-3288.
Tiller, T., et al. (2008) *J Immunol Methods* 329, 112-124.
Tomaras, G. D. et al. (2011) *Journal of virology* 85, 11502-11519.
Tong, T., et al. (2012) *Journal of virology* 86, 3574-3587.
Tran, E. E., et al. (2012) *PLoS pathogens* 8.
van Gils, M. J. et al. (2009) *AIDS* 23, 2405-2414.
van Loggerenberg, F. et al. (2008) *PLoS one* 3, e1954, doi:10.1371/journal.pone.0001954.
Verkoczy, L., et al. (2010) *Proc Natl Acad Sci* 107, 181-186.
Walker, L. M., et al. (2009) *Science* 326, 285-289.
Walker, L. M. et al. (2010) *PLoS* pathogens 6.
Walker, L. M., et al. (2011) *Nature* 477, 466-470.
Wardemann, H. et al. (2003) *Science* 301, 1374-1377.
Wei, X., et al. (2003) *Nature* 422, 307-312.
Wu, X. et al. (2010) *Science* 329, 856-861.
Wu, X. et al. (2011) *Science* 333, 1593-1602.
Zhou, T. et al. (2010) *Science* 329, 811-817.
Zhu, J. et al. (2012) *Frontiers in microbiology* 3, 315.
Zhu, J. et al. (2013) *Proc Natl Acad Sci.*

---

What is claimed is:

1. An isolated anti-HIV-1 antibody which binds to V1V2, wherein the antibody includes a heavy chain with a CDR1 comprising the amino acids at positions 31-35 of SEQ ID NO:172, a CDR2 comprising the amino acids at positions 50-66 of SEQ ID NO:172, and a CDR3 comprising the amino acids at positions 99-134 of SEQ ID NO:172, and a light chain with a CDR1 comprising the amino acids at positions 23-35 of SEQ ID NO:173, a CDR2 comprising the amino acids at positions 51-57 of SEQ ID NO:173, and a CDR3 comprising the amino acids at positions 90-101 of SEQ ID NO:173.

2. An isolated anti-HIV-1 antibody which binds to V1V2, wherein the antibody comprises:
    (i) a variable heavy chain sequence having the amino acid sequence of SEQ ID NO:172; and
    (ii) a variable light chain sequence having the amino acid sequence of SEQ ID NO:173.

3. An isolated anti-HIV-1 antibody of claim 1 or claim 2, wherein the antibody neutralizes autologous HIV-1 virus CAP256.SU at an $IC_{50}$ concentration of less than 0.5 μg/ml, or heterologous HIV-1 virus ZM53.12 at an $IC_{50}$ concentration of less than 0.5 μg/ml.

4. An isolated anti-HIV-1 antibody of claim 1 or claim 2, wherein the antibody is a Fab, Fab', a F(ab)'2, a single-chain Fv (scFv), an Fv fragment, or a linear antibody.

5. A composition comprising the isolated anti-HIV-1 antibody of claim 1 or claim 2, or a fragment thereof.

6. A pharmaceutical composition comprising an isolated anti-HIV-1 antibody of claim 1 or claim 2, or a fragment thereof, and a pharmaceutically acceptable carrier.

7. A method of inhibiting HIV-1 replication or reducing HIV-1 viral load in a subject the method comprising administering an isolated anti-HIV-1 antibody of claim 1 or claim 2, or a fragment thereof, to the subject.

8. The method of claim 7, further comprising the administration of a second therapeutic agent.

9. The method of claim 8, wherein said second therapeutic agent is an antiviral agent.

10. A kit comprising a container containing an isolated anti-HIV-1 antibody of claim 1 or claim 2, or fragment thereof.

\* \* \* \* \*

SEQUENCE LISTING

```
<160> NUMBER OF SEQ ID NOS: 229

<210> SEQ ID NO 1
<211> LENGTH: 474
<212> TYPE: PRT
<213> ORGANISM: Artificial sequence
<220> FEATURE:
<223> OTHER INFORMATION: Unmutated common ancestor

<400> SEQUENCE: 1

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Gly Glu Ser Glu Asn Glu Glu Trp Ala Thr Asp Tyr
            100                 105                 110

Tyr Asp Phe Ser Ile Gly Tyr Pro Gly Gln Asp Pro Arg Gly Val Val
        115                 120                 125

Gly Ala Phe Asp Ile Trp Gly Gln Gly Thr Met Val Thr Val Ser Ser
    130                 135                 140

Ala Ser Thr Lys Gly Pro Ser Val Phe Pro Leu Ala Pro Ser Ser Lys
145                 150                 155                 160
```

```
Ser Thr Ser Gly Gly Thr Ala Ala Leu Gly Cys Leu Val Lys Asp Tyr
            165                 170                 175

Phe Pro Glu Pro Val Thr Val Ser Trp Asn Ser Gly Ala Leu Thr Ser
        180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Leu Gly Thr Gln Thr
        210                 215                 220

Tyr Ile Cys Asn Val Asn His Lys Pro Ser Asn Thr Lys Val Asp Lys
225                 230                 235                 240

Lys Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
        290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Asp Glu
        370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
        450                 455                 460

Gln Lys Ser Leu Ser Leu Ser Pro Gly Lys
465                 470

<210> SEQ ID NO 2
<211> LENGTH: 217
<212> TYPE: PRT
<213> ORGANISM: Artificial sequence
<220> FEATURE:
<223> OTHER INFORMATION: Unmutated common ancestor

<400> SEQUENCE: 2

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
                20                  25                  30

Tyr Val Ser Trp Tyr Gln Gln Leu Pro Gly Thr Ala Pro Lys Leu Leu
            35                  40                  45
```

```
Ile Tyr Glu Asn Asn Lys Arg Pro Ser Gly Ile Pro Asp Arg Phe Ser
 50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Ser Leu
                 85                  90                  95

Ser Ala Gly Gly Val Phe Gly Thr Gly Thr Lys Val Thr Val Leu Gly
            100                 105                 110

Gln Pro Lys Ala Asn Pro Thr Val Thr Leu Phe Pro Pro Ser Ser Glu
        115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
210                 215

<210> SEQ ID NO 3
<211> LENGTH: 144
<212> TYPE: PRT
<213> ORGANISM: Artificial sequence
<220> FEATURE:
<223> OTHER INFORMATION: Unmutated common ancestor

<400> SEQUENCE: 3

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Leu Gly Glu Ser Glu Asn Glu Gly Trp Ala Thr Asp Tyr
            100                 105                 110

Tyr Asp Phe Ser Ile Gly Tyr Pro Gly Gln Asp Pro Arg Gly Val Val
        115                 120                 125

Gly Ala Phe Asp Ile Trp Gly Gln Gly Thr Met Val Thr Val Ser Ser
130                 135                 140

<210> SEQ ID NO 4
<211> LENGTH: 111
<212> TYPE: PRT
<213> ORGANISM: Artificial sequence
<220> FEATURE:
<223> OTHER INFORMATION: Unmutated common ancestor

<400> SEQUENCE: 4
```

```
Gln Ser Val Leu Thr Gln Pro Pro Ser Val Ala Ala Pro Gly Gln
1               5                   10                  15

Lys Val Thr Ile Ser Cys Ser Gly Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Glu Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Gly Gly Val Phe Gly Thr Gly Thr Lys Val Thr Val Leu
            100                 105                 110
```

<210> SEQ ID NO 5
<211> LENGTH: 474
<212> TYPE: PRT
<213> ORGANISM: Artificial sequence
<220> FEATURE:
<223> OTHER INFORMATION: Inferred intermediate sequence

<400> SEQUENCE: 5

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
                20                  25                  30

Ala Met Asp Trp Val Arg Gln Ala Pro Gly Lys Gly Leu Glu Trp Val
            35                  40                  45

Ala Val Ile Ser Ser Asp Gly Ser Asn Lys Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Gly Glu Asn Lys Asn Asp Glu Trp Ala Thr Asp Tyr
            100                 105                 110

Tyr Asp Leu Ser Ile Ala Tyr Pro Val Gln Asp Pro Arg Ala Val Val
    115                 120                 125

Gly Ala Phe Asp Ile Trp Gly Gln Gly Thr Met Val Thr Val Ser Ser
130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
    195                 200                 205

Leu Ser Ser Val Val Thr Val Pro Ser Ser Leu Gly Thr Gln Thr
210                 215                 220

Tyr Ile Cys Asn Val Asn His Lys Pro Ser Asn Thr Lys Val Asp Lys
225                 230                 235                 240

Lys Val Glu Pro Lys Ser Cys Asp Lys Thr His Thr Cys Pro Pro Cys
                245                 250                 255
```

```
Pro Ala Pro Glu Leu Gly Gly Pro Ser Val Phe Leu Phe Pro Pro
        260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
                340                 345                 350

Lys Ala Leu Pro Ala Pro Ile Glu Lys Thr Ile Ser Lys Ala Lys Gly
                355                 360                 365

Gln Pro Arg Glu Pro Gln Val Tyr Thr Leu Pro Pro Ser Arg Asp Glu
                370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
                420                 425                 430

Leu Tyr Ser Lys Leu Thr Val Asp Lys Ser Arg Trp Gln Gln Gly Asn
                435                 440                 445

Val Phe Ser Cys Ser Val Met His Glu Ala Leu His Asn His Tyr Thr
                450                 455                 460

Gln Lys Ser Leu Ser Leu Ser Pro Gly Lys
465                 470

<210> SEQ ID NO 6
<211> LENGTH: 217
<212> TYPE: PRT
<213> ORGANISM: Artificial sequence
<220> FEATURE:
<223> OTHER INFORMATION: Inferred intermediate sequence

<400> SEQUENCE: 6

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Lys Asn Asn Glu Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Thr Ser Leu
                85                  90                  95

Ser Ala Gly Gly Val Phe Gly Thr Gly Thr Lys Val Thr Val Leu Gly
            100                 105                 110

Gln Pro Lys Ala Asn Pro Thr Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140
```

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 7
<211> LENGTH: 144
<212> TYPE: PRT
<213> ORGANISM: Artificial sequence
<220> FEATURE:
<223> OTHER INFORMATION: Inferred intermediate sequence

<400> SEQUENCE: 7

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Ala Met Asp Trp Val Arg Gln Ala Pro Gly Lys Gly Leu Glu Trp Val
        35                  40                  45

Ala Val Ile Ser Ser Asp Gly Ser Asn Lys Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Gly Glu Asn Lys Asn Asp Trp Ala Thr Asp Tyr
            100                 105                 110

Tyr Asp Leu Ser Ile Ala Tyr Pro Val Gln Asp Pro Arg Ala Val Val
        115                 120                 125

Gly Ala Phe Asp Ile Trp Gly Gln Gly Thr Met Val Thr Val Ser Ser
    130                 135                 140

<210> SEQ ID NO 8
<211> LENGTH: 111
<212> TYPE: PRT
<213> ORGANISM: Artificial sequence
<220> FEATURE:
<223> OTHER INFORMATION: Inferred intermediate sequence

<400> SEQUENCE: 8

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Lys Asn Asn Glu Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Thr Ser Leu

```
                    85                  90                  95
Ser Ala Gly Gly Val Phe Gly Thr Gly Thr Lys Val Thr Val Leu
                100                 105                 110

<210> SEQ ID NO 9
<211> LENGTH: 474
<212> TYPE: PRT
<213> ORGANISM: Artificial sequence
<220> FEATURE:
<223> OTHER INFORMATION: Inferred intermediate sequence

<400> SEQUENCE: 9

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Asn Phe
                20                  25                  30

Ala Met Gly Trp Val Arg Gln Ala Pro Gly Lys Gly Leu Glu Trp Val
                35                  40                  45

Ala Phe Ile Ser Ser Asp Gly Ser Asn Lys Asn Tyr Gly Asp Ser Val
            50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Leu Tyr Tyr Cys
                85                  90                  95

Ala Lys Asp Val Gly Glu Tyr Lys Ser Asp Glu Trp Ala Thr Asp Tyr
                100                 105                 110

Tyr Asp Leu Ser Ile Ala Tyr Pro Ile Gln Asp Pro Arg Ala Met Val
            115                 120                 125

Gly Ala Phe Asp Ile Trp Gly Gln Gly Thr Met Val Thr Val Ser Ser
            130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
                180                 185                 190

Gly Val His Thr Phe Pro Ala Val Leu Gln Ser Ser Gly Leu Tyr Ser
            195                 200                 205

Leu Ser Ser Val Val Thr Val Pro Ser Ser Ser Leu Gly Thr Gln Thr
            210                 215                 220

Tyr Ile Cys Asn Val Asn His Lys Pro Ser Asn Thr Lys Val Asp Lys
225                 230                 235                 240

Lys Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
                260                 265                 270

Lys Pro Lys Asp Thr Leu Met Ile Ser Arg Thr Pro Glu Val Thr Cys
            275                 280                 285

Val Val Val Asp Val Ser His Glu Asp Pro Glu Val Lys Phe Asn Trp
            290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
```

```
                  340                 345                 350
Lys Ala Leu Pro Ala Pro Ile Glu Lys Thr Ile Ser Lys Ala Lys Gly
            355                 360                 365

Gln Pro Arg Glu Pro Gln Val Tyr Thr Leu Pro Pro Ser Arg Asp Glu
        370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly Lys
465                 470

<210> SEQ ID NO 10
<211> LENGTH: 217
<212> TYPE: PRT
<213> ORGANISM: Artificial sequence
<220> FEATURE:
<223> OTHER INFORMATION: Inferred intermediate sequence

<400> SEQUENCE: 10

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Thr Ile Gly Asn Asn
            20                  25                  30

Tyr Val Ser Trp Tyr Gln Leu Leu Pro Gly Thr Ala Pro Lys Leu Leu
        35                  40                  45

Ile Tyr Lys Asn Asp Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Thr Ser Leu
                85                  90                  95

Ser Ala Gly Gly Val Phe Gly Thr Gly Thr Lys Val Thr Val Leu Gly
            100                 105                 110

Gln Pro Lys Ala Asn Pro Thr Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215
```

```
<210> SEQ ID NO 11
<211> LENGTH: 144
<212> TYPE: PRT
<213> ORGANISM: Artificial sequence
<220> FEATURE:
<223> OTHER INFORMATION: Inferred intermediate sequence

<400> SEQUENCE: 11

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Phe
            20                  25                  30

Ala Met Gly Trp Val Arg Gln Ala Pro Gly Lys Gly Leu Glu Trp Val
        35                  40                  45

Ala Phe Ile Ser Ser Asp Gly Ser Asn Lys Asn Tyr Gly Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Leu Tyr Tyr Cys
                85                  90                  95

Ala Lys Asp Val Gly Glu Tyr Lys Ser Asp Glu Trp Ala Thr Asp Tyr
            100                 105                 110

Tyr Asp Leu Ser Ile Ala Tyr Pro Ile Gln Asp Pro Arg Ala Met Val
        115                 120                 125

Gly Ala Phe Asp Ile Trp Gly Gln Gly Thr Met Val Thr Val Ser Ser
    130                 135                 140

<210> SEQ ID NO 12
<211> LENGTH: 111
<212> TYPE: PRT
<213> ORGANISM: Artificial sequence
<220> FEATURE:
<223> OTHER INFORMATION: Inferred intermediate sequence

<400> SEQUENCE: 12

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Thr Ile Gly Asn Asn
            20                  25                  30

Tyr Val Ser Trp Tyr Gln Leu Leu Pro Gly Thr Ala Pro Lys Leu Leu
        35                  40                  45

Ile Tyr Lys Asn Asp Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Thr Ser Leu
                85                  90                  95

Ser Ala Gly Gly Val Phe Gly Thr Gly Thr Lys Val Thr Val Leu
            100                 105                 110

<210> SEQ ID NO 13
<211> LENGTH: 474
<212> TYPE: PRT
<213> ORGANISM: Homo sapiens

<400> SEQUENCE: 13

Glu Val Gln Val Val Glu Ser Gly Gly Gly Val Val Gln Pro Gly Arg
1               5                   10                  15

Ser Leu Arg Leu Ser Cys Thr Ala Ser Gly Phe Thr Phe Ser Asn Phe
```

```
                    20                  25                  30
Ala Met Gly Trp Val Arg Gln Ala Pro Gly Lys Gly Leu Glu Trp Val
                35                  40                  45
Ala Phe Ile Ser Ser Asp Gly Ser Asn Lys Asn Tyr Gly Asp Ser Val
            50                  55                  60
Lys Gly Arg Phe Thr Ile Ser Arg Asp Asn Ser Lys Asn Thr Val Phe
65                  70                  75                  80
Leu Gln Met Asn Ser Leu Arg Val Glu Asp Thr Ala Leu Tyr Tyr Cys
                85                  90                  95
Ala Lys Asp Val Gly Asp Tyr Lys Ser Asp Glu Trp Gly Thr Glu Tyr
                100                 105                 110
Tyr Asp Ile Ser Ile Ser Tyr Pro Ile Gln Asp Pro Arg Ala Met Val
                115                 120                 125
Gly Ala Phe Asp Leu Trp Gly Gln Gly Thr Met Val Thr Val Ser Pro
                130                 135                 140
Ala Ser Thr Lys Gly Pro Ser Val Phe Pro Leu Ala Pro Ser Ser Lys
145                 150                 155                 160
Ser Thr Ser Gly Gly Thr Ala Ala Leu Gly Cys Leu Val Lys Asp Tyr
                165                 170                 175
Phe Pro Glu Pro Val Thr Val Ser Trp Asn Ser Gly Ala Leu Thr Ser
                180                 185                 190
Gly Val His Thr Phe Pro Ala Val Leu Gln Ser Ser Gly Leu Tyr Ser
                195                 200                 205
Leu Ser Ser Val Val Thr Val Pro Ser Ser Ser Leu Gly Thr Gln Thr
                210                 215                 220
Tyr Ile Cys Asn Val Asn His Lys Pro Ser Asn Thr Lys Val Asp Lys
225                 230                 235                 240
Lys Val Glu Pro Lys Ser Cys Asp Lys Thr His Thr Cys Pro Pro Cys
                245                 250                 255
Pro Ala Pro Glu Leu Leu Gly Gly Pro Ser Val Phe Leu Phe Pro Pro
                260                 265                 270
Lys Pro Lys Asp Thr Leu Met Ile Ser Arg Thr Pro Glu Val Thr Cys
                275                 280                 285
Val Val Val Asp Val Ser His Glu Asp Pro Glu Val Lys Phe Asn Trp
                290                 295                 300
Tyr Val Asp Gly Val Glu Val His Asn Ala Lys Thr Lys Pro Arg Glu
305                 310                 315                 320
Glu Gln Tyr Asn Ser Thr Tyr Arg Val Val Ser Val Leu Thr Val Leu
                325                 330                 335
His Gln Asp Trp Leu Asn Gly Lys Glu Tyr Lys Cys Lys Val Ser Asn
                340                 345                 350
Lys Ala Leu Pro Ala Pro Ile Glu Lys Thr Ile Ser Lys Ala Lys Gly
                355                 360                 365
Gln Pro Arg Glu Pro Gln Val Tyr Thr Leu Pro Pro Ser Arg Asp Glu
                370                 375                 380
Leu Thr Lys Asn Gln Val Ser Leu Thr Cys Leu Val Lys Gly Phe Tyr
385                 390                 395                 400
Pro Ser Asp Ile Ala Val Glu Trp Glu Ser Asn Gly Gln Pro Glu Asn
                405                 410                 415
Asn Tyr Lys Thr Thr Pro Pro Val Leu Asp Ser Asp Gly Ser Phe Phe
                420                 425                 430
Leu Tyr Ser Lys Leu Thr Val Asp Lys Ser Arg Trp Gln Gln Gly Asn
                435                 440                 445
```

```
Val Phe Ser Cys Ser Val Met His Glu Ala Leu His Asn His Tyr Thr
    450                 455                 460
Gln Lys Ser Leu Ser Leu Ser Pro Gly Lys
465                 470
```

<210> SEQ ID NO 14
<211> LENGTH: 217
<212> TYPE: PRT
<213> ORGANISM: Homo sapiens

<400> SEQUENCE: 14

```
Gln Ser Val Leu Thr Gln Pro Pro Ser Val Ser Ala Ala Pro Gly Gln
1               5                   10                  15
Lys Val Thr Ile Ser Cys Ser Gly Ser Ser Thr Ile Gly Asn Asn
            20                  25                  30
Tyr Val Ser Trp Tyr Arg Leu Leu Pro Gly Thr Ala Pro Lys Leu Leu
            35                  40                  45
Ile Tyr Lys Asn Asp Asn Arg Pro Ser Gly Ile Pro Asp Arg Phe Ser
    50                  55                  60
Gly Ser Lys Ser Gly Thr Ser Ala Thr Leu Gly Ile Ser Gly Leu Gln
65                  70                  75                  80
Thr Gly Asp Glu Ala Asp Tyr Tyr Cys Gly Thr Trp Asp Thr Ser Leu
                85                  90                  95
Ser Gly Gly Gly Val Phe Gly Thr Gly Thr Lys Val Thr Val Leu Gly
            100                 105                 110
Gln Pro Lys Ala Asp Pro Thr Val Thr Leu Phe Pro Pro Ser Ser Glu
        115                 120                 125
Glu Leu Gln Ala Asn Lys Ala Thr Leu Val Cys Leu Ile Ser Asp Phe
    130                 135                 140
Tyr Pro Gly Ala Val Thr Val Ala Trp Lys Ala Asp Ser Ser Pro Val
145                 150                 155                 160
Lys Ala Gly Val Glu Thr Thr Thr Pro Ser Lys Gln Ser Asn Asn Lys
                165                 170                 175
Tyr Ala Ala Ser Ser Tyr Leu Ser Leu Thr Pro Glu Gln Trp Lys Ser
            180                 185                 190
His Arg Ser Tyr Ser Cys Gln Val Thr His Glu Gly Ser Thr Val Glu
        195                 200                 205
Lys Thr Val Ala Pro Thr Glu Cys Ser
    210                 215
```

<210> SEQ ID NO 15
<211> LENGTH: 144
<212> TYPE: PRT
<213> ORGANISM: Homo sapiens

<400> SEQUENCE: 15

```
Glu Val Gln Val Val Glu Ser Gly Gly Val Val Gln Pro Gly Arg
1               5                   10                  15
Ser Leu Arg Leu Ser Cys Thr Ala Ser Gly Phe Thr Phe Ser Asn Phe
            20                  25                  30
Ala Met Gly Trp Val Arg Gln Ala Pro Gly Lys Gly Leu Glu Trp Val
            35                  40                  45
Ala Phe Ile Ser Ser Asp Gly Ser Asn Lys Asn Tyr Gly Asp Ser Val
    50                  55                  60
Lys Gly Arg Phe Thr Ile Ser Arg Asp Asn Ser Lys Asn Thr Val Phe
65                  70                  75                  80
```

```
Leu Gln Met Asn Ser Leu Arg Val Glu Asp Thr Ala Leu Tyr Tyr Cys
                85                  90                  95

Ala Lys Asp Val Gly Asp Tyr Lys Ser Asp Glu Trp Gly Thr Glu Tyr
            100                 105                 110

Tyr Asp Ile Ser Ile Ser Tyr Pro Ile Gln Asp Pro Arg Ala Met Val
        115                 120                 125

Gly Ala Phe Asp Leu Trp Gly Gln Gly Thr Met Val Thr Val Ser Pro
    130                 135                 140
```

<210> SEQ ID NO 16
<211> LENGTH: 111
<212> TYPE: PRT
<213> ORGANISM: Homo sapiens

<400> SEQUENCE: 16

```
Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Thr Ile Gly Asn Asn
            20                  25                  30

Tyr Val Ser Trp Tyr Arg Leu Leu Pro Gly Thr Ala Pro Lys Leu Leu
        35                  40                  45

Ile Tyr Lys Asn Asp Asn Arg Pro Ser Gly Ile Pro Asp Arg Phe Ser
    50                  55                  60

Gly Ser Lys Ser Gly Thr Ser Ala Thr Leu Gly Ile Ser Gly Leu Gln
65                  70                  75                  80

Thr Gly Asp Glu Ala Asp Tyr Tyr Cys Gly Thr Trp Asp Thr Ser Leu
                85                  90                  95

Ser Gly Gly Gly Val Phe Gly Thr Gly Thr Lys Val Thr Val Leu
            100                 105                 110
```

<210> SEQ ID NO 17
<211> LENGTH: 474
<212> TYPE: PRT
<213> ORGANISM: Homo sapiens

<400> SEQUENCE: 17

```
Glu Val Gln Leu Val Glu Ser Gly Gly Gly Val Val Gln Pro Gly Arg
1               5                   10                  15

Ser Leu Arg Leu Ser Cys Ala Ala Ser Gln Phe Ser Phe Gly Asn Tyr
            20                  25                  30

Gly Met His Trp Val Arg Gln Ala Pro Gly Lys Gly Leu Glu Trp Val
        35                  40                  45

Ala Ala Ile Ser Phe Ala Gly Thr Lys Thr Asn Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Leu Tyr Phe Cys
                85                  90                  95

Ala Lys Asp Ile Arg Glu Tyr Glu Cys Glu Tyr Trp Thr Ser Asp Tyr
            100                 105                 110

Tyr Asp Phe Gly Arg Pro Gln Pro Cys Ile Asp Ser Arg Gly Val Val
        115                 120                 125

Gly Thr Phe Asp Val Trp Gly Gln Gly Thr Met Val Thr Val Ser Ser
    130                 135                 140

Ala Ser Thr Lys Gly Pro Ser Val Phe Pro Leu Ala Pro Ser Ser Lys
145                 150                 155                 160
```

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
210                 215                 220

Tyr Ile Cys Asn Val Asn His Lys Pro Ser Asn Thr Lys Val Asp Lys
225                 230                 235                 240

Lys Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Asp Glu
370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
450                 455                 460

Gln Lys Ser Leu Ser Leu Ser Pro Gly Lys
465                 470

<210> SEQ ID NO 18
<211> LENGTH: 214
<212> TYPE: PRT
<213> ORGANISM: Homo sapiens

<400> SEQUENCE: 18

Gln Ser Val Leu Thr Gln Pro Pro Ser Val Ser Ala Ala Pro Gly Gln
1               5                   10                  15

Lys Val Thr Ile Ser Cys Ser Gly Ser Asn Ser Asn Ile Gly Asn Lys
            20                  25                  30

Asp Val Ser Trp Tyr Gln Gln Ile Pro Ala Thr Ala Pro Lys Leu Leu
        35                  40                  45

Ile Tyr Glu Asn Asn Lys Arg Pro Ser Gly Ile Ser Asp Arg Phe Ser

```
                    50                  55                  60
Gly Ser Lys Ser Gly Thr Ser Ala Thr Leu Ala Ile Thr Gly Leu Gln
 65                  70                  75                  80

Thr Gly Asp Glu Ala Asp Tyr Tyr Cys Ala Thr Trp Asp Gly Arg Val
                 85                  90                  95

Ser Val Ile Gly Thr Gly Thr Asn Val Ile Val Leu Gly Gln Pro Lys
            100                 105                 110

Ala Asp Pro Thr Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 19
<211> LENGTH: 144
<212> TYPE: PRT
<213> ORGANISM: Homo sapiens

<400> SEQUENCE: 19

Glu Val Gln Leu Val Glu Ser Gly Gly Gly Val Val Gln Pro Gly Arg
 1               5                  10                  15

Ser Leu Arg Leu Ser Cys Ala Ala Ser Gln Phe Ser Phe Gly Asn Tyr
             20                  25                  30

Gly Met His Trp Val Arg Gln Ala Pro Gly Lys Gly Leu Glu Trp Val
         35                  40                  45

Ala Ala Ile Ser Phe Ala Gly Thr Lys Thr Asn Tyr Ala Asp Ser Val
     50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Ala Glu Asp Thr Ala Leu Tyr Phe Cys
                 85                  90                  95

Ala Lys Asp Ile Arg Glu Tyr Glu Cys Glu Tyr Trp Thr Ser Asp Tyr
            100                 105                 110

Tyr Asp Phe Gly Arg Pro Gln Pro Cys Ile Asp Ser Arg Gly Val Val
        115                 120                 125

Gly Thr Phe Asp Val Trp Gly Gln Gly Thr Met Val Thr Val Ser Ser
    130                 135                 140

<210> SEQ ID NO 20
<211> LENGTH: 108
<212> TYPE: PRT
<213> ORGANISM: Homo sapiens

<400> SEQUENCE: 20

Gln Ser Val Leu Thr Gln Pro Pro Ser Val Ser Ala Ala Pro Gly Gln
 1               5                  10                  15

Lys Val Thr Ile Ser Cys Ser Gly Ser Asn Ser Asn Ile Gly Asn Lys
```

```
                20                  25                  30
Asp Val Ser Trp Tyr Gln Gln Ile Pro Ala Thr Ala Pro Lys Leu Leu
         35                  40                  45

Ile Tyr Glu Asn Asn Lys Arg Pro Ser Gly Ile Ser Asp Arg Phe Ser
 50                  55                  60

Gly Ser Lys Ser Gly Thr Ser Ala Thr Leu Ala Ile Thr Gly Leu Gln
 65                  70                  75                  80

Thr Gly Asp Glu Ala Asp Tyr Tyr Cys Ala Thr Trp Asp Gly Arg Val
                 85                  90                  95

Ser Val Ile Gly Thr Gly Thr Asn Val Ile Val Leu
                100                 105

<210> SEQ ID NO 21
<211> LENGTH: 474
<212> TYPE: PRT
<213> ORGANISM: Homo sapiens

<400> SEQUENCE: 21

Glu Val Gln Leu Val Glu Ser Gly Gly Gly Val Val Gln Pro Gly Lys
 1               5                  10                  15

Ser Leu Arg Leu Ser Cys Ala Ala Ser Arg Phe Ser Phe Asn Arg Tyr
                20                  25                  30

Gly Met His Trp Val Arg Gln Ala Pro Gly Lys Gly Leu Glu Trp Val
             35                  40                  45

Ala Ala Ile Ser Tyr Asp Gly Thr Asp Lys Tyr His Ala Asp Lys Val
 50                  55                  60

Trp Gly Arg Phe Thr Ile Ser Arg Asp Asn Lys Asn Thr Leu Tyr
 65                  70                  75                  80

Leu Gln Met Asn Ser Leu Arg Ala Glu Asp Thr Ala Leu Tyr Tyr Cys
                 85                  90                  95

Ala Lys Asp Leu Arg Glu Asp Glu Cys Glu Glu Trp Trp Ser Asp Tyr
                100                 105                 110

Tyr Asp Phe Gly Lys Gln Leu Pro Cys Arg Lys Ser Arg Gly Val Ala
            115                 120                 125

Gly Ile Phe Asp Gly Trp Gly Gln Gly Thr Met Val Thr Val Ser Ser
        130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Leu Gly Thr Gln Thr
    210                 215                 220

Tyr Ile Cys Asn Val Asn His Lys Pro Ser Asn Thr Lys Val Asp Lys
225                 230                 235                 240

Lys Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285
```

Val Val Val Asp Val Ser His Glu Asp Pro Glu Val Lys Phe Asn Trp
            290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
                355                 360                 365

Gln Pro Arg Glu Pro Gln Val Tyr Thr Leu Pro Pro Ser Arg Asp Glu
    370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
                435                 440                 445

Val Phe Ser Cys Ser Val Met His Glu Ala Leu His Asn His Tyr Thr
    450                 455                 460

Gln Lys Ser Leu Ser Leu Ser Pro Gly Lys
465                 470

<210> SEQ ID NO 22
<211> LENGTH: 217
<212> TYPE: PRT
<213> ORGANISM: Homo sapiens

<400> SEQUENCE: 22

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Phe Val Ser Trp Tyr Gln Gln Arg Pro Gly Thr Ala Pro Lys Ile Leu
        35                  40                  45

Ile Tyr Glu Asn Asn Lys Arg Pro Ser Glu Thr Pro Asp Arg Phe Ser
    50                  55                  60

Gly Ser Lys Ser Gly Thr Ser Ala Thr Leu Ala Ile Thr Gly Leu Gln
65                  70                  75                  80

Thr Ala Asp Glu Ala Glu Tyr Tyr Cys Ala Thr Trp Ser Ala Ser Leu
                85                  90                  95

Ser Ser Ala Arg Val Phe Gly Thr Gly Thr Arg Ile Thr Val Leu Gly
            100                 105                 110

Gln Pro Lys Ala Asp Pro Thr Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
        210                 215

<210> SEQ ID NO 23
<211> LENGTH: 144
<212> TYPE: PRT
<213> ORGANISM: Homo sapiens

<400> SEQUENCE: 23

Glu Val Gln Leu Val Glu Ser Gly Gly Gly Val Val Gln Pro Gly Lys
1               5                   10                  15

Ser Leu Arg Leu Ser Cys Ala Ala Ser Arg Phe Ser Phe Asn Arg Tyr
            20                  25                  30

Gly Met His Trp Val Arg Gln Ala Pro Gly Lys Gly Leu Glu Trp Val
        35                  40                  45

Ala Ala Ile Ser Tyr Asp Gly Thr Asp Lys Tyr His Ala Asp Lys Val
    50                  55                  60

Trp Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Lys Asp Leu Arg Glu Asp Glu Cys Glu Glu Trp Trp Ser Asp Tyr
            100                 105                 110

Tyr Asp Phe Gly Lys Gln Leu Pro Cys Arg Lys Ser Arg Gly Val Ala
        115                 120                 125

Gly Ile Phe Asp Gly Trp Gly Gln Gly Thr Met Val Thr Val Ser Ser
    130                 135                 140

<210> SEQ ID NO 24
<211> LENGTH: 111
<212> TYPE: PRT
<213> ORGANISM: Homo sapiens

<400> SEQUENCE: 24

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Phe Val Ser Trp Tyr Gln Gln Arg Pro Gly Thr Ala Pro Lys Ile Leu
        35                  40                  45

Ile Tyr Glu Asn Asn Lys Arg Pro Ser Glu Thr Pro Asp Arg Phe Ser
    50                  55                  60

Gly Ser Lys Ser Gly Thr Ser Ala Thr Leu Ala Ile Thr Gly Leu Gln
65                  70                  75                  80

Thr Ala Asp Glu Ala Glu Tyr Tyr Cys Ala Thr Trp Ser Ala Ser Leu
                85                  90                  95

Ser Ser Ala Arg Val Phe Gly Thr Gly Thr Arg Ile Thr Val Leu
            100                 105                 110

<210> SEQ ID NO 25
<211> LENGTH: 474
<212> TYPE: PRT
<213> ORGANISM: Homo sapiens

<400> SEQUENCE: 25

```
Glu Val Gln Leu Val Glu Ser Gly Gly Gly Val Val Gln Pro Gly Lys
1               5                   10                  15

Ser Leu Arg Leu Ser Cys Ala Ala Ser Gln Phe Ser Phe Asn Arg Tyr
            20                  25                  30

Gly Met His Trp Val Arg Gln Ala Pro Gly Lys Gly Leu Glu Trp Val
        35                  40                  45

Ala Ala Ile Ser Tyr Asp Gly Thr Asp Lys Tyr His Ala Asp Lys Val
    50                  55                  60

Trp Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Lys Asp Leu Arg Glu Asp Glu Cys Glu Glu Trp Trp Ser Asp Tyr
        100                 105                 110

Tyr Asp Phe Gly Lys Gln Leu Pro Cys Arg Lys Ser Arg Gly Val Ala
        115                 120                 125

Gly Ile Phe Asp Lys Trp Gly Gln Gly Thr Met Val Ile Val Ser Ser
    130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
        180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Lys Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
        260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
        340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Asp Glu
    370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
```

```
            420             425             430
Leu Tyr Ser Lys Leu Thr Val Asp Lys Ser Arg Trp Gln Gln Gly Asn
            435                 440                 445

Val Phe Ser Cys Ser Val Met His Glu Ala Leu His Asn His Tyr Thr
        450                 455                 460

Gln Lys Ser Leu Ser Leu Ser Pro Gly Lys
465                 470

<210> SEQ ID NO 26
<211> LENGTH: 217
<212> TYPE: PRT
<213> ORGANISM: Homo sapiens

<400> SEQUENCE: 26

Gln Pro Val Leu Thr Gln Pro Pro Ser Val Ser Ala Ala Pro Gly Gln
1               5                   10                  15

Lys Val Thr Ile Ser Cys Ser Gly Ser Ser Asn Ile Gly Asn Asn
            20                  25                  30

Phe Val Ser Trp Tyr Gln Gln Arg Pro Gly Thr Ala Pro Ser Leu Leu
        35                  40                  45

Ile Tyr Glu Thr Asn Lys Arg Pro Ser Gly Ile Pro Asp Arg Phe Ser
    50                  55                  60

Gly Ser Lys Ser Ala Thr Ser Ala Thr Leu Ala Ile Thr Gly Leu Gln
65                  70                  75                  80

Thr Gly Asp Glu Ala Asp Tyr Tyr Cys Ala Thr Trp Ala Ala Ser Leu
                85                  90                  95

Thr Ser Ala Arg Val Phe Gly Thr Gly Thr Lys Val Ile Val Ser Gly
            100                 105                 110

Gln Pro Lys Ala Asp Pro Thr Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 27
<211> LENGTH: 144
<212> TYPE: PRT
<213> ORGANISM: Homo sapiens

<400> SEQUENCE: 27

Glu Val Gln Leu Val Glu Ser Gly Gly Gly Val Val Gln Pro Gly Lys
1               5                   10                  15

Ser Leu Arg Leu Ser Cys Ala Ala Ser Gln Phe Ser Phe Asn Arg Tyr
            20                  25                  30

Gly Met His Trp Val Arg Gln Ala Pro Gly Lys Gly Leu Glu Trp Val
        35                  40                  45

Ala Ala Ile Ser Tyr Asp Gly Thr Asp Lys Tyr His Ala Asp Lys Val
```

```
            50                  55                  60
Trp Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Leu Tyr Tyr Cys
                 85                  90                  95

Ala Lys Asp Leu Arg Glu Asp Glu Cys Glu Glu Trp Trp Ser Asp Tyr
                100                 105                 110

Tyr Asp Phe Gly Lys Gln Leu Pro Cys Arg Lys Ser Arg Gly Val Ala
            115                 120                 125

Gly Ile Phe Asp Lys Trp Gly Gln Gly Thr Met Val Ile Val Ser Ser
            130                 135                 140

<210> SEQ ID NO 28
<211> LENGTH: 111
<212> TYPE: PRT
<213> ORGANISM: Homo sapiens

<400> SEQUENCE: 28

Gln Pro Val Leu Thr Gln Pro Pro Ser Val Ser Ala Ala Pro Gly Gln
 1               5                  10                  15

Lys Val Thr Ile Ser Cys Ser Gly Ser Ser Ser Asn Ile Gly Asn Asn
                20                  25                  30

Phe Val Ser Trp Tyr Gln Gln Arg Pro Gly Thr Ala Pro Ser Leu Leu
            35                  40                  45

Ile Tyr Glu Thr Asn Lys Arg Pro Ser Gly Ile Pro Asp Arg Phe Ser
        50                  55                  60

Gly Ser Lys Ser Ala Thr Ser Ala Thr Leu Ala Ile Thr Gly Leu Gln
 65                  70                  75                  80

Thr Gly Asp Glu Ala Asp Tyr Tyr Cys Ala Thr Trp Ala Ala Ser Leu
                 85                  90                  95

Thr Ser Ala Arg Val Phe Gly Thr Gly Thr Lys Val Ile Val Ser
                100                 105                 110

<210> SEQ ID NO 29
<211> LENGTH: 474
<212> TYPE: PRT
<213> ORGANISM: Homo sapiens

<400> SEQUENCE: 29

Glu Val Gln Leu Val Glu Ser Gly Gly Gly Val Val Gln Pro Gly Arg
 1               5                  10                  15

Ser Leu Arg Leu Ser Cys Ala Ala Ser His Phe Ser Leu Ser Ser Tyr
                20                  25                  30

Gly Met His Trp Val Arg Gln Ala Pro Gly Lys Gly Leu Glu Trp Val
            35                  40                  45

Thr Gly Ile Ser Phe Ala Gly Thr Lys Thr Tyr Tyr Gly Asp Ser Val
        50                  55                  60

Arg Gly Arg Phe Thr Val Ser Arg Asp Ile Ser Lys Asn Thr Leu Phe
 65                  70                  75                  80

Leu Gln Met Asn Ser Leu Arg Pro Asp Asp Thr Ala Met Tyr Tyr Cys
                 85                  90                  95

Ala Arg Asp Gln Arg Tyr Glu Cys Glu Glu Trp Ala Ser Asp Tyr
                100                 105                 110

Tyr Asp Phe Gly Arg Glu Gln Pro Cys Leu Asp Pro Arg Gly Val Val
            115                 120                 125

Gly Ile Phe Asp Leu Trp Gly Gln Gly Thr Met Val Thr Val Ser Ser
```

```
            130                 135                 140
Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Lys Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Asp Glu
    370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly Lys
465                 470

<210> SEQ ID NO 30
<211> LENGTH: 214
<212> TYPE: PRT
<213> ORGANISM: Homo sapiens

<400> SEQUENCE: 30

Gln Ser Ala Leu Thr Gln Pro Pro Ser Val Ser Ala Ala Pro Gly Gln
1               5                   10                  15

Lys Val Thr Ile Ser Cys Ser Gly Asn Ile Gly Asn Asn Tyr Val Ser
            20                  25                  30
```

```
Trp Tyr Gln Gln Val Pro Gly Thr Ala Pro Lys Leu Leu Ile Tyr Glu
            35                  40                  45

Asn Asn Lys Arg Pro Ser Gly Ile Pro Asp Arg Phe Ser Gly Ser Lys
 50                  55                  60

Ser Gly Thr Ser Ala Thr Leu Val Ile Thr Gly Leu Gln Thr Gly Asp
 65                  70                  75                  80

Glu Ala Asp Phe Tyr Cys Gly Thr Trp Gly Gly Ser Leu Arg Thr Gly
                85                  90                  95

Gly Val Leu Gly Thr Gly Thr Arg Val Thr Val Leu Gly Gln Pro Lys
            100                 105                 110

Ala Asp Pro Thr Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
            195                 200                 205

Ala Pro Thr Glu Cys Ser
            210

<210> SEQ ID NO 31
<211> LENGTH: 144
<212> TYPE: PRT
<213> ORGANISM: Homo sapiens

<400> SEQUENCE: 31

Glu Val Gln Leu Val Glu Ser Gly Gly Gly Val Val Gln Pro Gly Arg
 1               5                  10                  15

Ser Leu Arg Leu Ser Cys Ala Ala Ser His Phe Ser Leu Ser Ser Tyr
            20                  25                  30

Gly Met His Trp Val Arg Gln Ala Pro Gly Lys Gly Leu Glu Trp Val
        35                  40                  45

Thr Gly Ile Ser Phe Ala Gly Thr Lys Thr Tyr Tyr Gly Asp Ser Val
 50                  55                  60

Arg Gly Arg Phe Thr Val Ser Arg Asp Ile Ser Lys Asn Thr Leu Phe
 65                  70                  75                  80

Leu Gln Met Asn Ser Leu Arg Pro Asp Asp Thr Ala Met Tyr Tyr Cys
                85                  90                  95

Ala Arg Asp Gln Arg Tyr Tyr Glu Cys Glu Glu Trp Ala Ser Asp Tyr
            100                 105                 110

Tyr Asp Phe Gly Arg Glu Gln Pro Cys Leu Asp Pro Arg Gly Val Val
            115                 120                 125

Gly Ile Phe Asp Leu Trp Gly Gln Gly Thr Met Val Thr Val Ser Ser
            130                 135                 140

<210> SEQ ID NO 32
<211> LENGTH: 108
<212> TYPE: PRT
<213> ORGANISM: Homo sapiens

<400> SEQUENCE: 32
```

```
Gln Ser Ala Leu Thr Gln Pro Pro Ser Val Ser Ala Pro Gly Gln
1               5                   10                  15

Lys Val Thr Ile Ser Cys Ser Gly Asn Ile Gly Asn Asn Tyr Val Ser
            20                  25                  30

Trp Tyr Gln Gln Val Pro Gly Thr Ala Pro Lys Leu Leu Ile Tyr Glu
        35                  40                  45

Asn Asn Lys Arg Pro Ser Gly Ile Pro Asp Arg Phe Ser Gly Ser Lys
50                  55                  60

Ser Gly Thr Ser Ala Thr Leu Val Ile Thr Gly Leu Gln Thr Gly Asp
65                  70                  75                  80

Glu Ala Asp Phe Tyr Cys Gly Thr Trp Gly Gly Ser Leu Arg Thr Gly
                85                  90                  95

Gly Val Leu Gly Thr Gly Thr Arg Val Thr Val Leu
            100                 105
```

<210> SEQ ID NO 33
<211> LENGTH: 475
<212> TYPE: PRT
<213> ORGANISM: Homo sapiens

<400> SEQUENCE: 33

```
Glu Val Gln Leu Ile Glu Ser Gly Gly Gly Val Val Gln Pro Gly Arg
1               5                   10                  15

Ser Leu Arg Leu Ser Cys Gly Ala Ser Gly Phe Ser Phe Asn Asn Tyr
            20                  25                  30

Gly Met His Trp Val Arg Gln Ala Pro Gly Lys Gly Leu Glu Trp Val
        35                  40                  45

Ala Gly Ile Ser Phe Ala Gly Ile Lys Lys Tyr Tyr Gly Thr Ser Val
50                  55                  60

Lys Gly Arg Phe Thr Ile Ser Arg Asp Asn Ser Lys Asn Asn Phe Tyr
65                  70                  75                  80

Leu Gln Met Asn Ser Leu Arg Val Glu Asp Thr Ala Leu Tyr Tyr Cys
                85                  90                  95

Ala Arg Asp Leu Arg Glu Leu Glu Cys Glu Glu Trp Thr Leu Tyr Asn
            100                 105                 110

Tyr Tyr Asp Phe Gly Ser Arg Gly Pro Cys Val Asp Pro Arg Gly Val
        115                 120                 125

Ala Gly Ser Phe Asp Val Trp Gly Gln Gly Thr Met Val Thr Val Ser
    130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Ser Leu Gly Thr Gln
    210                 215                 220

Thr Tyr Ile Cys Asn Val Asn His Lys Pro Ser Asn Thr Lys Val Asp
225                 230                 235                 240

Lys Lys Val Glu Pro Lys Ser Cys Asp Lys Thr His Thr Cys Pro Pro
                245                 250                 255

Cys Pro Ala Pro Glu Leu Leu Gly Gly Pro Ser Val Phe Leu Phe Pro
            260                 265                 270
```

```
Pro Lys Pro Lys Asp Thr Leu Met Ile Ser Arg Thr Pro Glu Val Thr
        275                 280                 285

Cys Val Val Asp Val Ser His Glu Asp Pro Glu Val Lys Phe Asn
290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Asp
    370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Lys
465                 470                 475

<210> SEQ ID NO 34
<211> LENGTH: 214
<212> TYPE: PRT
<213> ORGANISM: Homo sapiens

<400> SEQUENCE: 34

Gln Ser Val Leu Thr Gln Pro Pro Ser Val Ser Ala Ala Pro Gly Gln
1               5                   10                  15

Lys Val Thr Ile Ser Cys Ser Gly Ser Thr Ser Lys Ile Gly Gln Asn
            20                  25                  30

Ser Val Ser Trp Tyr Gln Gln Leu Pro Gly Thr Ala Pro Lys Leu Leu
        35                  40                  45

Ile Tyr Glu Asn Asp Arg Arg Pro Ser Gly Thr Pro Asp Arg Phe Ser
    50                  55                  60

Gly Ser Lys Ser Gly Thr Ser Ala Thr Leu Ala Ile Thr Gly Leu Gln
65                  70                  75                  80

Thr Gly Asp Glu Ala Glu Tyr Tyr Cys Glu Thr Trp Asp Gly Ser Gly
                85                  90                  95

Gly Val Phe Gly Thr Gly Thr Lys Val Thr Val Leu Gly Gln Pro Lys
            100                 105                 110

Ala Asp Pro Thr Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
```

165                 170                 175
Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
            195                 200                 205

Ala Pro Thr Glu Cys Ser
    210

<210> SEQ ID NO 35
<211> LENGTH: 145
<212> TYPE: PRT
<213> ORGANISM: Homo sapiens

<400> SEQUENCE: 35

Glu Val Gln Leu Ile Glu Ser Gly Gly Gly Val Val Gln Pro Gly Arg
1               5                   10                  15

Ser Leu Arg Leu Ser Cys Gly Ala Ser Gly Phe Ser Phe Asn Asn Tyr
            20                  25                  30

Gly Met His Trp Val Arg Gln Ala Pro Gly Lys Gly Leu Glu Trp Val
        35                  40                  45

Ala Gly Ile Ser Phe Ala Gly Ile Lys Lys Tyr Tyr Gly Thr Ser Val
    50                  55                  60

Lys Gly Arg Phe Thr Ile Ser Arg Asp Asn Ser Lys Asn Asn Phe Tyr
65                  70                  75                  80

Leu Gln Met Asn Ser Leu Arg Val Glu Asp Thr Ala Leu Tyr Tyr Cys
                85                  90                  95

Ala Arg Asp Leu Arg Glu Leu Glu Cys Glu Glu Trp Thr Leu Tyr Asn
            100                 105                 110

Tyr Tyr Asp Phe Gly Ser Arg Gly Pro Cys Val Asp Pro Arg Gly Val
        115                 120                 125

Ala Gly Ser Phe Asp Val Trp Gly Gln Gly Thr Met Val Thr Val Ser
    130                 135                 140

Ser
145

<210> SEQ ID NO 36
<211> LENGTH: 108
<212> TYPE: PRT
<213> ORGANISM: Homo sapiens

<400> SEQUENCE: 36

Gln Ser Val Leu Thr Gln Pro Pro Ser Val Ser Ala Ala Pro Gly Gln
1               5                   10                  15

Lys Val Thr Ile Ser Cys Ser Gly Ser Thr Ser Lys Ile Gly Gln Asn
            20                  25                  30

Ser Val Ser Trp Tyr Gln Gln Leu Pro Gly Thr Ala Pro Lys Leu Leu
        35                  40                  45

Ile Tyr Glu Asn Asp Arg Arg Pro Ser Gly Thr Pro Asp Arg Phe Ser
    50                  55                  60

Gly Ser Lys Ser Gly Thr Ser Ala Thr Leu Ala Ile Thr Gly Leu Gln
65                  70                  75                  80

Thr Gly Asp Glu Ala Glu Tyr Tyr Cys Glu Thr Trp Asp Gly Ser Gly
                85                  90                  95

Gly Val Phe Gly Thr Gly Thr Lys Val Thr Val Leu
            100                 105

```
<210> SEQ ID NO 37
<211> LENGTH: 474
<212> TYPE: PRT
<213> ORGANISM: Homo sapiens

<400> SEQUENCE: 37

Glu Val Gln Leu Val Glu Ser Gly Gly Gly Val Val Gln Pro Gly Arg
1               5                   10                  15

Ser Leu Arg Leu Ser Cys Val Gly Ser Gln Phe Ser Phe Asn Arg Tyr
                20                  25                  30

Gly Met His Trp Val Arg Gln Ala Pro Gly Lys Gly Leu Glu Trp Val
            35                  40                  45

Ala Gly Ile Ser Phe Asp Gly Thr Asp Arg Tyr His Ala Asp Asn Val
    50                  55                  60

Trp Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Leu Tyr Tyr Cys
                85                  90                  95

Ala Lys Asp Leu Arg Glu Asp Glu Cys Glu Glu Trp Trp Ser Asp Tyr
            100                 105                 110

Tyr Asp Phe Gly Lys Lys Leu Pro Cys Arg Lys Ser Arg Gly Val Ala
        115                 120                 125

Gly Val Phe Asp Lys Trp Gly Gln Gly Thr Met Val Thr Val Ser Ser
    130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Lys Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Asp Glu
    370                 375                 380
```

```
Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
            405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly Lys
465                 470
```

<210> SEQ ID NO 38
<211> LENGTH: 217
<212> TYPE: PRT
<213> ORGANISM: Homo sapiens

<400> SEQUENCE: 38

```
Gln Ala Val Leu Thr Gln Pro Pro Ser Val Ser Ala Ala Pro Gly Gln
1               5                   10                  15

Asn Val Thr Ile Ser Cys Ser Gly Ser Gly Ser Asn Ile Gly Asn Asn
            20                  25                  30

Phe Val Ser Trp Tyr Gln Gln Arg Pro Gly Thr Ala Pro Lys Leu Leu
        35                  40                  45

Ile Tyr Glu Ser Asn Lys Arg Pro Ser Gly Ile Pro Asp Arg Phe Ser
    50                  55                  60

Gly Ser Lys Ser Gly Thr Ser Ala Thr Leu Ala Ile Thr Gly Leu Gln
65                  70                  75                  80

Thr Gly Asp Glu Ala Tyr Tyr Tyr Cys Ala Thr Trp Ala Ala Arg Leu
                85                  90                  95

Asn Ser Ala Arg Val Phe Gly Thr Gly Thr Met Val Thr Val Leu Gly
            100                 105                 110

Gln Pro Lys Ala Asp Pro Thr Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215
```

<210> SEQ ID NO 39
<211> LENGTH: 144
<212> TYPE: PRT
<213> ORGANISM: Homo sapiens

<400> SEQUENCE: 39

```
Glu Val Gln Leu Val Glu Ser Gly Gly Gly Val Val Gln Pro Gly Arg
1               5                   10                  15
```

```
Ser Leu Arg Leu Ser Cys Val Gly Ser Gln Phe Ser Phe Asn Arg Tyr
            20                  25                  30

Gly Met His Trp Val Arg Gln Ala Pro Gly Lys Gly Leu Glu Trp Val
        35                  40                  45

Ala Gly Ile Ser Phe Asp Gly Thr Asp Arg Tyr His Ala Asp Asn Val
 50                  55                  60

Trp Gly Arg Phe Thr Ile Ser Arg Asp Asn Ser Lys Asn Thr Leu Tyr
 65                  70                  75                  80

Leu Gln Met Ser Ser Leu Arg Ala Glu Asp Thr Ala Leu Tyr Tyr Cys
                 85                  90                  95

Ala Lys Asp Leu Arg Glu Asp Glu Cys Glu Glu Trp Trp Ser Asp Tyr
            100                 105                 110

Tyr Asp Phe Gly Lys Lys Leu Pro Cys Arg Lys Ser Arg Gly Val Ala
            115                 120                 125

Gly Val Phe Asp Lys Trp Gly Gln Gly Thr Met Val Thr Val Ser Ser
        130                 135                 140

<210> SEQ ID NO 40
<211> LENGTH: 111
<212> TYPE: PRT
<213> ORGANISM: Homo sapiens

<400> SEQUENCE: 40

Gln Ala Val Leu Thr Gln Pro Pro Ser Val Ser Ala Ala Pro Gly Gln
1               5                   10                  15

Asn Val Thr Ile Ser Cys Ser Gly Ser Gly Ser Asn Ile Gly Asn Asn
            20                  25                  30

Phe Val Ser Trp Tyr Gln Gln Arg Pro Gly Thr Ala Pro Lys Leu Leu
        35                  40                  45

Ile Tyr Glu Ser Asn Lys Arg Pro Ser Gly Ile Pro Asp Arg Phe Ser
 50                  55                  60

Gly Ser Lys Ser Gly Thr Ser Ala Thr Leu Ala Ile Thr Gly Leu Gln
 65                  70                  75                  80

Thr Gly Asp Glu Ala Tyr Tyr Tyr Cys Ala Thr Trp Ala Ala Arg Leu
                 85                  90                  95

Asn Ser Ala Arg Val Phe Gly Thr Gly Thr Met Val Thr Val Leu
            100                 105                 110

<210> SEQ ID NO 41
<211> LENGTH: 476
<212> TYPE: PRT
<213> ORGANISM: Homo sapiens

<400> SEQUENCE: 41

Glu Val Gln Leu Val Glu Ser Gly Gly Gly Val Val Gln Pro Gly Arg
1               5                   10                  15

Ser Leu Thr Leu Ser Cys Ala Ala Ser Gln Phe Thr Phe Ser Asn Tyr
            20                  25                  30

Gly Met His Trp Val Arg Gln Ala Pro Gly Lys Gly Leu Glu Trp Val
        35                  40                  45

Ala Ser Val Ser Asn Asp Gly Thr Lys Lys Tyr His Gly Asp Ser Val
 50                  55                  60

Trp Gly Arg Phe Thr Ile Ser Arg Asp Asn Ser Lys Asn Thr Leu Phe
 65                  70                  75                  80

Leu Gln Met Ser Ser Leu Arg Ala Glu Asp Thr Ala Val Tyr Phe Cys
                 85                  90                  95
```

Val Arg Asp Gln Arg Glu Asp Glu Cys Glu Trp Trp Ser Asp Tyr
            100                 105                 110

Tyr Asp Phe Gly Arg Glu Leu Pro Cys Arg Lys Phe Arg Gly Leu Gly
        115                 120                 125

Leu Ala Gly Ile Phe Asp Ile Trp Gly His Gly Thr Met Val Thr Val
    130                 135                 140

Ser Ser Ala Ser Thr Lys Gly Pro Ser Val Phe Pro Leu Ala Pro Ser
145                 150                 155                 160

Ser Lys Ser Thr Ser Gly Gly Thr Ala Ala Leu Gly Cys Leu Val Lys
            165                 170                 175

Asp Tyr Phe Pro Glu Pro Val Thr Val Ser Trp Asn Ser Gly Ala Leu
        180                 185                 190

Thr Ser Gly Val His Thr Phe Pro Ala Val Leu Gln Ser Ser Gly Leu
    195                 200                 205

Tyr Ser Leu Ser Ser Val Val Thr Val Pro Ser Ser Ser Leu Gly Thr
    210                 215                 220

Gln Thr Tyr Ile Cys Asn Val Asn His Lys Pro Ser Asn Thr Lys Val
225                 230                 235                 240

Asp Lys Lys Val Glu Pro Lys Ser Cys Asp Lys Thr His Thr Cys Pro
            245                 250                 255

Pro Cys Pro Ala Pro Glu Leu Leu Gly Gly Pro Ser Val Phe Leu Phe
        260                 265                 270

Pro Pro Lys Pro Lys Asp Thr Leu Met Ile Ser Arg Thr Pro Glu Val
    275                 280                 285

Thr Cys Val Val Val Asp Val Ser His Glu Asp Pro Glu Val Lys Phe
    290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
            325                 330                 335

Val Leu His Gln Asp Trp Leu Asn Gly Lys Glu Tyr Lys Cys Lys Val
        340                 345                 350

Ser Asn Lys Ala Leu Pro Ala Pro Ile Glu Lys Thr Ile Ser Lys Ala
    355                 360                 365

Lys Gly Gln Pro Arg Glu Pro Gln Val Tyr Thr Leu Pro Pro Ser Arg
370                 375                 380

Asp Glu Leu Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
            405                 410                 415

Glu Asn Asn Tyr Lys Thr Thr Pro Pro Val Leu Asp Ser Asp Gly Ser
        420                 425                 430

Phe Phe Leu Tyr Ser Lys Leu Thr Val Asp Lys Ser Arg Trp Gln Gln
    435                 440                 445

Gly Asn Val Phe Ser Cys Ser Val Met His Glu Ala Leu His Asn His
    450                 455                 460

Tyr Thr Gln Lys Ser Leu Ser Leu Ser Pro Gly Lys
465                 470                 475

<210> SEQ ID NO 42
<211> LENGTH: 217
<212> TYPE: PRT
<213> ORGANISM: Homo sapiens

<400> SEQUENCE: 42

-continued

Gln Ser Ala Leu Thr Gln Pro Pro Ser Val Ser Ala Ala Pro Gly Gln
1               5                   10                  15

Lys Val Thr Ile Ser Cys Ser Gly Asn Ser Ser Asn Ile Gly Asn Asn
                20                  25                  30

Phe Val Ser Trp Tyr Gln Gln Val Pro Gly Thr Ala Pro Lys Leu Leu
                35                  40                  45

Leu Tyr Glu Thr Tyr Arg Arg Pro Ser Gly Ile Pro Asp Arg Phe Ser
        50                  55                  60

Gly Ser Lys Ser Gly Thr Ser Ala Thr Leu Ala Ile Thr Gly Leu Gln
65                  70                  75                  80

Thr Gly Asp Glu Ala Asp Tyr Tyr Cys Thr Val Trp Gly Val Arg Lys
                85                  90                  95

Gly Val Gly Ala Val Phe Gly Thr Gly Thr Lys Val Thr Val Leu Gly
                100                 105                 110

Gln Pro Lys Ala Asp Pro Thr Val Thr Leu Phe Pro Pro Ser Ser Glu
                115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
                180                 185                 190

His Arg Ser Tyr Ser Cys Gln Val Thr His Glu Gly Ser Thr Val Glu
        195                 200                 205

Lys Thr Val Ala Pro Thr Glu Cys Ser
210                 215

<210> SEQ ID NO 43
<211> LENGTH: 146
<212> TYPE: PRT
<213> ORGANISM: Homo sapiens

<400> SEQUENCE: 43

Glu Val Gln Leu Val Glu Ser Gly Gly Gly Val Val Gln Pro Gly Arg
1               5                   10                  15

Ser Leu Thr Leu Ser Cys Ala Ala Ser Gln Phe Thr Phe Ser Asn Tyr
                20                  25                  30

Gly Met His Trp Val Arg Gln Ala Pro Gly Lys Gly Leu Glu Trp Val
                35                  40                  45

Ala Ser Val Ser Asn Asp Gly Thr Lys Lys Tyr His Gly Asp Ser Val
        50                  55                  60

Trp Gly Arg Phe Thr Ile Ser Arg Asp Asn Ser Lys Asn Thr Leu Phe
65                  70                  75                  80

Leu Gln Met Ser Ser Leu Arg Ala Glu Asp Thr Ala Val Tyr Phe Cys
                85                  90                  95

Val Arg Asp Gln Arg Glu Asp Glu Cys Glu Glu Trp Trp Ser Asp Tyr
                100                 105                 110

Tyr Asp Phe Gly Arg Glu Leu Pro Cys Arg Lys Phe Arg Gly Leu Gly
                115                 120                 125

Leu Ala Gly Ile Phe Asp Ile Trp Gly His Gly Thr Met Val Thr Val
130                 135                 140

Ser Ser

<210> SEQ ID NO 44
<211> LENGTH: 111
<212> TYPE: PRT
<213> ORGANISM: Homo sapiens

<400> SEQUENCE: 44

Gln Ser Ala Leu Thr Gln Pro Pro Ser Val Ala Ala Pro Gly Gln
1               5                   10                  15

Lys Val Thr Ile Ser Cys Ser Gly Asn Ser Ser Asn Ile Gly Asn Asn
            20                  25                  30

Phe Val Ser Trp Tyr Gln Gln Val Pro Gly Thr Ala Pro Lys Leu Leu
        35                  40                  45

Leu Tyr Glu Thr Tyr Arg Arg Pro Ser Gly Ile Pro Asp Arg Phe Ser
50                  55                  60

Gly Ser Lys Ser Gly Thr Ser Ala Thr Leu Ala Ile Thr Gly Leu Gln
65                  70                  75                  80

Thr Gly Asp Glu Ala Asp Tyr Tyr Cys Thr Val Trp Gly Val Arg Lys
                85                  90                  95

Gly Val Gly Ala Val Phe Gly Thr Gly Thr Lys Val Thr Val Leu
            100                 105                 110

<210> SEQ ID NO 45
<211> LENGTH: 476
<212> TYPE: PRT
<213> ORGANISM: Homo sapiens

<400> SEQUENCE: 45

Glu Val Gln Leu Val Glu Ser Gly Gly Gly Val Val Gln Pro Gly Arg
1               5                   10                  15

Ser Leu Thr Leu Ser Cys Ala Ala Ser Gln Phe Asn Phe Ala Asn Tyr
            20                  25                  30

Gly Met His Trp Val Arg Gln Ala Pro Gly Lys Gly Leu Glu Trp Val
        35                  40                  45

Ala Ser Ile Ser Asn Asp Gly Thr Lys Lys Tyr His Glu Glu Ser Val
50                  55                  60

Trp Gly Arg Phe Thr Ile Ser Lys Asp Asn Ser Lys Ser Thr Leu Phe
65                  70                  75                  80

Leu Gln Met Asn Ser Leu Arg Ile Glu Asp Thr Ala Leu Tyr Phe Cys
                85                  90                  95

Val Lys Asp Gln Arg Glu Asp Glu Cys Glu Glu Trp Trp Ser Asp Tyr
            100                 105                 110

Tyr Asp Phe Gly Arg Glu Leu Pro Cys Arg Lys Ser Arg Gly Leu Gly
        115                 120                 125

Leu Ala Gly Ile Phe Asp Met Trp Gly His Gly Thr Met Val Thr Val
130                 135                 140

Ser Ser Ala Ser Thr Lys Gly Pro Ser Val Phe Pro Leu Ala Pro Ser
145                 150                 155                 160

Ser Lys Ser Thr Ser Gly Gly Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Ser Leu Gly Thr

```
            210                 215                 220
Gln Thr Tyr Ile Cys Asn Val Asn His Lys Pro Ser Asn Thr Lys Val
225                 230                 235                 240

Asp Lys Lys Val Glu Pro Lys Ser Cys Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
            275                 280                 285

Thr Cys Val Val Val Asp Val Ser His Glu Asp Pro Glu Val Lys Phe
        290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
        355                 360                 365

Lys Gly Gln Pro Arg Glu Pro Gln Val Tyr Thr Leu Pro Pro Ser Arg
        370                 375                 380

Asp Glu Leu Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
                420                 425                 430

Phe Phe Leu Tyr Ser Lys Leu Thr Val Asp Lys Ser Arg Trp Gln Gln
            435                 440                 445

Gly Asn Val Phe Ser Cys Ser Val Met His Glu Ala Leu His Asn His
        450                 455                 460

Tyr Thr Gln Lys Ser Leu Ser Leu Ser Pro Gly Lys
465                 470                 475

<210> SEQ ID NO 46
<211> LENGTH: 217
<212> TYPE: PRT
<213> ORGANISM: Homo sapiens

<400> SEQUENCE: 46

Gln Ser Ala Leu Thr Gln Pro Pro Ser Val Ser Ala Ala Pro Gly Gln
1               5                   10                  15

Lys Val Thr Ile Ser Cys Ser Gly Asn Ser Ser Asn Ile Gly Asn Asn
                20                  25                  30

Phe Val Ser Trp Tyr Gln Gln Leu Pro Gly Thr Ala Pro Lys Leu Leu
            35                  40                  45

Ile Tyr Glu Asn Asn Arg Arg Pro Ser Gly Ile Pro Asp Arg Phe Ser
        50                  55                  60

Gly Ser Lys Ser Gly Thr Ser Ala Thr Leu Ala Ile Ser Gly Leu Gln
65                  70                  75                  80

Thr Gly Asp Glu Ala Asp Tyr Trp Cys Ala Val Trp Gly Val Arg Arg
                85                  90                  95

Gly Ala Gly Ala Val Phe Gly Ala Gly Thr Lys Val Thr Val Leu Gly
            100                 105                 110
```

```
Gln Pro Lys Ala Asp Pro Thr Val Thr Leu Phe Pro Ser Ser Glu
            115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
210                 215

<210> SEQ ID NO 47
<211> LENGTH: 146
<212> TYPE: PRT
<213> ORGANISM: Homo sapiens

<400> SEQUENCE: 47

Glu Val Gln Leu Val Glu Ser Gly Gly Gly Val Val Gln Pro Gly Arg
1               5                   10                  15

Ser Leu Thr Leu Ser Cys Ala Ala Ser Gln Phe Asn Phe Ala Asn Tyr
            20                  25                  30

Gly Met His Trp Val Arg Gln Ala Pro Gly Lys Gly Leu Glu Trp Val
        35                  40                  45

Ala Ser Ile Ser Asn Asp Gly Thr Lys Lys Tyr His Glu Glu Ser Val
    50                  55                  60

Trp Gly Arg Phe Thr Ile Ser Lys Asp Asn Ser Lys Ser Thr Leu Phe
65                  70                  75                  80

Leu Gln Met Asn Ser Leu Arg Ile Glu Asp Thr Ala Leu Tyr Phe Cys
                85                  90                  95

Val Lys Asp Gln Arg Glu Asp Glu Cys Glu Glu Trp Trp Ser Asp Tyr
            100                 105                 110

Tyr Asp Phe Gly Arg Glu Leu Pro Cys Arg Lys Ser Arg Gly Leu Gly
        115                 120                 125

Leu Ala Gly Ile Phe Asp Met Trp Gly His Gly Thr Met Val Thr Val
    130                 135                 140

Ser Ser
145

<210> SEQ ID NO 48
<211> LENGTH: 111
<212> TYPE: PRT
<213> ORGANISM: Homo sapiens

<400> SEQUENCE: 48

Gln Ser Ala Leu Thr Gln Pro Pro Ser Val Ser Ala Ala Pro Gly Gln
1               5                   10                  15

Lys Val Thr Ile Ser Cys Ser Gly Asn Ser Ser Asn Ile Gly Asn Asn
            20                  25                  30

Phe Val Ser Trp Tyr Gln Gln Leu Pro Gly Thr Ala Pro Lys Leu Leu
        35                  40                  45

Ile Tyr Glu Asn Asn Arg Arg Pro Ser Gly Ile Pro Asp Arg Phe Ser
    50                  55                  60
```

```
Gly Ser Lys Ser Gly Thr Ser Ala Thr Leu Ala Ile Ser Gly Leu Gln
 65                  70                  75                  80

Thr Gly Asp Glu Ala Asp Tyr Trp Cys Ala Val Trp Gly Val Arg Arg
                 85                  90                  95

Gly Ala Gly Ala Val Phe Gly Ala Gly Thr Lys Val Thr Val Leu
            100                 105                 110

<210> SEQ ID NO 49
<211> LENGTH: 474
<212> TYPE: PRT
<213> ORGANISM: Homo sapiens

<400> SEQUENCE: 49

Gln Ala Ile Leu Val Glu Ser Gly Gly Val Val Gln Pro Gly Arg
 1               5                  10                  15

Ser Leu Arg Leu Ser Cys Ala Ala Ser Gln Phe Thr Phe Ser Gly His
                 20                  25                  30

Gly Leu His Trp Val Arg Gln Ala Pro Gly Lys Gly Leu Glu Trp Val
             35                  40                  45

Ala Ser Ile Ser Phe Ala Gly Thr Lys Met Asp Tyr Ala Asp Ser Val
 50                  55                  60

Lys Gly Arg Phe Ala Ile Ser Arg Asp Asn Ser Lys Asn Thr Leu Tyr
 65                  70                  75                  80

Leu Gln Met Asn Ser Leu Arg Val Glu Asp Thr Ala Leu Tyr Tyr Cys
                 85                  90                  95

Ala Lys Asp Met Arg Glu Tyr Glu Cys Glu Tyr Trp Thr Ser Asp Tyr
            100                 105                 110

Tyr Asp Phe Gly Arg Pro Gln Pro Cys Ile Asp Arg Arg Gly Val Val
            115                 120                 125

Gly Ile Phe Asp Met Trp Gly Gln Gly Thr Met Val Thr Val Ser Thr
            130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
            195                 200                 205

Leu Ser Ser Val Val Thr Val Pro Ser Ser Ser Leu Gly Thr Gln Thr
            210                 215                 220

Tyr Ile Cys Asn Val Asn His Lys Pro Ser Asn Thr Lys Val Asp Lys
225                 230                 235                 240

Lys Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
            275                 280                 285

Val Val Val Asp Val Ser His Glu Asp Pro Glu Val Lys Phe Asn Trp
            290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335
```

His Gln Asp Trp Leu Asn Gly Lys Glu Tyr Lys Cys Lys Val Ser Asn
                340                 345                 350

Lys Ala Leu Pro Ala Pro Ile Glu Lys Thr Ile Ser Lys Ala Lys Gly
            355                 360                 365

Gln Pro Arg Glu Pro Gln Val Tyr Thr Leu Pro Pro Ser Arg Asp Glu
370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
435                 440                 445

Val Phe Ser Cys Ser Val Met His Glu Ala Leu His Asn His Tyr Thr
            450                 455                 460

Gln Lys Ser Leu Ser Leu Ser Pro Gly Lys
465                 470

<210> SEQ ID NO 50
<211> LENGTH: 217
<212> TYPE: PRT
<213> ORGANISM: Homo sapiens

<400> SEQUENCE: 50

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asp Asn
            20                  25                  30

Tyr Val Ser Trp Tyr Gln His Leu Pro Gly Thr Ala Pro Lys Leu Leu
        35                  40                  45

Ile Tyr Glu Asn Thr Arg Arg Pro Ser Gly Ile Pro Asp Arg Phe Ser
    50                  55                  60

Gly Ser Lys Ser Gly Thr Ser Ala Thr Leu Ala Ile Thr Gly Leu Gln
65                  70                  75                  80

Thr Gly Asp Glu Ala Asp Tyr Tyr Cys Gly Thr Trp Asp Val Arg Pro
                85                  90                  95

Asn Arg Gly Ala Val Phe Gly Thr Gly Thr Lys Val Thr Val Leu Gly
            100                 105                 110

Gln Pro Lys Ala Asp Pro Thr Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
210                 215

<210> SEQ ID NO 51
<211> LENGTH: 144
<212> TYPE: PRT
<213> ORGANISM: Homo sapiens

<400> SEQUENCE: 51

```
Gln Ala Ile Leu Val Glu Ser Gly Gly Val Val Gln Pro Gly Arg
1               5                   10                  15

Ser Leu Arg Leu Ser Cys Ala Ala Ser Gln Phe Thr Phe Ser Gly His
                20                  25                  30

Gly Leu His Trp Val Arg Gln Ala Pro Gly Lys Gly Leu Glu Trp Val
            35                  40                  45

Ala Ser Ile Ser Phe Ala Gly Thr Lys Met Asp Tyr Ala Asp Ser Val
50                  55                  60

Lys Gly Arg Phe Ala Ile Ser Arg Asp Asn Ser Lys Asn Thr Leu Tyr
65                  70                  75                  80

Leu Gln Met Asn Ser Leu Arg Val Glu Asp Thr Ala Leu Tyr Tyr Cys
                85                  90                  95

Ala Lys Asp Met Arg Glu Tyr Glu Cys Glu Tyr Trp Thr Ser Asp Tyr
            100                 105                 110

Tyr Asp Phe Gly Arg Pro Gln Pro Cys Ile Asp Arg Gly Val Val
        115                 120                 125

Gly Ile Phe Asp Met Trp Gly Gln Gly Thr Met Val Thr Val Ser Thr
130                 135                 140
```

<210> SEQ ID NO 52
<211> LENGTH: 111
<212> TYPE: PRT
<213> ORGANISM: Homo sapiens

<400> SEQUENCE: 52

```
Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asp Asn
                20                  25                  30

Tyr Val Ser Trp Tyr Gln His Leu Pro Gly Thr Ala Pro Lys Leu Leu
            35                  40                  45

Ile Tyr Glu Asn Thr Arg Arg Pro Ser Gly Ile Pro Asp Arg Phe Ser
50                  55                  60

Gly Ser Lys Ser Gly Thr Ser Ala Thr Leu Ala Ile Thr Gly Leu Gln
65                  70                  75                  80

Thr Gly Asp Glu Ala Asp Tyr Tyr Cys Gly Thr Trp Asp Val Arg Pro
                85                  90                  95

Asn Arg Gly Ala Val Phe Gly Thr Gly Thr Lys Val Thr Val Leu
            100                 105                 110
```

<210> SEQ ID NO 53
<211> LENGTH: 473
<212> TYPE: PRT
<213> ORGANISM: Homo sapiens

<400> SEQUENCE: 53

```
Glu Val Gln Leu Val Glu Ser Gly Gly Val Val Pro Pro Gly Lys
1               5                   10                  15

Ser Leu Thr Leu Ser Cys Val Ala Ser Arg Phe Thr Phe Ser Ala Phe
                20                  25                  30

Gly Met His Trp Val Arg Gln Ala Pro Gly Lys Gly Leu Glu Trp Val
            35                  40                  45
```

```
Ala Ser Ile Ser Phe Ala Gly Ile Lys Lys Tyr Tyr Ala Asp Ser Val
 50                  55                  60
Lys Gly Arg Phe Ser Ile Ser Arg Asp Asn Ser Asn Thr Leu Phe Leu
 65                  70                  75                  80
Gln Met Asn Gly Leu Arg Gly Glu Asp Thr Gly Leu Tyr His Cys Val
                     85                  90                  95
Lys Asp Met Arg Glu Leu Glu Cys Glu Glu Trp Ala Ser Asp Tyr Tyr
                100                 105                 110
Asp Phe Gly Lys Pro Gln Pro Cys Leu Asp Arg Arg Gly Val Ser Gly
            115                 120                 125
Ile Ser Ala Trp Trp Gly Pro Gly Thr Met Val Thr Val Ser Ser Ala
        130                 135                 140
Ser Thr Lys Gly Pro Ser Val Phe Pro Leu Ala Pro Ser Ser Lys Ser
145                 150                 155                 160
Thr Ser Gly Gly Thr Ala Ala Leu Gly Cys Leu Val Lys Asp Tyr Phe
                165                 170                 175
Pro Glu Pro Val Thr Val Ser Trp Asn Ser Gly Ala Leu Thr Ser Gly
                180                 185                 190
Val His Thr Phe Pro Ala Val Leu Gln Ser Ser Gly Leu Tyr Ser Leu
            195                 200                 205
Ser Ser Val Val Thr Val Pro Ser Ser Ser Leu Gly Thr Gln Thr Tyr
        210                 215                 220
Ile Cys Asn Val Asn His Lys Pro Ser Asn Thr Lys Val Asp Lys Lys
225                 230                 235                 240
Val Glu Pro Lys Ser Cys Asp Lys Thr His Thr Cys Pro Pro Cys Pro
                245                 250                 255
Ala Pro Glu Leu Leu Gly Gly Pro Ser Val Phe Leu Phe Pro Pro Lys
                260                 265                 270
Pro Lys Asp Thr Leu Met Ile Ser Arg Thr Pro Glu Val Thr Cys Val
            275                 280                 285
Val Val Asp Val Ser His Glu Asp Pro Glu Val Lys Phe Asn Trp Tyr
        290                 295                 300
Val Asp Gly Val Glu Val His Asn Ala Lys Thr Lys Pro Arg Glu Glu
305                 310                 315                 320
Gln Tyr Asn Ser Thr Tyr Arg Val Val Ser Val Leu Thr Val Leu His
                325                 330                 335
Gln Asp Trp Leu Asn Gly Lys Glu Tyr Lys Cys Lys Val Ser Asn Lys
            340                 345                 350
Ala Leu Pro Ala Pro Ile Glu Lys Thr Ile Ser Lys Ala Lys Gly Gln
        355                 360                 365
Pro Arg Glu Pro Gln Val Tyr Thr Leu Pro Pro Ser Arg Asp Glu Leu
        370                 375                 380
Thr Lys Asn Gln Val Ser Leu Thr Cys Leu Val Lys Gly Phe Tyr Pro
385                 390                 395                 400
Ser Asp Ile Ala Val Glu Trp Glu Ser Asn Gly Gln Pro Glu Asn Asn
                405                 410                 415
Tyr Lys Thr Thr Pro Pro Val Leu Asp Ser Asp Gly Ser Phe Phe Leu
            420                 425                 430
Tyr Ser Lys Leu Thr Val Asp Lys Ser Arg Trp Gln Gln Gly Asn Val
        435                 440                 445
Phe Ser Cys Ser Val Met His Glu Ala Leu His Asn His Tyr Thr Gln
        450                 455                 460
```

```
Lys Ser Leu Ser Leu Ser Pro Gly Lys
465                 470
```

<210> SEQ ID NO 54
<211> LENGTH: 213
<212> TYPE: PRT
<213> ORGANISM: Homo sapiens

<400> SEQUENCE: 54

```
Gln Ser Val Leu Thr Gln Pro Pro Ser Val Ser Ala Ala Pro Gly Gln
1               5                   10                  15

Asn Val Thr Ile Ser Cys Ser Gly Pro Pro Ser His Ile Glu Lys Asn
            20                  25                  30

Asp Val Ser Trp Tyr Gln Arg Leu Pro Gly Met Ala Pro Lys Met Val
        35                  40                  45

Ile Tyr Glu Ser Lys Arg Arg Pro Leu Gly Ile Pro Val Arg Phe Ser
50                  55                  60

Ala Ser Arg Ser Gly Ser Ser Ala Thr Leu Val Ile Thr Gly Leu Gln
65                  70                  75                  80

Thr Ala Asp Glu Ala Asp Tyr Tyr Cys Gly Thr Trp Asp Gly Arg Met
                85                  90                  95

Asn Phe Gly Thr Gly Thr Thr Val Ser Val Leu Gly Gln Pro Lys Ala
            100                 105                 110

Asp Pro Thr Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210
```

<210> SEQ ID NO 55
<211> LENGTH: 143
<212> TYPE: PRT
<213> ORGANISM: Homo sapiens

<400> SEQUENCE: 55

```
Glu Val Gln Leu Val Glu Ser Gly Gly Gly Val Val Pro Pro Gly Lys
1               5                   10                  15

Ser Leu Thr Leu Ser Cys Val Ala Ser Arg Phe Thr Phe Ser Ala Phe
            20                  25                  30

Gly Met His Trp Val Arg Gln Ala Pro Gly Lys Gly Leu Glu Trp Val
        35                  40                  45

Ala Ser Ile Ser Phe Ala Gly Ile Lys Lys Tyr Tyr Ala Asp Ser Val
50                  55                  60

Lys Gly Arg Phe Ser Ile Ser Arg Asp Asn Ser Asn Thr Leu Phe Leu
65                  70                  75                  80

Gln Met Asn Gly Leu Arg Gly Glu Asp Thr Gly Leu Tyr His Cys Val
                85                  90                  95
```

```
Lys Asp Met Arg Glu Leu Glu Cys Glu Glu Trp Ala Ser Asp Tyr Tyr
                100                 105                 110

Asp Phe Gly Lys Pro Gln Pro Cys Leu Asp Arg Arg Gly Val Ser Gly
            115                 120                 125

Ile Ser Ala Trp Trp Gly Pro Gly Thr Met Val Thr Val Ser Ser
    130                 135                 140

<210> SEQ ID NO 56
<211> LENGTH: 107
<212> TYPE: PRT
<213> ORGANISM: Homo sapiens

<400> SEQUENCE: 56

Gln Ser Val Leu Thr Gln Pro Pro Ser Val Ser Ala Ala Pro Gly Gln
1               5                   10                  15

Asn Val Thr Ile Ser Cys Ser Gly Pro Ser His Ile Glu Lys Asn
            20                  25                  30

Asp Val Ser Trp Tyr Gln Arg Leu Pro Gly Met Ala Pro Lys Met Val
        35                  40                  45

Ile Tyr Glu Ser Lys Arg Arg Pro Leu Gly Ile Pro Val Arg Phe Ser
    50                  55                  60

Ala Ser Arg Ser Gly Ser Ser Ala Thr Leu Val Ile Thr Gly Leu Gln
65                  70                  75                  80

Thr Ala Asp Glu Ala Asp Tyr Tyr Cys Gly Thr Trp Asp Gly Arg Met
                85                  90                  95

Asn Phe Gly Thr Gly Thr Thr Val Ser Val Leu
                100                 105

<210> SEQ ID NO 57
<211> LENGTH: 474
<212> TYPE: PRT
<213> ORGANISM: Homo sapiens

<400> SEQUENCE: 57

Glu Val Gln Leu Val Gln Ser Gly Gly Gly Val Val Gln Pro Gly Arg
1               5                   10                  15

Ser Leu Arg Leu Ser Cys Ala Ala Pro Tyr Phe Glu Phe Gly Arg Tyr
            20                  25                  30

Gly Phe His Trp Val Arg Gln Ala Pro Gly Lys Gly Leu Glu Trp Val
        35                  40                  45

Ala Ser Ile Ser Phe Ala Gly Arg Asp Tyr Tyr His Ser Pro Ser Val
    50                  55                  60

Trp Gly Arg Phe Thr Ile Ser Arg Asp Asn Ser Lys Asn Thr Leu Tyr
65                  70                  75                  80

Leu Gln Met Asn Ser Leu Arg Ile Glu Asp Thr Ala Leu Tyr Phe Cys
                85                  90                  95

Ala Arg Asp Leu Arg Glu Ser Glu Cys Glu Glu Trp Glu Ser Asp Tyr
                100                 105                 110

Tyr Asp Phe Gly Lys Lys Gly Pro Cys Val Lys Pro Arg Gly Val Ala
            115                 120                 125

Gly Gly Leu Asp Leu Trp Gly Gln Gly Thr Met Val Ile Val Ser Ser
    130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175
```

Phe Pro Glu Pro Val Thr Val Ser Trp Asn Ser Gly Ala Leu Thr Ser
                180                 185                 190

Gly Val His Thr Phe Pro Ala Val Leu Gln Ser Gly Leu Tyr Ser
            195                 200                 205

Leu Ser Ser Val Val Thr Val Pro Ser Ser Ser Leu Gly Thr Gln Thr
210                 215                 220

Tyr Ile Cys Asn Val Asn His Lys Pro Ser Asn Thr Lys Val Asp Lys
225                 230                 235                 240

Lys Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
                260                 265                 270

Lys Pro Lys Asp Thr Leu Met Ile Ser Arg Thr Pro Glu Val Thr Cys
                275                 280                 285

Val Val Val Asp Val Ser His Glu Asp Pro Glu Val Lys Phe Asn Trp
290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
                340                 345                 350

Lys Ala Leu Pro Ala Pro Ile Glu Lys Thr Ile Ser Lys Ala Lys Gly
                355                 360                 365

Gln Pro Arg Glu Pro Gln Val Tyr Thr Leu Pro Pro Ser Arg Asp Glu
                370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
                420                 425                 430

Leu Tyr Ser Lys Leu Thr Val Asp Lys Ser Arg Trp Gln Gln Gly Asn
                435                 440                 445

Val Phe Ser Cys Ser Val Met His Glu Ala Leu His Asn His Tyr Thr
450                 455                 460

Gln Lys Ser Leu Ser Leu Ser Pro Gly Lys
465                 470

<210> SEQ ID NO 58
<211> LENGTH: 213
<212> TYPE: PRT
<213> ORGANISM: Homo sapiens

<400> SEQUENCE: 58

Gln Ser Val Leu Thr Gln Pro Pro Ser Val Ser Thr Ala Pro Gly Gln
1               5                   10                  15

Thr Val Thr Val Ser Cys Ser Gly Gly Thr Ser Asn Thr Gly Asn Asn
                20                  25                  30

Phe Val Ser Trp Tyr Gln His Leu Pro Gly Thr Ala Pro Lys Leu Leu
            35                  40                  45

Ile Tyr Glu Asn Asn Lys Arg Pro Leu Gly Val Pro Asp Arg Phe Ser
        50                  55                  60

Gly Ala Lys Ser Gly Thr Ser Ala Thr Leu Ala Ile Thr Gly Leu Gln
65                  70                  75                  80

```
Thr Gly Asp Glu Gly Asp Tyr Tyr Cys Ala Thr Trp Ser Gly Ser Leu
                85                  90                  95

Asn Ile Gly Thr Gly Thr Lys Val Ser Val Leu Gly Gln Pro Lys Ala
            100                 105                 110

Asp Pro Thr Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210
```

<210> SEQ ID NO 59
<211> LENGTH: 144
<212> TYPE: PRT
<213> ORGANISM: Homo sapiens

<400> SEQUENCE: 59

```
Glu Val Gln Leu Val Gln Ser Gly Gly Gly Val Val Gln Pro Gly Arg
1               5                   10                  15

Ser Leu Arg Leu Ser Cys Ala Ala Pro Tyr Phe Glu Phe Gly Arg Tyr
            20                  25                  30

Gly Phe His Trp Val Arg Gln Ala Pro Gly Lys Gly Leu Glu Trp Val
        35                  40                  45

Ala Ser Ile Ser Phe Ala Gly Arg Asp Tyr Tyr His Ser Pro Ser Val
    50                  55                  60

Trp Gly Arg Phe Thr Ile Ser Arg Asp Asn Ser Lys Asn Thr Leu Tyr
65                  70                  75                  80

Leu Gln Met Asn Ser Leu Arg Ile Glu Asp Thr Ala Leu Tyr Phe Cys
                85                  90                  95

Ala Arg Asp Leu Arg Glu Ser Glu Cys Glu Glu Trp Glu Ser Asp Tyr
            100                 105                 110

Tyr Asp Phe Gly Lys Lys Gly Pro Cys Val Lys Pro Arg Gly Val Ala
        115                 120                 125

Gly Gly Leu Asp Leu Trp Gly Gln Gly Thr Met Val Ile Val Ser Ser
    130                 135                 140
```

<210> SEQ ID NO 60
<211> LENGTH: 107
<212> TYPE: PRT
<213> ORGANISM: Homo sapiens

<400> SEQUENCE: 60

```
Gln Ser Val Leu Thr Gln Pro Pro Ser Val Ser Thr Ala Pro Gly Gln
1               5                   10                  15

Thr Val Thr Val Ser Cys Ser Gly Gly Thr Ser Asn Thr Gly Asn Asn
            20                  25                  30

Phe Val Ser Trp Tyr Gln His Leu Pro Gly Thr Ala Pro Lys Leu Leu
        35                  40                  45
```

```
Ile Tyr Glu Asn Asn Lys Arg Pro Leu Gly Val Pro Asp Arg Phe Ser
         50                  55                  60

Gly Ala Lys Ser Gly Thr Ser Ala Thr Leu Ala Ile Thr Gly Leu Gln
 65                  70                  75                  80

Thr Gly Asp Glu Gly Asp Tyr Tyr Cys Ala Thr Trp Ser Gly Ser Leu
                 85                  90                  95

Asn Ile Gly Thr Gly Thr Lys Val Ser Val Leu
            100                 105
```

```
<210> SEQ ID NO 61
<211> LENGTH: 1425
<212> TYPE: DNA
<213> ORGANISM: Artificial sequence
<220> FEATURE:
<223> OTHER INFORMATION: Unmutated common ancestor

<400> SEQUENCE: 61
caggtgcagc tggtggagtc tgggggaggc gtggtccagc ctgggaggtc cctgagactc      60
tcctgtgcag cctctggatt caccttcagt agctatggca tgcactgggt ccgccaggct     120
ccaggcaagg ggctggagtg ggtggcagtt atatcatatg atggaagtaa taaatactat     180
gcagactccg tgaagggccg attcaccatc tccagagaca attccaagaa cacgctgtat     240
ctgcaaatga acagcctgag agctgaggac acggctgtgt attactgtgc gaaagatctg     300
ggagaaagcg aaaatgaaga gtgggcgacg gattattacg atttttcgat tggttaccct     360
ggccaagacc cacggggcgt ggttggagct tttgatatct ggggccaagg acaatggtc      420
accgtctctt cagcgtcgac caagggccca tcggtcttcc ccctggcacc ctcctccaag     480
agcacctctg ggggcacagc ggccctgggc tgcctggtca aggactactt ccccgaaccc     540
gtgacggtgt cgtggaactc aggcgccctg accagcggcg tgcacacctt cccggctgtc     600
ctacagtcct caggactcta ctccctcagc agcgtggtga ccgtgccctc agcagcttg      660
ggcacccaga cctacatctg caacgtgaat cacaagccca gcaacaccaa ggtggacaag     720
aaagttgagc ccaaatcttg tgacaaaact cacacatgcc caccgtgccc agcacctgaa     780
ctcctggggg gaccgtcagt cttcctcttc cccccaaaac ccaaggacac cctcatgatc     840
tcccggaccc ctgaggtcac atgcgtggtg gtggacgtga gccacgaaga ccctgaggtc     900
aagttcaact ggtacgtgga cggcgtggag gtgcataatg ccaagacaaa gccgcgggag     960
gagcagtaca acagcacgta ccgtgtggtc agcgtcctca ccgtcctgca ccaggactgg    1020
ctgaatggca aggagtacaa gtgcaaggtc tccaacaaag ccctcccagc ccccatcgag    1080
aaaaccatct ccaaagccaa agggcagccc cgagaaccac aggtgtacac cctgccccca    1140
tcccgggatg agctgaccaa gaaccaggtc agcctgacct gcctggtcaa aggcttctat    1200
cccagcgaca tcgccgtgga gtgggagagc aatgggcagc cggagaacaa ctacaagacc    1260
acgcctcccg tgctggactc cgacggctcc ttcttcctct acagcaagct caccgtggac    1320
aagagcaggt ggcagcaggg gaacgtcttc tcatgctccg tgatgcatga ggctctgcac    1380
aaccactaca cgcagaagag cctctccctg tctccgggta aatga                    1425
```

```
<210> SEQ ID NO 62
<211> LENGTH: 654
<212> TYPE: DNA
<213> ORGANISM: Artificial sequence
<220> FEATURE:
<223> OTHER INFORMATION: Unmutated common ancestor
```

<400> SEQUENCE: 62

```
cagtctgtgt tgacgcagcc gccctcagtg tctgcggccc caggacagaa ggtcaccatc    60
tcctgctctg gaagcagctc caacattggg aataattatg tatcctggta ccagcagctc   120
ccaggaacag cccccaaact cctcatctat gaaaataata gcgaccctca gggattcct    180
gaccgattct ctggctccaa gtctggcacg tcagccaccc tgggcatcac cggactccag   240
actggggacg aggccgatta ttactgcgga acatgggata gcagcctgag tgctggcggt   300
gtcttcggaa ctgggaccaa agtcaccgtc ctaggtcagc ccaaggccaa ccccactgtc   360
actctgttcc cgccctcgag tgaggagctt caagccaaca ggccacact ggtgtgtctc    420
ataagtgact tctacccggg agccgtgaca gtggcctgga aggcagatag cagccccgtc   480
aaggcgggag tggagaccac cacaccctcc aaacaaagca caacaagta cgcggccagc    540
agctacctga gcctgacgcc tgagcagtgg aagtcccaca aagctacag ctgccaggtc    600
acgcatgaag ggagcaccgt ggagaagaca gtggccccta cagaatgttc atag         654
```

<210> SEQ ID NO 63
<211> LENGTH: 432
<212> TYPE: DNA
<213> ORGANISM: Artificial sequence
<220> FEATURE:
<223> OTHER INFORMATION: Unmutated common ancestor

<400> SEQUENCE: 63

```
caggtgcagc tggtggagtc tgggggaggc gtggtccagc ctgggaggtc cctgagactc    60
tcctgtgcag cctctggatt caccttcagt agctatggca tgcactgggt ccgccaggct   120
ccaggcaagg ggctggagtg ggtggcagtt atatcatatg atggaagtaa taaatactat   180
gcagactccg tgaagggccg attcaccatc tccagagaca attccaagaa cacgctgtat   240
ctgcaaatga acagcctgag agctgaggac acggctgtgt attactgtgc gaaagatctg   300
ggagaaagcg aaaatgaaga gtgggcgacg gattattacg atttttcgat tggttaccct   360
ggccaagacc cacggggcgt ggttggagct tttgatatct ggggccaagg gacaatggtc   420
accgtctctt ca                                                         432
```

<210> SEQ ID NO 64
<211> LENGTH: 333
<212> TYPE: DNA
<213> ORGANISM: Artificial sequence
<220> FEATURE:
<223> OTHER INFORMATION: Unmutated common ancestor

<400> SEQUENCE: 64

```
cagtctgtgt tgacgcagcc gccctcagtg tctgcggccc caggacagaa ggtcaccatc    60
tcctgctctg gaagcagctc caacattggg aataattatg tatcctggta ccagcagctc   120
ccaggaacag cccccaaact cctcatctat gaaaataata gcgaccctca gggattcct    180
gaccgattct ctggctccaa gtctggcacg tcagccaccc tgggcatcac cggactccag   240
actggggacg aggccgatta ttactgcgga acatgggata gcagcctgag tgctggcggt   300
gtcttcggaa ctgggaccaa agtcaccgtc cta                                  333
```

<210> SEQ ID NO 65
<211> LENGTH: 1425
<212> TYPE: DNA
<213> ORGANISM: Artificial sequence
<220> FEATURE:
<223> OTHER INFORMATION: Inferred intermediate sequence

<400> SEQUENCE: 65

```
caggtgcagc tggtggagtc tgggggaggc gtggtccagc ctgggaggtc cctgagactc    60
tcctgtgcag cctctggatt caccttcagt aactatgcca tggactgggt ccgccaggct   120
ccaggcaagg ggctggagtg ggtggcagtt atatcatctg atggaagtaa taaaaactat   180
gcagactccg tgaagggccg attcaccatc tccagagaca attccaagaa cacgctgtat   240
ctgcaaatga acagtctgag agctgaggac acggctgtgt attactgtgc gaaagatctg   300
ggagaaaaca aaaatgatga gtgggcgacg gattattatg atttgtcgat tgcttaccct   360
gtccaagacc cacgggccgt ggttggagct tttgatatct ggggccaagg gacaatggtc   420
accgtctctt cagcgtcgac caagggccca tcggtcttcc ccctggcacc ctcctccaag   480
agcacctctg ggggcacagc ggccctgggc tgcctggtca aggactactt ccccgaaccc   540
gtgacggtgt cgtggaactc aggcgccctg accagcggcg tgcacacctt cccggctgtc   600
ctacagtcct caggactcta ctccctcagc agcgtggtga ccgtgccctc cagcagcttg   660
ggcacccaga cctacatctg caacgtgaat cacaagccca gcaacaccaa ggtggacaag   720
aaagttgagc ccaaatcttg tgacaaaact cacacatgcc caccgtgccc agcacctgaa   780
ctcctggggg gaccgtcagt cttcctcttc cccccaaaac ccaaggacac cctcatgatc   840
tcccggaccc ctgaggtcac atgcgtggtg gtggacgtga gccacgaaga ccctgaggtc   900
aagttcaact ggtacgtgga cggcgtggag gtgcataatg ccaagacaaa gccgcgggag   960
gagcagtaca acagcacgta ccgtgtggtc agcgtcctca ccgtcctgca ccaggactgg  1020
ctgaatggca aggagtacaa gtgcaaggtc tccaacaaag ccctcccagc ccccatcgag  1080
aaaaccatct ccaaagccaa agggcagccc cgagaaccac aggtgtacac cctgcccca   1140
tcccgggatg agctgaccaa gaaccaggtc agcctgacct gcctggtcaa aggcttctat  1200
cccagcgaca tcgccgtgga gtgggagagc aatgggcagc cggagaacaa ctacaagacc  1260
acgcctcccg tgctggactc cgacggctcc ttcttcctct acagcaagct caccgtggac  1320
aagagcaggt ggcagcaggg gaacgtcttc tcatgctccg tgatgcatga ggctctgcac  1380
aaccactaca cgcagaagag cctctccctg tctccgggta aatga                  1425
```

<210> SEQ ID NO 66
<211> LENGTH: 654
<212> TYPE: DNA
<213> ORGANISM: Artificial sequence
<220> FEATURE:
<223> OTHER INFORMATION: Inferred intermediate sequence

<400> SEQUENCE: 66

```
cagtctgtgt tgacgcagcc gccctcagtg tctgcggccc caggacagaa ggtcaccatc    60
tcctgctctg gaagcagctc caacattggg aataattatg tatcctggta ccagcagctc   120
ccaggaacag cccccaaact cctcatctat aaaaataatg agcgaccctc agggattcct   180
gaccgattct ctggctccaa gtctggcacg tcagccaccc tgggcatcac cggactccag   240
actggggacg aggccgatta ttactgcgga acatgggata ccagcctgag tgctggcggt   300
gtcttcggaa ctgggaccaa ggtcaccgtc ctaggtcagc ccaaggccaa ccccactgtc   360
actctgttcc cgccctcgag tgaggagctt caagccaaca ggccacact ggtgtgtctc   420
ataagtgact tctacccggg agccgtgaca gtggcctgga aggcagatag cagccccgtc   480
aaggcgggag tggagaccac cacaccctcc aaacaaagca caacaagta cgcggccagc   540
```

| | |
|---|---|
| agctacctga gcctgacgcc tgagcagtgg aagtcccaca gaagctacag ctgccaggtc | 600 |
| acgcatgaag ggagcaccgt ggagaagaca gtggccccta cagaatgttc atag | 654 |

<210> SEQ ID NO 67
<211> LENGTH: 432
<212> TYPE: DNA
<213> ORGANISM: Artificial sequence
<220> FEATURE:
<223> OTHER INFORMATION: Inferred intermediate sequence

<400> SEQUENCE: 67

| | |
|---|---|
| caggtgcagc tggtggagtc tgggggaggc gtggtccagc ctgggaggtc cctgagactc | 60 |
| tcctgtgcag cctctggatt caccttcagt aactatgcca tggactgggt ccgccaggct | 120 |
| ccaggcaagg ggctgagtg gtggcagtt atatcatctg atggaagtaa taaaaactat | 180 |
| gcagactccg tgaagggccg attcaccatc tccagagaca attccaagaa cacgctgtat | 240 |
| ctgcaaatga acagtctgag agctgaggac acggctgtgt attactgtgc gaaagatctg | 300 |
| ggagaaaaca aaaatgatga gtgggcgacg gattattatg atttgtcgat tgcttaccct | 360 |
| gtccaagacc cacgggccgt ggttggagct tttgatatct ggggccaagg gacaatggtc | 420 |
| accgtctctt ca | 432 |

<210> SEQ ID NO 68
<211> LENGTH: 333
<212> TYPE: DNA
<213> ORGANISM: Artificial sequence
<220> FEATURE:
<223> OTHER INFORMATION: Inferred intermediate sequence

<400> SEQUENCE: 68

| | |
|---|---|
| cagtctgtgt tgacgcagcc gccctcagtg tctgcggccc caggacagaa ggtcaccatc | 60 |
| tcctgctctg gaagcagctc aacattggg aataattatg tatcctggta ccagcagctc | 120 |
| ccaggaacag cccccaaaact cctcatctat aaaaataatg agcgaccctc agggattcct | 180 |
| gaccgattct ctggctccaa gtctggcacg tcagccaccc tgggcatcac cggactccag | 240 |
| actggggacg aggccgatta ttactgcgga acatgggata ccagcctgag tgctggcggt | 300 |
| gtcttcggaa ctgggaccaa ggtcaccgtc cta | 333 |

<210> SEQ ID NO 69
<211> LENGTH: 1425
<212> TYPE: DNA
<213> ORGANISM: Artificial sequence
<220> FEATURE:
<223> OTHER INFORMATION: Inferred intermediate sequence

<400> SEQUENCE: 69

| | |
|---|---|
| caagtgcagc tggtggagtc tgggggaggc gtggtccagc ctgggaggtc cctgagactc | 60 |
| tcctgtgcag cctctggatt cactttcagt aactttgcca tgggctgggt ccgccaggct | 120 |
| ccgggcaagg gtctggagtg gtggcgtttt atatcatctg atggaagtaa taaaaactat | 180 |
| ggagactccg tgaagggccg attcaccatc tccagagaca attccaagaa cacgctgttc | 240 |
| ctgcaaatga acagtctgag agctgaggac acggctttgt attactgtgc gaaagatgtg | 300 |
| ggagaataca aaagtgatga gtgggcgacg gattattatg atctttcgat tgcttaccct | 360 |
| attcaagacc cacgggccat ggttggagct tttgatatct ggggccaagg gacaatggtc | 420 |
| accgtctctt cagcgtcgac caagggccca tcggtcttcc ccctggcacc ctcctccaag | 480 |
| agcacctctg ggggcacagc ggccctgggc tgcctggtca aggactactt ccccgaaccc | 540 |

```
gtgacggtgt cgtggaactc aggcgccctg accagcggcg tgcacacctt cccggctgtc    600
ctacagtcct caggactcta ctccctcagc agcgtggtga ccgtgccctc agcagcttg     660 ggcacccaga cctacatctg caacgtgaat cacaagccca gcaacaccaa ggtggacaag    720
aaagttgagc ccaaatcttg tgacaaaact cacacatgcc caccgtgccc agcacctgaa    780
ctcctggggg gaccgtcagt cttcctcttc cccccaaaac ccaaggacac cctcatgatc    840
tcccggaccc ctgaggtcac atgcgtggtg gtggacgtga gccacgaaga ccctgaggtc    900
aagttcaact ggtacgtgga cggcgtggag gtgcataatg ccaagacaaa gccgcgggag    960
gagcagtaca acagcacgta ccgtgtggtc agcgtcctca ccgtcctgca ccaggactgg   1020
ctgaatggca aggagtacaa gtgcaaggtc tccaacaaag ccctcccagc ccccatcgag   1080
aaaaccatct ccaaagccaa agggcagccc cgagaaccac aggtgtacac cctgccccca   1140
tcccgggatg agctgaccaa gaaccaggtc agcctgacct gcctggtcaa aggcttctat   1200
cccagcgaca tcgccgtgga gtgggagagc aatgggcagc cggagaacaa ctacaagacc   1260
acgcctcccg tgctggactc cgacggctcc ttcttcctct acagcaagct caccgtggac   1320
aagagcaggt ggcagcaggg gaacgtcttc tcatgctccg tgatgcatga ggctctgcac   1380
aaccactaca cgcagaagag cctctccctg tctccgggta aatga                   1425
```

<210> SEQ ID NO 70
<211> LENGTH: 654
<212> TYPE: DNA
<213> ORGANISM: Artificial sequence
<220> FEATURE:
<223> OTHER INFORMATION: Inferred intermediate sequence

<400> SEQUENCE: 70

```
cagtctgtgt tgacgcagcc gccctcagtg tctgcggccc caggacagaa ggtcaccatc     60
tcctgctctg gaagcagctc caccattggg aataattatg tatcctggta ccagctactc    120
ccaggaacag ccccccaaact cctcatctat aaaaatgata gcgaccctc agggattcct     180 gaccgattct ctggctccaa gtctggcacg tcagccaccc tgggcatcac cggactccag    240
actggggacg aggccgatta ttactgcgga acatgggata ccagcctgag tgctggcggt    300
gtcttcggaa ctgggaccaa ggtcaccgtc ctaggtcagc ccaaggccaa ccccactgtc    360
actctgttcc cgccctcgag tgaggagctt caagccaaca ggccacact ggtgtgtctc     420 ataagtgact tctacccggg agccgtgaca gtggcctgga aggcagatag cagccccgtc    480
aaggcgggag tggagaccac cacaccctcc aaacaaagca acaacaagta cgcggccagc    540
agctacctga gcctgacgcc tgagcagtgg aagtcccaca aagctacag ctgccaggtc      600 acgcatgaag ggagcaccgt ggagaagaca gtggccccta cagaatgttc atag          654
```

<210> SEQ ID NO 71
<211> LENGTH: 432
<212> TYPE: DNA
<213> ORGANISM: Artificial sequence
<220> FEATURE:
<223> OTHER INFORMATION: Inferred intermediate sequence

<400> SEQUENCE: 71

```
caagtgcagc tggtggagtc tgggggaggc gtggtccagc ctgggaggtc cctgagactc     60
tcctgtgcag cctctggatt cactttcagt aactttgcca tggctgggt ccgccaggct     120 ccgggcaagg gtctggagtg ggtggcgttt atatcatctg atggaagtaa taaaaactat    180
```

| | |
|---|---|
| ggagactccg tgaagggccg attcaccatc tccagagaca attccaagaa cacgctgttc | 240 |
| ctgcaaatga acagtctgag agctgaggac acggctttgt attactgtgc gaaagatgtg | 300 |
| ggagaataca aaagtgatga gtgggcgacg gattattatg atctttcgat tgcttaccct | 360 |
| attcaagacc cacgggccat ggttggagct tttgatatct ggggccaagg gacaatggtc | 420 |
| accgtctctt ca | 432 |

<210> SEQ ID NO 72
<211> LENGTH: 333
<212> TYPE: DNA
<213> ORGANISM: Artificial sequence
<220> FEATURE:
<223> OTHER INFORMATION: Inferred intermediate sequence

<400> SEQUENCE: 72

| | |
|---|---|
| cagtctgtgt tgacgcagcc gccctcagtg tctgcggccc caggacagaa ggtcaccatc | 60 |
| tcctgctctg gaagcagctc caccattggg aataattatg tatcctggta ccagctactc | 120 |
| ccaggaacag ccccccaaact cctcatctat aaaaatgata agcgaccctc agggattcct | 180 |
| gaccgattct ctggctccaa gtctggcacg tcagccaccc tgggcatcac cggactccag | 240 |
| actggggacg aggccgatta ttactgcgga acatgggata ccagcctgag tgctggcggt | 300 |
| gtcttcggaa ctgggaccaa ggtcaccgtc cta | 333 |

<210> SEQ ID NO 73
<211> LENGTH: 1425
<212> TYPE: DNA
<213> ORGANISM: Homo sapiens

<400> SEQUENCE: 73

| | |
|---|---|
| gaagtgcagg tggtggagtc tgggggaggc gtggtccagc ctgggaggtc cctgagactc | 60 |
| tcctgtacag cctctggatt cactttcagc aactttgcca tgggctgggt ccgccaggct | 120 |
| ccgggcaagg gtctggagtg gtggcctttt atatcatctg atggaagtaa taaaaactat | 180 |
| ggagactccg tgaagggccg attcaccatc tccagagaca attccaagaa cacggtgttc | 240 |
| ctgcaaatga acagtctgag agttgaggac acggctttgt attactgtgc gaaagatgtg | 300 |
| ggagactaca aaagtgatga gtggggacg gaatattatg atatttcgat ttcttaccct | 360 |
| attcaagacc cacgggccat ggttggagct tttgatctct ggggccaagg gacaatggtc | 420 |
| accgtctctc cagcgtcgac caagggccca tcggtcttcc ccctggcacc ctcctccaag | 480 |
| agcacctctg ggggcacagc ggccctgggc tgcctggtca aggactactt ccccgaaccc | 540 |
| gtgacggtgt cgtggaactc aggcgccctg accagcggcg tgcacacctt cccggctgtc | 600 |
| ctacagtcct caggactcta ctccctcagc agcgtggtga ccgtgccctc cagcagcttg | 660 |
| ggcacccaga cctacatctg caacgtgaat cacaagccca gcaacaccaa ggtggacaag | 720 |
| aaagttgagc ccaaatcttg tgacaaaact cacacatgcc caccgtgccc agcacctgaa | 780 |
| ctcctggggg gaccgtcagt cttcctcttc cccccaaaac ccaaggacac cctcatgatc | 840 |
| tcccggaccc ctgaggtcac atgcgtggtg gtggacgtga gccacgaaga ccctgaggtc | 900 |
| aagttcaact ggtacgtgga cggcgtggag gtgcataatg ccaagacaaa gccgcgggag | 960 |
| gagcagtaca acagcacgta ccgtgtggtc agcgtcctca ccgtcctgca ccaggactgg | 1020 |
| ctgaatggca aggagtacaa gtgcaaggtc tccaacaaag ccctcccagc ccccatcgag | 1080 |
| aaaaccatct ccaaagccaa agggcagccc cgagaaccac aggtgtacac cctgccccca | 1140 |
| tcccgggatg agctgaccaa gaaccaggtc agcctgacct gcctggtcaa aggcttctat | 1200 |

```
cccagcgaca tcgccgtgga gtgggagagc aatgggcagc cggagaacaa ctacaagacc    1260
acgcctcccg tgctggactc cgacggctcc ttcttcctct acagcaagct caccgtggac    1320
aagagcaggt ggcagcaggg gaacgtcttc tcatgctccg tgatgcatga ggctctgcac    1380
aaccactaca cgcagaagag cctctccctg tctccgggta aatga                    1425

<210> SEQ ID NO 74
<211> LENGTH: 654
<212> TYPE: DNA
<213> ORGANISM: Homo sapiens

<400> SEQUENCE: 74
cagtctgtgc tgacgcagcc gccctcagtg tctgcggccc caggacagaa ggtcaccatc     60
tcctgctctg gaagcagctc caccattggg aataattatg tctcctggta ccggctactc    120
ccaggaacag cccccaaact cctcatctat aaaaatgata accgaccctc agggattcct    180
gaccgattct ctggctccaa gtctggcacg tcagccaccc tgggcatcag cggactccag    240
actggggacg aggccgatta ttactgcgga acatgggata ccagcctgag tggtggcggt    300
gtcttcggaa ctgggaccaa ggtcaccgtc ctaggtcagc ccaaggccaa ccccactgtc    360
actctgttcc cgccctcgag tgaggagctt caagccaaca aggccacact ggtgtgtctc    420
ataagtgact tctacccggg agccgtgaca gtggcctgga aggcagatag cagccccgtc    480
aaggcgggag tggagaccac cacaccctcc aaacaaagca caacaagta cgcggccagc    540 agctacctga gcctgacgcc tgagcagtgg aagtcccaca aagctacag ctgccaggtc    600 acgcatgaag ggagcaccgt ggagaagaca gtggccccta cagaatgttc atag          654

<210> SEQ ID NO 75
<211> LENGTH: 432
<212> TYPE: DNA
<213> ORGANISM: Homo sapiens

<400> SEQUENCE: 75
gaagtgcagg tggtggagtc tggggggaggc gtggtccagc ctggggaggtc cctgagactc     60 tcctgtacag cctctggatt cactttcagc aactttgcca tgggctgggt ccgccaggct    120
ccgggcaagg gtctggagtg gtggccttt atatcatctg atggaagtaa taaaaactat    180
ggagactccg tgaagggccg attcaccatc tccagagaca attccaagaa cacggtgttc    240
ctgcaaatga acagtctgag agttgaggac acggctttgt attactgtgc gaaagatgtg    300
ggagactaca aaagtgatga gtgggggacg gaatatatg atatttcgat ttcttaccct    360
attcaagacc cacgggccat ggttggagct tttgatctct ggggccaagg gacaatggtc    420
accgtctctc ca                                                        432

<210> SEQ ID NO 76
<211> LENGTH: 333
<212> TYPE: DNA
<213> ORGANISM: Homo sapiens

<400> SEQUENCE: 76
cagtctgtgc tgacgcagcc gccctcagtg tctgcggccc caggacagaa ggtcaccatc     60
tcctgctctg gaagcagctc caccattggg aataattatg tctcctggta ccggctactc    120
ccaggaacag cccccaaact cctcatctat aaaaatgata accgaccctc agggattcct    180
gaccgattct ctggctccaa gtctggcacg tcagccaccc tgggcatcag cggactccag    240
```

```
actgggacg aggccgatta ttactgcgga acatgggata ccagcctgag tggtggcggt    300
gtcttcggaa ctgggaccaa ggtcaccgtc cta                                333
```

<210> SEQ ID NO 77
<211> LENGTH: 1425
<212> TYPE: DNA
<213> ORGANISM: Homo sapiens

<400> SEQUENCE: 77

```
gaggtgcagc tggtggagtc tgggggaggc gtggtccagc ctgggaggtc cctgagactc     60
tcctgtgcag cctctcaatt cagctttggt aactatggca tgcactgggt ccgccaggct    120
ccaggcaagg gactggagtg ggtggcagcc atttcatttg ctggaactaa gacaaactat    180
gcagattccg tgaagggccg attcaccatc tccagagaca attccaagaa cacggtctat    240
ctgcaaatga acagcctgcg cgctgaggac acggctctat atttctgtgc gaaagatatc    300
cgagaatacg aatgtgaata ttggacgtcg gattattacg attttgggag accgcaacct    360
tgtatagact cacggggggt ggttggaact tttgatgtct ggggccaagg gacaatggtc    420
accgtctctt cagcgtcgac caagggccca tcggtcttcc ccctggcacc ctcctccaag    480
agcacctctg gggcacagc ggccctgggc tgcctggtca aggactactt ccccgaaccc    540
gtgacggtgt cgtggaactc aggcgccctg accagcggcg tgcacacctt cccggctgtc    600
ctacagtcct caggactcta ctccctcagc agcgtggtga ccgtgccctc cagcagcttg    660
ggcacccaga cctacatctg caacgtgaat cacaagccca gcaacaccaa ggtggacaag    720
aaagttgagc ccaaatcttg tgacaaaact cacacatgcc caccgtgccc agcacctgaa    780
ctcctggggg gaccgtcagt cttcctcttc cccccaaaac ccaaggacac cctcatgatc    840
tcccggaccc ctgaggtcac atgcgtggtg gtggacgtga gccacgaaga ccctgaggtc    900
aagttcaact ggtacgtgga cggcgtggag gtgcataatg ccaagacaaa gccgcgggag    960
gagcagtaca acagcacgta ccgtgtggtc agcgtcctca ccgtcctgca ccaggactgg   1020
ctgaatggca aggagtacaa gtgcaaggtc tccaacaaag ccctcccagc ccccatcgag   1080
aaaaccatct ccaaagccaa agggcagccc cgagaaccac aggtgtacac cctgcccca   1140 tcccgggatg agctgaccaa gaaccaggtc agcctgacct gcctggtcaa aggcttctat   1200
cccagcgaca tcgccgtgga gtgggagagc aatgggcagc cggagaacaa ctacaagacc   1260
acgcctcccg tgctggactc cgacggctcc ttcttcctct acagcaagct caccgtggac   1320
aagagcaggt ggcagcaggg gaacgtcttc tcatgctccg tgatgcatga ggctctgcac   1380
aaccactaca cgcagaagag cctctccctg tctccgggta aatga              1425
```

<210> SEQ ID NO 78
<211> LENGTH: 645
<212> TYPE: DNA
<213> ORGANISM: Homo sapiens

<400> SEQUENCE: 78

```
cagtctgtgc tgacgcagcc gccctcagtg tctgcggccc caggacagaa ggtcaccatc     60
tcctgctctg gaagcaattc caacattggg aataaagatg tatcctggta ccaacagatc    120
ccagcaacag cccccaaact cctcatctat gaaaataaca gcgaccctc agggatttct    180 gaccgattct ctggctccaa gtctggcacg tcagccaccc tggccatcac cggactccag    240 actgggacg aggccgatta ttactgcgca acatgggatg gcagagtgag tgtcatcgga    300
actgggacca atgtcatcgt cctaggtcag cccaaggcca ccccactgt cactctgttc    360
```

| | |
|---|---|
| ccgccctcga gtgaggagct tcaagccaac aaggccacac tggtgtgtct cataagtgac | 420 |
| ttctacccgg gagccgtgac agtggcctgg aaggcagata gcagccccgt caaggcggga | 480 |
| gtggagacca ccacaccctc caaacaaagc aacaacaagt acgcggccag cagctacctg | 540 |
| agcctgacgc ctgagcagtg gaagtcccac agaagctaca gctgccaggt cacgcatgaa | 600 |
| gggagcaccg tggagaagac agtggcccct acagaatgtt catag | 645 |

<210> SEQ ID NO 79
<211> LENGTH: 432
<212> TYPE: DNA
<213> ORGANISM: Homo sapiens

<400> SEQUENCE: 79

| | |
|---|---|
| gaggtgcagc tggtggagtc tgggggaggc gtggtccagc ctgggaggtc cctgagactc | 60 |
| tcctgtgcag cctctcaatt cagctttggt aactatggca tgcactgggt ccgccaggct | 120 |
| ccaggcaagg gactggagtg ggtggcagcc atttcatttg ctggaactaa gacaaactat | 180 |
| gcagattccg tgaagggccg attcaccatc tccagagaca attccaagaa cacggtctat | 240 |
| ctgcaaatga acagcctgcg cgctgaggac acggctctat atttctgtgc gaaagatatc | 300 |
| cgagaatacg aatgtgaata ttggacgtcg gattattacg attttgggag accgcaacct | 360 |
| tgtatagact cacgggggt ggttggaact tttgatgtct ggggccaagg gacaatggtc | 420 |
| accgtctctt ca | 432 |

<210> SEQ ID NO 80
<211> LENGTH: 324
<212> TYPE: DNA
<213> ORGANISM: Homo sapiens

<400> SEQUENCE: 80

| | |
|---|---|
| cagtctgtgc tgacgcagcc gccctcagtg tctgcggccc caggacagaa ggtcaccatc | 60 |
| tcctgctctg gaagcaattc caacattggg aataaagatg tatcctggta ccaacagatc | 120 |
| ccagcaacag ccccaaaact cctcatctat gaaaataaca gcgaccctc agggatttct | 180 |
| gaccgattct ctggctccaa gtctggcacg tcagccaccc tggccatcac cggactccag | 240 |
| actggggacg aggccgatta ttactgcgca acatgggatg cagagtgag tgtcatcgga | 300 |
| actgggacca atgtcatcgt ccta | 324 |

<210> SEQ ID NO 81
<211> LENGTH: 1425
<212> TYPE: DNA
<213> ORGANISM: Homo sapiens

<400> SEQUENCE: 81

| | |
|---|---|
| gaggtgcagc tggtggagtc tgggggaggc gtggtccagc ctgggaagtc cctgagactc | 60 |
| tcctgtgcag cctctcgatt cagttttaat agatatggca tgcactgggt ccgccaggct | 120 |
| ccaggcaagg ggctggagtg ggtggcagcc atatcatatg atggaactga taaatatcat | 180 |
| gcagataaag tgtggggccg cttcaccatc tccagagaca attccaagaa cacactgtat | 240 |
| ctgcaaatga acagcctgcg agctgaggac acggctctct attactgtgc gaaagatttg | 300 |
| cgagaggacg aatgtgaaga gtggtggtcg gattattacg attttgggaa acagctccct | 360 |
| tgccgaaagt cacggggcgt ggctggaatt tttgatggct ggggccaagg gacaatggtc | 420 |
| accgtctctt cagcgtcgac caagggccca tcggtcttcc ccctggcacc ctcctccaag | 480 |

| | |
|---|---|
| agcacctctg ggggcacagc ggccctgggc tgcctggtca aggactactt ccccgaaccc | 540 |
| gtgacggtgt cgtggaactc aggcgccctg accagcggcg tgcacacctt cccggctgtc | 600 |
| ctacagtcct caggactcta ctccctcagc agcgtggtga ccgtgccctc agcagcttg | 660 |
| ggcacccaga cctacatctg caacgtgaat cacaagccca gcaacaccaa ggtggacaag | 720 |
| aaagttgagc ccaaatcttg tgacaaaact cacacatgcc caccgtgccc agcacctgaa | 780 |
| ctcctggggg gaccgtcagt cttcctcttc cccccaaaac ccaaggacac cctcatgatc | 840 |
| tcccggaccc ctgaggtcac atgcgtggtg gtggacgtga gccacgaaga ccctgaggtc | 900 |
| aagttcaact ggtacgtgga cggcgtggag gtgcataatg ccaagacaaa gccgcgggag | 960 |
| gagcagtaca acagcacgta ccgtgtggtc agcgtcctca ccgtcctgca ccaggactgg | 1020 |
| ctgaatggca aggagtacaa gtgcaaggtc tccaacaaag ccctcccagc ccccatcgag | 1080 |
| aaaaccatct ccaaagccaa agggcagccc cgagaaccac aggtgtacac cctgcccca | 1140 |
| tcccgggatg agctgaccaa gaaccaggtc agcctgacct gcctggtcaa aggcttctat | 1200 |
| cccagcgaca tcgccgtgga gtgggagagc aatgggcagc cggagaacaa ctacaagacc | 1260 |
| acgcctcccg tgctggactc cgacggctcc ttcttcctct acagcaagct caccgtggac | 1320 |
| aagagcaggt ggcagcaggg gaacgtcttc tcatgctccg tgatgcatga ggctctgcac | 1380 |
| aaccactaca cgcagaagag cctctccctg tctccgggta aatga | 1425 |

<210> SEQ ID NO 82
<211> LENGTH: 654
<212> TYPE: DNA
<213> ORGANISM: Homo sapiens

<400> SEQUENCE: 82

| | |
|---|---|
| cagtctgtgc tgactcagcc gccctcagtg tctgcggccc caggacagaa ggtcaccatc | 60 |
| tcctgctctg gaagcagctc aacattggc aataattttg tatcctggta ccagcagcgc | 120 |
| ccaggaacag cccccaagat cctcatttat gaaaataaca gcgaccctc agagactcct | 180 |
| gaccgattct ctggctccaa gtctggcacg tcagccaccc tggccatcac cggcctccag | 240 |
| actgcggacg aggccgaata ttactgcgcc acatggtctg ccagcctgag ctccgcgcgt | 300 |
| gtcttcggaa ctgggaccag gatcaccgtc ctaggtcagc ccaaggccaa ccccactgtc | 360 |
| actctgttcc cgccctcgag tgaggagctt caagccaaca ggccacact ggtgtgtctc | 420 |
| ataagtgact tctacccggg agccgtgaca gtggcctgga aggcagatag cagccccgtc | 480 |
| aaggcgggag tggagaccac cacaccctcc aaacaaagca acaacaagta cgcggccagc | 540 |
| agctacctga gcctgacgcc tgagcagtgg aagtcccaca aagctacag ctgccaggtc | 600 |
| acgcatgaag ggagcaccgt ggagaagaca gtggccccta cagaatgttc atag | 654 |

<210> SEQ ID NO 83
<211> LENGTH: 432
<212> TYPE: DNA
<213> ORGANISM: Homo sapiens

<400> SEQUENCE: 83

| | |
|---|---|
| gaggtgcagc tggtggagtc tgggggaggc gtggtccagc ctgggaagtc cctgagactc | 60 |
| tcctgtgcag cctctcgatt cagttttaat agatatggca tgcactgggt ccgccaggct | 120 |
| ccaggcaagg ggctggagtg ggtggcagcc atatcatatg atggaactga taaatatcat | 180 |
| gcagataaag tgtggggccg cttcaccatc tccagagaca attccaagaa cacactgtat | 240 |
| ctgcaaatga acagcctgcg agctgaggac acggctctct attactgtgc gaaagatttg | 300 |

```
cgagaggacg aatgtgaaga gtggtggtcg gattattacg attttgggaa acagctccct    360
tgccgaaagt cacggggcgt ggctggaatt tttgatggct ggggccaagg gacaatggtc    420
accgtctctt ca                                                         432
```

<210> SEQ ID NO 84
<211> LENGTH: 333
<212> TYPE: DNA
<213> ORGANISM: Homo sapiens

<400> SEQUENCE: 84

```
cagtctgtgc tgactcagcc gccctcagtg tctgcggccc caggacagaa ggtcaccatc     60
tcctgctctg gaagcagctc aacattggc aataattttg tatcctggta ccagcagcgc    120
ccaggaacag cccccaagat cctcatttat gaaaataaca gcgaccctc agagactcct    180 gaccgattct ctggctccaa gtctggcacg tcagccaccc tggccatcac cggcctccag    240
actgcggacg aggccgaata ttactgcgcc acatggtctg ccagcctgag ctccgcgcgt    300
gtcttcggaa ctgggaccag gatcaccgtc cta                                 333
```

<210> SEQ ID NO 85
<211> LENGTH: 1470
<212> TYPE: DNA
<213> ORGANISM: Homo sapiens

<400> SEQUENCE: 85

```
gaggtgcagc tggtggagtc tgggggaggc gtggtccagc ctgggaagtc cctgagactc     60
tcatgtgcag cctctcaatt cagttttaat agatatggca tgcactgggt ccgccaggct    120
ccaggcaagg ggctggagtg ggtggcagct atatcatatg atggaactga taaataccac    180
gctgataaag tgtggggccg cttcaccatc tccagagaca attccaagaa cacactgtat    240
ctgcaaatga acagcctgcg agctgaggac acggctctgt attactgtgc gaaagatttg    300
cgagaagacg agtgtgaaga gtggtggtcg gattattacg attttgggaa acaactccct    360
tgccgaaagt cacggggcgt ggctggaatt tttgataagt ggggccaagg gacaatggtc    420
atcgtctctt cagcgtcgac caagggccca tcggtcttcc ccctggcacc ctcctccgcg    480
tcgaccaagg gccatcggt cttccccctg gcaccctcct ccaagagcac ctctggggc    540 acagcggccc tgggctgcct ggtcaaggac tacttccccg aacccgtgac ggtgtcgtgg    600
aactcaggcg ccctgaccag cggcgtgcac accttcccgg ctgtcctaca gtcctcagga    660
ctctactccc tcagcagcgt ggtgaccgtg ccctccagca gcttgggcac ccagacctac    720
atctgcaacg tgaatcacaa gcccagcaac accaaggtgg acaagaaagt tgagcccaaa    780
tcttgtgaca aaactcacac atgcccaccg tgcccagcac ctgaactcct ggggggaccg    840
tcagtcttcc tcttcccccc aaaacccaag gacaccctca tgatctcccg gacccctgag    900
gtcacatgcg tggtggtgga cgtgagccac gaagaccctg aggtcaagtt caactggtac    960
gtggacggcg tggaggtgca taatgccaag acaaagccgc gggaggagca gtacaacagc    1020
acgtaccgtg tggtcagcgt cctcaccgtc ctgcaccagg actggctgaa tggcaaggag    1080
tacaagtgca aggtctccaa caaagccctc ccagccccca tcgagaaaac catctccaaa    1140
gccaaagggc agccccgaga accacaggtg tacaccctgc cccatcccg ggatgagctg    1200 accaagaacc aggtcagcct gacctgcctg gtcaaaggct tctatcccag cgacatcgcc    1260
gtggagtggg agagcaatgg gcagccggag aacaactaca agaccacgcc tcccgtgctg    1320
```

```
gactccgacg gctccttctt cctctacagc aagctcaccg tggacaagag caggtggcag    1380
caggggaacg tcttctcatg ctccgtgatg catgaggctc tgcacaacca ctacacgcag    1440
aagagcctct ccctgtctcc gggtaaatga                                     1470
```

<210> SEQ ID NO 86
<211> LENGTH: 654
<212> TYPE: DNA
<213> ORGANISM: Homo sapiens

<400> SEQUENCE: 86

```
cagcctgtgc tgactcagcc gccctcagtg tctgcggccc caggacagaa ggtcaccatc     60
tcctgctctg gaagcagctc caacattggc aataattttg tttcctggta ccagcagcgg    120
ccaggaacag cccccagcct cctcatttat gaaactaaca gcgaccctc aggaattcct     180 gaccgattct ctggctccaa gtctgccacg tcagccaccc tggccatcac cgggctccag    240
actggggacg aggccgatta ttactgcgcc acgtgggctg ccagcctgac ttccgcgcgt    300
gtcttcggaa ctgggaccaa ggtaatcgtc tcaggtcagc ccaaggccaa ccccactgtc    360
actctgttcc cgccctcgag tgaggagctt caagccaaca ggccacact ggtgtgtctc     420 ataagtgact tctacccggg agccgtgaca gtggcctgga aggcagatag cagccccgtc    480
aaggcgggag tggagaccac cacaccctcc aaacaaagca caacaagta cgcggccagc    540 agctacctga gcctgacgcc tgagcagtgg aagtcccaca aagctacag ctgccaggtc     600 acgcatgaag ggagcaccgt ggagaagaca gtggccccta cagaatgttc atag          654
```

<210> SEQ ID NO 87
<211> LENGTH: 477
<212> TYPE: DNA
<213> ORGANISM: Homo sapiens

<400> SEQUENCE: 87

```
gaggtgcagc tggtggagtc tgggggaggc gtggtccagc ctgggaagtc cctgagactc     60
tcatgtgcag cctctcaatt cagttttaat agatatggca tgcactgggt ccgccaggct    120
ccaggcaagg ggctggagtg ggtggcagct atatcatatg atggaactga taaataccac    180
gctgataaag tgtggggccg cttcaccatc tccagagaca attccaagaa cacactgtat    240
ctgcaaatga acagcctgcg agctgaggac acggctctgt attactgtgc gaaagatttg    300
cgagaagacg agtgtgaaga gtggtggtcg gattattacg attttgggaa caactccct    360 tgccgaaagt cacggggcgt ggctggaatt tttgataagt ggggccaagg gacaatggtc    420
atcgtctctt cagcgtcgac caagggccca tcggtcttcc cctggcacc ctcctcc       477
```

<210> SEQ ID NO 88
<211> LENGTH: 333
<212> TYPE: DNA
<213> ORGANISM: Homo sapiens

<400> SEQUENCE: 88

```
cagcctgtgc tgactcagcc gccctcagtg tctgcggccc caggacagaa ggtcaccatc     60
tcctgctctg gaagcagctc caacattggc aataattttg tttcctggta ccagcagcgg    120
ccaggaacag cccccagcct cctcatttat gaaactaaca gcgaccctc aggaattcct     180 gaccgattct ctggctccaa gtctgccacg tcagccaccc tggccatcac cgggctccag    240
actggggacg aggccgatta ttactgcgcc acgtgggctg ccagcctgac ttccgcgcgt    300
gtcttcggaa ctgggaccaa ggtaatcgtc tca                                 333
```

<210> SEQ ID NO 89
<211> LENGTH: 1425
<212> TYPE: DNA
<213> ORGANISM: Homo sapiens

<400> SEQUENCE: 89

| | | | | | |
|---|---|---|---|---|---|
| gaggtgcagc | tggtggagtc | tgggggaggc | gtggtccagc | ctgggaggtc | cctgagactc | 60 |
| tcctgtgcag | cctctcactt | ctcccttagt | agttatggca | tgcactgggt | ccgccaggct | 120 |
| ccaggcaagg | ggctggagtg | ggtgacaggt | atctcatttg | ctggaactaa | gacatactat | 180 |
| ggagattccg | tgaggggccg | tttcaccgtc | tccagagaca | tttccaagaa | cacgttgttc | 240 |
| ctgcaaatga | acagcctgcg | acctgacgac | acggctatgt | attactgtgc | gagagatcag | 300 |
| cgatattacg | agtgtgaaga | gtgggcgtcg | gattattacg | attttgggag | agagcaacct | 360 |
| tgcctagacc | cacggggcgt | ggttggaatt | ttcgatttgt | ggggccaagg | gacaatggtc | 420 |
| accgtctctt | cagcgtcgac | caagggccca | tcggtcttcc | ccctggcacc | ctcctccaag | 480 |
| agcacctctg | ggggcacagc | ggccctgggc | tgcctggtca | aggactactt | ccccgaaccc | 540 |
| gtgacggtgt | cgtggaactc | aggcgccctg | accagcggcg | tgcacacctt | cccggctgtc | 600 |
| ctacagtcct | caggactcta | ctccctcagc | agcgtggtga | ccgtgccctc | agcagcttg | 660 |
| ggcacccaga | cctacatctg | caacgtgaat | cacaagccca | gcaacaccaa | ggtggacaag | 720 |
| aaagttgagc | ccaaatcttg | tgacaaaact | cacacatgcc | caccgtgccc | agcacctgaa | 780 |
| ctcctggggg | gaccgtcagt | cttcctcttc | cccccaaaac | ccaaggacac | cctcatgatc | 840 |
| tcccggaccc | ctgaggtcac | atgcgtggtg | gtggacgtga | gccacgaaga | ccctgaggtc | 900 |
| aagttcaact | ggtacgtgga | cggcgtggag | gtgcataatg | ccaagacaaa | gccgcgggag | 960 |
| gagcagtaca | acagcacgta | ccgtgtggtc | agcgtcctca | ccgtcctgca | ccaggactgg | 1020 |
| ctgaatggca | aggagtacaa | gtgcaaggtc | tccaacaaag | ccctcccagc | ccccatcgag | 1080 |
| aaaaccatct | ccaaagccaa | agggcagccc | cgagaaccac | aggtgtacac | cctgccccca | 1140 |
| tcccgggatg | agctgaccaa | gaaccaggtc | agcctgacct | gcctggtcaa | aggcttctat | 1200 |
| cccagcgaca | tcgccgtgga | gtgggagagc | aatgggcagc | cggagaacaa | ctacaagacc | 1260 |
| acgcctcccg | tgctggactc | cgacggctcc | ttcttcctct | acagcaagct | caccgtggac | 1320 |
| aagagcaggt | ggcagcaggg | gaacgtcttc | tcatgctccg | tgatgcatga | ggctctgcac | 1380 |
| aaccactaca | cgcagaagag | cctctccctg | tctccgggta | aatga | | 1425 |

<210> SEQ ID NO 90
<211> LENGTH: 645
<212> TYPE: DNA
<213> ORGANISM: Homo sapiens

<400> SEQUENCE: 90

| | | | | | |
|---|---|---|---|---|---|
| cagtctgccc | tgactcagcc | gccctcagtg | tctgcggccc | caggacagaa | ggtcaccatc | 60 |
| tcctgctctg | gaaacattgg | gaataattat | gtttcttggt | accagcaagt | cccaggaaca | 120 |
| gcccccaaac | tcctcatcta | tgaaaataac | aagcgaccct | caggcattcc | tgaccgattc | 180 |
| tctggctcta | agtctggcac | gtcagccacc | ctggtcatca | ccggactcca | gactggggac | 240 |
| gaggccgatt | tttactgcgg | aacatggggt | ggcagcctga | gaactggcgg | tgtcctcgga | 300 |
| actgggacca | gggtcaccgt | cctaggtcag | cccaaggcca | accccactgt | cactctgttc | 360 |
| ccgccctcga | gtgaggagct | tcaagccaac | aaggccacac | tggtgtgtct | cataagtgac | 420 |

```
ttctacccgg gagccgtgac agtggcctgg aaggcagata gcagcccgt caaggcggga    480 gtggagacca ccacaccctc caaacaaagc aacaacaagt acgcggccag cagctacctg    540
agcctgacgc ctgagcagtg gaagtcccac agaagctaca gctgccaggt cacgcatgaa    600
gggagcaccg tggagaagac agtggcccct acagaatgtt catag                    645

<210> SEQ ID NO 91
<211> LENGTH: 432
<212> TYPE: DNA
<213> ORGANISM: Homo sapiens

<400> SEQUENCE: 91
gaggtgcagc tggtggagtc tgggggaggc gtggtccagc ctgggaggtc cctgagactc     60
tcctgtgcag cctctcactt ctcccttagt agttatggca tgcactgggt ccgccaggct    120
ccaggcaagg ggctggagtg ggtgacaggt atctcatttg ctggaactaa gacatactat    180
ggagattccg tgaggggccg tttcaccgtc tccagagaca tttccaagaa cacgttgttc    240
ctgcaaatga acagcctgcg acctgacgac acggctatgt attactgtgc gagagatcag    300
cgatattacg agtgtgaaga gtgggcgtcg gattattacg attttgggag agagcaacct    360
tgcctagacc cacggggcgt ggttggaatt ttcgatttgt ggggccaagg gacaatggtc    420
accgtctctt ca                                                        432

<210> SEQ ID NO 92
<211> LENGTH: 324
<212> TYPE: DNA
<213> ORGANISM: Homo sapiens

<400> SEQUENCE: 92
cagtctgccc tgactcagcc gccctcagtg tctgcggccc caggacagaa ggtcaccatc     60
tcctgctctg gaaacattgg gaataattat gtttcttggt accagcaagt cccaggaaca    120
gcccccaaac tcctcatcta tgaaaataac aagcgaccct caggcattcc tgaccgattc    180
tctggctcta agtctggcac gtcagccacc ctggtcatca ccggactcca gactggggac    240
gaggccgatt tttactgcgg aacatggggt ggcagcctga gaactggcgg tgtcctcgga    300
actgggacca gggtcaccgt ccta                                            324

<210> SEQ ID NO 93
<211> LENGTH: 1428
<212> TYPE: DNA
<213> ORGANISM: Homo sapiens

<400> SEQUENCE: 93
gaggtgcagc tgattgagtc gggggaggc gtggtccagc ctgggaggtc cctgagactc      60
tcctgtggag cgtctggatt cagcttcaat aactatggca tgcactgggt ccgccaggct    120
ccaggcaagg ggctggagtg ggtggcaggt atttcctttg ctggaatcaa gaaatactat    180
ggaacttccg tgaagggccg attcaccatc tcccgagaca attccaagaa caatttctat    240
ctgcaaatga acagcctgcg agttgaggac acggctctct attattgtgc gagagatctg    300
cgagaattgg aatgtgaaga gtggacacta tataattatt atgactttgg aagtcgaggc    360
ccttgtgtag acccacgggg cgtggctgga tcttttgatg tctggggcca ggggacaatg    420
gtgaccgtct cctcagcgtc gaccaagggc ccatcggtct tccccctggc acctcctcc    480 aagagcacct ctgggggcac agcggccctg ggctgcctgg tcaaggacta cttccccgaa    540
cccgtgacgg tgtcgtggaa ctcaggcgcc ctgaccagcg gcgtgcacac cttcccggct    600
```

```
gtcctacagt cctcaggact ctactccctc agcagcgtgg tgaccgtgcc ctccagcagc    660
ttgggcaccc agacctacat ctgcaacgtg aatcacaagc ccagcaacac caaggtggac    720
aagaaagttg agcccaaatc ttgtgacaaa actcacacat gcccaccgtg cccagcacct    780
gaactcctgg ggggaccgtc agtcttcctc ttccccccaa aacccaagga caccctcatg    840
atctcccgga cccctgaggt cacatgcgtg gtggtggacg tgagccacga agaccctgag    900
gtcaagttca actggtacgt ggacggcgtg gaggtgcata atgccaagac aaagccgcgg    960
gaggagcagt acaacagcac gtaccgtgtg gtcagcgtcc tcaccgtcct gcaccaggac   1020
tggctgaatg gcaaggagta caagtgcaag gtctccaaca aagcccctcc cagcccccatc  1080 gagaaaacca tctccaaagc caaagggcag ccccgagaac acaggtgta caccctgccc    1140 ccatcccggg atgagctgac caagaaccag gtcagcctga cctgcctggt caaaggcttc   1200
tatcccagcg acatcgccgt ggagtgggag agcaatgggc agccggagaa caactacaag   1260
accacgcctc ccgtgctgga ctccgacggc tccttcttcc tctacagcaa gctcaccgtg   1320
gacaagagca ggtggcagca ggggaacgtc ttctcatgct ccgtgatgca tgaggctctg   1380
cacaaccact acacgcagaa gagcctctcc ctgtctccgg gtaaatga                1428

<210> SEQ ID NO 94
<211> LENGTH: 645
<212> TYPE: DNA
<213> ORGANISM: Homo sapiens

<400> SEQUENCE: 94
cagtctgtgc tgactcagcc gccctcagtg tctgcggccc caggacagaa ggtcaccatc     60
tcctgctctg gaagcacttc caaaattggg caaaactctg tatcttggta ccagcaactc    120
ccaggaacag cccccaaact cctcatctat gaaaatgacc ggcgaccctc ggggactcct    180
gaccgattct ctggctccaa gtctggcacg tcagccaccc tggccatcac cggactccag    240
actggggacg aggccgaata ttactgcgaa acatgggatg gcagcggggg tgtcttcgga    300
actgggacca aggtcaccgt cctaggtcag cccaaggcca accccactgt cactctgttc    360
ccgccctcga gtgaggagct tcaagccaac aaggccacac tggtgtgtct cataagtgac    420
ttctacccgg gagccgtgac agtggcctgg aaggcagata gcagccccgt caaggcggga    480
gtggagacca ccacaccctc caaacaaagc aacaacaagt acgcggccag cagctacctg    540
agcctgacgc ctgagcagtg gaagtcccac agaagctaca gctgccaggt cacgcatgaa    600
gggagcaccg tggagaagac agtggcccct acagaatgtt catag                    645

<210> SEQ ID NO 95
<211> LENGTH: 435
<212> TYPE: DNA
<213> ORGANISM: Homo sapiens

<400> SEQUENCE: 95
gaggtgcagc tgattgagtc ggggggaggc gtggtccagc ctgggaggtc cctgagactc     60
tcctgtggag cgtctggatt cagcttcaat aactatggca tgcactgggt ccgccaggct    120
ccaggcaagg ggctggagtg ggtggcaggt atttcctttg ctggaatcaa gaatactat     180 ggaacttccg tgaagggccg attcaccatc tcccgagaca attccaagaa caatttctat    240
ctgcaaatga acagcctgcg agttgaggac acggctctct attattgtgc gagagatctg    300
cgagaattgg aatgtgaaga gtggacacta tataattatt atgactttgg aagtcgaggc    360
```

```
ccttgtgtag acccacgggg cgtggctgga tcttttgatg tctggggcca ggggacaatg    420
gtgaccgtct cctca                                                     435

<210> SEQ ID NO 96
<211> LENGTH: 324
<212> TYPE: DNA
<213> ORGANISM: Homo sapiens

<400> SEQUENCE: 96
cagtctgtgc tgactcagcc gccctcagtg tctgcggccc caggacagaa ggtcaccatc    60
tcctgctctg gaagcacttc caaaattggg caaaactctg tatcttggta ccagcaactc    120
ccaggaacag cccccaaact cctcatctat gaaaatgacc ggcgaccctc ggggactcct    180
gaccgattct ctggctccaa gtctggcacg tcagccaccc tggccatcac cggactccag    240
actggggacg aggccgaata ttactgcgaa acatgggatg gcagcggggg tgtcttcgga    300
actgggacca aggtcaccgt ccta                                           324

<210> SEQ ID NO 97
<211> LENGTH: 1425
<212> TYPE: DNA
<213> ORGANISM: Homo sapiens

<400> SEQUENCE: 97
gaggtgcagc tggtggagtc tgggggaggc gtggtccagc ctgggaggtc cctgagactc    60
tcctgtgtag gctctcaatt cagttttaat cgatatggca tgcactgggt ccgccaggct    120
ccaggcaagg ggctggagtg gtggcgggt atatcatttg atggaactga cagatatcat    180
gcagacaatg tgtggggccg cttcaccatc tccagagaca attccaagaa cacactgtat    240
ctacaaatga gcagcctgcg cgctgaggac acggctctct attattgtgc gaaagatttg    300
cgagaagacg aatgtgaaga gtggtggtcg gattattacg attttgggaa aaaactccct    360
tgccgaaagt cacggggcgt ggctggagtt tttgataagt ggggccaagg gacaatggtc    420
accgtctctt cagcgtcgac caagggccca tcggtcttcc ccctggcacc ctcctccaag    480
agcacctctg ggggcacagc ggccctgggc tgcctggtca aggactactt ccccgaaccc    540
gtgacggtgt cgtggaactc aggcgccctg accagcggcg tgcacacctt cccggctgtc    600
ctacagtcct caggactcta ctccctcagc agcgtggtga ccgtgccctc agcagcttg    660 ggcacccaga cctacatctg caacgtgaat cacaagccca gcaacaccaa ggtggacaag    720
aaagttgagc ccaaatcttg tgacaaaact cacacatgcc caccgtgccc agcacctgaa    780
ctcctggggg gaccgtcagt cttcctcttc cccccaaaac ccaaggacac cctcatgatc    840
tcccggaccc ctgaggtcac atgcgtggtg gtggacgtga gccacgaaga ccctgaggtc    900
aagttcaact ggtacgtgga cggcgtggag gtgcataatg ccaagacaaa gccgcgggag    960
gagcagtaca acagcacgta ccgtgtggtc agcgtcctca ccgtcctgca ccaggactgg   1020
ctgaatggca aggagtacaa gtgcaaggtc tccaacaaag ccctcccagc ccccatcgag   1080
aaaaccatct ccaaagccaa agggcagccc cgagaaccac aggtgtacac cctgccccca   1140
tcccgggatg agctgaccaa gaaccaggtc agcctgacct gcctggtcaa aggcttctat   1200
cccagcgaca tcgccgtgga gtgggagagc aatgggcagc cggagaacaa ctacaagacc   1260
acgcctcccg tgctggactc cgacggctcc ttcttcctct acagcaagct caccgtggac   1320
aagagcaggt ggcagcaggg gaacgtcttc tcatgctccg tgatgcatga ggctctgcac   1380
aaccactaca cgcagaagag cctctccctg tctccgggta aatga                   1425
```

<210> SEQ ID NO 98
<211> LENGTH: 654
<212> TYPE: DNA
<213> ORGANISM: Homo sapiens

<400> SEQUENCE: 98

```
caggctgtgc tgactcagcc gccctcagtg tctgcggccc caggacagaa cgtcaccatc      60
tcctgctctg gaagcggctc caacattggc aataattttg tatcctggta ccagcaacgc     120
ccaggaacag cccccaaact cctcatttat gagtctaaca agcgaccctc agggattcct     180
gaccgattct ctggctccaa gtctggcacg tcagccaccc tggccatcac cgggctccag     240
actggggacg aggcctatta ttactgcgcc acatgggctg ccaggctgaa ttccgcgcgt     300
gtcttcggaa ctgggaccat ggtcaccgtc ctaggtcagc ccaaggccaa ccccactgtc     360
actctgttcc cgccctcgag tgaggagctt caagccaaca aggccacact ggtgtgtctc     420
ataagtgact ctacccgggg agccgtgaca gtggcctgga aggcagatag cagccccgtc     480
aaggcgggag tggagaccac cacaccctcc aaacaaagca caacaagta cgcggccagc     540
agctacctga gcctgacgcc tgagcagtgg aagtcccaca aagctacag ctgccaggtc      600
acgcatgaag ggagcaccgt ggagaagaca gtggccccta cagaatgttc atag           654
```

<210> SEQ ID NO 99
<211> LENGTH: 432
<212> TYPE: DNA
<213> ORGANISM: Homo sapiens

<400> SEQUENCE: 99

```
gaggtgcagc tggtggagtc tgggggaggc gtggtccagc ctgggaggtc cctgagactc      60
tcctgtgtag gctctcaatt cagttttaat cgatatggca tgcactgggt ccgccaggct     120
ccagcaaggg ggctggagtg gtggcgggt atatcatttg atggaactga cagatatcat      180
gcagacaatg tgtggggccg cttcaccatc tccagagaca attccaagaa cacactgtat     240
ctacaaatga gcagcctgcg cgctgaggac acggctctct attattgtgc gaaagatttg     300
cgagaagacg aatgtgaaga gtggtggtcg gattattacg attttgggaa aaaactccct     360
tgccgaaagt cacggggcgt ggctggagtt tttgataagt ggggccaagg gacaatggtc     420
accgtctctt ca                                                         432
```

<210> SEQ ID NO 100
<211> LENGTH: 333
<212> TYPE: DNA
<213> ORGANISM: Homo sapiens

<400> SEQUENCE: 100

```
caggctgtgc tgactcagcc gccctcagtg tctgcggccc caggacagaa cgtcaccatc      60
tcctgctctg gaagcggctc caacattggc aataattttg tatcctggta ccagcaacgc     120
ccaggaacag cccccaaact cctcatttat gagtctaaca agcgaccctc agggattcct     180
gaccgattct ctggctccaa gtctggcacg tcagccaccc tggccatcac cgggctccag     240
actggggacg aggcctatta ttactgcgcc acatgggctg ccaggctgaa ttccgcgcgt     300
gtcttcggaa ctgggaccat ggtcaccgtc cta                                   333
```

<210> SEQ ID NO 101
<211> LENGTH: 1431
<212> TYPE: DNA

<213> ORGANISM: Homo sapiens

<400> SEQUENCE: 101

```
gaagtgcagc tggtggagtc tgggggaggc gtggtccagc ctgggaggtc cctgacactg      60
tcctgtgcag cctctcaatt cacttttcg aattatggca tgcactgggt ccgccaggct      120
ccaggcaagg gactggagtg ggtggcaagt gtatcaaatg atggaaccaa gaaatatcat     180
ggagattccg tgtggggccg attcaccatc tccagagaca attccaagaa cacactgttt     240
ctacaaatga gcagcctgcg agctgaggac acggctgtat atttctgtgt gagagatcaa     300
cgagaagacg agtgtgaaga gtggtggtcg gattattatg attttgggag agagctccct     360
tgccgaaaat tccggggcct gggcctggct ggaatttttg atatctgggg ccacgggaca     420
atggtcaccg tctcttcagc gtcgaccaag ggcccatcgg tcttccccct ggcaccctcc     480
tccaagagca cctctggggg cacagcggcc ctgggctgcc tggtcaagga ctacttcccc     540
gaacccgtga cggtgtcgtg gaactcaggc gccctgacca gcggcgtgca ccttcccg      600
gctgtcctac agtcctcagg actctactcc ctcagcagcg tggtgaccgt gccctccagc     660
agcttgggca cccagaccta catctgcaac gtgaatcaca agcccagcaa caccaaggtg     720
gacaagaaag ttgagcccaa atcttgtgac aaaactcaca catgcccacc gtgcccagca     780
cctgaactcc tggggggacc gtcagtcttc ctcttccccc caaaacccaa ggacaccctc     840
atgatctccc ggaccctga ggtcacatgc gtggtggtgg acgtgagcca cgaagaccct     900
gaggtcaagt tcaactggta cgtggacggc gtggaggtgc ataatgccaa gacaaagccg     960
cgggaggagc agtacaacag cacgtaccgt gtggtcagcg tcctcaccgt cctgcaccag    1020
gactggctga atggcaagga gtacaagtgc aaggtctcca acaaagccct cccagccccc    1080
atcgagaaaa ccatctccaa agccaaaggg cagccccgag aaccacaggt gtacaccctg    1140
cccccatccc gggatgagct gaccaagaac caggtcagcc tgacctgcct ggtcaaaggc    1200
ttctatccca gcgacatcgc cgtggagtgg gagagcaatg ggcagccgga gaacaactac    1260
aagaccacgc ctcccgtgct ggactccgac ggctccttct tcctctacag caagctcacc    1320
gtggacaaga gcaggtggca gcaggggaac gtcttctcat gctccgtgat gcatgaggct    1380
ctgcacaacc actacacgca gaagagcctc tccctgtctc cgggtaaatg a             1431
```

<210> SEQ ID NO 102
<211> LENGTH: 654
<212> TYPE: DNA
<213> ORGANISM: Homo sapiens

<400> SEQUENCE: 102

```
cagtctgccc tgactcagcc gccctcagtg tccgcggccc caggacagaa ggtcaccatc      60
tcctgctccg gaaacagctc caacattggg aataattttg tatcctggta ccagcaagtc     120
ccaggaacag cccccaaact cctcctgtat gaaacttaca gcgaccctc aggtattcct     180
gaccgattct ctggctccaa gtctggcacg tcagccaccc tggccatcac cggactccag     240
actggggacg aggccgacta ctactgcaca gtatggggtg tcaggaaggg tgtcggcgct     300
gtcttcggaa ctgggaccaa ggtcaccgtc ctaggtcagc ccaaggccaa ccccactgtc     360
actctgttcc cgccctcgag tgaggagctt caagccaaca aggccacact ggtgtgtctc     420
ataagtgact tctacccggg agccgtgaca gtggcctgga aggcagatag cagccccgtc     480
aaggcgggag tggagaccac cacaccctcc aaacaaagca caacaagta cgcggccagc     540
agctacctga gcctgacgcc tgagcagtgg aagtcccaca gaagctacag ctgccaggtc     600
```
acgcatgaag ggagcaccgt ggagaagaca gtggccccta cagaatgttc atag        654

<210> SEQ ID NO 103
<211> LENGTH: 438
<212> TYPE: DNA
<213> ORGANISM: Homo sapiens

<400> SEQUENCE: 103
gaagtgcagc tggtggagtc tgggggaggc gtggtccagc ctgggaggtc cctgacactg    60
tcctgtgcag cctctcaatt cacttttcg aattatggca tgcactgggt ccgccaggct   120
ccaggcaagg gactggagtg ggtggcaagt gtatcaaatg atggaaccaa gaaatatcat   180
ggagattccg tgtggggccg attcaccatc tccagagaca attccaagaa cacactgttt   240
ctacaaatga gcagcctgcg agctgaggac acggctgtat atttctgtgt gagagatcaa   300
cgagaagacg agtgtgaaga gtggtggtcg gattattatg attttgggag agagctccct   360
tgccgaaaat tccggggcct gggcctggct ggaattttg atatctgggg ccacgggaca    420
atggtcaccg tctcttca                                                 438

<210> SEQ ID NO 104
<211> LENGTH: 333
<212> TYPE: DNA
<213> ORGANISM: Homo sapiens

<400> SEQUENCE: 104
cagtctgccc tgactcagcc gccctcagtg tccgcggccc caggacagaa ggtcaccatc    60
tcctgctccg gaaacagctc caacattggg aataattttg tatcctggta ccagcaagtc   120
ccaggaacag ccccccaaact cctcctgtat gaaacttaca gcgaccctc aggtattcct   180 gaccgattct ctggctccaa gtctggcacg tcagccaccc tggccatcac cggactccag   240
actggggacg aggccgacta ctactgcaca gtatggggtg tcaggaaggg tgtcggcgct   300
gtcttcggaa ctgggaccaa ggtcaccgtc cta                                333

<210> SEQ ID NO 105
<211> LENGTH: 1431
<212> TYPE: DNA
<213> ORGANISM: Homo sapiens

<400> SEQUENCE: 105
gaggtgcagt tggtggagtc tgggggaggc gtggtccagc ctgggaggtc cctgacactg    60
tcctgtgcag cctctcaatt caattttgcg aattatggca tgcactgggt ccgccaggct   120
ccaggcaagg gattggagtg ggtggcaagt atatcaaatg atggaacgaa gaaatatcat   180
gaagaatccg tgtggggccg attcaccatc tccaaagaca attccaagag cacactattt   240
ctacaaatga acagcctgcg aattgaggac acggccctat atttctgtgt gaaagatcaa   300
cgagaggacg aatgtgaaga gtggtggtcg gattattatg attttgggag agagctccct   360
tgccgaaagt cccggggcct gggcctggct ggaatctttg atatgtgggg ccacgggaca   420
atggtcaccg tctcttcagc gtcgaccaag ggcccatcgg tcttcccct ggcaccctcc    480 tccaagagca cctctggggg cacagcggcc ctgggctgcc tggtcaagga ctacttcccc   540
gaacccgtga cggtgtcgtg gaactcaggc gccctgacca gcggcgtgca caccttcccg   600
gctgtcctac agtcctcagg actctactcc ctcagcagcg tggtgaccgt gccctccagc   660
agcttgggca cccagaccta catctgcaac gtgaatcaca agcccagcaa caccaaggtg   720

```
gacaagaaag ttgagcccaa atcttgtgac aaaactcaca catgcccacc gtgcccagca        780
cctgaactcc tggggggacc gtcagtcttc ctcttccccc caaaacccaa ggacaccctc        840
atgatctccc ggacccctga ggtcacatgc gtggtggtgg acgtgagcca cgaagaccct        900
gaggtcaagt tcaactggta cgtggacggc gtggaggtgc ataatgccaa gacaaagccg        960
cgggaggagc agtacaacag cacgtaccgt gtggtcagcg tcctcaccgt cctgcaccag       1020
gactggctga atggcaagga gtacaagtgc aaggtctcca acaaagccct cccagccccc       1080
atcgagaaaa ccatctccaa agccaaaggg cagccccgag aaccacaggt gtacaccctg       1140
cccccatccc gggatgagct gaccaagaac caggtcagcc tgacctgcct ggtcaaaggc       1200
ttctatccca gcgacatcgc cgtggagtgg gagagcaatg ggcagccgga gaacaactac       1260
aagaccacgc ctcccgtgct ggactccgac ggctccttct tcctctacag caagctcacc       1320
gtggacaaga gcaggtggca gcaggggaac gtcttctcat gctccgtgat gcatgaggct       1380
ctgcacaacc actacacgca gaagagcctc tccctgtctc cgggtaaatg a              1431

<210> SEQ ID NO 106
<211> LENGTH: 654
<212> TYPE: DNA
<213> ORGANISM: Homo sapiens

<400> SEQUENCE: 106
cagtctgccc tgactcagcc gccctcagtg tctgcggccc caggacagaa ggtcaccatc         60
tcctgctctg gaaatagttc caacattggg aataattttg tatcctggta ccagcaactc        120
ccggggacag ccccccaaact cctcatatat gaaaataaca gcgaccctc agggattcct        180 gaccgattct ctggctccaa gtctggcacg tcagccaccc tggccatcag cggactccag        240
actggggacg aggccgacta ttggtgcgct gtttggggtg tcaggcgggg tgccggcgct        300
gtcttcggag ctgggaccaa ggtcaccgtc ctaggtcagc ccaaggccaa ccccactgtc        360
actctgttcc cgccctcgag tgaggagctt caagccaaca aggccacact ggtgtgtctc        420
ataagtgact tctacccggg agccgtgaca gtggcctgga aggcagatag cagccccgtc        480
aaggcgggag tggagaccac cacacccctc aaacaaagca caacaagta cgcggccagc        540 agctacctga gcctgacgcc tgagcagtgg aagtcccaca gaagctacag ctgccaggtc        600
acgcatgaag ggagcaccgt ggagaagaca gtggccccta cagaatgttc atag             654

<210> SEQ ID NO 107
<211> LENGTH: 438
<212> TYPE: DNA
<213> ORGANISM: Homo sapiens

<400> SEQUENCE: 107
gaggtgcagt tggtggagtc tggggggaggc gtggtccagc ctgggaggtc cctgacactg         60
tcctgtgcag cctctcaatt caattttgcg aattatggca tgcactgggt ccgccaggct        120
ccaggcaagg gattggagtg ggtggcagtt atatcaaatg atggaacgaa gaaatatcat        180
gaagaatccg tgtgggggccg attcaccatc tccaaagaca attccaagag cacactattt        240
ctacaaatga acagcctgcg aattgaggac acggccctat atttctgtgt gaaagatcaa        300
cgagaggacg aatgtgaaga gtggtggtcg gattattatg attttgggag agagctccct        360
tgccgaaagt cccgggggcct gggcctggct ggaatctttg atatgtgggg ccacgggaca        420
atggtcaccg tctcttca                                                      438
```

<210> SEQ ID NO 108
<211> LENGTH: 333
<212> TYPE: DNA
<213> ORGANISM: Homo sapiens

<400> SEQUENCE: 108

```
cagtctgccc tgactcagcc gccctcagtg tctgcggccc caggacagaa ggtcaccatc      60
tcctgctctg gaaatagttc aacattggg aataattttg tatcctggta ccagcaactc     120
ccggggacag cccccaaact cctcatatat gaaaataaca gcgaccctc agggattcct     180
gaccgattct ctggctccaa gtctggcacg tcagccaccc tggccatcag cggactccag     240
actggggacg aggccgacta ttggtgcgct gtttggggtg tcaggcgggg tgccggcgct     300
gtcttcggag ctgggaccaa ggtcaccgtc cta                                  333
```

<210> SEQ ID NO 109
<211> LENGTH: 1425
<212> TYPE: DNA
<213> ORGANISM: Homo sapiens

<400> SEQUENCE: 109

```
caggcgatcc tggtggaatc tggggggaggc gtggtccagc ctgggaggtc cctgagactc      60
tcctgtgcag cctcgcaatt cacatttagt ggacatggcc tgcactgggt ccgccaggct     120
ccaggcaagg ggctggagtg gtggcctct atttcttttg ctggaactaa aatgactat       180
gcagattccg tgaagggccg attcgccatc tccagagaca actccaagaa cacgttgtat     240
ctgcaaatga acagcctgcg agttgaggac acggctctat attactgtgc aaaagatatg     300
cgagaatatg aatgtgaata ttggacgtcg gattattacg attttgggag acctcaaccg     360
tgcatagacc gacggggcgt ggttggaatt tttgatatgt ggggccaagg acaatggtc      420
accgtctcta cagcgtcgac caagggccca tcggtcttcc cctggcacc tcctccaag      480
agcacctctg ggggcacagc ggccctgggc tgcctggtca aggactactt ccccgaaccc     540
gtgacggtgt cgtggaactc aggcgccctg accagcggcg tgcacacctt cccggctgtc     600
ctacagtcct caggactcta ctccctcagc agcgtggtga ccgtgccctc cagcagcttg     660
ggcacccaga cctacatctg caacgtgaat cacaagccca gcaacaccaa ggtggacaag     720
aaagttgagc ccaaatcttg tgacaaaact cacacatgcc caccgtgccc agcacctgaa     780
ctcctggggg gaccgtcagt cttcctcttc ccccaaaac ccaaggacac cctcatgatc      840
tcccggaccc ctgaggtcac atgcgtggtg gtggacgtga gccacgaaga ccctgaggtc     900
aagttcaact ggtacgtgga cggcgtggag gtgcataatg ccaagacaaa gccgcgggag     960
gagcagtaca acagcacgta ccgtgtggtc agcgtcctca ccgtcctgca ccaggactgg    1020
ctgaatggca aggagtacaa gtgcaaggtc tccaacaaag ccctcccagc ccccatcgag    1080
aaaaccatct ccaaagccaa agggcagccc cgagaaccac aggtgtacac cctgccccca    1140
tcccgggatg agctgaccaa gaaccaggtc agcctgacct gcctggtcaa aggcttctat    1200
cccagcgaca tcgccgtgga gtgggagagc aatgggcagc cggagaacaa ctacaagacc    1260
acgcctcccg tgctggactc cgacggctcc ttcttcctct acagcaagct caccgtggac    1320
aagagcaggt ggcagcaggg gaacgtcttc tcatgctccg tgatgcatga ggctctgcac    1380
aaccactaca cgcagaagag cctctccctg tctccgggta aatga                    1425
```

<210> SEQ ID NO 110
<211> LENGTH: 654
<212> TYPE: DNA

<213> ORGANISM: Homo sapiens

<400> SEQUENCE: 110

```
cagtctgtgc tgacgcagcc gccctcagtg tctgcggccc caggacagaa ggtcaccatc      60
tcctgctctg gaagcagctc caacattggg gataattatg tgtcctggta ccagcacctc     120
ccaggaacag cccccaaact cctcatctat gaaaatacca ggcgaccctc agggattcct     180
gaccgattct ctggctccaa gtctggcacg tcagccaccc tggccatcac cggactccag     240
actggggacg aggccgatta ttactgcgga acatgggatg tcagaccgaa tcgtggcgct     300
gtcttcggaa ctgggacgaa ggtcaccgtc ctaggtcagc ccaaggccaa ccccactgtc     360
actctgttcc cgccctcgag tgaggagctt caagccaaca aggccacact ggtgtgtctc     420
ataagtgact ctacccgggg agccgtgaca gtggcctgga aggcagatag cagccccgtc     480
aaggcgggag tggagaccac cacaccctcc aaacaaagca caacaagta cgcggccagc     540
agctacctga gcctgacgcc tgagcagtgg aagtcccaca agctacag ctgccaggtc      600
acgcatgaag ggagcaccgt ggagaagaca gtggccccta cagaatgttc atag           654
```

<210> SEQ ID NO 111
<211> LENGTH: 432
<212> TYPE: DNA
<213> ORGANISM: Homo sapiens

<400> SEQUENCE: 111

```
caggcgatcc tggtggaatc tggggaggc gtggtccagc ctgggaggtc cctgagactc       60
tcctgtgcag cctcgcaatt cacatttagt ggacatggcc tgcactgggt ccgccaggct     120
ccaggcaagg gctggagtg ggtggcctct atttctttg ctggaactaa aatggactat       180
gcagattccg tgaagggccg attcgccatc tccagagaca actccaagaa cacgttgtat     240
ctgcaaatga acagcctgcg agttgaggac acggctctat attactgtgc aaaagatatg     300
cgagaatatg aatgtgaata ttggacgtcg gattattacg attttgggag acctcaaccg     360
tgcatagacc gacgggggcgt ggttggaatt tttgatatgt ggggccaagg gacaatggtc     420
accgtctcta ca                                                         432
```

<210> SEQ ID NO 112
<211> LENGTH: 333
<212> TYPE: DNA
<213> ORGANISM: Homo sapiens

<400> SEQUENCE: 112

```
cagtctgtgc tgacgcagcc gccctcagtg tctgcggccc caggacagaa ggtcaccatc      60
tcctgctctg gaagcagctc caacattggg gataattatg tgtcctggta ccagcacctc     120
ccaggaacag cccccaaact cctcatctat gaaaatacca ggcgaccctc agggattcct     180
gaccgattct ctggctccaa gtctggcacg tcagccaccc tggccatcac cggactccag     240
actggggacg aggccgatta ttactgcgga acatgggatg tcagaccgaa tcgtggcgct     300
gtcttcggaa ctgggacgaa ggtcaccgtc cta                                  333
```

<210> SEQ ID NO 113
<211> LENGTH: 1422
<212> TYPE: DNA
<213> ORGANISM: Homo sapiens

<400> SEQUENCE: 113

```
gaggtgcagc tggtggagtc tgggggaggc gtggtccgc ctggggaagtc cctgacactc       60
```

```
tcctgtgtag cctctcgatt caccttttagt gcctttggga tgcactgggt ccgccaggct    120
ccagggaagg ggctggagtg ggtggcaagt atatcatttg ctggaattaa gaaatattat    180
gcagattccg tgaagggccg attcagcatc tccagagaca attccaacac actgtttctc    240
caaatgaatg gcctgcgagg agaagacacg ggtctatatc actgtgtcaa agatatgcga    300
gagttggagt gtgaagagtg ggcgtcggat tactacgatt ttgggaagcc tcagccttgt    360
ctggaccgac ggggcgtgtc tggaatctct gcttggtggg gtcctgggac aatggtcacc    420
gtctcttcag cgtcgaccaa gggcccatcg gtcttccccc tggcaccctc ctccaagagc    480
acctctgggg gcacagcggc cctgggctgc ctggtcaagg actacttccc cgaacccgtg    540
acggtgtcgt ggaactcagg cgccctgacc agcggcgtgc acaccttccc ggctgtccta    600
cagtcctcag gactctactc cctcagcagc gtggtgaccg tgccctccag cagcttgggc    660
acccagacct acatctgcaa cgtgaatcac aagcccagca acaccaaggt ggacaagaaa    720
gttgagccca atcttgtgac aaaactcac acatgcccac cgtgcccagc acctgaactc    780
ctggggggac cgtcagtctt cctcttcccc ccaaaaccca aggacaccct catgatctcc    840
cggacccctg aggtcacatg cgtggtggtg gacgtgagcc acgaagaccc tgaggtcaag    900
ttcaactggt acgtggacgg cgtggaggtg cataatgcca agacaaagcc gcgggaggag    960
cagtacaaca gcacgtaccg tgtggtcagc gtcctcaccg tcctgcacca ggactggctg   1020
aatggcaagg agtacaagtg caaggtctcc aacaaagccc tcccagcccc catcgagaaa   1080
accatctcca aagccaaagg gcagcccga gaaccacagg tgtacaccct gcccccatcc   1140
cgggatgagc tgaccaagaa ccaggtcagc ctgacctgcc tggtcaaagg cttctatccc   1200
agcgacatcg ccgtggagtg ggagagcaat gggcagccgg agaacaacta caagaccacg   1260
cctcccgtgc tggactccga cggctccttc ttcctctaca gcaagctcac cgtggacaag   1320
agcaggtggc agcaggggaa cgtcttctca tgctccgtga tgcatgaggc tctgcacaac   1380
cactacacgc agaagagcct ctccctgtct ccgggtaaat ga                      1422

<210> SEQ ID NO 114
<211> LENGTH: 642
<212> TYPE: DNA
<213> ORGANISM: Homo sapiens

<400> SEQUENCE: 114
cagtctgtgc tgacgcagcc gccctcagtg tctgcggccc caggacagaa cgtcaccatc     60
tcctgctctg gaccccgtc ccacattgag aagaatgatg tgtcgtggta ccaacgcctc    120
ccaggaatgg cccccaaaat ggtcatttat gaaagtaaaa ggcgacctct cgggatccct    180
gtccgattct ctgcctccag gtctggctcg tcagccaccc tggtcatcac cggactccag    240
actgccgacg aggccgatta ttactgcgga acatgggatg cagaatgaa ttttgggact    300 gggaccacgg tctccgtcct aggtcagccc aaggccaacc ccactgtcac tctgttcccg    360
ccctcgagtg aggagcttca agccaacaag gccacactgg tgtgtctcat aagtgacttc    420
tacccgggag ccgtgacagt ggcctggaag gcagatagca gccccgtcaa ggcgggagtg    480
gagaccacca cacctccaa acaaagcaac aacaagtacg cggccagcag ctacctgagc    540
ctgacgcctg agcagtggaa gtcccacaga agctacagct gccaggtcac gcatgaaggg    600
agcaccgtgg agaagacagt ggcccctaca gaatgttcat ag                      642

<210> SEQ ID NO 115
```

```
<211> LENGTH: 429
<212> TYPE: DNA
<213> ORGANISM: Homo sapiens

<400> SEQUENCE: 115
gaggtgcagc tggtggagtc tgggggaggc gtggtcccgc ctgggaagtc cctgacactc        60
tcctgtgtag cctctcgatt cacctttagt gcctttggga tgcactgggt ccgccaggct       120
ccagggaagg ggctggagtg ggtggcaagt atatcatttg ctggaattaa gaaatattat       180
gcagattccg tgaagggccg attcagcatc tccagagaca attccaacac actgtttctc       240
caaatgaatg gcctgcgagg agaagacacg ggtctatatc actgtgtcaa agatatgcga       300
gagttggagt gtgaagagtg ggcgtcggat tactacgatt tgggaagcc tcagccttgt       360 ctggaccgac ggggcgtgtc tggaatctct gcttggtggg gtcctgggac aatggtcacc       420
gtctcttca                                                              429

<210> SEQ ID NO 116
<211> LENGTH: 321
<212> TYPE: DNA
<213> ORGANISM: Homo sapiens

<400> SEQUENCE: 116
cagtctgtgc tgacgcagcc gccctcagtg tctgcggccc caggacagaa cgtcaccatc        60
tcctgctctg gaccccgtc ccacattgag aagaatgatg tgtcgtggta ccaacgcctc       120
ccaggaatgg cccccaaaat ggtcatttat gaaagtaaaa ggcgacctct cgggatccct       180
gtccgattct ctgcctccag gtctggctcg tcagccaccc tggtcatcac cggactccag       240
actgccgacg aggccgatta ttactgcgga acatgggatg cagaatgaa ttttgggact       300 gggaccacgg tctccgtcct a                                                 321

<210> SEQ ID NO 117
<211> LENGTH: 1425
<212> TYPE: DNA
<213> ORGANISM: Homo sapiens

<400> SEQUENCE: 117
gaagtgcagc tggtgcagtc tgggggaggc gtggtccagc ctgggaggtc cctgagactc        60
tcctgtgcag cccgtatttt cgagtttggt agatatggct tccactgggt ccgccaggct       120
ccaggcaagg gtctggagtg ggtggcaagt atatcatttg ctggaagaga ttattaccac       180
tcaccatccg tgtggggccg cttcaccatc tccagagaca attccaagaa cacactatat       240
ttgcaaatga acagcctgcg aattgaagac acggctctct atttctgtgc gagagatctg       300
agagaaagcg aatgtgaaga gtgggagtcg gactattatg attttgggaa aaagggccct       360
tgtgttaagc cgcggggcgt ggctggaggt ttggatctct ggggccaagg gacaatggtc       420
atcgtctcat cagcgtcgac caagggccca tcggtcttcc ccctggcacc ctcctccaag       480
agcacctctg ggggcacagc ggccctgggc tgcctggtca aggactactt ccccgaaccc       540
gtgacggtgt cgtggaactc aggcgccctg accagcggcg tgcacacctt cccggctgtc       600
ctacagtcct caggactcta ctccctcagc agcgtggtga ccgtgccctc agcagcttg       660 ggcacccaga cctacatctg caacgtgaat cacaagccca gcaacaccaa ggtggacaag       720
aaagttgagc ccaaatcttg tgacaaaact cacacatgcc caccgtgccc agcacctgaa       780
ctcctggggg gaccgtcagt cttcctcttc cccccaaaac ccaaggacac cctcatgatc       840
tcccggaccc ctgaggtcac atgcgtggtg gtggacgtga gccacgaaga ccctgaggtc       900
```

```
aagttcaact ggtacgtgga cggcgtggag gtgcataatg ccaagacaaa gccgcgggag    960
gagcagtaca acagcacgta ccgtgtggtc agcgtcctca ccgtcctgca ccaggactgg   1020
ctgaatggca aggagtacaa gtgcaaggtc tccaacaaag ccctcccagc ccccatcgag   1080
aaaaccatct ccaaagccaa agggcagccc cgagaaccac aggtgtacac cctgccccca   1140
tcccgggatg agctgaccaa gaaccaggtc agcctgacct gcctggtcaa aggcttctat   1200
cccagcgaca tcgccgtgga gtgggagagc aatgggcagc cggagaacaa ctacaagacc   1260
acgcctcccg tgctggactc cgacggctcc ttcttcctct acagcaagct caccgtggac   1320
aagagcaggt ggcagcaggg gaacgtcttc tcatgctccg tgatgcatga ggctctgcac   1380
aaccactaca cgcagaagag cctctccctg tctccgggta aatga               1425

<210> SEQ ID NO 118
<211> LENGTH: 642
<212> TYPE: DNA
<213> ORGANISM: Homo sapiens

<400> SEQUENCE: 118
cagtctgtgc tgacgcagcc gccctcagtg tctacggccc caggacagac ggtcaccgtc     60
tcctgctccg gaggcaccct caacactggg aataattttg tctcctggta ccaacacctc    120
ccaggaacag cccccaaact tctcatctat gaaaataaca gcgacccctt aggggttcct    180
gaccgattct ctggcgccaa gtctggcacg tcagccaccc tggccatcac cggactccag    240
actggggacg agggcgatta ttactgcgca acatggagtg gcagtctgaa catcgggact    300
gggaccaaag tctccgtcct aggtcagccc aaggccaacc ccactgtcac tctgttcccg    360
ccctcgagtg aggagcttca agccaacaag gccacactgg tgtgtctcat aagtgacttc    420
tacccgggag ccgtgacagt ggcctggaag gcagatagca gccccgtcaa ggcgggagtg    480
gagaccacca cacctccaa acaaagcaac aacaagtacg cggccagcag ctacctgagc    540
ctgacgcctg agcagtggaa gtcccacaga agctacagct gccaggtcac gcatgaaggg    600
agcaccgtgg agaagacagt ggcccctaca gaatgttcat ag                       642

<210> SEQ ID NO 119
<211> LENGTH: 432
<212> TYPE: DNA
<213> ORGANISM: Homo sapiens

<400> SEQUENCE: 119
gaagtgcagc tggtgcagtc tggggaggc gtggtccagc ctgggaggtc cctgagactc      60
tcctgtgcag ccccgtattt cgagtttggt agatatggct tccactgggt ccgccaggct    120
ccaggcaagg gtctggagtg ggtggcaagt atatcatttg ctggaagaga ttattaccac    180
tcaccatccg tgtggggccg cttcaccatc tccagagaca attccaagaa cacactatat    240
ttgcaaatga acagcctgcg aattgaagac acggctctct attttctgtgc gagagatctg    300 agagaaagcg aatgtgaaga gtgggagtcg gactatatg attttgggaa aagggccct     360 tgtgttaagc cgcggggcgt ggctggaggt ttggatctct ggggccaagg gacaatggtc    420
atcgtctcat ca                                                        432

<210> SEQ ID NO 120
<211> LENGTH: 321
<212> TYPE: DNA
<213> ORGANISM: Homo sapiens
```

<400> SEQUENCE: 120

```
cagtctgtgc tgacgcagcc gccctcagtg tctacggccc caggacagac ggtcaccgtc      60
tcctgctccg gaggcacctc caacactggg aataattttg tctcctggta ccaacacctc     120
ccaggaacag cccccaaact tctcatctat gaaaataaca agcgaccctt aggggttcct     180
gaccgattct ctggcgccaa gtctggcacg tcagccaccc tggccatcac cggactccag     240
actggggacg agggcgatta ttactgcgca acatggagtg gcagtctgaa catcgggact     300
gggaccaaag tctccgtcct a                                                321
```

<210> SEQ ID NO 121
<211> LENGTH: 147
<212> TYPE: PRT
<213> ORGANISM: Artificial sequence
<220> FEATURE:
<223> OTHER INFORMATION: Synthetic VH consensus sequence
<220> FEATURE:
<221> NAME/KEY: misc_feature
<222> LOCATION: (1)..(6)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (23)..(26)
<223> OTHER INFORMATION: Xaa can be any naturally occurring amino acid
<220> FEATURE:
<221> NAME/KEY: misc_feature
<222> LOCATION: (28)..(35)
<223> OTHER INFORMATION: Xaa can be any naturally occurring amino acid
<220> FEATURE:
<221> NAME/KEY: misc_feature
<222> LOCATION: (49)..(51)
<223> OTHER INFORMATION: Xaa can be any naturally occurring amino acid
<220> FEATURE:
<221> NAME/KEY: misc_feature
<222> LOCATION: (53)..(54)
<223> OTHER INFORMATION: Xaa can be any naturally occurring amino acid
<220> FEATURE:
<221> NAME/KEY: misc_feature
<222> LOCATION: (56)..(63)
<223> OTHER INFORMATION: Xaa can be any naturally occurring amino acid
<220> FEATURE:
<221> NAME/KEY: misc_feature
<222> LOCATION: (65)..(65)
<223> OTHER INFORMATION: Xaa can be any naturally occurring amino acid
<220> FEATURE:
<221> NAME/KEY: misc_feature
<222> LOCATION: (69)..(70)
<223> OTHER INFORMATION: Xaa can be any naturally occurring amino acid
<220> FEATURE:
<221> NAME/KEY: misc_feature
<222> LOCATION: (72)..(72)
<223> OTHER INFORMATION: Xaa can be any naturally occurring amino acid
<220> FEATURE:
<221> NAME/KEY: misc_feature
<222> LOCATION: (74)..(74)
<223> OTHER INFORMATION: Xaa can be any naturally occurring amino acid
<220> FEATURE:
<221> NAME/KEY: misc_feature
<222> LOCATION: (76)..(80)
<223> OTHER INFORMATION: Xaa can be any naturally occurring amino acid
<220> FEATURE:
<221> NAME/KEY: misc_feature

```
<222> LOCATION: (84)..(85)
<223> OTHER INFORMATION: Xaa can be any naturally occurring amino acid
<220> FEATURE:
<221> NAME/KEY: misc_feature
<222> LOCATION: (88)..(89)
<223> OTHER INFORMATION: Xaa can be any naturally occurring amino acid
<220> FEATURE:
<221> NAME/KEY: misc_feature
<222> LOCATION: (92)..(93)
<223> OTHER INFORMATION: Xaa can be any naturally occurring amino acid
<220> FEATURE:
<221> NAME/KEY: misc_feature
<222> LOCATION: (95)..(95)
<223> OTHER INFORMATION: Xaa can be any naturally occurring amino acid
<220> FEATURE:
<221> NAME/KEY: misc_feature
<222> LOCATION: (97)..(98)
<223> OTHER INFORMATION: Xaa can be any naturally occurring amino acid
<220> FEATURE:
<221> NAME/KEY: misc_feature
<222> LOCATION: (100)..(107)
<223> OTHER INFORMATION: Xaa can be any naturally occurring amino acid
<220> FEATURE:
<221> NAME/KEY: misc_feature
<222> LOCATION: (109)..(112)
<223> OTHER INFORMATION: Xaa can be any naturally occurring amino acid
<220> FEATURE:
<221> NAME/KEY: misc_feature
<222> LOCATION: (116)..(120)
<223> OTHER INFORMATION: Xaa can be any naturally occurring amino acid
<220> FEATURE:
<221> NAME/KEY: misc_feature
<222> LOCATION: (122)..(125)
<223> OTHER INFORMATION: Xaa can be any naturally occurring amino acid
<220> FEATURE:
<221> NAME/KEY: misc_feature
<222> LOCATION: (127)..(131)
<223> OTHER INFORMATION: Xaa can be any naturally occurring amino acid
<220> FEATURE:
<221> NAME/KEY: misc_feature
<222> LOCATION: (133)..(136)
<223> OTHER INFORMATION: Xaa can be any naturally occurring amino acid
<220> FEATURE:
<221> NAME/KEY: misc_feature
<222> LOCATION: (139)..(139)
<223> OTHER INFORMATION: Xaa can be any naturally occurring amino acid
<220> FEATURE:
<221> NAME/KEY: misc_feature
<222> LOCATION: (144)..(144)
<223> OTHER INFORMATION: Xaa can be any naturally occurring amino acid
<220> FEATURE:
<221> NAME/KEY: misc_feature
<222> LOCATION: (147)..(147)
<223> OTHER INFORMATION: Xaa can be any naturally occurring amino acid

<400> SEQUENCE: 121

Xaa Xaa Xaa Xaa Xaa Xaa Ser Gly Gly Gly Val Val Xaa Pro Gly Xaa
1               5                   10                  15

Ser Leu Xaa Leu Ser Cys Xaa Xaa Xaa Xaa Phe Xaa Xaa Xaa Xaa Xaa
            20                  25                  30

Xaa Xaa Xaa Trp Val Arg Gln Ala Pro Gly Lys Gly Leu Glu Trp Val
        35                  40                  45

Xaa Xaa Xaa Ser Xaa Xaa Gly Xaa Xaa Xaa Xaa Xaa Xaa Xaa Xaa Val
    50                  55                  60

Xaa Gly Arg Phe Xaa Xaa Ser Xaa Asp Xaa Ser Xaa Xaa Xaa Xaa Xaa
65                  70                  75                  80

Leu Gln Met Xaa Xaa Leu Arg Xaa Xaa Asp Thr Xaa Xaa Tyr Xaa Cys
                85                  90                  95

Xaa Xaa Asp Xaa Xaa Xaa Xaa Xaa Xaa Xaa Trp Xaa Xaa Xaa Xaa
                100                 105                 110

Tyr Tyr Asp Xaa Xaa Xaa Xaa Xaa Pro Xaa Xaa Xaa Xaa Arg Xaa Xaa
```

```
            115                 120                 125
Xaa Xaa Xaa Gly Xaa Xaa Xaa Xaa Trp Gly Xaa Gly Thr Met Val Xaa
        130                 135                 140

Val Ser Xaa
145

<210> SEQ ID NO 122
<211> LENGTH: 111
<212> TYPE: PRT
<213> ORGANISM: Artificial sequence
<220> FEATURE:
<223> OTHER INFORMATION: Synthetic VL consensus sequence
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (25)..(33)
<223> OTHER INFORMATION: Xaa can be any naturally occurring amino acid
<220> FEATURE:
<221> NAME/KEY: misc_feature
<222> LOCATION: (38)..(40)
<223> OTHER INFORMATION: Xaa can be any naturally occurring amino acid
<220> FEATURE:
<221> NAME/KEY: misc_feature
<222> LOCATION: (42)..(43)
<223> OTHER INFORMATION: Xaa can be any naturally occurring amino acid
<220> FEATURE:
<221> NAME/KEY: misc_feature
<222> LOCATION: (46)..(49)
<223> OTHER INFORMATION: Xaa can be any naturally occurring amino acid
<220> FEATURE:
<221> NAME/KEY: misc_feature
<222> LOCATION: (51)..(54)
<223> OTHER INFORMATION: Xaa can be any naturally occurring amino acid
<220> FEATURE:
<221> NAME/KEY: misc_feature
<222> LOCATION: (57)..(61)
<223> OTHER INFORMATION: Xaa can be any naturally occurring amino acid
<220> FEATURE:
<221> NAME/KEY: misc_feature
<222> LOCATION: (65)..(67)
<223> OTHER INFORMATION: Xaa can be any naturally occurring amino acid
<220> FEATURE:
<221> NAME/KEY: misc_feature
<222> LOCATION: (69)..(70)
<223> OTHER INFORMATION: Xaa can be any naturally occurring amino acid
<220> FEATURE:
<221> NAME/KEY: misc_feature
<222> LOCATION: (75)..(75)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (85)..(88)
<223> OTHER INFORMATION: Xaa can be any naturally occurring amino acid
```

<220> FEATURE:
<221> NAME/KEY: misc_feature
<222> LOCATION: (90)..(91)
<223> OTHER INFORMATION: Xaa can be any naturally occurring amino acid
<220> FEATURE:
<221> NAME/KEY: misc_feature
<222> LOCATION: (93)..(102)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid
<220> FEATURE:
<221> NAME/KEY: misc_feature
<222> LOCATION: (107)..(109)
<223> OTHER INFORMATION: Xaa can be any naturally occurring amino acid
<220> FEATURE:
<221> NAME/KEY: misc_feature
<222> LOCATION: (111)..(111)
<223> OTHER INFORMATION: Xaa can be any naturally occurring amino acid

<400> SEQUENCE: 122

Gln Xaa Xaa Leu Thr Gln Pro Pro Ser Val Ser Xaa Ala Pro Gly Gln
1               5                   10                  15

Xaa Val Thr Xaa Ser Cys Ser Gly Xaa Xaa Xaa Xaa Xaa Xaa Xaa
            20                  25                  30

Xaa Val Ser Trp Tyr Xaa Xaa Xaa Pro Xaa Xaa Ala Pro Xaa Xaa Xaa
            35                  40                  45

Xaa Tyr Xaa Xaa Xaa Xaa Arg Pro Xaa Xaa Xaa Xaa Arg Phe Ser
50                  55                  60

Xaa Xaa Xaa Ser Xaa Xaa Ser Ala Thr Leu Xaa Ile Xaa Gly Leu Gln
65                  70                  75                  80

Thr Xaa Asp Glu Xaa Xaa Xaa Xaa Cys Xaa Xaa Trp Xaa Xaa Xaa Xaa
                85                  90                  95

Xaa Xaa Xaa Xaa Xaa Xaa Gly Xaa Gly Thr Xaa Xaa Xaa Val Xaa
            100                 105                 110

<210> SEQ ID NO 123
<211> LENGTH: 47
<212> TYPE: DNA
<213> ORGANISM: Artificial sequence
<220> FEATURE:
<223> OTHER INFORMATION: Oligonucleotide primer XLR-A_VH3 LEADER-A

<400> SEQUENCE: 123
ccatctcatc cctgcgtgtc tccgactcag taaaaggtgt ccagtgt                47

<210> SEQ ID NO 124
<211> LENGTH: 47
<212> TYPE: DNA
<213> ORGANISM: Artificial sequence
<220> FEATURE:
<223> OTHER INFORMATION: Oligonucleotide primer XLR-A_VH3 LEADER-B

<400> SEQUENCE: 124
ccatctcatc cctgcgtgtc tccgactcag taagaggtgt ccagtgt                47

<210> SEQ ID NO 125
<211> LENGTH: 47
<212> TYPE: DNA
<213> ORGANISM: Artificial sequence
<220> FEATURE:
<223> OTHER INFORMATION: Oligonucleotide primer XLR-A_VH3 LEADER-C

<400> SEQUENCE: 125
ccatctcatc cctgcgtgtc tccgactcag tagaaggtgt ccagtgt                47

<210> SEQ ID NO 126
<211> LENGTH: 54
<212> TYPE: DNA
<213> ORGANISM: Artificial sequence
<220> FEATURE:
<223> OTHER INFORMATION: Oligonucleotide primer XLR-A_VH3 LEADER-D

<400> SEQUENCE: 126
ccatctcatc cctgcgtgtc tccgactcag gctatttta aggtgtcca gtgt        54

<210> SEQ ID NO 127
<211> LENGTH: 47
<212> TYPE: DNA
<213> ORGANISM: Artificial sequence
<220> FEATURE:
<223> OTHER INFORMATION: Oligonucleotide primer XLR-A_VH3 LEADER-E

<400> SEQUENCE: 127
ccatctcatc cctgcgtgtc tccgactcag tacaaggtgt ccagtgt               47

<210> SEQ ID NO 128
<211> LENGTH: 47
<212> TYPE: DNA
<213> ORGANISM: Artificial sequence
<220> FEATURE:
<223> OTHER INFORMATION: Oligonucleotide primer XLR-A_VH3 LEADER-F

<400> SEQUENCE: 128
ccatctcatc cctgcgtgtc tccgactcag ttaaagctgt ccagtgt               47

<210> SEQ ID NO 129
<211> LENGTH: 54
<212> TYPE: DNA
<213> ORGANISM: Artificial sequence
<220> FEATURE:
<223> OTHER INFORMATION: Oligonucleotide primer XLR-B_3xwCgammaCH1-2

<400> SEQUENCE: 129
cctatcccct gtgtgccttg gcagtctcag ggggaagacc gatgggccct tggt        54

<210> SEQ ID NO 130
<211> LENGTH: 51
<212> TYPE: DNA
<213> ORGANISM: Artificial sequence
<220> FEATURE:
<223> OTHER INFORMATION: Oligonucleotide primer XLR-B_3CmuCH1

<400> SEQUENCE: 130
cctatcccct gtgtgccttg gcagtctcag gggaattctc acaggagacg a           51

<210> SEQ ID NO 131
<211> LENGTH: 54
<212> TYPE: DNA
<213> ORGANISM: Artificial sequence
<220> FEATURE:
<223> OTHER INFORMATION: Oligonucleotide primer XLR-A_5L-VL1/2

<400> SEQUENCE: 131
ccatctcatc cctgcgtgtc tccgactcag gcacagggtc ctgggcccag tctg        54

<210> SEQ ID NO 132
<211> LENGTH: 53
<212> TYPE: DNA
<213> ORGANISM: Artificial sequence
<220> FEATURE:

<223> OTHER INFORMATION: Oligonucleotide primer XLR-A_5L-VL3

<400> SEQUENCE: 132
ccatctcatc cctgcgtgtc tccgactcag gctctgtgac ctcctatgag ctg    53

<210> SEQ ID NO 133
<211> LENGTH: 53
<212> TYPE: DNA
<213> ORGANISM: Artificial sequence
<220> FEATURE:
<223> OTHER INFORMATION: Oligonucleotide primer XLR-A_5L-VL4/5

<400> SEQUENCE: 133
ccatctcatc cctgcgtgtc tccgactcag ggtctctctc scagcytgtg ctg    53

<210> SEQ ID NO 134
<211> LENGTH: 53
<212> TYPE: DNA
<213> ORGANISM: Artificial sequence
<220> FEATURE:
<223> OTHER INFORMATION: Oligonucleotide primer XLR-A_5L-VL6

<400> SEQUENCE: 134
ccatctcatc cctgcgtgtc tccgactcag gttcttgggc caattttatg ctg    53

<210> SEQ ID NO 135
<211> LENGTH: 53
<212> TYPE: DNA
<213> ORGANISM: Artificial sequence
<220> FEATURE:
<223> OTHER INFORMATION: Oligonucleotide primer XLR-A_5L-VL7/8

<400> SEQUENCE: 135
ccatctcatc cctgcgtgtc tccgactcag gagtggattc tcagactgtg gtg    53

<210> SEQ ID NO 136
<211> LENGTH: 54
<212> TYPE: DNA
<213> ORGANISM: Artificial sequence
<220> FEATURE:
<223> OTHER INFORMATION: Oligonucleotide primer XLR-A_5MP-VL1

<400> SEQUENCE: 136
ccatctcatc cctgcgtgtc tccgactcag gctcactgca cagggtcctg ggcc    54

<210> SEQ ID NO 137
<211> LENGTH: 54
<212> TYPE: DNA
<213> ORGANISM: Artificial sequence
<220> FEATURE:
<223> OTHER INFORMATION: Oligonucleotide primer XLR-A_5MP-VL3-1

<400> SEQUENCE: 137
ccatctcatc cctgcgtgtc tccgactcag gcttactgca caggatccgt ggcc    54

<210> SEQ ID NO 138
<211> LENGTH: 54
<212> TYPE: DNA
<213> ORGANISM: Artificial sequence
<220> FEATURE:
<223> OTHER INFORMATION: Oligonucleotide primer XLR-A_5MP-VL3-19

<400> SEQUENCE: 138
ccatctcatc cctgcgtgtc tccgactcag actctttgca taggttctgt ggtt    54

```
<210> SEQ ID NO 139
<211> LENGTH: 54
<212> TYPE: DNA
<213> ORGANISM: Artificial sequence
<220> FEATURE:
<223> OTHER INFORMATION: Oligonucleotide primer XLR-A_5MP-VL3-21

<400> SEQUENCE: 139
ccatctcatc cctgcgtgtc tccgactcag tctcactgca caggctctgt gacc          54

<210> SEQ ID NO 140
<211> LENGTH: 53
<212> TYPE: DNA
<213> ORGANISM: Artificial sequence
<220> FEATURE:
<223> OTHER INFORMATION: Oligonucleotide primer XLR-A_5MP-VL7-43

<400> SEQUENCE: 140
ccatctcatc cctgcgtgtc tccgactcag acttgctgcc cagggtccaa ttc           53

<210> SEQ ID NO 141
<211> LENGTH: 54
<212> TYPE: DNA
<213> ORGANISM: Artificial sequence
<220> FEATURE:
<223> OTHER INFORMATION: Oligonucleotide primer XLR-B_3CL

<400> SEQUENCE: 141
cctatcccct gtgtgccttg gcagtctcag caccagtgtg gccttgttgg cttg          54

<210> SEQ ID NO 142
<211> LENGTH: 54
<212> TYPE: DNA
<213> ORGANISM: Artificial sequence
<220> FEATURE:
<223> OTHER INFORMATION: Oligonucleotide primer XLR-A_5L-VH1

<400> SEQUENCE: 142
ccatctcatc cctgcgtgtc tccgactcag acaggtgccc actcccaggt gcag          54

<210> SEQ ID NO 143
<211> LENGTH: 53
<212> TYPE: DNA
<213> ORGANISM: Artificial sequence
<220> FEATURE:
<223> OTHER INFORMATION: Oligonucleotide primer XLR-A_5L-VH3

<400> SEQUENCE: 143
ccatctcatc cctgcgtgtc tccgactcag aaggtgtcca gtgtgargtg cag           53

<210> SEQ ID NO 144
<211> LENGTH: 57
<212> TYPE: DNA
<213> ORGANISM: Artificial sequence
<220> FEATURE:
<223> OTHER INFORMATION: Oligonucleotide primer XLR-A_5L-VH4/6

<400> SEQUENCE: 144
ccatctcatc cctgcgtgtc tccgactcag cccagatggg tcctgtccca ggtgcag       57

<210> SEQ ID NO 145
<211> LENGTH: 54
<212> TYPE: DNA
<213> ORGANISM: Artificial sequence
<220> FEATURE:
<223> OTHER INFORMATION: Oligonucleotide primer XLR-A_5L-VH5
```

<400> SEQUENCE: 145
ccatctcatc cctgcgtgtc tccgactcag caaggagtct gttccgaggt gcag     54

<210> SEQ ID NO 146
<211> LENGTH: 51
<212> TYPE: DNA
<213> ORGANISM: Artificial sequence
<220> FEATURE:
<223> OTHER INFORMATION: Oligonucleotide primer XLR-A_5xwL-VH1

<400> SEQUENCE: 146
ccatctcatc cctgcgtgtc tccgactcag gcagccacag gtgcccactc c     51

<210> SEQ ID NO 147
<211> LENGTH: 52
<212> TYPE: DNA
<213> ORGANISM: Artificial sequence
<220> FEATURE:
<223> OTHER INFORMATION: Oligonucleotide primer XLR-A_5xwL-VH1-24

<400> SEQUENCE: 147
ccatctcatc cctgcgtgtc tccgactcag cagcagctac aggcacccac gc     52

<210> SEQ ID NO 148
<211> LENGTH: 55
<212> TYPE: DNA
<213> ORGANISM: Artificial sequence
<220> FEATURE:
<223> OTHER INFORMATION: Oligonucleotide primer XLR-A_5xwL-VH1-69

<400> SEQUENCE: 148
ccatctcatc cctgcgtgtc tccgactcag ggcagcagct acaggtgtcc agtcc     55

<210> SEQ ID NO 149
<211> LENGTH: 54
<212> TYPE: DNA
<213> ORGANISM: Artificial sequence
<220> FEATURE:
<223> OTHER INFORMATION: Oligonucleotide primer XLR-A_VH3-L1-MP

<400> SEQUENCE: 149
ccatctcatc cctgcgtgtc tccgactcag gctattttaa aaggtgtcca atgt     54

<210> SEQ ID NO 150
<211> LENGTH: 56
<212> TYPE: DNA
<213> ORGANISM: Artificial sequence
<220> FEATURE:
<223> OTHER INFORMATION: Oligonucleotide primer XLR-A_VH3/4-L1-MP

<400> SEQUENCE: 150
ccatctcatc cctgcgtgtc tccgactcag gtggcagctc ccagatgggt cctgtc     56

<210> SEQ ID NO 151
<211> LENGTH: 56
<212> TYPE: DNA
<213> ORGANISM: Artificial sequence
<220> FEATURE:
<223> OTHER INFORMATION: Oligonucleotide primer XLR-A_VH3/4-L3-MP

<400> SEQUENCE: 151
ccatctcatc cctgcgtgtc tccgactcag gttgcagttt taaaaggtgt ccagtg     56

<210> SEQ ID NO 152
<211> LENGTH: 54

```
<212> TYPE: DNA
<213> ORGANISM: Artificial sequence
<220> FEATURE:
<223> OTHER INFORMATION: Oligonucleotide primer XLR-A_VH5-L1-MP

<400> SEQUENCE: 152
ccatctcatc cctgcgtgtc tccgactcag gctgttctcc aaggagtctg ttcc            54

<210> SEQ ID NO 153
<211> LENGTH: 56
<212> TYPE: DNA
<213> ORGANISM: Artificial sequence
<220> FEATURE:
<223> OTHER INFORMATION: Oligonucleotide primer XLR-A_5xwL-VK1/2

<400> SEQUENCE: 153
ccatctcatc cctgcgtgtc tccgactcag atgaggstcc cygctcagct cctggg         56

<210> SEQ ID NO 154
<211> LENGTH: 58
<212> TYPE: DNA
<213> ORGANISM: Artificial sequence
<220> FEATURE:
<223> OTHER INFORMATION: Oligonucleotide primer XLR-A_5L-VK3

<400> SEQUENCE: 154
ccatctcatc cctgcgtgtc tccgactcag ctcttcctcc tgctactctg gctcccag      58

<210> SEQ ID NO 155
<211> LENGTH: 55
<212> TYPE: DNA
<213> ORGANISM: Artificial sequence
<220> FEATURE:
<223> OTHER INFORMATION: Oligonucleotide primer XLR-A_5L-VK4

<400> SEQUENCE: 155
ccatctcatc cctgcgtgtc tccgactcag atttctctgt tgctctggat ctctg          55

<210> SEQ ID NO 156
<211> LENGTH: 54
<212> TYPE: DNA
<213> ORGANISM: Artificial sequence
<220> FEATURE:
<223> OTHER INFORMATION: Oligonucleotide primer XLR-A_5L-VL1/2

<400> SEQUENCE: 156
ccatctcatc cctgcgtgtc tccgactcag gcacagggtc ctgggcccag tctg           54

<210> SEQ ID NO 157
<211> LENGTH: 53
<212> TYPE: DNA
<213> ORGANISM: Artificial sequence
<220> FEATURE:
<223> OTHER INFORMATION: Oligonucleotide primer XLR-A_5L-VL3

<400> SEQUENCE: 157
ccatctcatc cctgcgtgtc tccgactcag gctctgtgac ctcctatgag ctg            53

<210> SEQ ID NO 158
<211> LENGTH: 53
<212> TYPE: DNA
<213> ORGANISM: Artificial sequence
<220> FEATURE:
<223> OTHER INFORMATION: Oligonucleotide primer XLR-A_5L-VL4/5

<400> SEQUENCE: 158
```

```
ccatctcatc cctgcgtgtc tccgactcag ggtctctctc scagcytgtg ctg        53
```

<210> SEQ ID NO 159
<211> LENGTH: 53
<212> TYPE: DNA
<213> ORGANISM: Artificial sequence
<220> FEATURE:
<223> OTHER INFORMATION: Oligonucleotide primer XLR-A_5L-VL6

<400> SEQUENCE: 159

```
ccatctcatc cctgcgtgtc tccgactcag gttcttgggc aattttatg ctg         53
```

<210> SEQ ID NO 160
<211> LENGTH: 53
<212> TYPE: DNA
<213> ORGANISM: Artificial sequence
<220> FEATURE:
<223> OTHER INFORMATION: Oligonucleotide primer XLR-A_5L-VL7/8

<400> SEQUENCE: 160

```
ccatctcatc cctgcgtgtc tccgactcag gagtggattc tcagactgtg gtg        53
```

<210> SEQ ID NO 161
<211> LENGTH: 54
<212> TYPE: DNA
<213> ORGANISM: Artificial sequence
<220> FEATURE:
<223> OTHER INFORMATION: Oligonucleotide primer XLR-A_5MP-VL1

<400> SEQUENCE: 161

```
ccatctcatc cctgcgtgtc tccgactcag gctcactgca cagggtcctg ggcc       54
```

<210> SEQ ID NO 162
<211> LENGTH: 54
<212> TYPE: DNA
<213> ORGANISM: Artificial sequence
<220> FEATURE:
<223> OTHER INFORMATION: Oligonucleotide primer XLR-A_5MP-VL3-1

<400> SEQUENCE: 162

```
ccatctcatc cctgcgtgtc tccgactcag gcttactgca caggatccgt ggcc       54
```

<210> SEQ ID NO 163
<211> LENGTH: 54
<212> TYPE: DNA
<213> ORGANISM: Artificial sequence
<220> FEATURE:
<223> OTHER INFORMATION: Oligonucleotide primer XLR-A_5MP-VL3-19

<400> SEQUENCE: 163

```
ccatctcatc cctgcgtgtc tccgactcag actctttgca taggttctgt ggtt       54
```

<210> SEQ ID NO 164
<211> LENGTH: 54
<212> TYPE: DNA
<213> ORGANISM: Artificial sequence
<220> FEATURE:
<223> OTHER INFORMATION: Oligonucleotide primer XLR-A_5MP-VL3-21

<400> SEQUENCE: 164

```
ccatctcatc cctgcgtgtc tccgactcag tctcactgca caggctctgt gacc       54
```

<210> SEQ ID NO 165
<211> LENGTH: 53
<212> TYPE: DNA
<213> ORGANISM: Artificial sequence

```
<220> FEATURE:
<223> OTHER INFORMATION: Oligonucleotide primer XLR-A_5MP-VL7-43

<400> SEQUENCE: 165
ccatctcatc cctgcgtgtc tccgactcag acttgctgcc cagggtccaa ttc          53

<210> SEQ ID NO 166
<211> LENGTH: 57
<212> TYPE: DNA
<213> ORGANISM: Artificial sequence
<220> FEATURE:
<223> OTHER INFORMATION: Oligonucleotide primer XLR-B_3xwCK1

<400> SEQUENCE: 166
cctatcccct gtgtgccttg gcagtctcag cagcaggcac acaacagagg cagttcc      57

<210> SEQ ID NO 167
<211> LENGTH: 54
<212> TYPE: DNA
<213> ORGANISM: Artificial sequence
<220> FEATURE:
<223> OTHER INFORMATION: Oligonucleotide primer XLR-B_3CL

<400> SEQUENCE: 167
cctatcccct gtgtgccttg gcagtctcag caccagtgtg gccttgttgg cttg         54

<210> SEQ ID NO 168
<211> LENGTH: 29
<212> TYPE: DNA
<213> ORGANISM: Artificial sequence
<220> FEATURE:
<223> OTHER INFORMATION: Oligonucleotide primer EnvM

<400> SEQUENCE: 168
tagcccttcc agtccccccct tttcttttta                                    29

<210> SEQ ID NO 169
<211> LENGTH: 33
<212> TYPE: DNA
<213> ORGANISM: Artificial sequence
<220> FEATURE:
<223> OTHER INFORMATION: Oligonucleotide primer EnvAstop

<400> SEQUENCE: 169
caccggctta ggcatctcct atggcaggaa gaa                                 33

<210> SEQ ID NO 170
<211> LENGTH: 494
<212> TYPE: PRT
<213> ORGANISM: Homo sapiens

<400> SEQUENCE: 170

Met Gly Trp Ser Cys Ile Ile Leu Phe Leu Val Ala Thr Ala Thr Gly
1               5                   10                  15

Val His Ser Gln Val Gln Leu Val Glu Ser Gly Gly Gly Val Val Gln
            20                  25                  30

Pro Gly Thr Ser Leu Arg Leu Ser Cys Ala Ala Ser Gln Phe Arg Phe
        35                  40                  45

Asp Gly Tyr Gly Met His Trp Val Arg Gln Ala Pro Gly Lys Gly Leu
    50                  55                  60

Glu Trp Val Ala Ser Ile Ser His Asp Gly Ile Lys Lys Tyr His Ala
65                  70                  75                  80

Glu Lys Val Trp Gly Arg Phe Thr Ile Ser Arg Asp Asn Ser Lys Asn
```

```
                    85                  90                  95
Thr Leu Tyr Leu Gln Met Asn Ser Leu Arg Pro Glu Asp Thr Ala Leu
            100                 105                 110
Tyr Tyr Cys Ala Lys Asp Leu Arg Glu Asp Cys Glu Glu Trp Trp
            115                 120                 125
Ser Asp Tyr Tyr Asp Phe Gly Lys Gln Leu Pro Cys Ala Lys Ser Arg
            130                 135                 140
Gly Gly Leu Val Gly Ile Ala Asp Asn Trp Gly Gln Gly Thr Met Val
145                 150                 155                 160
Thr Val Ser Ser Ala Ser Thr Lys Gly Pro Ser Val Phe Pro Leu Ala
            165                 170                 175
Pro Ser Ser Lys Ser Thr Ser Gly Gly Thr Ala Ala Leu Gly Cys Leu
            180                 185                 190
Val Lys Asp Tyr Phe Pro Glu Pro Val Thr Val Ser Trp Asn Ser Gly
            195                 200                 205
Ala Leu Thr Ser Gly Val His Thr Phe Pro Ala Val Leu Gln Ser Ser
            210                 215                 220
Gly Leu Tyr Ser Leu Ser Ser Val Val Thr Val Pro Ser Ser Ser Leu
225                 230                 235                 240
Gly Thr Gln Thr Tyr Ile Cys Asn Val Asn His Lys Pro Ser Asn Thr
                245                 250                 255
Lys Val Asp Lys Lys Val Glu Pro Lys Ser Cys Asp Lys Thr His Thr
                260                 265                 270
Cys Pro Pro Cys Pro Ala Pro Glu Leu Leu Gly Gly Pro Ser Val Phe
            275                 280                 285
Leu Phe Pro Pro Lys Pro Lys Asp Thr Leu Met Ile Ser Arg Thr Pro
290                 295                 300
Glu Val Thr Cys Val Val Val Asp Val Ser His Glu Asp Pro Glu Val
305                 310                 315                 320
Lys Phe Asn Trp Tyr Val Asp Gly Val Glu Val His Asn Ala Lys Thr
                325                 330                 335
Lys Pro Arg Glu Glu Gln Tyr Asn Ser Thr Tyr Arg Val Val Ser Val
            340                 345                 350
Leu Thr Val Leu His Gln Asp Trp Leu Asn Gly Lys Glu Tyr Lys Cys
            355                 360                 365
Lys Val Ser Asn Lys Ala Leu Pro Ala Pro Ile Glu Lys Thr Ile Ser
            370                 375                 380
Lys Ala Lys Gly Gln Pro Arg Glu Pro Gln Val Tyr Thr Leu Pro Pro
385                 390                 395                 400
Ser Arg Asp Glu Leu Thr Lys Asn Gln Val Ser Leu Thr Cys Leu Val
                405                 410                 415
Lys Gly Phe Tyr Pro Ser Asp Ile Ala Val Glu Trp Glu Ser Asn Gly
                420                 425                 430
Gln Pro Glu Asn Asn Tyr Lys Thr Thr Pro Pro Val Leu Asp Ser Asp
            435                 440                 445
Gly Ser Phe Phe Leu Tyr Ser Lys Leu Thr Val Asp Lys Ser Arg Trp
450                 455                 460
Gln Gln Gly Asn Val Phe Ser Cys Ser Val Met His Glu Ala Leu His
465                 470                 475                 480
Asn His Tyr Thr Gln Lys Ser Leu Ser Leu Ser Pro Gly Lys
                485                 490

<210> SEQ ID NO 171
```

<211> LENGTH: 236
<212> TYPE: PRT
<213> ORGANISM: Homo sapiens

<400> SEQUENCE: 171

Met Gly Trp Ser Cys Ile Ile Leu Phe Leu Val Ala Thr Ala Thr Gly
1               5                   10                  15

Ser Trp Ala Gln Ser Val Leu Thr Gln Pro Pro Ser Val Ser Ala Ala
            20                  25                  30

Pro Gly Gln Lys Val Thr Ile Ser Cys Ser Gly Asn Thr Ser Asn Ile
        35                  40                  45

Gly Asn Asn Phe Val Ser Trp Tyr Gln Gln Arg Pro Gly Arg Ala Pro
    50                  55                  60

Gln Leu Leu Ile Tyr Glu Thr Asp Lys Arg Pro Ser Gly Ile Pro Asp
65                  70                  75                  80

Arg Phe Ser Ala Ser Lys Ser Gly Thr Ser Gly Thr Leu Ala Ile Thr
                85                  90                  95

Gly Leu Gln Thr Gly Asp Glu Ala Asp Tyr Tyr Cys Ala Thr Trp Ala
            100                 105                 110

Ala Ser Leu Ser Ser Ala Arg Val Phe Gly Thr Gly Thr Gln Val Ile
        115                 120                 125

Val Leu Gly Gln Pro Lys Val Asn Pro Thr Val Thr Leu Phe Pro Pro
130                 135                 140

Ser Ser Glu Glu Leu Gln Ala Asn Lys Ala Thr Leu Val Cys Leu Ile
145                 150                 155                 160

Ser Asp Phe Tyr Pro Gly Ala Val Thr Val Ala Trp Lys Ala Asp Ser
                165                 170                 175

Ser Pro Val Lys Ala Gly Val Glu Thr Thr Thr Pro Ser Lys Gln Ser
            180                 185                 190

Asn Asn Lys Tyr Ala Ala Ser Ser Tyr Leu Ser Leu Thr Pro Glu Gln
        195                 200                 205

Trp Lys Ser His Arg Ser Tyr Ser Cys Gln Val Thr His Glu Gly Ser
210                 215                 220

Thr Val Glu Lys Thr Val Ala Pro Thr Glu Cys Ser
225                 230                 235

<210> SEQ ID NO 172
<211> LENGTH: 145
<212> TYPE: PRT
<213> ORGANISM: Homo sapiens

<400> SEQUENCE: 172

Gln Val Gln Leu Val Glu Ser Gly Gly Gly Val Val Gln Pro Gly Thr
1               5                   10                  15

Ser Leu Arg Leu Ser Cys Ala Ala Ser Gln Phe Arg Phe Asp Gly Tyr
            20                  25                  30

Gly Met His Trp Val Arg Gln Ala Pro Gly Lys Gly Leu Glu Trp Val
        35                  40                  45

Ala Ser Ile Ser His Asp Gly Ile Lys Lys Tyr His Ala Glu Lys Val
    50                  55                  60

Trp Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Ala Lys Asp Leu Arg Glu Asp Glu Cys Glu Glu Trp Trp Ser Asp Tyr
            100                 105                 110

```
Tyr Asp Phe Gly Lys Gln Leu Pro Cys Ala Lys Ser Arg Gly Gly Leu
        115                 120                 125

Val Gly Ile Ala Asp Asn Trp Gly Gln Gly Thr Met Val Thr Val Ser
130                 135                 140

Ser
145

<210> SEQ ID NO 173
<211> LENGTH: 122
<212> TYPE: PRT
<213> ORGANISM: Homo sapiens

<400> SEQUENCE: 173

Gln Ser Val Leu Thr Gln Pro Pro Ser Val Ser Ala Ala Pro Gly Gln
1               5                   10                  15

Lys Val Thr Ile Ser Cys Ser Gly Asn Thr Ser Asn Ile Gly Asn Asn
            20                  25                  30

Phe Val Ser Trp Tyr Gln Gln Arg Pro Gly Arg Ala Pro Gln Leu Leu
        35                  40                  45

Ile Tyr Glu Thr Asp Lys Arg Pro Ser Gly Ile Pro Asp Arg Phe Ser
50                  55                  60

Ala Ser Lys Ser Gly Thr Ser Gly Thr Leu Ala Ile Thr Gly Leu Gln
65                  70                  75                  80

Thr Gly Asp Glu Ala Asp Tyr Tyr Cys Ala Thr Trp Ala Ala Ser Leu
                85                  90                  95

Ser Ser Ala Arg Val Phe Gly Thr Gly Thr Gln Val Ile Val Leu Gly
            100                 105                 110

Gln Pro Lys Val Asn Pro Thr Val Thr Leu
        115                 120

<210> SEQ ID NO 174
<211> LENGTH: 1485
<212> TYPE: DNA
<213> ORGANISM: Homo sapiens

<400> SEQUENCE: 174
atgggatggt catgtatcat cctttttcta gtagcaactg caaccggtgt acattctcag      60
gtgcagctgg tggagtctgg gggaggcgtg gtccagcctg ggacgtccct gagactctcc    120
tgtgcagcct ctcaattcag gtttgatggt tatggcatgc actgggtccg ccaggcccca    180
ggcaaggggc tggagtgggt ggcatctata tcacatgatg gaattaaaaa gtatcacgca    240
gaaaaagtgt ggggccgctt caccatctcc agagacaatt ccaagaacac actgtatcta    300
caaatgaaca gcctgcgacc tgaggacacg gctctctact actgtgcgaa agatttgcga    360
gaagacgaat gtgaagagtg gtggtcggat tattacgatt ttgggaaaca actcccttgc    420
gcaaagtcac gcggcggctt ggttggaatt gctgataact ggggccaagg acaatggtc    480 accgtctctt cagcgtcgac caagggccca tcggtcttcc cctggcacc tcctccaag     540 agcacctctg ggggcacagc ggccctgggc tgcctggtca aggactactt ccccgaaccc    600
gtgacggtgt cgtggaactc aggcgccctg accagcggcg tgcacacctt ccggctgtc    660 ctacagtcct caggactcta ctccctcagc agcgtggtga ccgtgccctc agcagcttg    720 ggcacccaga cctacatctg caacgtgaat cacaagccca gcaacaccaa ggtggacaag    780
aaagttgagc ccaaatcttg tgacaaaact cacacatgcc caccgtgccc agcacctgaa    840
ctcctggggg gaccgtcagt cttcctcttc cccccaaaac ccaaggacac cctcatgatc    900
```

```
tcccggaccc ctgaggtcac atgcgtggtg gtggacgtga gccacgaaga ccctgaggtc      960
aagttcaact ggtacgtgga cggcgtggag gtgcataatg ccaagacaaa gccgcgggag     1020
gagcagtaca acagcacgta ccgtgtggtc agcgtcctca ccgtcctgca ccaggactgg     1080
ctgaatggca aggagtacaa gtgcaaggtc tccaacaaag ccctcccagc ccccatcgag     1140
aaaaccatct ccaaagccaa agggcagccc cgagaaccac aggtgtacac cctgccccca     1200
tcccgggatg agctgaccaa gaaccaggtc agcctgacct gcctggtcaa aggcttctat     1260
cccagcgaca tcgccgtgga gtgggagagc aatgggcagc cggagaacaa ctacaagacc     1320
acgcctcccg tgctggactc cgacggctcc ttcttcctct acagcaagct caccgtggac     1380
aagagcaggt ggcagcaggg gaacgtcttc tcatgctccg tgatgcatga ggctctgcac     1440
aaccactaca cgcagaagag cctctccctg tctccgggta aatga                    1485

<210> SEQ ID NO 175
<211> LENGTH: 711
<212> TYPE: DNA
<213> ORGANISM: Homo sapiens

<400> SEQUENCE: 175
atgggatggt catgtatcat cctttttcta gtagcaactg caaccggttc ctgggcccag       60
tctgtgctga ctcagccgcc ctcagtgtct gcggccccag gacagaaggt caccatctcc      120
tgctctggaa acacctccaa cattggtaat aattttgtgt cctggtacca acagcgcccc      180
ggcagagccc cccaactcct catttatgaa actgacaagc gaccctcagg gattcctgac      240
cgattctctg cttccaagtc tggtacgtca ggcaccctgg ccatcaccgg ctgcagact      300 ggggacgagg ccgactatta ctgcgccaca tgggctgcca gctgagttc cgcgcgtgtc      360 ttcggaactg ggaccaggt catcgtccta ggtcagccca aggtcaaccc cactgtcact      420
ctgttcccgc cctcgagtga ggagcttcaa gccaacaagg ccacactggt gtgtctcata      480
agtgacttct acccgggagc cgtgacagtg gcctggaagg cagatagcag ccccgtcaag      540
gcgggagtgg agaccaccac accctccaaa caaagcaaca caagtacgcg gccagcagc      600 tacctgagcc tgacgcctga cagtggaag tcccacagaa gctacagctg ccaggtcacg      660
catgaaggga gcaccgtgga gaagacagtg gcccctacag aatgttcata g              711

<210> SEQ ID NO 176
<211> LENGTH: 435
<212> TYPE: DNA
<213> ORGANISM: Homo sapiens

<400> SEQUENCE: 176
caggtgcagc tggtggagtc tgggggaggc gtggtccagc ctgggacgtc cctgagactc       60
tcctgtgcag cctctcaatt caggtttgat ggttatggca tgcactgggt ccgccaggcc      120
ccaggcaagg ggctggagtg ggtggcatct atatcacatg atggaattaa aaagtatcac      180
gcagaaaaag tgtggggccg cttcaccatc tccagagaca attccaagaa cacactgtat      240
ctacaaatga acagcctgcg acctgaggac acggctctct actactgtgc gaaagatttg      300
cgagaagacg aatgtgaaga gtggtggtcg gattattacg attttgggaa caactccct      360 tgcgcaaagt cacgcggcgg cttggttgga attgctgata ctggggcca agggacaatg      420 gtcaccgtct cttca                                                     435

<210> SEQ ID NO 177
```

<211> LENGTH: 366
<212> TYPE: DNA
<213> ORGANISM: Homo sapiens

<400> SEQUENCE: 177

```
cagtctgtgc tgactcagcc gccctcagtg tctgcggccc caggacagaa ggtcaccatc      60
tcctgctctg gaaacacctc caacattggt aataattttg tgtcctggta ccaacagcgc     120
cccggcagag cccccaact cctcatttat gaaactgaca agcgaccctc agggattcct      180
gaccgattct ctgcttccaa gtctggtacg tcaggcaccc tggccatcac cgggctgcag     240
actggggacg aggccgacta ttactgcgcc acatgggctg ccagcctgag ttccgcgcgt     300
gtcttcggaa ctgggaccca ggtcatcgtc ctaggtcagc ccaaggtcaa ccccactgtc     360
actctg                                                                366
```

<210> SEQ ID NO 178
<211> LENGTH: 476
<212> TYPE: PRT
<213> ORGANISM: Homo sapiens

<400> SEQUENCE: 178

```
Glu Val Gln Leu Val Glu Ser Gly Gly Gly Ile Val Gln Pro Gly Arg
1               5                   10                  15

Ser Leu Thr Leu Ser Cys Val Ala Ser Gln Phe Ala Phe Ser His Tyr
            20                  25                  30

Gly Met His Trp Val Arg Gln Ala Pro Gly Lys Gly Leu Glu Trp Val
        35                  40                  45

Ala Ser Ile Ser Arg Asp Glu Thr Lys Lys Tyr His Gly Asp Ser Val
    50                  55                  60

Trp Asp Arg Phe Ser Ile Ser Arg Asp Asn Ser Lys Asn Thr Leu Phe
65                  70                  75                  80

Leu Gln Met Asn Ser Leu Arg Ala Glu Asp Thr Ala Leu Tyr Phe Cys
                85                  90                  95

Val Arg Asp Gln Arg Glu Asp Glu Cys Glu Glu Trp Trp Ser Asp Tyr
            100                 105                 110

Tyr Asp Phe Gly Lys Glu Leu Pro Cys Arg Lys Phe Arg Gly Leu Gly
        115                 120                 125

Leu Ala Gly Ile Phe Asp Val Trp Gly His Gly Thr Met Val Ile Val
    130                 135                 140

Ser Ser Ala Ser Thr Lys Gly Pro Ser Val Phe Pro Leu Ala Pro Ser
145                 150                 155                 160

Ser Lys Ser Thr Ser Gly Gly Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Ser Leu Gly Thr
    210                 215                 220

Gln Thr Tyr Ile Cys Asn Val Asn His Lys Pro Ser Asn Thr Lys Val
225                 230                 235                 240

Asp Lys Lys Val Glu Pro Lys Ser Cys Asp Lys Thr His Thr Cys Pro
                245                 250                 255

Pro Cys Pro Ala Pro Glu Leu Leu Gly Gly Pro Ser Val Phe Leu Phe
            260                 265                 270
```

Pro Pro Lys Pro Lys Asp Thr Leu Met Ile Ser Arg Thr Pro Glu Val
            275                 280                 285

Thr Cys Val Val Val Asp Val Ser His Glu Asp Pro Glu Val Lys Phe
    290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
        355                 360                 365

Lys Gly Gln Pro Arg Glu Pro Gln Val Tyr Thr Leu Pro Pro Ser Arg
    370                 375                 380

Asp Glu Leu Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
            420                 425                 430

Phe Phe Leu Tyr Ser Lys Leu Thr Val Asp Lys Ser Arg Trp Gln Gln
        435                 440                 445

Gly Asn Val Phe Ser Cys Ser Val Met His Glu Ala Leu His Asn His
    450                 455                 460

Tyr Thr Gln Lys Ser Leu Ser Leu Ser Pro Gly Lys
465                 470                 475

<210> SEQ ID NO 179
<211> LENGTH: 217
<212> TYPE: PRT
<213> ORGANISM: Homo sapiens

<400> SEQUENCE: 179

Gln Ser Ala Leu Thr Gln Pro Pro Ser Val Ser Ala Ala Pro Gly Gln
1               5                   10                  15

Lys Val Ser Ile Ser Cys Ser Gly Asn Asn Ser Asn Ile Gly Asn Asn
            20                  25                  30

Phe Ile Ser Trp Phe Gln Gln Phe Pro Gly Thr Ala Pro Lys Pro Leu
        35                  40                  45

Ile Tyr Glu Thr Tyr Lys Arg His Ser Gly Ile Pro Asp Arg Phe Ser
    50                  55                  60

Gly Ser Lys Ser Gly Thr Ser Ala Thr Leu Ala Ile Thr Gly Leu Gln
65                  70                  75                  80

Thr Gly Asp Glu Ala Asp Tyr Tyr Cys Ala Thr Trp Gly Val Arg Gln
                85                  90                  95

Gly Val Gly Ala Leu Phe Gly Thr Gly Thr Lys Val Thr Val Leu Gly
            100                 105                 110

Gln Pro Lys Ala Asn Pro Thr Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
                180                 185                 190

His Arg Ser Tyr Ser Cys Gln Val Thr His Glu Gly Ser Thr Val Glu
            195                 200                 205

Lys Thr Val Ala Pro Thr Glu Cys Ser
210                 215

<210> SEQ ID NO 180
<211> LENGTH: 146
<212> TYPE: PRT
<213> ORGANISM: Homo sapiens

<400> SEQUENCE: 180

Glu Val Gln Leu Val Glu Ser Gly Gly Gly Ile Val Gln Pro Gly Arg
1               5                   10                  15

Ser Leu Thr Leu Ser Cys Val Ala Ser Gln Phe Ala Phe Ser His Tyr
            20                  25                  30

Gly Met His Trp Val Arg Gln Ala Pro Gly Lys Gly Leu Glu Trp Val
        35                  40                  45

Ala Ser Ile Ser Arg Asp Glu Thr Lys Lys Tyr His Gly Asp Ser Val
50                  55                  60

Trp Asp Arg Phe Ser Ile Ser Arg Asp Asn Ser Lys Asn Thr Leu Phe
65                  70                  75                  80

Leu Gln Met Asn Ser Leu Arg Ala Glu Asp Thr Ala Leu Tyr Phe Cys
                85                  90                  95

Val Arg Asp Gln Arg Glu Asp Glu Cys Glu Gly Trp Trp Ser Asp Tyr
            100                 105                 110

Tyr Asp Phe Gly Lys Glu Leu Pro Cys Arg Lys Phe Arg Gly Leu Gly
        115                 120                 125

Leu Ala Gly Ile Phe Asp Val Trp Gly His Gly Thr Met Val Ile Val
    130                 135                 140

Ser Ser
145

<210> SEQ ID NO 181
<211> LENGTH: 111
<212> TYPE: PRT
<213> ORGANISM: Homo sapiens

<400> SEQUENCE: 181

Gln Ser Ala Leu Thr Gln Pro Pro Ser Val Ser Ala Ala Pro Gly Gln
1               5                   10                  15

Lys Val Ser Ile Ser Cys Ser Gly Asn Asn Ser Asn Ile Gly Asn Asn
            20                  25                  30

Phe Ile Ser Trp Phe Gln Gln Phe Pro Gly Thr Ala Pro Lys Pro Leu
        35                  40                  45

Ile Tyr Glu Thr Tyr Lys Arg His Ser Gly Ile Pro Asp Arg Phe Ser
    50                  55                  60

Gly Ser Lys Ser Gly Thr Ser Ala Thr Leu Ala Ile Thr Gly Leu Gln
65                  70                  75                  80

Thr Gly Asp Glu Ala Asp Tyr Tyr Cys Ala Thr Trp Gly Val Arg Gln
                85                  90                  95

Gly Val Gly Ala Leu Phe Gly Thr Gly Thr Lys Val Thr Val Leu
            100                 105                 110

<210> SEQ ID NO 182

```
<211> LENGTH: 1431
<212> TYPE: DNA
<213> ORGANISM: Homo sapiens

<400> SEQUENCE: 182
gaggtgcagc tggtggagtc tgggggaggc atagtccagc ctgggaggtc cctgacactg      60
tcttgtgtag cctctcaatt cgcttttcg cattatggca tgcactgggt ccgccaggct     120
ccaggcaagg gactggagtg ggtggccagt atctcaaggg atgagaccaa gaaatatcat    180
ggagattccg tgtgggaccg attcagtatc tccagagaca attccaagaa taccctgttt    240
ctacaaatga acagcctgcg agctgaggac acggcactat atttctgtgt gagagatcag    300
cgagaagacg aatgtgagga gtggtggtcg gactattatg attttgggaa agaactccct    360
tgccgaaaat tccggggcct gggcctggct ggaattttg atgtctgggg ccacgggaca     420
atggtcatcg tctcttcagc gtcgaccaag ggcccatcgg tcttccccct ggcaccctcc    480
tccaagagca cctctggggg cacagcggcc ctgggctgcc tggtcaagga ctacttcccc    540
gaacccgtga cggtgtcgtg aactcaggc gccctgacca cgcgcgtgca caccttcccg     600
gctgtcctac agtcctcagg actctactcc ctcagcagcg tggtgaccgt gccctccagc    660
agcttgggca cccagaccta catctgcaac gtgaatcaca agcccagcaa caccaaggtg    720
gacaagaaag ttgagcccaa atcttgtgac aaaactcaca catgcccacc gtgcccagca    780
cctgaactcc tggggggacc gtcagtcttc ctcttccccc caaaacccaa ggacaccctc    840
atgatctccc ggacccctga ggtcacatgc gtggtggtgg acgtgagcca cgaagaccct    900
gaggtcaagt tcaactggta cgtggacggc gtggaggtgc ataatgccaa gacaaagccg    960
cgggaggagc agtacaacag cacgtaccgt gtggtcagcg tcctcaccgt cctgcaccag   1020
gactggctga atggcaagga gtacaagtgc aaggtctcca caaagccct cccagccccc   1080 atcgagaaaa ccatctccaa agccaaaggg cagccccgag aaccacaggt gtacaccctg   1140
cccccatccc gggatgagct gaccaagaac caggtcagcc tgacctgcct ggtcaaaggc   1200
ttctatccca gcgacatcgc cgtggagtgg gagagcaatg ggcagccgga gaacaactac   1260
aagaccacgc ctcccgtgct ggactccgac ggctccttct cctctacag caagctcacc    1320 gtggacaaga gcaggtggca gcaggggaac gtcttctcat gctccgtgat gcatgaggct   1380
ctgcacaacc actacacgca gaagagcctc tccctgtctc cgggtaaatg a            1431

<210> SEQ ID NO 183
<211> LENGTH: 654
<212> TYPE: DNA
<213> ORGANISM: Homo sapiens

<400> SEQUENCE: 183
cagtctgccc tgactcagcc gccctcagtg tctgcggccc caggacagaa ggtctccatc      60
tcctgctctg gaacaactc aaacattggg aataactta tatcctggtt ccagcaattc     120
ccaggaacag cccccaaacc cctcatatat gaaacttaca gcgacactc aggtattcct     180 gaccgattct ctggctccaa gtctggcacg tcagccaccc tggccatcac cggactccag    240
actggggacg aggccgacta ttactgcgca acatggggtg tcaggcaggg tgtcggcgct    300
ctcttcggaa ctgggactaa ggtcaccgtc ctaggtcagc ccaaggccaa ccccactgtc    360
actctgttcc cgccctcgag tgaggagctt caagccaaca aggccacact ggtgtgtctc    420
ataagtgact tctaccccggg agccgtgaca gtggcctgga aggcagatag cagccccgtc    480
aaggcgggag tggagaccac cacaccctcc aaacaaagca caacaagta cgcggccagc    540
```

```
agctacctga gcctgacgcc tgagcagtgg aagtcccaca gaagctacag ctgccaggtc    600
acgcatgaag ggagcaccgt ggagaagaca gtggcccct a cagaatgttc atag         654
```

<210> SEQ ID NO 184
<211> LENGTH: 438
<212> TYPE: DNA
<213> ORGANISM: Homo sapiens

<400> SEQUENCE: 184

```
gaggtgcagc tggtggagtc tgggggaggc atagtccagc ctggg aggtc cctgacactg    60 tcttgtgtag cctctcaatt cgcttttcg cattatggca tgcactgggt ccgccaggct    120
ccaggcaagg gactggagtg ggtggccagt atctcaaggg atgagaccaa gaaatatcat    180
ggagattccg tgtgggaccg attcagtatc tccagagaca attccaagaa taccctgttt    240
ctacaaatga acagcctgcg agctgaggac acggcactat atttctgtgt gagagatcag    300
cgagaagacg aatgtgagga gtggtggtcg gactattatg attttgggaa agaactccct    360
tgccgaaaat tccggggcct gggcctggct ggaattttg atgtctgggg ccacgggaca    420
atggtcatcg tctcttca                                                 438
```

<210> SEQ ID NO 185
<211> LENGTH: 333
<212> TYPE: DNA
<213> ORGANISM: Homo sapiens

<400> SEQUENCE: 185

```
cagtctgccc tgactcagcc gccctcagtg tctgcggccc caggacagaa ggtctccatc    60
tcctgctctg gaacaactc aaacattggg ataactttta tatcctggtt ccagcaattc    120
ccaggaacag cccccaaacc cctcatatat gaaacttaca gcgacactc aggtattcct    180 gaccgattct ctggctccaa gtctggcacg tcagccaccc tggccatcac cggactccag    240
actggggacg aggccgacta ttactgcgca acatggggtg tcaggcaggg tgtcggcgct    300
ctcttcggaa ctgggactaa ggtcaccgtc cta                                333
```

<210> SEQ ID NO 186
<211> LENGTH: 476
<212> TYPE: PRT
<213> ORGANISM: Homo sapiens

<400> SEQUENCE: 186

Gln Lys Gln Leu Val Glu Ser Gly Gly Gly Val Val Gln Pro Gly Arg
1               5                   10                  15

Ser Leu Thr Leu Ser Cys Ala Ala Ser Gln Phe Pro Phe Ser His Tyr
            20                  25                  30

Gly Met His Trp Val Arg Gln Ala Pro Gly Lys Gly Leu Glu Trp Val
        35                  40                  45

Ala Ser Ile Thr Asn Asp Gly Thr Lys Lys Tyr His Gly Glu Ser Val
    50                  55                  60

Trp Asp Arg Phe Arg Ile Ser Arg Asp Asn Ser Lys Asn Thr Leu Phe
65                  70                  75                  80

Leu Gln Met Asn Ser Leu Arg Ala Glu Asp Thr Ala Leu Tyr Phe Cys
                85                  90                  95

Val Arg Asp Gln Arg Glu Asp Glu Cys Glu Glu Trp Trp Ser Asp Tyr
            100                 105                 110

Tyr Asp Phe Gly Lys Glu Leu Pro Cys Arg Lys Phe Arg Gly Leu Gly

```
            115                 120                 125
Leu Ala Gly Ile Phe Asp Ile Trp Gly His Gly Thr Met Val Ile Val
    130                 135                 140

Ser Ser Ala Ser Thr Lys Gly Pro Ser Val Phe Pro Leu Ala Pro Ser
145                 150                 155                 160

Ser Lys Ser Thr Ser Gly Gly Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Ser Leu Gly Thr
    210                 215                 220

Gln Thr Tyr Ile Cys Asn Val Asn His Lys Pro Ser Asn Thr Lys Val
225                 230                 235                 240

Asp Lys Lys Val Glu Pro Lys Ser Cys Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
        275                 280                 285

Thr Cys Val Val Val Asp Val Ser His Glu Asp Pro Glu Val Lys Phe
    290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
        355                 360                 365

Lys Gly Gln Pro Arg Glu Pro Gln Val Tyr Thr Leu Pro Pro Ser Arg
    370                 375                 380

Asp Glu Leu Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
            420                 425                 430

Phe Phe Leu Tyr Ser Lys Leu Thr Val Asp Lys Ser Arg Trp Gln Gln
        435                 440                 445

Gly Asn Val Phe Ser Cys Ser Val Met His Glu Ala Leu His Asn His
    450                 455                 460

Tyr Thr Gln Lys Ser Leu Ser Leu Ser Pro Gly Lys
465                 470                 475

<210> SEQ ID NO 187
<211> LENGTH: 217
<212> TYPE: PRT
<213> ORGANISM: Homo sapiens

<400> SEQUENCE: 187

Gln Ser Val Leu Thr Gln Pro Pro Ser Val Ser Ala Ala Pro Gly Gln
1               5                   10                  15
```

```
Lys Val Ser Ile Ser Cys Ser Gly Asn Asn Ser Asn Ile Gly Asn Asn
             20                  25                  30

Phe Ile Ser Trp Phe Gln Gln Phe Pro Gly Thr Ala Pro Lys Pro Leu
         35                  40                  45

Ile Tyr Glu Thr Tyr Arg Arg His Ser Gly Ile Pro Asp Arg Phe Ser
 50                      55                  60

Gly Ser Lys Ser Gly Thr Ser Ala Thr Leu Ala Ile Thr Gly Leu Gln
 65                  70                  75                  80

Thr Gly Asp Glu Ala Asp Tyr Tyr Cys Ala Thr Trp Gly Val Arg Gln
                 85                  90                  95

Gly Val Gly Ala Leu Phe Gly Thr Gly Thr Lys Val Thr Val Leu Gly
             100                 105                 110

Gln Pro Lys Ala Asn Pro Thr Val Thr Leu Phe Pro Pro Ser Ser Glu
         115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                 165                 170                 175

Tyr Ala Ala Ser Ser Tyr Leu Ser Leu Thr Pro Glu Gln Trp Lys Ser
             180                 185                 190

His Arg Ser Tyr Ser Cys Gln Val Thr His Glu Gly Ser Thr Val Glu
         195                 200                 205

Lys Thr Val Ala Pro Thr Glu Cys Ser
210                 215

<210> SEQ ID NO 188
<211> LENGTH: 146
<212> TYPE: PRT
<213> ORGANISM: Homo sapiens

<400> SEQUENCE: 188

Gln Lys Gln Leu Val Glu Ser Gly Gly Gly Val Val Gln Pro Gly Arg
 1               5                  10                  15

Ser Leu Thr Leu Ser Cys Ala Ala Ser Gln Phe Pro Phe Ser His Tyr
             20                  25                  30

Gly Met His Trp Val Arg Gln Ala Pro Gly Lys Gly Leu Glu Trp Val
         35                  40                  45

Ala Ser Ile Thr Asn Asp Gly Thr Lys Lys Tyr His Gly Glu Ser Val
 50                  55                  60

Trp Asp Arg Phe Arg Ile Ser Arg Asp Asn Ser Lys Asn Thr Leu Phe
 65                  70                  75                  80

Leu Gln Met Asn Ser Leu Arg Ala Glu Asp Thr Ala Leu Tyr Phe Cys
                 85                  90                  95

Val Arg Asp Gln Arg Glu Asp Glu Cys Glu Glu Trp Trp Ser Asp Tyr
             100                 105                 110

Tyr Asp Phe Gly Lys Glu Leu Pro Cys Arg Lys Phe Arg Gly Leu Gly
         115                 120                 125

Leu Ala Gly Ile Phe Asp Ile Trp Gly His Gly Thr Met Val Ile Val
     130                 135                 140

Ser Ser
145

<210> SEQ ID NO 189
```

<211> LENGTH: 111
<212> TYPE: PRT
<213> ORGANISM: Homo sapiens

<400> SEQUENCE: 189

Gln Ser Val Leu Thr Gln Pro Pro Ser Val Ser Ala Ala Pro Gly Gln
1               5                   10                  15

Lys Val Ser Ile Ser Cys Ser Gly Asn Asn Ser Asn Ile Gly Asn Asn
            20                  25                  30

Phe Ile Ser Trp Phe Gln Gln Phe Pro Gly Thr Ala Pro Lys Pro Leu
        35                  40                  45

Ile Tyr Glu Thr Tyr Arg Arg His Ser Gly Ile Pro Asp Arg Phe Ser
    50                  55                  60

Gly Ser Lys Ser Gly Thr Ser Ala Thr Leu Ala Ile Thr Gly Leu Gln
65                  70                  75                  80

Thr Gly Asp Glu Ala Asp Tyr Tyr Cys Ala Thr Trp Gly Val Arg Gln
                85                  90                  95

Gly Val Gly Ala Leu Phe Gly Thr Gly Thr Lys Val Thr Val Leu
            100                 105                 110

<210> SEQ ID NO 190
<211> LENGTH: 1431
<212> TYPE: DNA
<213> ORGANISM: Homo sapiens

<400> SEQUENCE: 190

```
cagaagcagt tggtggagtc tgggggaggc gtagtccagc ctgggaggtc cctgacactg      60
tcctgtgcag cctctcaatt ccctttttcg cattatggca tgcactgggt ccgccaggct     120
ccaggcaagg ggctggagtg ggtggcaagt attacaaatg atgggaccaa gaaatatcat     180
ggagagtccg tgtgggaccg attcaggatc tccagagaca attccaagaa tacactcttt     240
ctacaaatga acagcctgcg agctgaggac acggcactat atttctgtgt gagagatcag     300
cgagaagacg aatgtgaaga gtggtggtcg gattattatg attttgggaa agaactccct     360
tgccgaaaat tccggggcct gggcctggct ggaattttg atatctgggg ccacgggaca     420
atggtcatcg tctcatcagc gtcgaccaag ggcccatcgg tcttcccct ggcaccctcc      480
tccaagagca cctctggggg cacagcggcc ctgggctgcc tggtcaagga ctacttcccc     540
gaacccgtga cggtgtcgtg aactcaggc gccctgacca gcggcgtgca ccttcccg       600
gctgtcctac agtcctcagg actctactcc ctcagcagcg tggtgaccgt gccctccagc     660
agcttgggca cccagaccta catctgcaac gtgaatcaca agcccagcaa caccaaggtg     720
gacaagaaag ttgagcccaa atcttgtgac aaaactcaca catgcccacc gtgcccagca     780
cctgaactcc tggggggacc gtcagtcttc ctcttccccc caaaacccaa ggacaccctc     840
atgatctccc ggacccctga ggtcacatgc gtggtggtgg acgtgagcca cgaagaccct     900
gaggtcaagt tcaactggta cgtggacggc gtggaggtgc ataatgccaa gacaaagccg     960
cgggaggagc agtacaacag cacgtaccgt gtggtcagcg tcctcaccgt cctgcaccag    1020
gactggctga atggcaagga gtacaagtgc aaggtctcca acaaagccct cccagccccc    1080
atcgagaaaa ccatctccaa agccaaaggg cagccccgag aaccacaggt gtacaccctg    1140
cccccatccc gggatgagct gaccaagaac caggtcagcc tgacctgcct ggtcaaaggc    1200
ttctatccca gcgacatcgc cgtggagtgg gagagcaatg ggcagccgga gaacaactac    1260
aagaccacgc ctcccgtgct ggactccgac ggctccttct tcctctacag caagctcacc    1320
```

```
gtggacaaga gcaggtggca gcaggggaac gtcttctcat gctccgtgat gcatgaggct    1380
ctgcacaacc actacacgca gaagagcctc tccctgtctc cgggtaaatg a             1431

<210> SEQ ID NO 191
<211> LENGTH: 654
<212> TYPE: DNA
<213> ORGANISM: Homo sapiens

<400> SEQUENCE: 191
cagtctgtgc tgacgcagcc gccctcagtg tctgcggccc caggacagaa ggtctccatc      60
tcctgctctg gaaacaattc aaacattggg aataacttta tatcctggtt ccagcaattc     120
ccaggaacag cccccaaacc cctcatatat gaaacttaca ggcgacactc aggtattcct     180
gaccgattct ctggctccaa gtctggcacg tcagccaccc tggccatcac cggactccag     240
actggggacg aggccgacta ttactgcgca acatggggtg tcaggcaggg tgtcggcgct     300
ctcttcggaa ctgggactaa ggtcaccgtc ctaggtcagc ccaaggccaa ccccactgtc     360
actctgttcc cgccctcgag tgaggagctt caagccaaca ggccacact ggtgtgtctc      420 ataagtgact tctacccggg agccgtgaca gtggcctgga aggcagatag cagccccgtc     480
aaggcgggag tggagaccac cacaccctcc aaacaaagca caacaagta cgcggccagc      540 agctacctga gcctgacgcc tgagcagtgg aagtcccaca agctacag ctgccaggtc       600 acgcatgaag ggagcaccgt ggagaagaca gtggccccta cagaatgttc atag           654

<210> SEQ ID NO 192
<211> LENGTH: 438
<212> TYPE: DNA
<213> ORGANISM: Homo sapiens

<400> SEQUENCE: 192
cagaagcagt tggtggagtc tgggggaggc gtagtccagc ctgggaggtc cctgacactg      60
tcctgtgcag cctctcaatt ccctttttcg cattatggca tgcactgggt ccgccaggct    120
ccaggcaagg ggctggagtg ggtggcaagt attacaaatg atgggaccaa gaaatatcat    180
ggagagtccg tgtgggaccg attcaggatc tccagagaca attccaagaa tacactcttt    240
ctacaaatga acagcctgcg agctgaggac acggcactat atttctgtgt gagagatcag    300
cgagaagacg aatgtgaaga gtggtggtcg gattattatg attttgggaa agaactccct    360
tgccgaaaat tccggggcct gggcctggct ggaattttg atatctgggg ccacgggaca     420
atggtcatcg tctcatca                                                  438

<210> SEQ ID NO 193
<211> LENGTH: 333
<212> TYPE: DNA
<213> ORGANISM: Homo sapiens

<400> SEQUENCE: 193
cagtctgtgc tgacgcagcc gccctcagtg tctgcggccc caggacagaa ggtctccatc      60
tcctgctctg gaaacaattc aaacattggg aataacttta tatcctggtt ccagcaattc     120
ccaggaacag cccccaaacc cctcatatat gaaacttaca ggcgacactc aggtattcct     180
gaccgattct ctggctccaa gtctggcacg tcagccaccc tggccatcac cggactccag     240
actggggacg aggccgacta ttactgcgca acatggggtg tcaggcaggg tgtcggcgct     300
ctcttcggaa ctgggactaa ggtcaccgtc cta                                  333
```

<210> SEQ ID NO 194
<211> LENGTH: 144
<212> TYPE: PRT
<213> ORGANISM: Homo sapiens

<400> SEQUENCE: 194

Gln Val Gln Leu Val Gln Ser Gly Gly Gly Val Val Gln Pro Gly Arg
1               5                   10                  15

Ser Leu Arg Leu Ser Cys Ala Ala Pro Tyr Phe Glu Phe Gly Arg Tyr
                20                  25                  30

Gly Phe His Trp Val Arg Gln Ala Pro Gly Lys Gly Leu Glu Trp Val
            35                  40                  45

Ala Ser Ile Ser Phe Ala Gly Arg Asp Tyr Tyr His Ser Pro Ser Val
        50                  55                  60

Trp Gly Arg Phe Thr Ile Ser Arg Asp Asn Ser Lys Asn Thr Leu Tyr
65                  70                  75                  80

Leu Gln Met Asn Ser Leu Arg Ile Glu Asp Thr Ala Leu Tyr Phe Cys
                85                  90                  95

Ala Arg Asp Leu Arg Glu Ser Glu Cys Glu Glu Trp Glu Ser Asp Tyr
                100                 105                 110

Tyr Asp Phe Gly Lys Lys Gly Pro Cys Val Lys Pro Arg Gly Val Ala
            115                 120                 125

Gly Gly Leu Asp Leu Trp Gly Gln Gly Thr Met Val Ile Val Ser Ser
        130                 135                 140

<210> SEQ ID NO 195
<211> LENGTH: 144
<212> TYPE: PRT
<213> ORGANISM: Homo sapiens

<400> SEQUENCE: 195

Gln Val Gln Leu Met Glu Ser Gly Gly Gly Val Val Gln Pro Gly Arg
1               5                   10                  15

Ser Leu Arg Leu Ser Cys Ala Ala Ser Gly Phe Asn Phe Gly Gly Tyr
                20                  25                  30

Gly Met His Trp Val Arg Gln Ala Pro Gly Lys Gly Leu Glu Trp Val
            35                  40                  45

Ala Ala Ile Ser Phe Val Gly Leu Lys Asn Tyr Tyr Ser Asn Ser Val
        50                  55                  60

Arg Gly Arg Phe Thr Ile Ser Arg Asp Asn Ser Lys Asn Ile Leu Tyr
65                  70                  75                  80

Leu Gln Met Glu Ser Leu Arg Ala Glu Asp Thr Ala Leu Tyr Tyr Cys
                85                  90                  95

Ala Arg Asp Val Arg Glu Met Glu Cys Glu Glu Trp Ala Ser Asp Tyr
                100                 105                 110

Tyr Asp Phe Gly Arg Gly Gly Pro Cys Arg Asp Phe Arg Gly Val Val
            115                 120                 125

Gly Ile Leu Asp Ile Trp Gly Pro Gly Thr Met Val Ser Val Ser Ser
        130                 135                 140

<210> SEQ ID NO 196
<211> LENGTH: 144
<212> TYPE: PRT
<213> ORGANISM: Homo sapiens

<400> SEQUENCE: 196

Glu Val Gln Leu Val Glu Ser Gly Gly Gly Val Val Gln Pro Gly Arg
1               5                   10                  15

```
Ser Leu Arg Leu Ser Cys Ala Ala Ser Gln Phe Thr Phe Ser Asn Tyr
            20                  25                  30

Gly Met His Trp Val Arg Gln Ala Pro Gly Lys Gly Leu Glu Trp Val
        35                  40                  45

Ala Gly Ile Ser Phe Val Gly Ile Arg Lys Tyr Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Ala Asp Thr Ala Leu Tyr Phe Cys
                85                  90                  95

Ala Arg Asp Leu Arg Glu Tyr Glu Cys Glu Leu Trp Ala Ser Asp Tyr
            100                 105                 110

Tyr Asp Phe Gly Lys Pro Gln Pro Cys Glu Asp Pro Arg Gly Val Val
                115                 120                 125

Gly Thr Ser Asp Ile Trp Gly Gln Gly Thr Met Val Thr Val Ser Ser
        130                 135                 140

<210> SEQ ID NO 197
<211> LENGTH: 144
<212> TYPE: PRT
<213> ORGANISM: Homo sapiens

<400> SEQUENCE: 197

Glu Val Gln Leu Met Glu Ser Gly Gly Gly Val Val Gln Pro Gly Arg
1               5                   10                  15

Ser Leu Arg Leu Ser Cys Ala Ala Ser Gly Phe Asn Phe Gly Gly Tyr
            20                  25                  30

Gly Met His Trp Val Arg Gln Ala Pro Gly Lys Gly Leu Glu Trp Val
        35                  40                  45

Ala Ala Ile Ser Phe Val Gly Leu Lys Asn Tyr Tyr Thr Asn Ser Val
 50                  55                  60

Arg Gly Arg Phe Thr Ile Ser Arg Asp Asn Ser Lys Asn Ile Leu Tyr
65                  70                  75                  80

Leu Gln Met Glu Ser Leu Arg Ala Glu Asp Thr Ala Leu Tyr Tyr Cys
                85                  90                  95

Ala Arg Asp Val Arg Glu Met Glu Cys Glu Glu Trp Ala Ser Asp Tyr
            100                 105                 110

Tyr Asp Phe Gly Arg Gly Pro Cys Arg Asp Phe Arg Gly Val Val
                115                 120                 125

Gly Ile Leu Asp Ile Trp Gly Pro Gly Thr Met Val Thr Val Ser Ser
        130                 135                 140

<210> SEQ ID NO 198
<211> LENGTH: 144
<212> TYPE: PRT
<213> ORGANISM: Homo sapiens

<400> SEQUENCE: 198

Glu Val Gln Leu Glu Glu Ser Gly Gly Gly Val Val Gln Pro Gly Arg
1               5                   10                  15

Ser Leu Arg Leu Ser Cys Ala Ala Ser Gly Phe Ser Phe Gly Arg Tyr
            20                  25                  30

Gly Met His Trp Val Arg Gln Ala Pro Gly Lys Gly Leu Glu Trp Val
        35                  40                  45

Ala Gly Val Ser Phe Val Gly Leu Arg Lys Tyr His Ala Asn Ser Val
 50                  55                  60
```

Arg Gly Arg Phe Thr Ile Ser Arg Asp Asn Ser Lys Asn Ile Leu Tyr
65                  70                  75                  80

Leu Gln Met Asp Ser Leu Arg Gly Glu Asp Thr Ala Leu Tyr Tyr Cys
                85                  90                  95

Ala Arg Asp Met Arg Glu Met Glu Cys Glu Glu Trp Ala Ser Asp Tyr
            100                 105                 110

Tyr Asp Phe Gly Arg Pro Gly Pro Cys Arg Asp Leu Arg Gly Val Val
        115                 120                 125

Gly Thr Phe Asp Ile Trp Gly Pro Gly Thr Met Val Thr Val Ser Ser
    130                 135                 140

<210> SEQ ID NO 199
<211> LENGTH: 144
<212> TYPE: PRT
<213> ORGANISM: Homo sapiens

<400> SEQUENCE: 199

Glu Val Gln Leu Glu Glu Ser Gly Gly Asp Val Val Gln Pro Gly Arg
1               5                   10                  15

Ser Leu Arg Leu Ser Cys Ala Ala Ser Gly Phe Ser Phe Gly Asn Tyr
            20                  25                  30

Gly Met His Trp Val Arg Gln Ala Pro Gly Lys Gly Leu Glu Trp Val
        35                  40                  45

Ala Ala Ile Ser Phe Ile Gly Leu Lys Lys Tyr Tyr Glu Asn Ser Val
    50                  55                  60

Arg Gly Arg Phe Thr Ile Ser Arg Asp Asn Ser Lys Asn Ile Leu Tyr
65                  70                  75                  80

Leu Gln Met Asp Ser Leu Arg Gly Glu Asp Thr Ala Leu Tyr Tyr Cys
                85                  90                  95

Ala Arg Asp Met Arg Glu Met Glu Cys Glu Glu Trp Ala Ser Asp Tyr
            100                 105                 110

Tyr Asp Phe Gly Arg Ser Gly Pro Cys Arg Asp Phe Arg Gly Val Val
        115                 120                 125

Gly Val Phe Asp Ile Trp Gly Pro Gly Thr Met Val Thr Val Ser Ser
    130                 135                 140

<210> SEQ ID NO 200
<211> LENGTH: 144
<212> TYPE: PRT
<213> ORGANISM: Homo sapiens

<400> SEQUENCE: 200

Glu Val Gln Leu Val Glu Ser Gly Gly Val Val Gln Pro Gly Arg
1               5                   10                  15

Ser Leu Arg Leu Ser Cys Val Ala Ser Gln Phe Thr Phe Ser Gly His
            20                  25                  30

Gly Met His Trp Leu Arg Gln Ala Pro Gly Lys Gly Leu Glu Trp Val
        35                  40                  45

Ala Ser Thr Ser Phe Ala Gly Thr Lys Ser His Tyr Ala Asn Ser Val
    50                  55                  60

Arg Gly Arg Phe Thr Ile Ser Arg Asp Asn Ser Lys Asn Thr Leu Tyr
65                  70                  75                  80

Leu Gln Met Asn Asn Leu Arg Ala Glu Asp Thr Ala Leu Tyr Tyr Cys
                85                  90                  95

Ala Arg Asp Ser Arg Glu Tyr Glu Cys Glu Leu Trp Thr Ser Asp Tyr
            100                 105                 110

```
Tyr Asp Phe Gly Lys Pro Gln Pro Cys Ile Asp Thr Arg Asp Val Gly
        115                 120                 125

Gly Leu Phe Asp Met Trp Gly Gln Gly Thr Met Val Thr Val Ser Ser
        130                 135                 140

<210> SEQ ID NO 201
<211> LENGTH: 146
<212> TYPE: PRT
<213> ORGANISM: Homo sapiens

<400> SEQUENCE: 201

Glu Val Gln Leu Val Glu Ser Gly Gly Gly Val Val Gln Pro Gly Lys
1               5                   10                  15

Ser Leu Thr Leu Ser Cys Ala Ala Ser Gln Phe Ala Phe Ser Asn Tyr
            20                  25                  30

Gly Met His Trp Val Arg Gln Ala Pro Gly Lys Gly Leu Glu Trp Val
        35                  40                  45

Gly Ser Ile Thr Asn Asp Gly Asn Lys Lys Tyr His Gly Asp Ser Val
    50                  55                  60

Trp Asp Arg Phe Thr Ile Ser Arg Asp Asn Ser Lys Asn Thr Leu Phe
65                  70                  75                  80

Leu Gln Met Asn Ser Leu Arg Val Glu Asp Thr Ala Arg Tyr Phe Cys
                85                  90                  95

Val Arg Asp Gln Arg Glu Asp Cys Glu Arg Trp Ser Asp Tyr
            100                 105                 110

Tyr His Phe Gly Arg Val Leu Pro Cys Arg Lys Tyr Arg Gly Leu Gly
        115                 120                 125

Leu Ala Gly Val Phe Asp Ile Trp Gly His Gly Thr Met Val Ile Val
        130                 135                 140

Ser Ser
145

<210> SEQ ID NO 202
<211> LENGTH: 146
<212> TYPE: PRT
<213> ORGANISM: Homo sapiens

<400> SEQUENCE: 202

Gln Met Leu Leu Val Glu Ser Gly Gly Gly Val Val Glu Pro Gly Arg
1               5                   10                  15

Ser Leu Thr Leu Ser Cys Ala Thr Ser Gln Phe Thr Phe Ser His Tyr
            20                  25                  30

Gly Met His Trp Val Arg Gln Thr Pro Gly Arg Gly Leu Glu Trp Val
        35                  40                  45

Ala Ser Ile Ser Asn Glu Gly Asn Lys Lys Tyr His Gly Glu Ser Val
    50                  55                  60

Trp Gly Arg Phe Ile Ile Ser Arg Asp Asn Ser Lys Asn Thr Leu Phe
65                  70                  75                  80

Leu His Met Ser Asn Leu Arg Ala Asp Asp Ser Ala Leu Tyr Phe Cys
                85                  90                  95

Val Arg Asp Arg Gln Glu Asp Cys Glu Glu Trp Trp Ser Asp Tyr
            100                 105                 110

Tyr Ala Phe Gly Arg Gly Gly Pro Cys Arg Lys Tyr His Gly Gln Gly
        115                 120                 125

Leu Ala Gly Ile Phe Asp Ile Trp Gly Arg Gly Thr Met Val Thr Val
        130                 135                 140
```

```
Ser Ser
145

<210> SEQ ID NO 203
<211> LENGTH: 146
<212> TYPE: PRT
<213> ORGANISM: Homo sapiens

<400> SEQUENCE: 203

Glu Val Gln Leu Val Glu Ser Gly Gly Gly Val Val Gln Pro Gly Thr
1               5                   10                  15

Ser Leu Thr Leu Ser Cys Thr Ala Ser Gln Phe Ser Phe Ser Asn Tyr
            20                  25                  30

Gly Met His Trp Val Arg Gln Ala Pro Gly Lys Gly Leu Glu Trp Val
        35                  40                  45

Ala Ser Ile Ser Asn Asp Gly Ser Lys Arg Tyr His Gly Asp Ala Val
    50                  55                  60

Trp Ala Arg Phe Ile Ile Ser Arg Asp Asn Ser Lys Asn Thr Val Phe
65                  70                  75                  80

Leu Gln Met Thr Ser Leu Arg Thr Glu Asp Thr Ala Leu Tyr Phe Cys
                85                  90                  95

Val Arg Asp Arg Gln Glu Asp Glu Cys Val Glu Trp Trp Ser Asp Tyr
            100                 105                 110

Tyr Asn Phe Gly Arg Glu Leu Pro Cys Ser Lys Phe Arg Gly Leu Gly
        115                 120                 125

Leu Ala Gly Ile Phe Asp Ile Trp Gly His Gly Thr Met Val Thr Val
    130                 135                 140

Ser Ser
145

<210> SEQ ID NO 204
<211> LENGTH: 144
<212> TYPE: PRT
<213> ORGANISM: Homo sapiens

<400> SEQUENCE: 204

Gln Val His Leu Val Ala Ser Gly Gly Gly Val Val Pro Pro Gly Arg
1               5                   10                  15

Ser Leu Thr Leu Ser Cys Val Ala Ser Gln Phe Thr Phe Ser Ser Cys
            20                  25                  30

Gly Leu His Trp Val Arg Gln Ala Pro Gly Lys Gly Leu Glu Trp Val
        35                  40                  45

Ala Ala Ile Ser Phe Ala Gly Thr Lys Lys His Tyr Gly Asn Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Lys Asp Leu Arg Glu Tyr Glu Cys Glu Glu Trp Arg Ser Asp Tyr
            100                 105                 110

Tyr Asp Phe Gly Arg Asp Gln Pro Cys Ile Asp Ser Gln Gly Val Val
        115                 120                 125

Gly Ile Leu Asp Ile Trp Gly Gln Gly Thr Met Val Thr Val Ser Ser
    130                 135                 140

<210> SEQ ID NO 205
```

<211> LENGTH: 144
<212> TYPE: PRT
<213> ORGANISM: Homo sapiens

<400> SEQUENCE: 205

Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Thr Tyr
            20                  25                  30
Ala Met His Trp Val Arg Gln Ala Pro Gly Lys Gly Leu Glu Trp Val
        35                  40                  45
Ala Leu Ile Ser Tyr Asp Ala Thr Asn Lys Tyr Tyr Val Asp Ser Val
    50                  55                  60
Lys Gly Arg Phe Thr Ile Ser Arg Asp Asn Ser Lys Asn Thr Leu Tyr
65                  70                  75                  80
Leu Gln Val Ser Ser Leu Thr Ala Glu Asp Thr Ala Val Tyr Tyr Cys
                85                  90                  95
Ala Lys Asp Leu Gly Gly Ile Lys Asn Asp Glu Trp Gly Thr Asp Tyr
            100                 105                 110
Tyr Asp Ile Ser Val Ser Tyr Pro Val Gln Asp Pro Arg Ala Val Ala
        115                 120                 125
Gly Ile Phe Asp Val Trp Gly His Gly Thr Met Val Ser Val Ser Ser
    130                 135                 140

<210> SEQ ID NO 206
<211> LENGTH: 146
<212> TYPE: PRT
<213> ORGANISM: Homo sapiens

<400> SEQUENCE: 206

Glu Val Gln Leu Val Glu Ser Gly Gly Gly Val Val Gln Pro Gly Thr
1               5                   10                  15
Ser Leu Thr Leu Ser Cys Ala Ala Ser Gln Phe Thr Phe Ser Asn Tyr
            20                  25                  30
Gly Met His Trp Val Arg Gln Ala Pro Gly Lys Gly Leu Glu Trp Val
        35                  40                  45
Ala Ser Ile Ser Asn Asp Gly Asn Lys Lys Tyr His Gly Asp Ala Val
    50                  55                  60
Trp Ala Arg Phe Ile Ile Ser Arg Asp Asn Ser Lys Asn Thr Val Phe
65                  70                  75                  80
Leu Gln Leu Thr Ser Leu Arg Ala Glu Asp Thr Ala Leu Tyr Phe Cys
                85                  90                  95
Val Arg Asp Arg Gln Glu Asp Glu Cys Val Glu Trp Trp Ser Asp Tyr
            100                 105                 110
Tyr Asn Phe Gly Arg Glu Leu Pro Cys Ser Lys Phe Arg Gly Leu Gly
        115                 120                 125
Leu Ala Gly Ile Phe Asp Ile Trp Gly Leu Gly Thr Met Val Thr Val
    130                 135                 140
Ser Ser
145

<210> SEQ ID NO 207
<211> LENGTH: 146
<212> TYPE: PRT
<213> ORGANISM: Homo sapiens

<400> SEQUENCE: 207

Glu Val Gln Leu Val Glu Ser Gly Gly Gly Val Val Gln Pro Gly Thr
1               5                   10                  15

Ser Leu Thr Leu Ser Cys Ala Ala Ser Gln Phe Ser Phe Ser Asn Tyr
            20                  25                  30

Gly Met His Trp Val Arg Gln Ala Pro Gly Lys Gly Leu Glu Trp Val
        35                  40                  45

Ala Ser Ile Ser Asn Asp Gly Ser Lys Arg Tyr His Gly Asp Ala Val
    50                  55                  60

Trp Ala Arg Phe Ile Ile Ser Arg Asp Asn Ser Lys Asn Thr Val Phe
65                  70                  75                  80

Leu Gln Met Thr Ser Leu Arg Ala Glu Asp Thr Ala Leu Tyr Phe Cys
                85                  90                  95

Val Arg Asp Arg Gln Glu Asp Glu Cys Val Glu Trp Trp Ser Asp Tyr
                100                 105                 110

Tyr Asn Phe Gly Arg Glu Leu Pro Cys Ser Lys Phe Arg Gly Leu Gly
            115                 120                 125

Leu Ala Gly Ile Phe Asp Ile Trp Gly His Gly Thr Met Val Thr Val
        130                 135                 140

Ser Ser
145

<210> SEQ ID NO 208
<211> LENGTH: 146
<212> TYPE: PRT
<213> ORGANISM: Homo sapiens

<400> SEQUENCE: 208

Glu Val Gln Leu Val Glu Ser Gly Gly Gly Glu Val Gln Pro Gly Thr
1               5                   10                  15

Ser Leu Thr Leu Ser Cys Ala Ala Ser Gln Phe Thr Phe Ser Asn Tyr
            20                  25                  30

Gly Met His Trp Val Arg Gln Ala Pro Gly Lys Gly Leu Glu Trp Val
        35                  40                  45

Ala Ser Ile Ser Asn Glu Gly Asn Lys Lys Tyr His Gly Asp Ser Val
    50                  55                  60

Trp Ala Arg Phe Ile Ile Ser Arg Asp Asn Ser Lys Asn Thr Val Phe
65                  70                  75                  80

Leu Gln Met Thr Ser Leu Arg Ala Glu Asp Thr Ala Leu Tyr Phe Cys
                85                  90                  95

Val Arg Asp Arg Gln Glu Asp Glu Cys Glu Glu Trp Trp Ser Asp Tyr
                100                 105                 110

Tyr Asn Phe Gly Arg Glu Leu Pro Cys Arg Lys Phe Arg Gly Gln Gly
            115                 120                 125

Leu Ala Gly Ile Phe Asp Ile Trp Gly His Gly Thr Met Val Thr Val
        130                 135                 140

Ser Ser
145

<210> SEQ ID NO 209
<211> LENGTH: 146
<212> TYPE: PRT
<213> ORGANISM: Homo sapiens

<400> SEQUENCE: 209

Glu Val Gln Leu Val Glu Ser Gly Gly Gly Val Val Gln Pro Gly Met
1               5                   10                  15

-continued

Ser Leu Thr Leu Ser Cys Ala Ala Ser His Phe Thr Phe Ser Asn Tyr
            20                  25                  30

Gly Met His Trp Val Arg Gln Ala Pro Gly Lys Gly Leu Glu Trp Val
            35                  40                  45

Ala Ser Ile Ser Asn Glu Gly Asn Lys Lys Tyr His Gly Asp Ser Val
        50                  55                  60

Trp Gly Arg Phe Ile Ile Ser Arg Asp Asn Ser Lys Asn Thr Leu Phe
65                  70                  75                  80

Leu His Met Ser Ser Leu Arg Val Glu Asp Thr Ala Leu Tyr Phe Cys
                85                  90                  95

Val Arg Asp Arg Gln Glu Asp Glu Cys Glu Gly Trp Trp Ser Asp Tyr
            100                 105                 110

Tyr Asn Phe Gly Arg Glu Leu Pro Cys Arg Lys Phe Arg Gly Pro Gly
            115                 120                 125

Leu Ala Gly Ile Phe Asp Ile Trp Gly His Gly Thr Met Val Thr Val
        130                 135                 140

Ser Ser
145

<210> SEQ ID NO 210
<211> LENGTH: 144
<212> TYPE: PRT
<213> ORGANISM: Homo sapiens

<400> SEQUENCE: 210

Glu Val Gln Leu Val Glu Ser Gly Gly Gly Val Val Pro Pro Gly Lys
1               5                   10                  15

Ser Leu Arg Leu Ser Cys Val Ala Ser Arg Phe Thr Phe Ser Ala Phe
            20                  25                  30

Gly Met His Trp Val Arg Gln Ala Pro Gly Lys Gly Leu Glu Trp Val
            35                  40                  45

Ala Gly Ile Ser Phe Ala Gly Ile Lys Tyr Tyr Tyr Ala Asp Ser Val
        50                  55                  60

Lys Gly Arg Phe Thr Ile Ser Arg Asp Asn Ser Lys Asn Thr Leu Phe
65                  70                  75                  80

Leu Gln Met Asn Gly Leu Arg Gly Asp Asp Thr Ala Leu Tyr Tyr Cys
                85                  90                  95

Val Lys Asp Leu Arg Glu Leu Gly Cys Glu Gly Trp Thr Ser Asp Tyr
            100                 105                 110

Tyr Asp Phe Gly Arg Pro Gln Pro Cys Ile Asp Pro Arg Gly Val Ser
            115                 120                 125

Gly Ile Ser Ala Met Trp Gly Gln Gly Thr Met Val Thr Ile Ser Ser
        130                 135                 140

<210> SEQ ID NO 211
<211> LENGTH: 144
<212> TYPE: PRT
<213> ORGANISM: Homo sapiens

<400> SEQUENCE: 211

Glu Val Gln Leu Val Glu Ser Gly Gly Gly Val Val Gln Pro Gly Arg
1               5                   10                  15

Ser Leu Arg Leu Ser Cys Ala Ala Ser His Phe Ser Leu Ser Ser Tyr
            20                  25                  30

Gly Met His Trp Val Arg Gln Ala Pro Gly Lys Gly Leu Glu Trp Val
            35                  40                  45

Ala Gly Glu Ser Phe Ala Ala Thr Asn Lys Tyr Tyr Ala Asp Ser Val
         50                  55                  60

Lys Gly Arg Phe Ile Val Ser Arg Asp Ile Ser Lys Asn Thr Leu Tyr
 65                  70                  75                  80

Leu Glu Val Asn Ser Leu Arg Thr Glu Asp Thr Ala Leu Tyr Tyr Cys
                 85                  90                  95

Ala Arg Asp Gln Arg Tyr Tyr Glu Cys Glu Glu Trp Ala Ser Asp Tyr
             100                 105                 110

Tyr Asp Phe Gly Arg Glu Gln Pro Cys Gln Asp Pro Arg Gly Val Val
             115                 120                 125

Gly Ile Phe Asp Ile Trp Gly Gln Gly Thr Met Val Thr Val Ser Ser
130                 135                 140

<210> SEQ ID NO 212
<211> LENGTH: 107
<212> TYPE: PRT
<213> ORGANISM: Homo sapiens

<400> SEQUENCE: 212

Gln Ser Ala Leu Thr Gln Pro Pro Ser Val Ser Thr Ala Pro Gly Gln
 1               5                  10                  15

Thr Val Thr Val Ser Cys Ser Gly Gly Thr Ser Asn Thr Gly Asn Asn
                 20                  25                  30

Phe Val Ser Trp Tyr Gln His Leu Pro Gly Thr Ala Pro Lys Leu Leu
             35                  40                  45

Ile Tyr Glu Asn Asn Lys Arg Pro Leu Gly Val Pro Asp Arg Phe Ser
         50                  55                  60

Gly Ala Lys Ser Gly Thr Ser Ala Thr Leu Ala Ile Thr Gly Leu Gln
 65                  70                  75                  80

Thr Gly Asp Glu Gly Asp Tyr Tyr Cys Ala Thr Trp Ser Gly Ser Leu
                 85                  90                  95

Asn Ile Gly Thr Gly Thr Lys Val Ser Val Leu
            100                 105

<210> SEQ ID NO 213
<211> LENGTH: 111
<212> TYPE: PRT
<213> ORGANISM: Homo sapiens

<400> SEQUENCE: 213

Gln Ser Val Leu Thr Gln Pro Pro Ser Val Ser Ala Ala Pro Gly Gln
 1               5                  10                  15

Asn Val Thr Ile Ser Cys Ser Gly Ser Ala Ser Asn Ile Gly Lys Asn
                 20                  25                  30

Phe Ala Ser Trp Tyr Gln Gln Leu Pro Gly Thr Ala Pro Lys Leu Leu
             35                  40                  45

Ile Tyr Glu Asn Asn Arg Arg Pro Ser Gly Thr Pro Asp Arg Phe Ser
         50                  55                  60

Gly Ser Lys Ser Gly Thr Ser Ala Thr Leu Ala Ile Ser Gly Leu Gln
 65                  70                  75                  80

Thr Gly Asp Gly Ala Asp Tyr Tyr Cys Gly Thr Trp Asp Asn Ser Leu
                 85                  90                  95

Asn Ser Ser Pro Leu Ile Gly Pro Gly Thr Lys Val Thr Val Leu
            100                 105                 110

<210> SEQ ID NO 214
<211> LENGTH: 108

```
<212> TYPE: PRT
<213> ORGANISM: Homo sapiens

<400> SEQUENCE: 214

Gln Ser Val Leu Thr Gln Pro Pro Ser Val Ser Ala Ala Pro Gly Gln
1               5                   10                  15

Lys Val Thr Ile Ser Cys Ser Gly Ser Ser Asn Ile Gly Ser Asn
            20                  25                  30

Tyr Val Ser Trp Tyr Gln His Val Pro Gly Thr Ala Pro Lys Leu Leu
        35                  40                  45

Ile Tyr Glu Asn Asn Arg Arg Pro Ser Gly Thr Pro Asp Arg Phe Ser
    50                  55                  60

Gly Ser Lys Ser Gly Thr Ser Ala Thr Leu Ala Ile Thr Gly Leu Arg
65                  70                  75                  80

Thr Gly Asp Glu Ala Asp Tyr Tyr Cys Gly Thr Trp Leu Asn Ser Gly
                85                  90                  95

Gly Val Phe Gly Thr Gly Thr Arg Val Asn Val Leu
            100                 105

<210> SEQ ID NO 215
<211> LENGTH: 111
<212> TYPE: PRT
<213> ORGANISM: Homo sapiens

<400> SEQUENCE: 215

Gln Ser Val Leu Thr Gln Pro Pro Ser Val Ser Glu Ala Pro Gly Gln
1               5                   10                  15

Lys Val Thr Ile Ser Cys Ser Gly Ser Ala Ser Asn Ile Gly Lys Asn
            20                  25                  30

Phe Val Ser Trp Tyr Gln Gln Phe Pro Gly Thr Ala Pro Lys Leu Val
        35                  40                  45

Ile Tyr Glu Asn Asn Arg Arg Pro Ser Gly Thr Pro Asp Arg Phe Ser
    50                  55                  60

Gly Ser Lys Ser Gly Thr Ser Ala Thr Leu Ala Ile Ser Gly Leu Gln
65                  70                  75                  80

Thr Gly Asp Glu Ala Asp Tyr Tyr Cys Gly Thr Trp Asp Asn Ser Leu
                85                  90                  95

Asn Ser Ser Pro Val Phe Gly Thr Gly Thr Lys Val Thr Val Leu
            100                 105                 110

<210> SEQ ID NO 216
<211> LENGTH: 111
<212> TYPE: PRT
<213> ORGANISM: Homo sapiens

<400> SEQUENCE: 216

Gln Ser Val Leu Thr Gln Pro Pro Ser Val Ser Ala Ala Pro Gly Gln
1               5                   10                  15

Lys Val Thr Ile Ser Cys Ser Gly Ser Ala Ser Asn Ile Gly Lys Asn
            20                  25                  30

Phe Val Ser Trp Tyr Gln Gln Leu Pro Gly Thr Ala Pro Lys Leu Ile
        35                  40                  45

Ile Tyr Glu Asn Asn Arg Arg Pro Ser Gly Thr Pro Asp Arg Phe Ser
    50                  55                  60

Gly Ser Lys Ser Gly Thr Ser Gly Thr Leu Ala Ile Ser Gly Leu Gln
65                  70                  75                  80

Thr Asp Asp Glu Ala Asp Tyr Tyr Cys Ala Thr Trp Asp Asn Thr Leu
```

-continued

```
                85                  90                  95
Asp Ser Ser Pro Leu Ile Gly Pro Gly Thr Lys Val Thr Val Leu
            100                 105                 110

<210> SEQ ID NO 217
<211> LENGTH: 111
<212> TYPE: PRT
<213> ORGANISM: Homo sapiens

<400> SEQUENCE: 217

Gln Ser Val Leu Thr Gln Pro Pro Ser Val Ser Ala Ala Pro Gly Gln
1               5                   10                  15

Arg Val Thr Ile Ser Cys Ser Gly Ser Ala Ser Asp Ile Gly Lys Asn
            20                  25                  30

Ser Val Ser Trp Tyr Gln Gln Leu Pro Gly Thr Ala Pro Lys Leu Leu
        35                  40                  45

Ile Tyr Glu Asn Asn Arg Arg Pro Ser Gly Thr Pro Asp Arg Phe Ser
    50                  55                  60

Gly Ser Lys Ser Gly Thr Ser Ala Thr Leu Ala Ile Ser Gly Leu Gln
65                  70                  75                  80

Thr Gly Asp Glu Ala Asp Tyr Tyr Cys Gly Thr Trp Asp Asn Ser Leu
                85                  90                  95

Gly Ser Ser Pro Leu Ile Gly Ser Gly Thr Lys Val Thr Val Leu
            100                 105                 110

<210> SEQ ID NO 218
<211> LENGTH: 111
<212> TYPE: PRT
<213> ORGANISM: Homo sapiens

<400> SEQUENCE: 218

Gln Ser Val Leu Thr Gln Pro Pro Ser Val Ser Ala Thr Pro Gly Gln
1               5                   10                  15

Lys Val Thr Ile Ser Cys Ser Gly Ser Asn Ser Asn Ile Gly Thr Lys
            20                  25                  30

Tyr Val Ser Trp Tyr Gln His Val Pro Gly Thr Ala Pro Lys Leu Leu
        35                  40                  45

Ile Phe Glu Ser Asp Arg Arg Pro Thr Gly Ile Pro Asp Arg Phe Ser
    50                  55                  60

Gly Ser Lys Ser Ala Thr Ser Ala Thr Leu Thr Ile Thr Gly Leu Gln
65                  70                  75                  80

Thr Gly Asp Glu Ala Ile Tyr Tyr Cys Gly Thr Tyr Gly Asp Ser Arg
                85                  90                  95

Thr Pro Gly Gly Leu Phe Gly Thr Gly Thr Lys Leu Thr Val Leu
            100                 105                 110

<210> SEQ ID NO 219
<211> LENGTH: 111
<212> TYPE: PRT
<213> ORGANISM: Homo sapiens

<400> SEQUENCE: 219

Gln Ser Val Leu Thr Gln Pro Pro Ser Val Ser Ala Ala Pro Gly Gln
1               5                   10                  15

Lys Val Ser Ile Ser Cys Ser Gly Asn Asn Ser Asn Ile Gly Asn Asn
            20                  25                  30

Phe Ile Ser Trp Phe Gln Gln Phe Pro Gly Thr Ala Pro Lys Pro Leu
        35                  40                  45
```

Ile Phe Glu Thr Tyr Arg Arg His Ser Gly Ile Ser Asp Arg Phe Ser
 50                  55                  60

Ala Ser Lys Ser Gly Thr Ser Ala Thr Leu Ala Ile Thr Gly Leu Gln
 65                  70                  75                  80

Pro Gly Asp Glu Ala Asp Tyr Tyr Cys Ala Thr Trp Gly Val Arg Gln
                 85                  90                  95

Gly Val Gly Ala Leu Phe Gly Thr Gly Thr Lys Val Thr Val Leu
             100                 105                 110

<210> SEQ ID NO 220
<211> LENGTH: 111
<212> TYPE: PRT
<213> ORGANISM: Homo sapiens

<400> SEQUENCE: 220

Gln Ser Val Leu Thr Gln Pro Pro Ser Val Ser Ala Ala Pro Gly Gln
 1               5                  10                  15

Lys Val Ile Ile Ser Cys Ser Gly Asp Asn Ser Thr Ile Gly Ser Lys
                 20                  25                  30

Phe Val Ser Trp Tyr Gln Gln Val Pro Gly Thr Ala Pro Lys Leu Leu
             35                  40                  45

Val Tyr Glu Thr Asn Arg Arg Pro Ser Gly Ile Pro Asp Arg Phe Ser
 50                  55                  60

Gly Ser Lys Ser Gly Thr Ser Ala Thr Leu Ala Ile Thr Gly Leu Gln
 65                  70                  75                  80

Thr Gly Asp Glu Ala Asp Tyr Phe Cys Thr Val Trp Gly Val Arg Lys
                 85                  90                  95

Gly Val Gly Ala Leu Phe Gly Thr Gly Thr Lys Val Thr Val Leu
             100                 105                 110

<210> SEQ ID NO 221
<211> LENGTH: 111
<212> TYPE: PRT
<213> ORGANISM: Homo sapiens

<400> SEQUENCE: 221

Gln Ser Val Leu Thr Gln Pro Pro Ser Val Ser Ala Ala Pro Gly Gln
 1               5                  10                  15

Lys Val Ile Ile Ser Cys Ser Gly Asn Asn Ser Thr Ile Gly Asn Asn
                 20                  25                  30

Phe Val Ser Trp Tyr Gln Gln Val Pro Gly Thr Ala Pro Lys Leu Leu
             35                  40                  45

Val Tyr Glu Thr Tyr Arg Arg Pro Ser Gly Ile Pro Asp Arg Phe Ser
 50                  55                  60

Gly Ser Lys Ser Gly Thr Thr Ala Thr Leu Ala Ile Ser Gly Leu Gln
 65                  70                  75                  80

Thr Gly Asp Glu Ala Asp Tyr His Cys Thr Val Trp Gly Val Arg Lys
                 85                  90                  95

Gly Val Ala Ala Val Phe Gly Thr Gly Thr Lys Val Thr Val Leu
             100                 105                 110

<210> SEQ ID NO 222
<211> LENGTH: 108
<212> TYPE: PRT
<213> ORGANISM: Homo sapiens

<400> SEQUENCE: 222

Gln Ser Val Leu Thr Gln Pro Pro Ser Val Ser Ala Ala Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Tyr Leu Pro Gly Thr Ala Pro Lys Leu Leu
            35                  40                  45

Ile Tyr Glu Asn Gly Lys Arg Pro Ser Gly Ile Pro Asp Arg Phe Ser
            50                  55                  60

Ala Ser Lys Ser Gly Thr Ser Ala Thr Leu Ala Ile Thr Gly Leu Gln
65                  70                  75                  80

Thr Gly Asp Glu Ala Asp Tyr Tyr Cys Gly Thr Trp Met Thr Thr Gly
                85                  90                  95

Gly Val Phe Gly Ser Gly Thr Lys Val Thr Val Leu
            100                 105

<210> SEQ ID NO 223
<211> LENGTH: 111
<212> TYPE: PRT
<213> ORGANISM: Homo sapiens

<400> SEQUENCE: 223

Gln Ser Val Leu Thr Gln Pro Pro Ser Val Ser Ala Ala Pro Gly Gln
1               5                   10                  15

Lys Val Thr Ile Ser Cys Ser Gly Thr Ser Ser Asn Ile Arg Asn Asn
            20                  25                  30

Tyr Val Ser Trp Tyr Gln Gln Leu Pro Gly Thr Ala Pro Lys Leu Leu
            35                  40                  45

Ile Tyr Glu Asn Asn Lys Arg Pro Ser Gly Ile Pro Asp Arg Phe Ser
            50                  55                  60

Gly Ser Lys Ser Gly Thr Ser Ala Thr Leu Ala Ile Thr Gly Leu Gln
65                  70                  75                  80

Thr Gly Asp Glu Ala Asp Tyr Tyr Cys Gly Thr Trp Asp Asn Ser Leu
                85                  90                  95

Asn Thr Gly Gly Val Phe Gly Ala Gly Thr Lys Val Thr Val Leu
            100                 105                 110

<210> SEQ ID NO 224
<211> LENGTH: 111
<212> TYPE: PRT
<213> ORGANISM: Homo sapiens

<400> SEQUENCE: 224

Gln Ser Val Leu Thr Gln Pro Pro Ser Val Ser Ala Ala Pro Gly Gln
1               5                   10                  15

Lys Val Ile Ile Ser Cys Ser Gly Asn Asn Ser Thr Ile Gly Asn Asn
            20                  25                  30

Phe Val Ser Trp Tyr Gln Gln Val Pro Gly Thr Ala Pro Lys Leu Leu
            35                  40                  45

Val Tyr Glu Thr Tyr Arg Arg Pro Ser Gly Ile Pro Asp Arg Phe Ser
            50                  55                  60

Gly Ser Lys Ser Gly Thr Ser Ala Thr Leu Ala Ile Thr Gly Leu Gln
65                  70                  75                  80

Thr Gly Asp Glu Ala Asp Tyr Tyr Cys Thr Val Trp Gly Val Arg Lys
                85                  90                  95

Gly Val Ala Val Phe Gly Thr Gly Thr Lys Val Thr Val Leu
            100                 105                 110

<210> SEQ ID NO 225
<211> LENGTH: 111
<212> TYPE: PRT
<213> ORGANISM: Homo sapiens

<400> SEQUENCE: 225

Gln Ser Val Leu Thr Gln Pro Pro Ser Val Ser Ala Ala Pro Gly Gln
1               5                   10                  15

Lys Val Ile Ile Ser Cys Ser Gly Asn Asn Ser Thr Ile Gly Asn Asn
            20                  25                  30

Phe Val Ser Trp Tyr Gln Gln Val Pro Gly Thr Ala Pro Lys Leu Leu
        35                  40                  45

Val Tyr Glu Thr Tyr Arg Arg Pro Ser Gly Ile Pro Asp Arg Phe Ser
    50                  55                  60

Gly Ser Lys Ser Gly Thr Thr Ala Thr Leu Ala Ile Ser Gly Leu Gln
65                  70                  75                  80

Thr Gly Asp Glu Ala Asp Tyr His Cys Thr Val Trp Gly Val Arg Lys
                85                  90                  95

Gly Val Ala Ala Val Phe Gly Thr Gly Thr Lys Val Thr Val Leu
            100                 105                 110

<210> SEQ ID NO 226
<211> LENGTH: 111
<212> TYPE: PRT
<213> ORGANISM: Homo sapiens

<400> SEQUENCE: 226

Gln Ser Val Leu Thr Gln Pro Pro Ser Val Ser Ala Ala Pro Gly Gln
1               5                   10                  15

Lys Val Ile Ile Ser Cys Ser Gly Asn Asn Ser Thr Val Gly Asn Asn
            20                  25                  30

Phe Val Ser Trp Tyr Gln Gln Val Pro Gly Thr Ala Pro Lys Leu Leu
        35                  40                  45

Val Tyr Glu Thr Tyr Arg Arg Pro Ser Gly Ile Pro Asp Arg Phe Ser
    50                  55                  60

Gly Ser Lys Ser Gly Thr Ser Ala Thr Leu Ala Ile Thr Gly Leu Gln
65                  70                  75                  80

Ala Gly Asp Glu Ala Asp Tyr Tyr Cys Thr Val Trp Gly Val Arg Lys
                85                  90                  95

Gly Val Ala Ala Val Phe Gly Thr Gly Thr Lys Val Thr Val Leu
            100                 105                 110

<210> SEQ ID NO 227
<211> LENGTH: 111
<212> TYPE: PRT
<213> ORGANISM: Homo sapiens

<400> SEQUENCE: 227

Gln Ser Val Leu Thr Gln Pro Pro Ser Val Ser Ala Ala Pro Gly Gln
1               5                   10                  15

Arg Val Thr Ile Ser Cys Ser Gly Asn Asn Ser Thr Ile Gly Asn Asn
            20                  25                  30

Phe Val Ser Trp Tyr Gln Gln Val Pro Gly Thr Ala Pro Lys Leu Leu
        35                  40                  45

Val Tyr Glu Thr Tyr Arg Arg Pro Ser Gly Ile Pro Asp Arg Phe Ser
    50                  55                  60

Gly Ser Lys Ser Gly Thr Ser Ala Thr Leu Ala Ile Thr Gly Leu Gln

```
                65                  70                  75                  80
Thr Gly Asp Glu Ala Asp Tyr Tyr Cys Thr Val Trp Gly Ile Arg Lys
                    85                      90                  95

Gly Val Ala Ala Val Phe Gly Thr Gly Thr Lys Val Thr Val Leu
                100                 105                 110

<210> SEQ ID NO 228
<211> LENGTH: 107
<212> TYPE: PRT
<213> ORGANISM: Homo sapiens

<400> SEQUENCE: 228

Gln Ser Val Leu Thr Gln Pro Pro Ser Val Ser Ala Ala Pro Gly Gln
1               5                   10                  15

Asn Val Thr Ile Ser Cys Ser Gly Pro Pro Ser His Ile Glu Lys Asn
                20                  25                  30

Asp Val Ser Trp Tyr Gln Arg Phe Pro Gly Met Ala Pro Lys Met Leu
            35                  40                  45

Ile Tyr Glu Ser Tyr Arg Arg Pro Ala Gly Ile Pro Ala Arg Phe Ser
        50                  55                  60

Ala Ser Arg Ser Gly Lys Ser Ala Thr Leu Thr Ile Thr Gly Leu Gln
65                  70                  75                  80

Thr Gly Asp Glu Ala Asp Tyr Tyr Cys Gly Thr Trp Asn Gly Arg Met
                85                  90                  95

Asn Phe Gly Thr Gly Thr Val Thr Val Leu
                100                 105

<210> SEQ ID NO 229
<211> LENGTH: 108
<212> TYPE: PRT
<213> ORGANISM: Homo sapiens

<400> SEQUENCE: 229

Gln Ser Ala Leu Thr Gln Pro Pro Ser Val Ser Ala Ala Pro Gly Gln
1               5                   10                  15

Lys Val Thr Ile Ser Cys Ser Gly Ser Ile Gly Asn Asn Tyr Ile Ser
                20                  25                  30

Trp Tyr Gln Gln Val Pro Gly Thr Ala Pro Lys Leu Leu Ile Tyr Glu
            35                  40                  45

Asn Tyr Lys Arg Pro Ser Gly Ile Pro Asp Arg Phe Ser Gly Ser Lys
        50                  55                  60

Ser Gly Thr Ser Ala Thr Leu Ala Ile Thr Gly Leu Gln Thr Gly Asp
65                  70                  75                  80

Glu Ala Asp Phe Tyr Cys Ala Thr Trp Gly Gly Ser Leu Thr Thr Gly
                85                  90                  95

Gly Val Ile Gly Thr Gly Thr Lys Val Thr Val Leu
                100                 105
```